US011578141B2

(12) United States Patent
Neijssen et al.

(10) Patent No.: US 11,578,141 B2
(45) Date of Patent: Feb. 14, 2023

(54) BISPECIFIC ANTIBODIES AGAINST HER2 AND CD3

(71) Applicant: GENMAB A/S, Copenhagen V (DK)

(72) Inventors: Joost J. Neijssen, Werkhoven (NL); Joyce I. Meesters, Utrecht (NL); Bart De Goeij, Utrecht (NL); Aran Frank Labrijn, Nigtevecht (NL); Paul Parren, Odijk (NL); Janine Schuurman, Diemen (NL)

(73) Assignee: GENMAB A/S, Copenhagen V (DK)

( * ) Notice: Subject to any disclaimer, the term of this patent is extended or adjusted under 35 U.S.C. 154(b) by 0 days.

(21) Appl. No.: 16/667,369

(22) Filed: Oct. 29, 2019

(65) Prior Publication Data

US 2020/0270366 A1 Aug. 27, 2020

Related U.S. Application Data

(63) Continuation of application No. 15/599,395, filed on May 18, 2017, now abandoned, which is a continuation of application No. 14/112,859, filed as application No. PCT/EP2012/057307 on Apr. 20, 2012, now abandoned.

(60) Provisional application No. 61/552,286, filed on Oct. 27, 2011.

(30) Foreign Application Priority Data

| | | |
|---|---|---|
| Apr. 20, 2011 | (DK) | PA201100312 |
| Apr. 20, 2011 | (WO) | PCT/EP2011/056388 |
| May 27, 2011 | (WO) | PCT/EP2011/058772 |
| May 27, 2011 | (WO) | PCT/EP2011/058779 |
| Oct. 27, 2011 | (DK) | PA201100824 |

(51) Int. Cl.

| | |
|---|---|
| ***C07K 16/46*** | (2006.01) |
| ***C07K 16/10*** | (2006.01) |
| ***C07K 16/28*** | (2006.01) |
| ***C07K 16/32*** | (2006.01) |
| ***A61K 47/68*** | (2017.01) |
| ***A61K 39/395*** | (2006.01) |
| ***C07K 1/113*** | (2006.01) |
| ***A61K 39/00*** | (2006.01) |

(52) U.S. Cl.

CPC ........ *C07K 16/468* (2013.01); *A61K 39/3955* (2013.01); *A61K 47/6803* (2017.08); *A61K 47/6813* (2017.08); *A61K 47/6829* (2017.08); *A61K 47/6849* (2017.08); *A61K 47/6851* (2017.08); *A61K 47/6855* (2017.08); *A61K 47/6879* (2017.08); *C07K 1/113* (2013.01); *C07K 16/1063* (2013.01); *C07K 16/2803* (2013.01); *C07K 16/2809* (2013.01); *C07K 16/32* (2013.01); *A61K 2039/505* (2013.01); *C07K 16/2863* (2013.01); *C07K 2317/21* (2013.01); *C07K 2317/31* (2013.01); *C07K 2317/41* (2013.01); *C07K 2317/52* (2013.01); *C07K 2317/526* (2013.01); *C07K 2317/73* (2013.01); *C07K 2317/732* (2013.01); *C07K 2317/74* (2013.01); *C07K 2317/75* (2013.01); *C07K 2317/76* (2013.01); *C07K 2317/77* (2013.01); *C07K 2317/92* (2013.01)

(58) Field of Classification Search

CPC .. C07K 16/468; C07K 1/113; C07K 16/1063; C07K 16/2863; C07K 16/2803; C07K 16/2809; C07K 16/32; C07K 2317/21; C07K 2317/31; C07K 2317/41; C07K 2317/52; C07K 2317/526; C07K 2317/73; C07K 2317/732; C07K 2317/74; C07K 2317/75; C07K 2317/76; C07K 2317/77; C07K 2317/92; A61K 39/3955; A61K 47/6803; A61K 47/6813; A61K 47/6829; A61K 47/6849; A61K 47/6851; A61K 47/6855; A61K 47/6879; A61K 2039/505; A61P 35/00; A61P 43/00

See application file for complete search history.

(56) References Cited

U.S. PATENT DOCUMENTS

| | | | | |
|---|---|---|---|---|
| 5,705,157 | A | 1/1998 | Greene | |
| 6,123,939 | A | 9/2000 | Shawver et al. | |
| 6,270,765 | B1 | 8/2001 | Deo et al. | |
| 7,309,486 | B1 | 12/2007 | Zamoyski | |
| 9,150,663 | B2 | 10/2015 | Labrijn et al. | |
| 9,714,294 | B2 * | 7/2017 | De Goeij | C07K 16/32 |
| 9,862,769 | B2 * | 1/2018 | De Goeij | C07K 16/32 |

(Continued)

FOREIGN PATENT DOCUMENTS

| | | | |
|---|---|---|---|
| CN | 101633695 | A | 1/2010 |
| CN | 101721700 | A | 6/2010 |

(Continued)

OTHER PUBLICATIONS

U.S. Appl. No. 17/149,019, filed Jan. 14, 2021, Bart De Goeij.

(Continued)

*Primary Examiner* — Phuong Huynh

(74) *Attorney, Agent, or Firm* — Nelson Mullins Riley & Scarborough LLP; Jane E. Remillard, Esq.; Christopher L. Frank

(57) ABSTRACT

Bispecific antibodies which comprise one antigen-binding region binding to an epitope of human epidermal growth factor receptor 2 (HER2) and one antigen-binding region binding to human CD3, and related antibody-based compositions and molecules, are disclosed. Pharmaceutical compositions comprising the antibodies and methods for preparing and using the antibodies are also disclosed.

11 Claims, 45 Drawing Sheets

Specification includes a Sequence Listing.

(56) References Cited

U.S. PATENT DOCUMENTS

| | | | |
|---|---|---|---|
| 10,597,464 B2 | 3/2020 | Labrijn et al. | |
| 10,793,640 B2 | 10/2020 | De Goeij et al. | |
| 11,046,771 B2 * | 6/2021 | De Goeij | A61P 43/00 |
| 11,091,553 B2 * | 8/2021 | De Goeij | C07K 16/2809 |
| 2003/0118583 A1 | 6/2003 | Emery et al. | |
| 2006/0121604 A1 | 6/2006 | Handa et al. | |
| 2009/0202532 A1 | 8/2009 | Kumagai et al. | |
| 2009/0317869 A1 | 12/2009 | Alley et al. | |
| 2010/0015157 A1 | 1/2010 | Andya et al. | |
| 2010/0286374 A1 | 11/2010 | Kannan et al. | |
| 2012/0149876 A1 | 6/2012 | Von Kreudenstein et al. | |
| 2013/0039913 A1 | 2/2013 | Labrijn et al. | |
| 2013/0171148 A1 | 7/2013 | De Goeij et al. | |
| 2013/0189271 A1 | 7/2013 | De Goeij et al. | |
| 2014/0170148 A1 | 6/2014 | De Goeij et al. | |
| 2016/0046727 A1 | 2/2016 | Labrijn et al. | |
| 2017/0233497 A1 | 8/2017 | Labrijn et al. | |
| 2017/0369590 A1 | 12/2017 | De Goeij et al. | |
| 2017/0369594 A1 | 12/2017 | Neijssen et al. | |
| 2018/0022816 A1 | 1/2018 | De Goeij et al. | |
| 2018/0179286 A1 | 6/2018 | De Goeij et al. | |
| 2018/0194845 A1 | 7/2018 | De Goeij et al. | |
| 2018/0215827 A1 | 8/2018 | De Goeij et al. | |
| 2020/0262932 A1 | 8/2020 | Labrijn et al. | |
| 2021/0122830 A1 | 4/2021 | De Goeij et al. | |
| 2021/0324105 A1 | 10/2021 | De Goeij et al. | |
| 2022/0169738 A1 | 6/2022 | De Goeij et al. | |

FOREIGN PATENT DOCUMENTS

| | | | | |
|---|---|---|---|---|
| EP | 1980626 A1 | 10/2008 | | |
| WO | 89/06692 A1 | 7/1989 | | |
| WO | 97/35885 A1 | 10/1997 | | |
| WO | 98/17797 A1 | 4/1998 | | |
| WO | 99/31140 A1 | 6/1999 | | |
| WO | 99/44645 A1 | 9/1999 | | |
| WO | 1999/048527 A1 | 9/1999 | | |
| WO | 99/55367 A1 | 11/1999 | | |
| WO | 00/69460 A1 | 11/2000 | | |
| WO | 01/000238 A1 | 1/2001 | | |
| WO | 01/00244 A2 | 1/2001 | | |
| WO | 01/00245 A2 | 1/2001 | | |
| WO | 2001/009187 A2 | 2/2001 | | |
| WO | 01/89566 A1 | 11/2001 | | |
| WO | 02/082041 A2 | 10/2002 | | |
| WO | 02/100348 A2 | 12/2002 | | |
| WO | 03/101491 A1 | 12/2003 | | |
| WO | 2004/032960 A1 | 4/2004 | | |
| WO | 2004/035607 A2 | 4/2004 | | |
| WO | 2005/034733 A2 | 4/2005 | | |
| WO | WO-2005070963 A1 * | 8/2005 | | C07K 16/2896 |
| WO | 2005/117973 A2 | 12/2005 | | |
| WO | 2005/118635 A2 | 12/2005 | | |
| WO | 2006/033386 A1 | 3/2006 | | |
| WO | 2006/033700 A2 | 3/2006 | | |
| WO | 2006/063042 A2 | 6/2006 | | |
| WO | 2006/091693 A2 | 8/2006 | | |
| WO | 2006/116107 A2 | 11/2006 | | |
| WO | 2007/059782 A1 | 5/2007 | | |
| WO | 2007/084181 A2 | 7/2007 | | |
| WO | 2007147901 A1 | 12/2007 | | |
| WO | 2008/019290 A2 | 2/2008 | | |
| WO | 2008/22746 A1 | 2/2008 | | |
| WO | 2008/031531 A1 | 3/2008 | | |
| WO | 2008/088861 A2 | 7/2008 | | |
| WO | 2008/097229 A1 | 8/2008 | | |
| WO | 2008/109440 A2 | 9/2008 | | |
| WO | 2008/119353 A1 | 10/2008 | | |
| WO | 2008/119493 A1 | 10/2008 | | |
| WO | 2008/127710 A2 | 10/2008 | | |
| WO | 2008/130910 A1 | 10/2008 | | |
| WO | 2008/145142 A1 | 12/2008 | | |
| WO | 2008/148546 A2 | 12/2008 | | |
| WO | 2008/150485 A2 | 12/2008 | | |
| WO | 2008/154249 A2 | 12/2008 | | |
| WO | 2009026681 A1 | 3/2009 | | |
| WO | 09/055074 A2 | 4/2009 | | |
| WO | 2009/068625 A2 | 6/2009 | | |
| WO | 2009/099829 A1 | 8/2009 | | |
| WO | 2009/100110 A1 | 8/2009 | | |
| WO | 2009/105230 A2 | 8/2009 | | |
| WO | 2009/106096 A1 | 9/2009 | | |
| WO | 2009/151356 A1 | 12/2009 | | |
| WO | 2009/154651 A1 | 12/2009 | | |
| WO | 2010/001251 A2 | 1/2010 | | |
| WO | 2010/002862 A2 | 1/2010 | | |
| WO | 2010/027981 A1 | 3/2010 | | |
| WO | 2010/066803 A2 | 6/2010 | | |
| WO | 2010/070117 A1 | 6/2010 | | |
| WO | 2011/147986 A1 | 12/2011 | | |

OTHER PUBLICATIONS

U.S. Appl. No. 15/599,393, filed May 18, 2017, Bart De Goeij.
U.S. Appl. No. 14/112,848, filed Feb. 7, 2014, Bart De Goeij.
U.S. Appl. No. 15/599,395, filed May 18, 2017, Joost J. Neijssen.
U.S. Appl. No. 13/642,253, filed Oct. 24, 2012, Aran Frank Labrijn.
U.S. Appl. No. 14/830,336, filed Aug. 19, 2015, Aran Frank Labrijn.
U.S. Appl. No. 15/414,122, filed Jan. 24, 2017, Aran Frank Labrijn.
U.S. Appl. No. 16/777,053, filed Jan. 30, 2020, Aran Frank Labrijn.
U.S. Appl. No. 17/369,542, filed Jul. 7, 2021, Bart De Goeij.
U.S. Appl. No. 15/832,421, filed Dec. 5, 2017, Bart De Goeij.
U.S. Appl. No. 15/832,366, filed Dec. 5, 2017, Bart De Goeij.
U.S. Appl. No. 15/832,337, filed Dec. 5, 2017, Bart De Goeij.
U.S. Appl. No. 13/700,341, filed Mar. 14, 2013, Bart De Goeij.
U.S. Appl. No. 13/700,246, filed Mar. 21, 2013, Bart De Goeij.
U.S. Appl. No. 15/627,921, filed Jun. 20, 2017, Bart De Goeij.
U.S. Appl. No. 17/003,442, filed Aug. 26, 2020, Bart De Goeij.
Oshima, CT., et al., "C-erbB-2 oncoprotein in gastric carcinoma: correlation with clinical stage and prognosis," Int J Biol Markers, vol. 16(4) pp. 250-254 (2001).
Osman, I., et al., "Serum levels of shed Her2/neu protein in men with prostate cancer correlate with disease progression," J Urol., vol. 174(6), pp. 2174-2177 (2005).
Parren, PW., et al., "Induction of T-cell proliferation by recombinant mouse and chimeric mouse/human anti-CD3 monoclonal antibodies," Res Immunol., vol. 142 (9), pp. 749-763 (1991).
Pedersen, NM., et al., "Expression of epidermal growth factor receptor or ErbB3 facilitates geldanamycin-induced down-regulation of ErbB2," Mol Cancer Res., 7(2), pp. 275-284 (2009).
Perez, E.A., et al., "Efficacy and Safety of Trastuzumab-DM1 versus Trastuzumab Plus Docetaxel In Her2-Positive Metastatic Breast Cancer Patients with No Prior Chemotherapy for Metastatic Disease: Preliminary Results of A Randomized, Multicenter, Open Label Phase 2 Study (TDM4450G)," Abstract BA3, European Society for Medical Oncology Meeting 2010, Annals of Oncology, vol. 21(Supp. 8), 12 pages (2010).
Reese, DM. et al., "HER-2/neu signal transduction in human breast and ovarian cancer.," Stem Cells, vol. 15(1), pp. 1-8 (1997).
Riese, DJ., et al, "Specificity within the EGF family/ErbB receptor family signaling network," Bioessays, vol. 20 (1), pp. 41-48 (1998).
Robinson, MK. et al., "Targeting ErbB2 and ErbB3 with a bispecific single-chain Fv enhances targeting selectivity and induces a therapeutic effect in vitro," British Journal of Cancer, vol. 99(9), pp. 1415-1425 (2008).
Rockberg J. et al.,"Discovery of epitopes for targeting the human epidermal growth factor receptor 2 (HER2) with antibodies," Molecular Oncology, vol. 3(3), pp. 238-247 (2009).
Ross, JS., et al., "The Her-2/neu gene and protein in breast cancer 2003: biomarker and target of therapy," Oncologist, vol. 8(4), pp. 307-325 (2003).
Routledge, EG. et al., "A humanized monovalent CD3 antibody which can activate homologous complement," Eur J Immunol., vol. 21(11), pp. 2717-2725 (1991).
Rudikoff S. et al, "Single amino acid substitution altering antigen-binding specificity," PNAS, vol. 79, pp. 1979-1983.

(56) References Cited

OTHER PUBLICATIONS

Scheuer, W. et al., "Strongly enhanced antitumor activity of Trastuzumab and Pertuzumab combination treatment on HER2 positive human xenograft tumor models," Cancer Research, vol. 69 (24), pp. 9330-9336 (2009).
Schmitz, KR. et al., "Interaction of antibodies with ErbB receptor extracellular regions," Exp Cell Res., vol. 315(4), pp. 659-670 (2009).
Slamon, DJ., et al., "Human breast cancer: correlation of relapse and survival with amplification of the HER-2/neu oncogene," Science, vol. 235 (4785), pp. 177-182 (1987).
Spiridon, C. et al., "Targeting Multiple Her-2 Epitopes with Monoclonal Antibodies Results in Improved Antigrowth Activity of a Human Breast Cancer Cell Line in Vitro and in Vivo," Clinical Cancer Research, vol. 8, pp. 1720-1730 (2002).
Staerz, U. et al., "Hybrid Antibodies can Target Sites for Attack by T Cells," Nature, vol. 314, pp. 628-631 (1985).
Tao, R.H. et al., "All EGF(ErbB) receptors have preformed homo- and heterodimeric structures in living cells," J Cell Sci., vol. 121, pp. 3207-3217 (2008).
Turken, O. et al., "Prevalence and prognostic value of c-erbB2 expression in non-small cell lung cancer (NSCLC)," Neoplasma, vol. 50 (4), pp. 257-261 (2003).
Van Berkel, PH. et al, "Rapid production of recombinant human IgG With improved ADCC effector function in a transient expression system," Biotechnology and Bioengineering, vol. 105(2), pp. 350-357 (2010).
Van der Neut Kolfschoten, M. et al., "Anti-inflammatory activity of human IgG4 antibodies by dynamic Fab arm exchange," Science, vol. 317(5844), pp. 1554-1557 (2007).
Van Spriel, A.B.et al., "Immunotherapeutic perspectives for bispecific antibodies," Immunology Today, vol. 21(8), pp. 391-397 (2000).
Wehrman, TS., et al., "A system for quantifying dynamic protein interactions defines a role for Herceptin in modulating ErbB2 interactions," PNAS USA, vol. 103(50), pp. 19063-19068 (2006).
Zhu, Z. et al., "Engineering High Affinity Humanized Anti-P185HER2/Anti-CD3 Bispecific F(AB')2 for Efficient Lysis of P185HER2 Overexpressing Tumor Cells," International Journal of Cancer, vol. 62(3), pp. 319-324 (1995).
Agus DB., et al., "Targeting ligand-activated ErbB2 signaling inhibits breast and prostate tumor growth," Cancer Cell, vol. 2: pp. 127-137 (2002).
Andrechek E. et al., "Amplification of the neuy erbB-2 oncogene in a mouse model of mammary tumorigenesis," Proc Natl Acad Sci USA, vol. 97(7), pp. 3444-3449 (2000).
Baeuerle, P. et al., "Bispecific T-Cell Engaging Antibodies for Cancer Therapy," Cancer Research, vol. 69 (12), 5 pages, (2009).
Baeuerle, P. et al., BiTE Teaching antibodies to engage T-cells for Cancer Therapy, Current Opinion in Molecular Therapeutics, vol. 11, pp. 22-30 (2009).
Bargou, R. et al., "Tumor Regression in Cancer Patients by Very Low Doses of a T Cell-Engaging Antibody," Science, vol. 321, pp. 974-977, (2008).
Baselga, J. et al., "Phase II Trial of Pertuzumab and Trastuzumab in Patients With Human Epidermal Growth Factor Receptor 2-Positive Metastatic Breast Cancer That Progressed During Prior Trastuzumab Therapy," J Clin Oncol, vol. 28(7), pp. 1138-1144 (2010).
Baulida, J. et al., "All ErbB receptors other than the epidermal growth factor receptor are endocytosis impaired," J Biol Chem, vol. 271(9), pp. 5251-5257 (1996).
Ben-Kasus, T. et al., "Persistent elimination of ErbB-2/HER2-overexpressing tumors using combinations of monoclonal antibodies: relevance of receptor endocytosis," Proc Natl Acad Sci USA , vol. 106, pp. 3294-3299 (2009).
Bolt, S. et al., "The generation of a humanized, non-mitogenic CD3 monoclonal antibody which retains in vitro immunosuppressive properties," Eur J Immunol, vol. 23(2), pp. 403-411 (1993).
Boyer , CM. et al., "Relative cytotoxic activity of immunotoxins reactive with different epitopes on the extracellular domain of the c-erbB-2 (HER-2/neu) gene product p185," Int J Cancer vol. 82, pp. 525-531 (1999).
Burris, H. et al, Phase II study of the antibody drug conjugate trastuzumab-DM1 for the treatment of human epidermal growth factor receptor 2 (HER2)-positive breast cancer after prior HER2-directed therapy, J Clin Oncol, vol. 29(4), pp. 398-405 (2011).
Chames, P. et al., "Bispecific antibodies for cancer therapy," Current Opinion in Drug Discovery & Development, vol. 12 (2), pp. 276-283 (2009).
Dho, HS et al., "Structure of the extracellular region of HER2 alone and in complex with the Herceptin Fab," Nature, 421(6924), pp. 756-760 (2003).
Database Geneseq [online], Jan. 11, 2007, "Human anti-IL8 monoclonal antibody mAb 809 Vk".
Database Geneseq [online], Aug. 6, 2009, Human anti-RG-1 Monoclonal antibody 34E1 VL, Seq ID No. 16.
Database Geneseq [online], Mar. 20, 2008, Human HER2 specific antibody VL Seq ID No. 639.
Database Geneseq [online], Feb. 23, 2006, Antibody 28F10 light chain variable region SEQ ID No. 8.
Dinh, P. et al., "Trastuzumab for early breast cancer: current status and future directions," Clin Adv Hematol Oncol, vol. 5(9), pp. 707-717 (2007).
Emde, A. et al., "Combining Epitope-distinct antibodies to HER2, Cooperative inhibitory effects on invasive growth," Oncogene, vol. 30, pp. 1631-1642 (2011).
Franklin, M. et al., "Insights into ErbB signaling from the structure of the ErbB2-pertuzumab complex," Cancer Cell, vol. 5 (4), pp. 317-328 (2004).
Friedman, M. et al., "Engineering and characterization of a bispecific HER2 x EGFR-binding affibody molecule," Biotechnol. Appl. Biochem., vol. 54(2), pp. 121-131 (2009).
Garcia de Palazzo, I. et al.,"Immunohistochemical detection of c-erbB-2 expression by neoplastic human tissue using monospecific and bispecific monoclonal antibodies.," Int J Biol Markers, vol. 8(4), pp. 233-239; (1993).
Graus-Porta, D. et al., "ErbB-2, the preferred heterodimerization partner of all ErbB receptors, is a mediator of lateral signaling," Embo J, vol. 16, pp. 1647-1655 (1997).
Guillemard, V. et al., HER2-mediated internalization of a targeted prodrug cytotoxic conjugate is dependent on the valency of the targeting ligand, DNA Cell Biol., vol. 24(6), pp. 350-358 (2005).
Harwerth, IM, et al., "Monoclonal antibodies directed to the erbB-2 receptor inhibit in vivo tumour cell growth," Br J Cancer, vol. 68, pp. 1140-1145 (1993).
Hu, S , et al: "Epitope mapping and structural analysis of an anti-ErbB2 antibody A21: Molecular basis for tumor inhibitory mechanism", Proteins: Structure, Function and Bioinformatics, vol. 70 (3), pp. 938-949 (2008).
Huang, Z. et al., "A pan-HER approach for cancer therapy: background, current status and future development," Expert Opin Biol Ther., vol. 9(1), pp. 97-110 (2009).
Hudis, C., "Drug therapy: Trastuzumab—Mechanism of action and use in clinical practice," New England Journal of Medicine, vol. 357(1), pp. 39-51 (2007).
Hughes, JB et al., "Pertuzumab increases epidermal growth factor receptor down-regulation by counteracting epidermal growth factor receptor-ErbB2 heterodimerization," Mol Cancer Ther., vol. 8 (7), pp. 1885-1892 (2009).
Hynes, NE, et al., "PI3K inhibition overcomes trastuzumab resistance: blockade of ErbB2/ErbB3 is not always enough," Cancer Cell, vol. 15(5), pp. 353-355 (2009).
Jasinska, J. et al: "Inhibition of tumor cell growth by antibodies induced after vaccination with peptides derived from the extracellular domain of Her-2/neu," International Journal of Cancer, vol. 107(6), pp. 976-983 (2003).
Jones, KL. et al., "Evolving novel anti-HER2 strategies," Lancet Oncol., vol. 10 (12), pp. 1179-1187 (2009).

(56) References Cited

OTHER PUBLICATIONS

Junttila TT., et al., "Ligand-independent HER2/HER3/PI3K complex is disrupted by trastuzumab and is effectively inhibited by the PI3K inhibitor GDC-0941," Cancer Cell, vol. 15 (5), pp. 429-440 (2009).
Kapitanovic, S. et al, "The expression of p185(HER-2/neu) correlates with the stage of disease and survival in colorectal cancer," Gastroenterology, vol. 112 (4), pp. 1103-1113 (1997).
Kiewe, P. et al., "Phase I trial of the trifunctional anti-HER2 x anti-CD3 antibody ertumaxomab in metastatic breast cancer," Clin Cancer Res., vol. 12(10), pp. 3085-3091 (2006).
Klapper LN, et al., "A subclass of tumor-inhibitory monoclonal antibodies to ErbB-2/HER2 blocks crosstalk with growth factor receptors," Oncogene, vol. 14, pp. 2099-2109 (1997).
Klein, C. et al., "Epitope Interactions of monoclonal antibodies targeting CD2+ and their relationship to functional properties," mAbs vol. 5(1), pp. 22-33 (2013).
Langdon S P et al: "Pertuzumab—Humanized anti-HER2 monoclonal antibody HER dimerization inhibitor oncolytic," Drugs of the Future, Prous Science, vol. 33(2), pp. 123-130 (2008).
Larsen, SS., et al., "Acquired antiestrogen resistance in MCF-7 human breast cancer sublines is not accomplished by altered expression of receptors in the ErbB-family.," Breast Cancer Res Treat., vol. 58(1), pp. 41-56 (1999).
Lewis, P. et al., "Targeting HER2-positive breast cancer with trastuzumab-DM1, an antibody-cytotoxic drug conjugate," Cancer Res., vol. 68(22), pp. 9280-9290 (2008).
Li, J. et al., "A Biparatopic HER2-Targeting Antibody-Drug Conjugate Induces Tumor Regression in Primary Models Refractory to or Ineligible for HER2-Targeted Therapy," Cancer Cell, vol. 29, pp. 117-129 (2016).
Lum, G. et al., "Phase I/II study of treatment of stage IV breast cancer with OKT3 x trastuzumab-armed activated T cells," Clinical Breast Cancer, vol. 4:212-217 (2003).
Maccallum RM., et al: "Antibody-antigen interactions: Contact analysis and binding site topography," Journal of Molecular Biology, vol. 262(5), pp. 732-745 (1996).
Montgomery, RB. et al: "Endogenous anti-HER2 antibodies block HER2 phosphorylation and signaling througth extracellular signal-regulated kinase," Cancer Research, American Association for Cancer Research, vol. 65(2), pp. 650-656 (2005).
Moore, PA et al., "Application of dual affinity retargeting molecules to achieve optimal redirected T-cell killing of B-cell lymphoma," Blood, vol. 117(17), pp. 4542-4551 (2011).
Muller, D. et al., "Bispecific antibodies for cancer immunotherapy: Current perspectives," BioDrugs, vol. 24(2), pp. 89-98 (2010).
Nahta, R. et al., "Mechanisms of Disease: Understanding Resistance to HER2-targeted; therapy in human breast cancer," Nature Clinical Practice Oncology, vol. 3(5), pp. 269-280 (2006).
Nahta, R. et al., "Trastuzumab: triumphs and tribulations," Oncogene, vol. 26(25) pp. 3637-3643 (2007).
Natsume, A., et al., "Engineered anti-CD20 antibodies with enhanced complement-activating capacity mediate potent anti-lymphoma activity," Cancer Science, vol. 100 (12), pp. 2411-2418 (2009).
Oral Presentations, Experimental Hematology, Elsevier, Inc.; vol. 33(7), 34 pages, (2005).

* cited by examiner

FIG. 1A

IgHV3-23-01 / IGHJ4-02 – VH alignment (Group 1)

```
IgHV1-23-01  EVQLLESGGGLVQPGGSLRLSCAASGFTFSSYAMSWVRQAPGKGLEWVSAISGSGGSTYYADSVKG
TH1014-050   EVQLLESGGGLVQPGGSLRLSCAASGFTFSSYAMNWVRQAPGKGLEWVSAISGRGGTTYYADSVKG
VH1014-049   EVQLLESGGDLVQPGGSLRLSCAASGFTFSSYAMSWVRQAPGKGLEWVSAISGRGGTTYYADSVKG
VH1014-051   EVQLLESGGDLVQPGGSLRLSCAASGFTFSSYAMSWVRQAPGKGLEWVSAISGRGGTTYYADSVKG
VH1014-055   EVQLLESGGGLVQPGGSLRLSCAASGFTFSSYAMNWVRQAPGKGLEWVSAISGRGGTTYYADSVKG
Consensus    EVQLLESGGXLVQPGGSLRLSCAASGFTFSSYAMXWVRQAPGKGLEWVSAISGXGGXTYYADSVKG

IgHV1-23-01  RFTISRDNSKNTLYLQMNSLRAEDTAVYYCAK------YFDYWGQGTLVTVSS
TH1014-050   RFTISRDNSKNTLYLQMSLRAEDTAVYYCAKARANWDYFDYWGQGTLVTVSS
VH1014-049   RFTISRDNSKSTLCLQMNSLRAEDTAVYYCAKARANWDYFDYWGQGTLVTVSS
VH1014-051   RFTISRDNSKSTLCLQMNSLRAEDTAVYYCAKARANWDYFDYWGQGTLVTVSS
VH1014-055   RFTISRDNSKSTLCLQMNSLRAEDTAVYYCAKARANWDYFDYWGQGTLVTVSS
Consensus    RFTISRDNSKXTLXLQMXSLRAEDTAVYYCAKARANWDYFDYWGQGTLVTVSS
```

FIG. 1B

IgHV1-69-04 / IGHJ6-02 – VH alignment (Group 1)

```
IgHV1-69-04  QVQLVQSGAEVKKPGSSVKVSCKASGGTFSSYAISWVRQAPGQGLEWMGRIIPILGIANYAQKFQG
TH1014-084   QVQLVQSGAEVKKPGSSVKVSCKASGGTFRTYAINWVRQAPGQGLEWMGRINTVLGIVNHAQKFQG
Consensus    QVQLVQSGAEVKKPGSSVKVSCKASGGTFXXYAISWVRQAPGQGLEWMGRIXXXLGIXNXAQKFQG

IgHV1-69-04  RVTITADKSTSTAYMELSSLRSEDTAVYYCAR--------GMDVWGQGTTVTVSS
TH1014-084   RVTITADKSTNTAYMELNSLRSEDTAVYYCAREKGVDYYYGIEVWGQGTTVTVSS
Consensus    RVTITADKSTXTAYMELXSLRSEDTAVYYCAREKGVDYYYGXXVWGQGTTVTVSS
```

FIG. 1C

IgHV1-18-01 / IGHJ4-02 – VH alignment (Group 1)

```
IgHV1-18-01  QVQLVQSGAEVKKPGASVKVSCKASGYTFTSYGISWVRQAPGQGLEWMGWISAYNGNTNYAQKLQG
TH1014-169   QVQLVQSGAEVKKPGASVKVSCKASGYTFTNYGISWVRQAPGQGLEWMGWLSAYSGNTIYAQKLQG
VH1014-123   QVQLVQSGAEVKKPGASVKVSCKAAGYTFTNYGISWVRQAPGQALEWMGWITTYSSNTIYAQKLQG
VH1014-161   QVQLVQSGAEVKKPGASVKVSCKASGYTFTNYGISWVRQAPGQGLEWMGWLSAYSGNTIYAQKLQG
VH1014-124   QVQLVQSGAEVKKPGASVKVSCKAAGYTFTNYGISWVRQAPGQGLEWMGWIITYNGNTIYAQRFQD
Consensus    QVQLVQSGAEVKKPGASVKVSCKASGYTFTXYGISWVRQAPGQXLEWMGWIXXYXGNTXYAQXXQG

IgHV1-18-01  RVTMTTDTSTSTAYMELRSLRSDDTAVYYCAR--------YFDYWGQGTLVTVSS
TH1014-169   RVTMTTDTSTTTAYMELRSLRSDDTAVYYCARDRIVVRPDYFDYWGQGTLVTVSS
VH1014-123   RVTMTTDTSTSTAYMELRSLRSDDTAVYYCARDRVVVRPDYFDYWGQGTLVTVSS
VH1014-161   RVTMTTDTSTTTAYMELRSLRSDDTAVYYCARDRIVVRPDYFDYWGQGTLVTVSS
VH1014-124   RVTMTTDTSTSTAYMELRSLRSDDTAVYYCARDRIIVRPDYFDYWGQGTLVTVSS
Consensus    RVTMTTDTSTXTAYMELRSLRSDDTAVYYCARDRXXVRPDYFDYWGQGTLVTVSS
```

FIG. 1D

IgHV4-34-01 / IGHJ4-02 – VH alignment (Group 2, No. 1)

```
IgHV4-34-01  QVQLQQWGAGLLKPSETLSLTCAVYGGSFSGYYWSWIRQPPGKGLEWIGEINHSGSTNYNPSLKSR
TH1014-025   QVQLQQWGAGLLKPSETLSLTCAVYGGSFSDYYWNWIRQPPGKGLEWIGEIHHSGSTNYNPSLKSR
VH1014-001   QVQLQQWGAGLLKPSETLSLTCAVYGGSFSGYYWNWIRQPPGKGLEWIGEINHSGSTNYNPSLKSR
VH1014-143   QVQLQQWGAGLLKPSETLSLTCAVYGGSFSGYYWNWIRQPPGKGLEWIGEIHHSGSANYNPSLMSR
VH1014-019   QVQLQQWGAGLLKPSETLSLTCAVYGGSFSDYYWNWIRQPPGKGLEWIGEIHHVGSTNYNPSLKSR
VH1014-021   QVQLQQWGAGLLKPSETLSLTCAVYGGSFSDYYWNWIRQPPGKGLEWIGEIHHSGSTNYNPSLKSR
VH1014-027   QVQLQQWGAGLLKPSETLSLTCAVYGGSFSDYFWNWIRQPPGKGLEWIGEIHHSGSTNYNPSLKSR
Consensus    QVQLQQWGAGLLKPSETLSLTCAVYGGSFSXYXWXWIRQPPGKGLEWIGEIXHXGSXNYNPSLXSR

IgHV4-34-01  VTISVDTSKNQFSLKLSSVTAADTAVYYCAR---------YFDYWGQGTLVTVSS
TH1014-025   VTISVDTSKNQFSLKLSSVTAADTAVYYCARGYYDSGVYYFDYWAQGTLVTVSS
VH1014-001   VTISVDTSKNQFSLKLSSVTAADTAVYYCARGNYGSGYYYFDLWGRGTQVTVSS
VH1014-143   VTISVDTSKNQFSLQLSSVTAADTAVYYCARGYYGSGYYYFDYWGQGTLVTVSS
VH1014-019   VTISVDTSKSQFSLKLSSVTAADTAVYYCARGYYDSGVYYFDYWAQGTLVTVSS
VH1014-021   VTISVDTSKNQFSLKLSSVTAADTAVYYCARGYYASGVYYFDYWGQGTLVTVSS
VH1014-027   VTISVDTSKNQFSLNLSSVTAADTAVYYCARGLIGSGYYYFDYWDQGTLVTVSS
Consensus    VTISVDTSKXQFSLXLSSVTAADTAVYYCARGXXXSGXYYFDXWXXGTXVTVSS
```

FIG. 1E

IgHV4-34-01 / IGHJ4-02 – VH alignment (Group 2, No. 2)

```
IgHV4-34-01  QVQLQQWGAGLLKPSETLSLTCAVYGGSFSGYYWSWIRQPPGKGLEWIGEINHSGSTNYNPSLKSR
TH1014-091   QVQLQQWGAGLLKPSETLSLTCAVSGGSFSGYYWTWIRQPPGKGLEWIGEIYHSGDTNYNPSLKSR
VH1014-032   QVQLQQWGAGLLKPSETLSLTCAVYGGSFSGYYWSWIRQPPGKGLEWIGEINHSGDTNYNPSLTSR
VH1014-035   QVQLQQWGAGLLKPSETLSLTCAIYGGSFSGYYWSWIRQPPGKGLEWIGEINHSGDTNYNPSLTSR
VH1014-036   QVQLQQWGAGLLKPSETLSLTCAVYGGSFSDYYWSWIRQPPGKGLEWIGEINHSGSTNYNPSLKSR
VH1014-054   QVQLQQWGAGLLKPSETLSLTCAVYGGSFSGYYWSWIRQPPGKGLEWIGEIHHSGSTNYNPSLKSR
VH1014-094   QVQLQQWGAGLLKPSETLSLTCAVSGGSFSGYYWTWIRQPPGKGLEWIGEIYHSGDTNYNPSLKSR
Consensus    QVQLQQWGAGLLKPSETLSLTCAXXGGSFSXYYWXWIRQPPGKGLEWIGEIXHSGXTNYNPSLXSR

IgHV4-34-01  VTISVDTSKNQFSLKLSSVTAADTAVYYCAR--------YFDYWGQGTLVTVSS
TH1014-091   VTISVDTSKNQFSLKLYSVTAADTAVYYCARLYFGSGIYYLDYWGQGTLVTVSS
VH1014-032   VTISVDTSKNQFSLKLSSVTAADTAVYYCARLFYGSGIYYFDYWGQGTLVTVSS
VH1014-035   VTISVDTSKNQFSLKLSSVTAADTAVYYCARLFYGSGIYYFDYWGQGTLVTVSS
VH1014-036   VTISVDTSKNQFSLKLSSVTAADTAVYYCARLYYGSGTYYFDYWGQGTLVTVSS
VH1014-054   VTISVDTSKNQFSLKLSSVTAADTAVYYCARLWYGSGSYYFDYWGQGTLVTVSS
VH1014-094   VTISVDTSKNQFSLKLYSVTAADTAVYYCARLYFGSGIYYLDYWGQGTLVTVSS
Consensus    VTISVDTSKNQFSLKLXSVTAADTAVYYCARLXXGSGXYYXDYWGQGTLVTVSS
```

FIG. 1F

IgHV3-30-3-01 / IGHJ4-02 – VH alignment (Group 2)

```
IgHV1-30-...  QVQLVESGGGVVQPGRSLRLSCAASGFTFSSYAMHWVRQAPGKGLEWVAVISYDGSNKYYADSVKGR
TH1014-129    QVQLVESGGGVVQPGRSLRLSCAASGFTFSTFAIHWVRQAPGKGLEWVAVISYDGGHKFYADSVKGR
Consensus     QVQLVESGGGVVQPGRSLRLSCAASGFTFSXXAXHWVRQAPGKGLEWVAVISYDGXXKXYADSVKGR

IgHV3-30-...  FTISRDNSKNTLYLQMNSLRAEDTAVYYCAR------YFDYWGQGTLVTVSS
TH1014-129    FTISRDNSKNTLYLQMNSLRAEDTAMYYCARGLGVWGAFDYWGQGTLVTVSS
Consensus     FTISRDNSKNTLYLQMNSLRAEDTAXYYCARGLGVWGXFDYWGQGTLVTVSS
```

FIG. 1G

IgHV3-23-1 / IGHJ4-02 – VH alignment (Group 3a)

```
IgHV3-23-1   EVQLLESGGGLVQPGGSLRLSCAASGFTFSSYAMSWVRQAPGKGLEWVSAISGSGGSTYYADSVKG
TH1014-098   EVQLLESGGGLVQPGGSLRLSCAASGFTFSNYGMSWVRQAPGKGLEWVSAISGSAYSTYYADSVKG
VH1014-105   EVQLLESGGGLVQPGGSLRLSCAASGFTFSNYGMSWVRQAPGKGLEWVSAISGSAYSTYYADSVKG
VH1014-100   EVQLLESGGGLVQPGGSLRLSCAASGFTFNNYGMNWVRQAPGKGLEWVSAISGTGYSTYYADSVKG
VH1014-125   EVQLLESGGGLVQPGGSLRLSCAASGFTFTDYAMNWVRQAPGKGLEWVSTISGSGYATYYADSVKG
VH1014-162   EVQLWESGGGSVQPGGSLRLSCAASGFTFSSYGMSWVRQAPGKGLEWVSGISGSGYSTYYADSVKG
Consensus    EVQLXESGGGXVQPGGSLRLSCAASGFTFXXYXMXWVRQAPGKGLEWVSXISGXXXXTYYADSVKG

IgHV3-23-1   RFTISRDNSKNTLYLQMNSLRAEDTAVYYCAK-----------YFDYWGQGTLVTVSS
TH1014-098   RFTISRDNSKNTLWLQMNSLRAEDTAVYYCAKAHYHGSGSYYTLFDYWGQGTLVTVSS
VH1014-105   RFTISRDNSKNTLWLQMNSLRAEDTAVYYCAKAHYHGSGSYYTLFDYWGQGTLVTVSS
VH1014-100   RFTISRDNSKNTLYLQMNSLRAEDTAVYYCAKAHYFGSGSYYTLFDYWGQGTLVTVSS
VH1014-125   RFTISRDNSKTTLYLQMNSLRAEDTAVYYCAKGHTLGSGSYYTLFDYWGQGTLVTVSS
VH1014-162   RFTISRDNSKNTLYLQMNSLRAEDTAVYYCAKGYYHGSGSYYTSFDYWGQGTLVTVSS
Consensus    RFTISRDNSKXTLXLQMNSLRAEDTAVYYCAKXXXXGSGSYYTXFDYWGQGTLVTVSS
```

FIG. 1H

IgHV5-51-01 / IGHJ2-01 – VH alignment (Group 3a, No. 1)

```
IgHV5-51-01  EVQLVQSGAEVKKPGESLKISCKGSGYSFTSYWIGWVRQMPGKGLEWMGIIYPGDSDTRYSPSFQG
TH1014-127   EVQLVQSGAEVKKPGESLTISCKGSGYSFSIYWIGWVRQMPGKGLEWMGIIFPGDSDIRYSPSFQG
Consensus    EVQLVQSGAEVKKPGESLXISCKGSGYSFXXYWIGWVRQMPGKGLEWMGIIXPGDSDXRYSPSFQG

IgHV5-51-01  QVTISADKSISTAYLQWSSLKASDTAMYYCAR----------YFDLWGRGTLVTVSS
TH1014-127   QVTISADKSISTAYLQWSSLKASDTAMYYCARQPGDWSPRHWYFDLWGRGTLVTVSS
Consensus    QVTISADKSISTAYLQWSSLKASDTAMYYCARQPGDWSPRHWYFDLWGRGTLVTVSS
```

FIG. 1I

IgHV5-51-01-01 / IGHJ5-02 – VH alignment (Group 3a, No. 2)

```
IgHV5-51-01  EVQLVQSGAEVKKPGESLKISCKGSGYSFTSYWIGWVRQMPGKGLEWMGIIYPGDSDTRYSPSFQG
TH1014-159   EVQLVQSGAEVKKPGESLKISCKGSGYNFTSYWIGWVRQMPGKGLEWMGIIYPGDSDTRYSPSFQG
Consensus    EVQLVQSGAEVKKPGESLKISCKGSGYXFTSYWIGWVRQMPGKGLEWMGIIYPGDSDTRYSPSFQG

IgHV5-51-01  QVTISADKSISTAYLQWSSLKASDTAMYYCAR------------NWFDPWGQGTLVTVSS
TH1014-159   QVTISADKSISTAYLQWSSLKASDTAMYYCARWGTYYDILTGYFNWFDPWGQGTLVTVSS
Consensus    QVTISADKSISTAYLQWSSLKASDTAMYYCARWGTYYDILTGYFNWFDPWGQGTLVTVSS
```

FIG. 1J

IgHV1-18-01 / IGHJ6-02 – VH alignment (Group 3b)

```
IgHV1-18-01  QVQLVQSGAEVKKPGASVKVSCKASGYTFTSYGISWVRQAPGQGLEWMGWISAYNGNTNYAQKLQG
TH1014-132   QVQLVQSGAEVKKPGASVKVSCKASGYTFTSYGISWVRQAPGQGLEWMGWISAYNGNSNYVQKFQG
Consensus    QVQLVQSGAEVKKPGASVKVSCKASGYTFTSYGISWVRQAPGQGLEWMGWISAYNGNXNYXQKXQG

IgHV1-18-01  RVTMTTDTSTSTAYMELRSLRSDDTAVYYCAR------------GMDVWGQGTTVTVSS
TH1014-132   RVTMTTDTTTSTAYMELRSLTSDDTAVYYCAREYSYDSGTYFYYGMDVWGQGTTVTVSS
Consensus    RVTMTTDTSTSTAYMELRSLRSDDTAVYYCAREYSYDSGTYFYYGMDVWGQGTTVTVSS
```

FIG. 1K

IgHV3-30-3-01 / IGHJ4-02 – VH alignment (Group 3b)

```
IgHV3-30...  QVQLVESGGGVVQPGRSLRLSCAASGFTFSSYAMHWVRQAPGKGLEWVAVISYDGSNKYYADSVKG
TH1014-153   QVQLVESGGGVVQPGRSLRLSCAASGFTFSDYVIHWVRQAPGKGLEWVTVISYDGSNKYYADSVKG
VH1014-033   QVQLVESGGGVVQTGRSLRLSCAASGFTFSSHAMHWVRQAPGKGLEWVAAISYDGSNKYYADSVKG
VH1014-160   QVQLVESGGGVVQPGRSLRLSCAASGFTFSSHAMHWVRQAPGKGLEWVAAISYDGSNKYYADSVKG
VH1014-166   QVQLVESGGGVVQPGRSLRLSCAASGFTFSSYAMHWVRQAPGKGLEWVAVISYDGSNEYYADSVKG
VH1014-152   QVQVVESGGGVVQPGRSLRLSCAASGFTFSSYAMHWVRQAPGKGLEWVAVISYDGSYKYYADSVKG
VH1014-167   QVQLVESGGGVVQPGRSLRLSCAASGFTFSSYAIHWVRQAPGKGLEWVAVISYDGSNKYYADSVKG
Consensus    QVQLVESGGGVVQXGRSLRLSCAASGFTFSXXXXHWVRQAPGKGLEWVXXISYDGSXXYYADSVKG

IgHV3-30...  RFTISRDNSKNTLYLQMNSLRAEDTAVYYCAR--------YFDYWGQGTLVTVSS
TH1014-153   RFTISRDNSKNTLYLQMNSLSAEDTAMYYCARGGITGTTGVFDYWGQGTLVTVSS
VH1014-033   RFTISRDNSKNTLYLQMNSLRAEDTAVYYCARGDYISSSGVFDYWGQGTLVTVSS
VH1014-160   RFTISRDNSKNTMYLQMNSLRAEDTAMCYCARGSITGSTGVFDYWGQGTLVTVSS
VH1014-166   RFTISRDNSKNTLYLQMNSLRAEDTAVYYCARGSIIGSTGVFDYWGQGTLVTVSS
VH1014-152   RFTISRDNSKNTLYLQMNSLRAEDTAVYYCARGSITGSTGVFDYWGQGTLVTVSS
VH1014-167   RFTISRDNSKNTLYLQMNSLRAEDTAVYYCARGSITGSTGVFDYWGQGTLVTVSS
Consensus    RFTISRDNSKNTXYLQMNSLXAEDTAXXYCARGXXXXXXGXFDYWGQGTLVTVSS
```

FIG. 1L

IgHV5-51-1 / IGHJ6-02 – VH alignment

| | |
|---|---|
| IgHV5-51-1 | EVQLVQSGAEVKKPGESLKISCKGSGYSFTSYWIGWVRQMPGKGLEWMGIIYPGDSDTRYSPSFQ |
| **TH1014-005** | EVQLVQSGAEVKKPGESLKISCKASGYSFHFYWIGWVRQMPGKGLEWMGSIYPGDSDTRYRPSFQ |
| **TH1014-060** | EVQLVQSGAEVKKPGESLKISCKGSGYRFTSYWIGWVRQMPGKGLEWMGSIYPGDSYTRNSPSFQ |
| **TH1014-106** | EVQLVQSGAEVKKPGESLKISCKGSGYSFTRYWIGWVRQMPGKGLEWMGIIYPGDSDTRYSPSFQ |
| VH1014-041 | EVQLVQSGAEVKKPGESLKISCKGSGYSFTSYWIGWVRQMPGKGLEWMGSIYPGDSHTRYRPSFQ |
| VH1014-150 | EVQLVQSGAEVKKPGESLKISCKGSGYSFTSYWIGWVRQMPGKGLEWMGSIYPGDSHTRYRPSFQ |
| VH1014-067 | EVQLVQSGAEVKKPGESLKISCKGSGYSFTSYWIGWVRQMPGKGLEWMGIIYPGDSDTRYSPSFQ |
| VH1014-072 | EVQLVQSGAEVKKPGESLKISCKGSGYSFTSYWIGWVRQMPGKGLEWMGIIYPGDSDTRYSPSFQ |
| VH1014-163 | EVQLVQSGAEVKKPGESLKISCQGSGYRFISYWIGWVRQMPGKGLEWMGRIYPGDSDTRYSPSFQ |
| VH1014-093 | EVQLVQSGAEVKKPGESLKISCKGSGYSFTSYWIGWVRQMPGKGLEWMGRIYPGDSDTRYSPSFQ |
| VH1014-044 | EVQLVQSGAEVKKPGESLKISCKGSGYRFSSYWIGWVRQMPGKGLEWMGSIFPGDSDTRYSPSFQ |
| Consensus | EVQLVQSGAEVKKPGESLKISCXXSGYXFXXYWIGWVRQMPGKGLEWMGXIXPGDSXTRXXPSFQ |

| | |
|---|---|
| IgHV5-51-1 | GQVTISADKSISTAYLQWSSLKASDTAMYYCAR-----------GMDVWGQGTTVTVSS |
| **TH1014-005** | GQVTISADKSISTAYLQWTSLKASDTAIYYCARQRGD--YYYFYGMDVWGQGTTVTVSS |
| **TH1014-060** | GQVTISADKSIATAYLQWNSLKASDTAMYYCARHAGD--FYYFDGLDVWGQGTTVTVSS |
| **TH1014-106** | GQVTISADKSISTAYLQWSSLKASDTAMYYCARLTGDRGFDYYSGMDVWGQGTTVTVSS |
| VH1014-041 | GQVTISADKSISTAYLQWSSLKASDTAMYYCARQKGD--FYYFFGLDVWGQGTAITVSS |
| VH1014-150 | GQVTISADKSISTAYLQWSSLKASDTAMYYCARQAGD--YYYYNGMDVWGQGTTVTVSS |
| VH1014-067 | GQVTISVDKSISTAYLQWSSLKASDTAMYYCARQKGD--YYYHYGLDVWGQGTTVTVSS |
| VH1014-072 | GQVTISADKSISTAYLQWSSLKASDTAMYYCARQKGD--YYYFNGLDVWGQGTTVTVSS |
| VH1014-163 | GQVTISVDKSISTAYLQWSSLKASDTAMYYCARQRGD--YYYFNGLDVWGQGTTVTVSS |
| VH1014-093 | GQVTISADKSITTAYLQWSSLRASDTAMYYCARQRGD--YYYFFGLDIWGQGTTVTVSL |
| VH1014-044 | GQVTISADKSITTAYLQWSSLKASDTAMYYCARQAGD--YYYYNGMDVWGQGTTVTVSS |
| Consensus | GQVTISXDKSIXTAYLQWXSLXASDTAXYYCARXXXXXXXXYXXGXDXWGQGTXXTVSX |

FIG. 1M

IgHV3-23-1 / IGHJ4-02 – VH alignment

```
IgHV3-23-1   EVQLLESGGGLVQPGGSLRLSCAASGFTFSSYAMSWVRQAPGKGLEWVSAISGSGGSTYYADSVKG
TH1014-006   EVQLLESGGGLVQPGGSLRLSCAASGFTFSNYALIWVRQAPGKGLEWVSTIRGGAGSTYYADSVKG
Consensus    EVQLLESGGGLVQPGGSLRLSCAASGFTFSXYAXXWVRQAPGKGLEWVSXIXGXXGSTYYADSVKG

IgHV3-23-1   RFTISRDNSKNTLYLQMNSLRAEDTAVYYCAK------YFDYWGQGTLVTVSS
TH1014-006   RFTISRDNSKNTLYLQMNSLRAEDTAVYYCAKARIWGPLFDYWGQGTLVTVSS
Consensus    RFTISRDNSKNTLYLQMNSLRAEDTAVYYCAKARIWGPXFDYWGQGTLVTVSS
```

FIG. 1N

IgHV1-18-1 / IGHJ4-02 – VH alignment

```
IgHV1-18-1   QVQLVQSGAEVKKPGASVKVSCKASGYTFTSYGISWVRQAPGQGLEWMGWISAYNGNTNYAQKLQG
TH1014-059   QVQLVQSGAEVKKPGASVRVPCKASGYTFTRYGISWVRQAPGQGLEWMGWISAYNGKTYYAQKLQG
Consensus    QVQLVQSGAEVKKPGASVXVXCKASGYTFTXYGISWVRQAPGQGLEWMGWISAYNGXTXYAQKLQG

IgHV1-18-1   RVTMTTDTSTSTAYMELRSLRSDDTAVYYCAR---------YFDYWGQGTLVTVSS
TH1014-059   RVTMTTDTSTSTAYMELRSLRSDDTAVYYCARSPLLWFEELYFDYWGQGTLVTVSS
Consensus    RVTMTTDTSTSTAYMELRSLRSDDTAVYYCARSPLLWFEELYFDYWGQGTLVTVSS
```

FIG. 1O

IgHV1-69-4 / IGHJ4-02 – VH alignment

```
IgHV1-69-4   QVQLVQSGAEVKKPGSSVKVSCKASGGTFSSYAISWVRQAPGQGLEWMGRIIPILGIANYAQKFQG
TH1014-111   QVQLVQSGAEVKKPGSSVKVSCKASGGTFSSYGISWVRQAPGPGLEWMGRIIPILGIANYAQKFQG
Consensus    QVQLVQSGAEVKKPGSSVKVSCKASGGTFSSYXISWVRQAPGXGLEWMGRIIPILGIANYAQKFQG

IgHV1-69-4   RVTITADKSTSTAYMELSSLRSEDTAVYYCAR------YFDYWGQGTLVTVSS
TH1014-111   RVTITADKSTNTAYMELSSLRSEDTAVYYCARDQEYSSNWYYWGQGTLVTVSS
Consensus    RVTITADKSTXTAYMELSSLRSEDTAVYYCARDQEYSSXXXYWGQGTLVTVSS
```

FIG. 2A

IgKV1-12-01 / IGKJ5-01 – VL alignment (Group 1)

| | |
|---|---|
| IgKV1-12-01 | DIQMTQSPSSVSASVGDRVTITCRASQGISSWLAWYQQKPGKAPKLLIYAASSLQSGVPSRFSGSG |
| **VL1014-050** | DIQMTQSPSSVSASVGDRVTITCRASQGISSWLAWYQHKPGKAPKLLIYAASILQSGVPSRFSGSG |
| **VL1014-084** | DIQMTQSPSSVSASVGDRVTITCRASQGISSWLAWYQHKPGKAPKLLIYVASTLQSGVPSRFSGSG |
| VL1014-049 | DIQMTQSPSSVSASVGDRVTITCRASQGISSWLAWYQHKPGKAPKLLIYAASILQSGVPSRFSGSG |
| VL1014-051 | DIQMTQSPSSVSASVGDRVTITCRASQGISSWLAWYQHKPGKAPKLLIYAASILQSGVPSRFSGSG |
| VL1014-055 | DIQMTQSPSSVSASVGDRVTITCRASQGISSWLAWYQHKPGKAPKLLIYAASILQSGVPSRFSGSG |
| Consensus | DIQMTQSPSSVSASVGDRVTITCRASQGISSWLAWYQXKPGKAPKLLIYXASXLQSGVPSRFSGSG |

| | |
|---|---|
| IgKV1-12-01 | SGTDFTLTISSLQPEDFATYYCQQANSFPITFGQGTRLEIK |
| **VL1014-050** | SGTDFTLTISSLQPEDFATYYCQQANSFPITFGQGTRLEIK |
| **VL1014-084** | SGTDFTLTISSLQPEDFATYYCQQANSFPLTFGGGTKVEIK |
| VL1014-049 | SGTDFTLTISSLRPEDFATYYCQQANSFPITFGQGTRLEIK |
| VL1014-051 | SGTDFTLTISSLRPEDFATYYCQQANSFPITFGQGTRLEIK |
| VL1014-055 | SGTDFTLTISSLRPEDFATYYCQQANSFPITFGQGTRLEIK |
| Consensus | SGTDFTLTISSLXPEDFATYYCQQANSFPXTFGXGTRXEIK |

FIG. 2B

IgKV3-11-01 / IGKJ1-01 – VL alignment (Group 1)

| | |
|---|---|
| IgKV3-11-01 | EIVLTQSPATLSLSPGERATLSCRASQSVSSYLAWYQQKPGQAPRLLIYDASNRATGIPARFSGSG |
| **VL1014-169** | EIVLTQSPATLSLSPGERATLSCRASQSVSSYLAWYQQKPGQAPRLLIYDASNRATGIPARFSGSG |
| VL1014-124 | EIVLTQSPATLSLSPGERATLSCRASQSVSSYLAWYQQKPGQAPRLLIYDASNRATGIPARFSGSG |
| VL1014-161 | EIVLTQSPATLSLSPGERATLSCRASQSVSSYLAWYQQKPGQAPRLLIYDASNRATGIPARFSGSG |
| VL1014-123 | EIVLTQSPATLSLSPGERATLSCRASQSVSSYLAWYQQKPGQAPRLLIYDTSNRATGIPARFSGSG |
| Consensus | EIVLTQSPATLSLSPGERATLSCRASQSVSSYLAWYQQKPGQAPRLLIYDXSNRATGIPARFSGSG |

| | |
|---|---|
| IgKV3-11-01 | SGTDFTLTISSLEPEDFAVYYCQQRSNWPWTFGQGTKVEIK |
| **VL1014-169** | SGTDFTLTISSLEPEDFAVYYCQQRSNWPRTFGQGTKVEIK |
| VL1014-124 | SGTDFTLTISSLEPEDFAVYYCQQRSNWPRTFGQGTKVEIK |
| VL1014-161 | SGTDFTLTISSLEPEDFAVYYCQQRSNWPRTFGQGTKVEIK |
| VL1014-123 | SGTDFTLTISSLEPEDFAVYYCQQRSHWPRTFGQGTKVEIK |
| Consensus | SGTDFTLTISSLEPEDFAVYYCQQRSXWPRTFGQGTKVEIK |

FIG. 2C

IgKV1D-16-01 / IGKJ5-01– VL alignment (Group 2, No. 1)

```
IgKV1D-16 ...  DIQMTQSPSSLSASVGDRVTITCRASQGISSWLAWYQQKPEKAPKSLIYAASSLQSGVPSRFSGSG
VL1014-025     DIQMTQSPSSLSASVGDRVTITCRASQGISRWLAWYQQKPEKAPKSLIYAASSLRSGVPSRFSGSG
VL1014-001     DIQMTQSPSSLSASVGDRVTITCRASQGISSWLAWYQQKPEKAPKSLIFAASSLQSGVPSRFSGSG
VL1014-019     DIQMTQSPSSLSASVGDRVTITCRASQGISRWLAWYQQKPEKAPKSLIYAASSLRSGVPSRFSGSG
VL1014-143     DIQMTQSPSSLSASVGDRVTITCRASQGISSWLAWYQQKPEKAPKSLIYAASRLQSGVPSRFSGSG
VL1014-021     DIQMTQSPSSLSASVGDRVTITCRASQGISSWLAWYQQKPEKAPKSLIYAASSLQSGVPSRFSGSG
VL1014-027     DIQMTQSPSSLSASVGDRVTITCRASQGISSWLAWYQQKPEKAPKSLIYAASSLQSGVPSRFSGSG
Consensus      DIQMTQSPSSLSASVGDRVTITCRASQGISXWLAWYQQKPEKAPKSLIXAASXLXSGVPSRFSGSG

IgKV1D-16 ...  SGTDFTLTISSLQPEDFATYYCQQYNSYPITFGQGTRLEIK
VL1014-025     SGTDFTLTISSLQPEDFATYYCQQYNSYPITFGQGTRLEIK
VL1014-001     SGTDFTLTISSLQPEDFATYYCQQYISFPITFGQGTRLEIK
VL1014-019     SGTDFTLTISSLQPEDFATYYCQQYNSYPITFGQGTRLEIK
VL1014-143     SGTDFTLTISSLQPEDFATYYCQQYNSYPITFGQGTRLEIK
VL1014-021     SGTDFTLTISSLQPEDFATYYCQQYNSYPITFGQGTRLEIK
VL1014-027     SGTDFTLTISSLQPEDFATYYCQQYNSYPITFGQGTRLEIK
Consensus      SGTDFTLTISSLQPEDFATYYCQQYNSXPITFGQGTRLEIK
```

FIG. 2D

IgKV1D-16-01 / IGKJ1-01– VL alignment (Group 2, No. 2)

```
IgKV1D-16 ...  DIQMTQSPSSLSASVGDRVTITCRASQGISSWLAWYQQKPEKAPKSLIYAASSLQSGVPSRFSGSG
VL1014-091     DIQMTQSPSSLSASVGDRVTITCRASQGISSWLVWYQQKPEKAPKSLIYAASSLQSGVPSRFSGSG
VL1014-032     DIQMTQSPSSLSASVGDRVTITCRASQGISSWLAWYQQKPEKAPKSLIYATFRLQSGVPSRFSGSG
VL1014-035     DIQMTQSPSSLSASVGDRVTITCRASQGISSWLAWYQQKPEKAPKSLIYATFRLQSGVPSRFSGSG
VL1014-036     DIQMTQSPSSLSASVGDRVTITCRASQGISSWLTWYQQKPEKAPKSLIYAASRLQSGVPSRFSGSG
VL1014-054     DIQMTQSPSSLSASVGDRVTITCRASQGISSWLAWYQQKPEKAPKSLIYAASSLQSGVPSRFSGSG
VL1014-094     DIQMTQSPSSLSASVGDRVTITCRASQGISSWLVWYQQKPEKAPKSLIYAASSLQSGVPSRFSGSG
Consensus      DIQMTQSPSSLSASVGDRVTITCRASQGISSWLXWYQQKPEKAPKSLIYAXXXLQSGVPSRFSGSG

IgKV1D-16 ...  SGTDFTLTISSLQPEDFATYYCQQYNSYPWTFGQGTKVEIK
VL1014-091     SGTDFTLTISSLQPEDFATYYCQQYNSFPPTFGQGTKVEIK
VL1014-032     SGTDFTLTISSLQPEDFATYYCQQYNSFPPTFGQGTKVEIK
VL1014-035     SGTDFTLTISSLQPEDFATYYCQQYNSFPPTFGQGTKVEIK
VL1014-036     SGTDFTLTISSLQPEDFATYYCQQYNSFPPTFGQGTKVEIK
VL1014-054     SGTDFTLTISSLQPEDFATYYCQQYNSFPPTFGGGTKVEIK
VL1014-094     SGTDFTLTISSLQPEDFATYYCQQYNSFPPTFGQGTKVEIK
Consensus      SGTDFTLTISSLQPEDFATYYCQQYNSFPPTFGXGTKVEIK
```

FIG. 2E

IgKV1D-16-01 / IGKJ2-01 – VL alignment (Group 3a)

```
IgKV1D-16 ...  DIQMTQSPSSLSASVGDRVTITCRASQGISSWLAWYQQKPEKAPKSLIYAASSLQSGVPSRFSGSG
VL1014-098     DIQMTQSPSSLSASVGDRVTITCRASQGISSWLAWYQQKPEKAPKSLIYAASSLQSGVPSRFSGSG
VL1014-100     DIQMTQSPSSLSASVGDRVTITCRASQGISSWLAWYQQKPEKAPKSLIYAASSLQSGVPSRFSGSG
VL1014-105     DIQMTQSPSSLSASVGDRVTITCRASQGISSWLAWYQQKPEKAPKSLIYAASSLQSGVPSRFSGSG
VL1014-125     DIQMTQSPSSLSASVGDRVTITCRASQGINSWLAWYQQKPEKAPKSLIYAASSLQSGVPSRFSGSG
VL1014-162     DIQMTQSPSSLSASVGDRVTITCRASQGISSWLAWYQQKPEKAPKSLIYAASSLQSGVPSRFSGSG
Consensus      DIQMTQSPSSLSASVGDRVTITCRASQGIXSWLAWYQQKPEKAPKSLIYAASSLQSGVPSRFSGSG

IgKV1D-16 ...  SGTDFTLTISSLQPEDFATYYCQQYNSYPYTFGQGTKLEIK
VL1014-098     SGTDFTLTISSLQPEDFATYYCQQYNSYPYTFGQGTKLEIK
VL1014-100     SGTDFTLTISSLQPEDFATYYCQQYNSYPYTFGQGTKLEIK
VL1014-105     SGTDFTLTISSLQPEDFATYYCQQYNSYPYTFGQGTKLEIK
VL1014-125     SGTDFTLTISSLQPEDFATYYCQQYNSYPYTFGQGTKLEIK
VL1014-162     SGTDFTLTISSLQPEDFATYYCQQYNSYPLTFGGGTKVEIK
Consensus      SGTDFTLTISSLQPEDFATYYCQQYNSYPXTFGXGTKXEIK
```

FIG. 2F

IgKV1D-16-01 / IGKJ5-01 – VL alignment (Group 3b)

```
IgKV1D-16 ...  DIQMTQSPSSLSASVGDRVTITCRASQGISSWLAWYQQKPEKAPKSLIYAASSLQSGVPSRFSGSG
VL1014-153     DIQMTQSPSSLSASVGDRVTITCRASQGISSWLAWYQQKPEKAPKSLIYDASSLQSGVPSRFSGSG
VL1014-152     DIQMTQSPSSLSASVGDRVTITCRASQGINSWLAWYQQKPEKAPKSLIYDASSLQSGVPSRFSGSG
VL1014-166     DIQMTQSPSSLSASVGDRVTITCRASQGISNWLAWYQQKPEKAPKSLIYDASSLQSGVPSRFSGSG
VL1014-167     DIQMTQSPSSLSASVGDRVTITCRASQGISNWLAWYQQKPEKAPKSLIYDASSLQSGVPSRFSGSG
VL1014-160     DIQMTQSPSSLSASVGDRVTITCRASQDISSWLAWYQQKPEKAPKSLIYAASSLQSGVPSRFSGSG
VL1014-033     DIQMTQSPSSLSASVGDRVTITCRASQGISSWLAWYQQKPEKAPKSLIYAASSLQSGVPSRFSGSG
Consensus      DIQMTQSPSSLSASVGDRVTITCRASQGIXXWLAWYQQKPEKAPKSLIYXASSLQSGVPSRFSGSG

IgKV1D-16 ...  SGTDFTLTISSLQPEDFATYYCQQYNSYPITFGQGTRLEIK
VL1014-153     YGTDFSLTISSLQPEDFAIYYCQQYKSYPITFGQGTRLEIK
VL1014-152     SGTDFTLTISSLQPENFATYYCQQYNSYPITFGQGTRLEIK
VL1014-166     SGTDFTLTISSLQPEDFATYYCQQYNSYPITFGQGTRLEIK
VL1014-167     SGTDFTLTISSLQPEDFATYYCQQYNSYPITFGQGTRLEIK
VL1014-160     SGTDFTLTISSLQPEDFATYYCQQYNSYPITFGQGTRLEIK
VL1014-033     SGTDFTLTISSLQPEDFATYYCQQYNSYPITFGQGTRLEIK
Consensus      XGTDFXLTISSLQPEXFAXYYCQQYXSYPITFGQGTRLEIK
```

FIG. 2G

IgKV3-20-01 / IGKJ4-01 – VL alignment

IgKV3-20-01 EIVLTQSPGTLSLSPGERATLSCRASQSVSSSYLAWYQQKPGQAPRLLIYGASSRATGIPDRFSGS
VL1014-005 EIVLTQSPGTLSLSPGERATLSCRASQSVSSSYLAWYQQKPGQVPRLLIYGASSRATGIPDRFSGS
VL1014-059 EIVLTQSPGTLSLSPGERATLSCRASQSVSSTYLAWYQQKPGQAPRLLIYGASSRATGIPDRFSGS
VL1014-060 EIVLTQSPGTLSLSPGERATLSCRASQSVSSSYLAWYQQKPGQAPRLLIYGASSRATGIPDRFSGS
VL1014-106 EIVLTQSPGTLSLSPGERATLSCRASQSVSSSYLAWYQQKPGQAPRLLIYGASSRATGIPDRFSGS
VL1014-111 EIVLTQSPGTLSLSPGERATLSCRASQSVRSSYLAWYQQKPGQAPRLLIYGASSRATGIPDRFSGS
VL1014-041 EIVLTQSPGTLSLSPGERATLSCRASQSVSSSYLAWYQQKPGQAPRLLIYGASSRATGIPDRFSGS
VL1014-150 EIVLTQSPGTLSLSPGERATLSCRASQSVSSSYLTWYQQKPGQAPRLLIYGASSRATGIPDRFSGS
VL1014-067 EIVLTQSPGTLSLSPGERATLSCRASQSVSSSYLAWYQQKPGQAPRLLIYGASSRATGIPDRFSGS
VL1014-072 EIVLTQSPGTLSLSPGERATLSCRASQSVSSSYLAWYQQKPGQAPRLLIYGASSRATGIPDRFSGS
VL1014-163 EIVLTQSPGTLSLSPGERATLSCRASQSVSSSYLAWYQQKPGQAPRLLIYGASSRATGIPDRFSGS
VL1014-093 EIVLTQSPGTLSLSPGERATLSCRASQSVSSSYLAWYQQKPGQAPRLLIYGASSRATGIPDRFSGS
VL1014-044 EIVLTQSPGTLSLSPGERATLSCRASQSVSSSYLAWYQQKPGQAPRLLIYGASSRATGIPDRFSGS
Consensus EIVLTQSPGTLSLSPGERATLSCRASQSVXSXYLXWYQQKPGQXPRLLIYGASSRATGIPDRFSGS IgKV3-20-01 GSGTDFTLTISRLEPEDFAVYYCQQYGSSP-LTFGGGTKVEIK
VL1014-005 GSGTDFTLTISRLEPEDFAVYYCQQYGSS--LTFGGGTKVEIK
VL1014-059 GSGTDFTLTISRLEPEDFAVYYCQQYGTS-LFTFGPGTKVDIK
VL1014-060 GSGTDFTLTISRLEPEDFAVYYCQQYGSSPPITFGQGTRLEIK
VL1014-106 GSGTDFTLTISRLEPEDFAVYYCQQYGSS--FTFGPGTKVDIK
VL1014-111 GSGTDFTLTISRLEPEDFAVYYCQLYGSSP--TFGPGTKVDIK
VL1014-041 GSGTDFTLTISRLEPEDFAVYYCQQYGSS--LTFGGGTKVEIK
VL1014-150 GSGTDFTLTISRLEPEDFAVYYCQQYGSS--LTFGGGTKVEIK
VL1014-067 GSGTDFTLTISRLEPEDFAVYYCQQYGSSPRLTFGGGTKVEIK
VL1014-072 GSGTDFTLTISRLEPEDFAVYYCQQYGSSPRLTFGGGTKVEIK
VL1014-163 GSGTDFTLTISRLEPEDFAVYYCQQYGSS--LTFGGGTKVEIK
VL1014-093 GSGTDFTLTISRLEPEDFAVYYCQQYGSS--LTFGGGTKVEIK
VL1014-044 GSGTDFTLTISRLEPEDFAVYYCQQYGSS--LTFGGGTKVEIK
Consensus GSGTDFTLTISRLEPEDFAVYYCQXYGXSXXXTFGXGTXXXIK

FIG. 2H

IgKV3-11-01 / IGKJ4-01 – VL alignment

```
IgKV3-11-01  EIVLTQSPATLSLSPGERATLSCRASQSVSSYLAWYQQKPGQAPRLLIYDASNRATGIPARFSGS
VL1014-006   EIVLTQSPATLSLSPGERATLSCRASQSVSSYLAWYQQKPGQAPRLLIYDASNRATGIPARFSGS
Consensus    EIVLTQSPATLSLSPGERATLSCRASQSVSSYLAWYQQKPGQAPRLLIYDASNRATGIPARFSGS

IgKV3-11-01  GSGTDFTLTISSLEPEDFAVYYCQQRSNWPPLTFGGGTKVEIK
VL1014-006   GSGTDFTLTISSLEPEDFAVYYCQQRSNWPPLTFGGGTKVEIK
Consensus    GSGTDFTLTISSLEPEDFAVYYCQQRSNWPPLTFGGGTKVEIK
```

BISPECIFIC ANTIBODIES AGAINST HER2 AND CD3

RELATED APPLICATIONS

This application is a continuation of U.S. patent application Ser. No. 15/599,395, filed May 18, 2017, which is a continuation of U.S. patent application Ser. No. 14/112,859, filed Feb. 12, 2014, which is a 35 U.S.C. 371 national stage filing of International Application No. PCT/EP2012/057307, filed Apr. 20, 2012, which claims priority to International Patent Application Nos. PCT/EP2011/056388, filed Apr. 20, 2011; PCT/EP2011/058779, filed May 27, 2011; and PCT/EP2011/058772, filed May 27, 2011; Danish Patent Application Nos. PA 2011 00824, filed Oct. 27, 2011, and PA 2011 00312, filed Apr. 20, 2011; and U.S. Provisional Patent Application No. 61/552,286, filed Oct. 27, 2011. The entire contents of the aforementioned applications are incorporated herein by reference.

SEQUENCE LISTING

The instant application contains a Sequence Listing which has been submitted electronically in ASCII format and is hereby incorporated by reference in its entirety. Said ASCII copy, created on Oct. 29, 2019, is named GMI_145USCN2_Sequence_Listing.txt and is 171,511 bytes in size.

FIELD OF THE INVENTION

The present invention relates to bispecific antibodies directed to human epidermal growth factor receptor 2 (HER2) and cluster determinant 3 (CD3) and to uses of such antibodies, in particular their use in the treatment of cancer.

BACKGROUND OF THE INVENTION

HER2 is a 185-kDa cell surface receptor tyrosine kinase and member of the epidermal growth factor receptor (EGFR) family that comprises four distinct receptors: EGFR/ErbB-1, HER2/ErbB-2, HER3/ErbB-3, and HER4/ErbB-4. Both homo- and heterodimers are formed by the four members of the EGFR family, with HER2 being the preferred and most potent dimerization partner for other ErbB receptors (Graus-Porta et al., Embo J 1997; 16:1647-1655; Tao et al., J Cell Sci 2008; 121:3207-3217). HER2 can be activated by overexpression or by heterodimerization with other ErbBs that can be activated by ligand binding (Riese and Stern, Bioessays 1998; 20:41-48). For HER2, no ligand has been identified. HER2 activation leads to receptor phosphorylation, which triggers a cascade of downstream signals through multiple signaling pathways, such as MAPK, phosphoinositol 3-kinase/AKT, JAK/STAT and PKC, which ultimately results in the regulation of multiple cellular functions, such as growth, survival and differentiation (Huang et al., Expert Opin Biol Ther 2009; 9:97-110).

Much of the attention on HER2 in tumors has been focused on its role in breast cancer, in which HER2 overexpression is reported in approximately 20% of the cases and is correlated with poor prognosis (Reese et al., Stem Cells 1997; 15:1-8; Andrechek et al., Proc Natl Acad Sci USA 2000; 97:3444-3449; and Slamon et al., Science 1987; 235:177-182). Besides breast cancer, HER2 expression has also been associated with other human carcinoma types, including prostate cancer, non-small cell lung cancer, bladder cancer, ovarian cancer, gastric cancer, colon cancer, esophageal cancer and squamous cell carcinoma of the head & neck (Garcia de Palazzo et al., Int 3 Biol Markers 1993; 8:233-239; Ross et al., Oncologist 2003; 8:307-325; Osman et al., J Urol 2005; 174:2174-2177; Kapitanovic et al., Gastroenterology 1997; 112:1103-1113; Turken et al., Neoplasma 2003; 50:257-261; and Oshima et al., Int J Biol Markers 2001; 16:250-254).

Trastuzumab (Herceptin®) is a recombinant, humanized monoclonal antibody directed against domain IV of the HER2 protein, thereby blocking ligand-independent HER2 homodimerization, and to a lesser extend heterodimerization of HER2 with other family members in cells with high HER2 overexpression (Cho et al., Nature 2003; 421:756-760 and Wehrman et al., Proc Natl Acad Sci USA 2006; 103: 19063-19068). In cells with modest HER2 expressing levels, trastuzumab was found to inhibit the formation of HER2/EGFR heterodimers (Wehrman et al., (2006), supra; Schmitz et al., Exp Cell Res 2009; 315:659-670). Trastuzumab mediates antibody-dependent cellular cytotoxicity (ADCC) and prevents ectodomain shedding, which would otherwise result in the formation of a truncated constitutively active protein in HER2 overexpressing cells. Also inhibition of both in vitro and in vivo proliferation of tumor cells expressing high levels of HER2 has been reported for trastuzumab (reviewed in Nahta and Esteva, Oncogene 2007; 26:3637-3643). Herceptin® has been approved both for first-line and adjuvant treatment of HER2 overexpressing metastatic breast cancer, either in combination with chemotherapy, or as a single agent following one or more chemotherapy regimens. Trastuzumab has been found to be effective only in 20-50% of HER2 overexpressing breast tumor patients and many of the initial responders show relapse after a few months (Dinh et al., Clin Adv Hematol Oncol 2007; 5:707-717).

Pertuzumab (Omnitarg™) is another humanized monoclonal antibody. It is directed against domain II of the HER2 protein, resulting in inhibition of ligand-induced heterodimerization (i.e., HER2 dimerizing with another member of the ErbB family to which a ligand has bound); a mechanism reported to not strictly require high HER2 expression levels (Franklin et al., Cancer Cell 2004; 5:317-328.). Although pertuzumab also mediates ADCC, the main mechanism of action of pertuzumab relies on its dimerization blockade (Hughes et al., Mol Cancer Ther 2009; 8:1885-1892). Moreover, pertuzumab was found to enhance EGFR internalization and downregulation by inhibiting the formation of EGFR/HER2 heterodimers, which otherwise tethers EGFR at the plasma membrane (Hughes et al., 2009, supra). This correlates with the observation that EGFR homodimers internalize more efficient than EGFR/HER2 dimers (Pedersen et al., Mol Cancer Res 2009; 7:275-284. The complementary mechanisms of action of pertuzumab and trastuzumab reportedly results in enhanced anti-tumor effects and efficacy when combined in patients who progressed during prior trastuzumab therapy (Baselga et al., J Clin Oncol 2010; 28:1138-1144), and a phase III trial to evaluate this antibody combination together with Docetaxel in previously untreated HER2-positive metastatic breast cancer is underway.

An alternative approach to improve targeted antibody therapy is by delivering cytotoxic cells or drugs specifically to the antigen-expressing cancer cells. This concept of using T-cell for efficient killing of tumor cells has been described already in 1985 (Stearz at al. Nature 1985, 314:628-631). For example, the so-called trifunctional antibodies are bispecific antibodies, targeting with one arm the antigen on the tumor cell and with the other arm for instance CD3 on T cells, and provide Fc receptor binding by the Fc region. Upon binding, a complex of T cells, tumor cells and effector cells that bind the antibody Fc domain is formed, leading to killing of the tumor cells (Muller and Kontermann, BioDrugs 2010; 24:89-98.). Ertumaxomab is one such trifunctional antibody against HER2 and CD3, which induces cytotoxicity in cell lines with low HER2 expression and which is in Phase II clinical development in metastatic breast cancer (Jones et al., Lancet Oncol 2009; 10:1179-1187 and Kiewe et al., Clin Cancer Res 2006; 12:3085-3091).

Alternatively, a complex of T cells and tumor cells are formed, leading to killing of the tumor cells (Muller and Kontermann, BioDrugs 2010; 24:89-98, Baeuerle and Reinhardt 2009, Cancer Research 96: 4941) by an dual targeting antibody fragment (e.g. dual targeting single chain antibodies). Blinatumomab (Bargou et al, Science 2008, 321:974-976) is a single chain antibody construct named BITE which induces cytotoxicity by targeting CD19 and CD3. Other antibody fragment based T-cell engaging bispecifics have been described (Moore et al. 2011, Blood 117:4542-4551, Baeuerle et el. Current opinion in Molecular Therapeutics 2009, 11:22-30).

The complex mechanisms regulating the function of HER2 warrant further research on new and optimized therapeutic strategies against this proto-oncogene. Accordingly, there remains a need for effective and safe products for treating HER2-related diseases, such as cancer.

SUMMARY OF THE INVENTION

It is an object of the present invention to provide novel effective bispecific antibodies comprising a first antigen-binding region derived from a HER2 antibody and a second region having a binding specificity for CD3, for medical use. Typically, the second region is an antigen-binding region derived from a CD3 antibody, optionally a known CD3 antibody.

As shown herein, the novel bispecific HER2×CD3 antibodies are capable of dose-dependent killing of HER2-expressing cells in in vitro cytoxicity assays, effectively prevent tumor growth in vivo, and/or have other advantages over monospecific HER2 or CD3 antibodies. In one aspect, the monospecific HER2 antibodies from which the HER2-binding region is derived exhibit HER2 binding characteristics or variable region sequences that differ from HER2 antibodies described in the art.

In preferred embodiments, the bispecific HER2×CD3 antibodies of the invention are prepared from HER2 antibodies that are fully human or humanized, bind to novel epitopes, and/or have favorable properties for therapeutic use in human patients. Each Fab-arm of the bispecific antibodies may further include an Fc-region, optionally comprising modifications promoting the formation of the bispecific antibody, modifications affecting Fc-mediated effector functions, and/or other features described herein.

These and other aspects of the invention are described in further detail below.

BRIEF DESCRIPTION OF THE DRAWINGS

FIGS. 1A-1O: Alignment of HER2 HuMab heavy chain variable region (VH) sequences with germline (reference) sequences (FIGS. 1A-1O). In each VH sequence, the amino acids that differ from those of the germline (reference) at specific positions are highlighted. Consensus VH sequences are shown, where "X" indicates positions at which alternative amino acids (selected from those aligned at each position) are possible. The CDR1, CDR2, and CDR3 sequences are underlined in each VH sequence. The consensus CDR sequences are further defined in Table 4.

FIGS. 2A-2H: Alignment of HuMab light chain variable region (VL) sequences with germline (reference) sequences (FIGS. 2A-2H). In each VL sequence, the amino acids that differ from those of the germline (reference) at specific positions are highlighted. In, e.g., FIG. 2A, all VL sequences derived from the same V-segment (IgKV1-12-01), but the closest J-segment differed between antibodies. Consensus VL sequences are shown, where "X" indicates positions at which alternative amino acids (selected from those aligned at the indicated position) are possible. The CDR1, CDR2, and CDR3 sequences are underlined in each VL sequence. The consensus CDR sequences are further defined in Table 4.

(FIG. 8A, FIG. 8B) Data shown are fluorescence intensities (FI) of one representative experiment with AU565 cells treated with non-conjugated and anti-kappa-ETA'-conjugated HER2 antibodies. (FIG. 8C, FIG. 8D) Data shown are mean fluorescence intensities (MFI) of one representative experiment with A431 cells treated with non-conjugated and anti-kappa-ETA'-conjugated HER2 antibodies. See Example 18 for details.

4) to labeled AU565 cells (CFSE—Y-axis) and Jurkat cells (PKH26—X-asis), thereby creating doublets of interconnected cells as shown by the double-positive cells in FACS dot plot (Q2). (FIG. 10B) Representative examples of FACS experiments showing the double positive events in Q2 (dotted line) representing the cells simultanously bound via the bispecific HER2×CD antibody.

(FIG. 11A) huOKT3, (FIG. 11B) HUM291, (FIG. 11C) YTH12.5 and (FIG. 11D) huCLB-T3/4. See Example 21 for details.

(FIG. 26A) A concentration series (total antibody) of 0-20 μg/mL was analyzed. The positive control is a purified batch of bispecific antibody, derived from IgG1-2F8-ITL×IgG4-7D8-CPPC. (FIG. 26B) The exchange is presented as bispecific binding at 20 μg/mL relative to the positive control (black bar). Dark grey bars represents the bispecific binding between the IgG4 control (IgG4-7D8×IgG4-2F8), the negative control (IgG1-2F8×IgG1-7D8-K409R) and between IgG1-2F8-ITL and IgG4-7D8-CPPC. Light grey bars represent results from simultaneously performed Fab-arm-exchange reactions between the indicated IgG1-7D8-K409X mutants and IgG1-2F8-ITL.

(FIG. 27A) A concentration series (total antibody) of 0-20 μg/mL was analyzed in the ELISA. The positive control is a purified batch of bispecific antibody, derived from IgG1-2F8-F405L×IgG1-7D8-K409R. (FIG. 27B) The exchange is presented as bispecific binding at 20 μg/mL antibody concentration relative to the positive control (black bar). Dark grey bars represents the bispecific binding between the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-F405X mutants and IgG1-7D8-K409R or controls.

(FIG. 28A) A concentration series (total antibody) of 0-20 μg/mL was analyzed in the ELISA. The positive control is a purified batch of bispecific antibody, derived from IgG1-2F8-F405L×IgG1-7D8-K409R. (FIG. 28B) The exchange is presented as bispecific binding at 20 μg/mL antibody concentration relative to the positive control (black bar). Dark grey bars represents the bispecific binding between the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-Y407X mutants and IgG1-7D8-K409R or controls.

(FIG. 29B) Bispecific binding at 20 μg/mL relative to the positive control (black bar). Dark grey bars represents the bispecific binding between the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-L368X mutants and IgG1-7D8-K409R.

(FIG. 30B) Bispecific binding at 20 μg/mL relative to the positive control (black bar). Dark grey bars represents the bispecific binding between the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-D370X mutants and IgG1-7D8-K409R.

(FIG. 31B) Bispecific binding at 20 μg/mL antibody concentration relative to the positive control (black bar). Dark grey bars represents the bispecific binding between the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-D399X mutants and IgG1-7D8-K409R.

(FIG. 32B) The bispecific binding at 20 μg/mL antibody concentration relative to the positive control (black bar). Dark grey bars represents the bispecific binding between the IgG4 control (IgG4-7D8×IgG4-2F8) and the negative control (IgG1-2F8×IgG1-7D8-K409R). Light grey bars represent results from simultaneously performed Fab-arm-exchange reactions between the indicated IgG1-2F8-T366X mutants and IgG1-7D8-K409R.

DETAILED DESCRIPTION OF THE INVENTION

Definitions

Figure 3A:
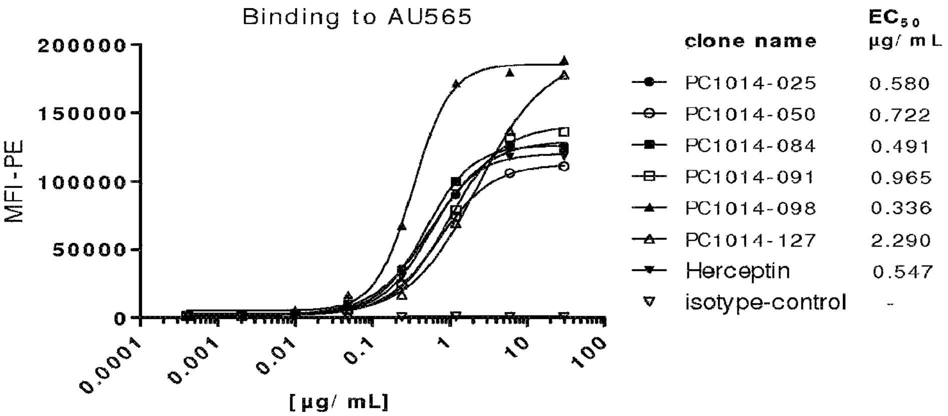
FIGS. 3A-3F: Binding curves of HER2 antibodies to (FIG. 3A, FIG. 3B, FIG. 3E) high (AU565) and (FIG. 3C, FIG. 3D, FIG. 3F) low (A431) HER2 expressing cell lines, determined as described in Example 12. Data shown are mean fluorescence intensities (MFI) of one representative experiment for each cell line. The $EC_{50}$ values indicate the apparent affinities.
Figure 3B:
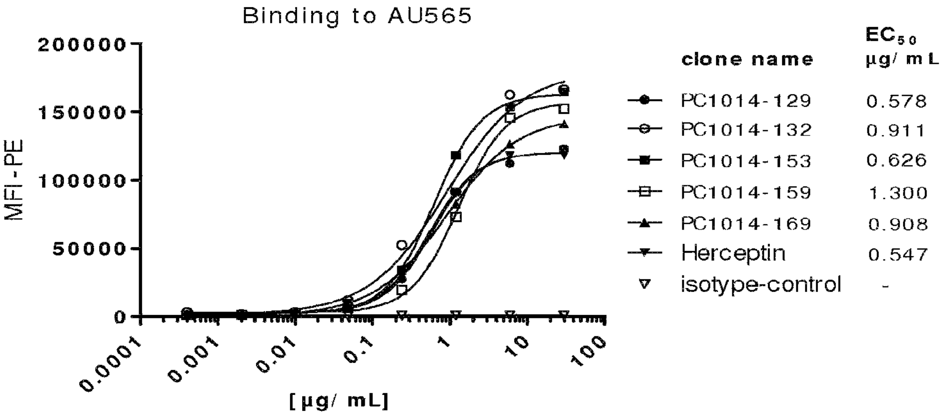
Figure 3C:
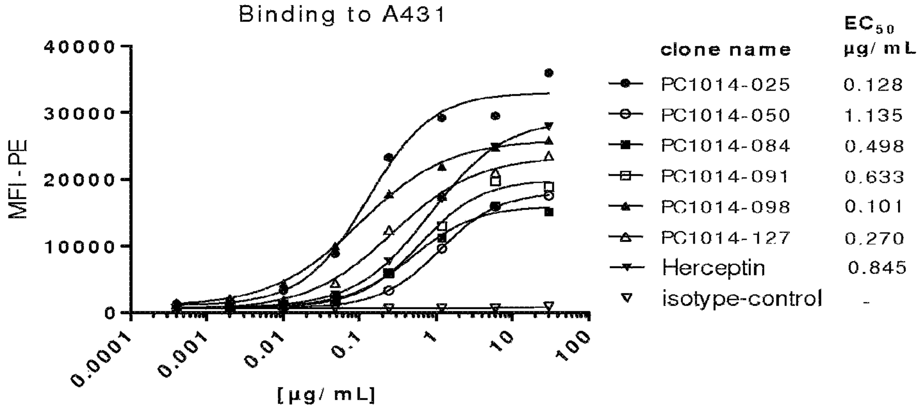
Figure 3D:
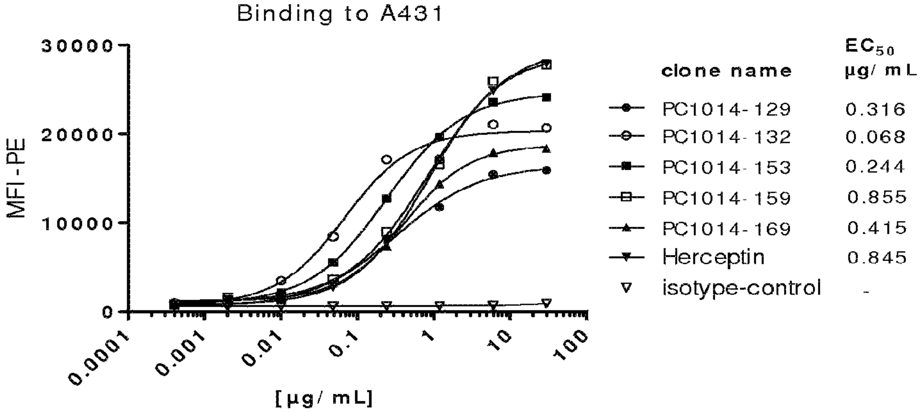

The term "HER2" (also known as ErbB-2, NEU, HER-2, and CD340), when used herein, refers to human epidermal growth factor receptor 2 (SwissProt P04626) and includes any variants, isoforms and species homologs of HER2 which are naturally expressed by cells, including tumor cells, or are expressed on cells transfected with the HER2 gene or cDNA. Species homologs include rhesus monkey HER2 (macaca mulatta; Genbank accession No. GI:109114897).

The term "CD3" refers to the human CD3 protein complex, which is composed of six distinct chains (a CD3γ chain (SwissProt P09693), a CD3δ chain (SwissProt P04234), two CD3ε chains (SwissProt P07766), and one CD3 zeta chain homodimer (SwissProt P20963) (ε γ: ε δ:ζζ), and which is associated with the T cell receptor α and β chain. The term includes any CD3 variants, isoforms and species homologs which are naturally expressed by cells, including T cells, or are expressed on cells transfected with genes or cDNA encoding the aforementioned chains.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH or VH) and a heavy chain constant region. The heavy chain constant region typically is comprised of three domains, $C_H1$, $C_H2$, and $C_H3$. Each light chain typically is comprised of a light chain variable region (abbreviated herein as $V_L$ or $V_L$) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Unless otherwise stated or contradicted by context, CDR sequences herein are identified according to IMGT rules (Brochet X., Nucl Acids Res. 2008; 36:W503-508 and Lefranc M P., Nucleic Acids Research 1999; 27:209-212; see also internet http address imgt.cines.fr/IMGT_vquest/vquest?livret=0&Option=humanIg. However, the numbering of amino acid residues in an antibody sequence can also be performed by the method described in Kabat et al., Sequences of Proteins of Immunological Interest, 5th Ed. Public Health Service, National Institutes of Health, Bethesda, Md. (1991) (phrases such as "variable domain residue numbering as in Kabat", "Kabat position" or "according to Kabat" herein refer to this numbering system). Particularly, for numbering of amino acids in the constant region, the EU index numbering system (Kabat et al, supra), can be used. The Kabat numbering of residues may be determined for a given antibody as described in Kabat et al., supra.

In the present invention reference to amino acid positions is, unless contradicted by the context, according to the EU-index as described in Kabat et al., Sequences of Proteins of Immunological Interest, 5th Ed. Public Health Service, National Institutes of Health, Bethesda, Md. (1991).

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. A HER2 antibody may also be a multispecific antibody, such as a bispecific antibody, diabody, or similar molecule (see for instance PNAS USA 90(14), 6444-8 (1993) for a description of diabodies). Indeed, bispecific antibodies, diabodies, and the like, provided by the present invention may bind any suitable target in addition to a portion of HER2. As indicated above, the term antibody herein, unless otherwise stated or clearly contradicted by context, includes fragments of an antibody that are antigen-binding fragments, i.e., retain the ability to specifically bind to the antigen. It has been shown that the antigen-binding function of an antibody may be performed by fragments of a full-length antibody. Examples of antigen-binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab); (ii) $F(ab')_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a VH domain and also called domain antibodies (Holt et al; Trends Biotechnol. 2003 November; 21(11):484-90); (vi) camelid or nanobodies (Revets etas Expert Opin Biol Ther. 2005 January; 5(1):111-24) and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention, as well as bispecific formats of such fragments, are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

The term "bispecific antibody" is in the context of the present invention to be understood as an antibody having two different antigen-binding regions defined by different antibody sequences. This can be understood as different target binding but includes as well binding to different epitopes in one target.

The term "bispecific antibody" is in the context of the present invention to be understood as an antibody with two different antigen-binding regions (based on sequence information). This can mean different target binding but includes as well binding to different epitopes in one target.

When used herein, unless contradicted by context, the term "Fab-arm" or "arm" refers to one heavy chain-light chain pair.

When used herein, unless contradicted by context, the term "Fc region" refers to an antibody region comprising at least a hinge region, a CH2 domain, and a CH3 domain.

As used herein, "isotype" refers to the immunoglobulin class (for instance IgG1, IgG2, IgG3, IgG4, IgD, IgA, IgE, or IgM) that is encoded by heavy chain constant region genes.

The term "monovalent antibody" means in the context of the present invention that an antibody molecule is capable of binding a single molecule of the antigen, and thus is not able of antigen crosslinking.

An "antibody deficient in effector function" or an "effector-function-deficient antibody" refers to an antibody which has a significantly reduced or no ability to activate one or more effector mechanisms, such as complement activation or Fc receptor binding. Thus, effector-function deficient antibodies have significantly reduced or no ability to mediate antibody-dependent cell-mediated cytotoxicity (ADCC) and/or complement-dependent cytotoxicity (CDC). An example of such an antibody is IgG4. Another example is the introduction of mutations in Fc-region which can strongly reduce the interaction with complement proteins and Fc-receptors. See, for example, Bolt S et al., Eur J Immunol 1993, 23:403-411; Oganesyan, Acta Crys. 2008, D64, 700-704; and Shields et al., J B C 2001, 276: 6591-6604.

A "HER2 antibody" or "anti-HER2 antibody" is an antibody as described above, which binds specifically to the antigen HER2.

A "HER2×CD3 antibody" or "anti-HER2×CD3 antibody" is a multispecific antibody, optionally a bispecific antibody, which comprises two different antigen-binding regions, one of which binds specifically to the antigen HER2 and one of which binds specifically to CD3.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline immunoglobulin gene. Typically, outside the heavy chain CDR3, a human antibody derived from a particular human germline sequence will display no more than 20 amino acid differences, e.g. no more than 10 amino acid differences, such as no more than 9, 8, 7, 6 or 5, for instance no more than 4, 3, 2, or 1 amino acid difference from the amino acid sequence encoded by the germline immunoglobulin gene.

When used herein, the term "heavy chain antibody" or "heavy-chain antibody" refers to an antibody which consists only of two heavy chains and lacks the two light chains usually found in antibodies. Heavy chain antibodies, which naturally occur in e.g. camelids, can bind antigens despite their lack of VL domains.

In a preferred embodiment, the antibody of the invention is isolated. An "isolated antibody," as used herein, is intended to refer to an antibody which is substantially free of other antibodies having different antigenic specificities (for instance an isolated antibody that specifically binds to HER2 is substantially free of antibodies that specifically bind antigens other than HER2). An isolated antibody that specifically binds to an epitope, isoform or variant of HER2 may, however, have cross-reactivity to other related antigens, for instance from other species (such as HER2 species homologs). Moreover, an isolated antibody may be substantially free of other cellular material and/or chemicals. In one embodiment of the present invention, two or more "isolated" monoclonal antibodies having different antigen-binding specificities are combined in a well-defined composition.

When used herein in the context of two or more antibodies, the term "competes with" or "cross-competes with" indicates that the two or more antibodies compete for binding to HER2, e.g. compete for HER2 binding in the assay described in Example 14. An antibody "blocks" or "cross-blocks" one or more other antibodies from binding to HER2 if the antibody competes with the one or more other antibodies 25% or more, with 25%-74% representing "partial block" and 75%-100% representing "full block", preferably as determined using the assay of Example 14. For some pairs of antibodies, competition or blocking in the assay of the Examples is only observed when one antibody is coated on the plate and the other is used to compete, and not vice versa. Unless otherwise defined or negated by context, the terms "competes with", "cross-competes with", "blocks" or "cross-blocks" when used herein is also intended to cover such pairs of antibodies.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked or covered by the specifically antigen binding peptide (in other words, the amino acid residue is within the footprint of the specifically antigen binding peptide).

The term "monoclonal antibody" as used herein refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

As used herein, the term "binding" in the context of the binding of an antibody to a predetermined antigen or epitope typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "IQ" ($sec^{-1}$), as used herein, refers to the dissociation rate constant of a particular antibody-antigen interaction. Said value is also referred to as the $k_{off}$ value.

The term "$k_a$" ($M^{-1}\times sec^{-1}$), as used herein, refers to the association rate constant of a particular antibody-antigen interaction.

The term "$K_D$" (M), as used herein, refers to the dissociation equilibrium constant of a particular antibody-antigen interaction.

The term "$K_A$" ($M^{-1}$), as used herein, refers to the association equilibrium constant of a particular antibody-antigen interaction and is obtained by dividing the $k_a$ by the $k_d$.

When used herein the term "heterodimeric interaction between the first and second CH3 regions" refers to the interaction between the first CH3 region and the second CH3 region in a first-CH3/second-CH3 heterodimeric protein.

When used herein the term "homodimeric interactions of the first and second CH3 regions" refers to the interaction between a first CH3 region and another first CH3 region in a first-CH3/first-CH3 homodimeric protein and the interaction between a second CH3 region and another second CH3 region in a second-CH3/second-CH3 homodimeric protein.

The term "reducing conditions" or "reducing environment" refers to a condition or an environment in which a substrate, here a cysteine residue in the hinge region of an antibody, is more likely to become reduced than oxidized.

As used herein, the term "inhibits proliferation" (e.g. referring to cells, such as tumor cells) is intended to include any substantial decrease in the cell proliferation when contacted with a HER2 antibody as compared to the proliferation of the same cells not in contact with a HER2 antibody, e.g., the inhibition of proliferation of a cell culture by at least about 10%, at least about 20% or at least about 30%, or at least as much as a reference antibody such as trastuzumab, e.g., as determined by an assay in the Examples, e.g. Example 16.

As used herein, the term "promotes proliferation" (e.g. referring to cells, such as tumor cells) is intended to include any substantial increase in the cell proliferation when contacted with a HER2 antibody as compared to the proliferation of the same cells not in contact with a HER2 antibody, e.g., the promotion of proliferation of a cell culture by at least about 10%, at least about 20% or at least about 30%, or at least as much as a reference antibody as F5, e.g., as determined by an assay in the Examples.

As used herein, the term "internalization", when used in the context of a HER2 antibody includes any mechanism by which the antibody is internalized into a HER2-expressing cell from the cell-surface and/or from surrounding medium, e.g., via endocytosis. The internalization of an antibody can be evaluated using a direct assay measuring the amount of internalized antibody (such as, e.g., the fab-CypHer5E assay described in Example 19), or an indirect assay where the effect of an internalized antibody-toxin conjugate is measured (such as, e.g., the anti-kappa-ETA' assay of Example 18).

The present invention also provides antibodies comprising functional variants of the $V_L$ region, $V_H$ region, or one or more CDRs of the antibodies of the examples. A functional variant of a $V_L$, $V_H$, or CDR used in the context of a HER2 antibody still allows the antibody to retain at least a substantial proportion (at least about 50%, 60%, 70%, 80%, 90%, 95% or more) of the affinity/avidity and/or the specificity/selectivity of the parent antibody and in some cases such a HER2 antibody may be associated with greater affinity, selectivity and/or specificity than the parent antibody.

Such functional variants typically retain significant sequence identity to the parent antibody. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

Exemplary variants include those which differ from a parent antibody VH and/or VL sequence shown in FIGS. 1 and 2 at one or more "variant" amino acid positions, denoted "X" in the corresponding consensus sequence. Preferred variants are those in which the new amino acid is selected from those at the corresponding position in one of the aligned sequences in FIG. 1 or 2 (for details on CDR sequence variants, see Table 4). Alternatively or additionally, the sequence of VH, VL or CDR variants may differ from the sequence of the VH, VL or CDR of the parent antibody sequences mainly by conservative substitutions; for instance at least 10, such as at least 9, 8, 7, 6, 5, 4, 3, 2 or 1 of the substitutions in the variant are conservative amino acid residue replacements.

In the context of the present invention, conservative substitutions may be defined by substitutions within the classes of amino acids reflected in the following table:

Amino acid residue classes for conservative substitutions

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

In the context of the present invention the following notations are, unless otherwise indicated, used to describe a mutation; i) substitution of an amino acid in a given position is written as e.g. K405R which means a substitution of a Lysine in position 405 with an Arginine; and ii) for specific variants the specific three or one letter codes are used, including the codes Xaa and X to indicate any amino acid residue. Thus, the substitution of Arginine for Lysine in position 405 is designated as: K405R, or the substitution of any amino acid residue for Lysine in position 405 is designated as K405X. In case of deletion of Lysine in position 405 it is indicated by K405*.

The term "recombinant host cell" (or simply "host cell"), as used herein, is intended to refer to a cell into which an expression vector has been introduced, e.g. an expression vector encoding an antibody of the invention. Recombinant host cells include, for example, transfectomas, such as CHO cells, HEK293 cells, NS/0 cells, and lymphocytic cells.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human HER2 antibodies when immunized with HER2 antigen and/or cells expressing HER2. The human heavy chain transgene may be integrated into the chromosomal DNA of the mouse, as is the case for transgenic mice, for instance HuMAb® mice, such as HCo7, HCo12, or HCo17 mice, or the human heavy chain transgene may be maintained extrachromosomally, as is the case for transchromosomal KM mice as described in WO02/43478. Similar mice, having a larger human Ab gene repertoire, include HCo7 and HCo20 (see e.g. WO2009097006). Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, nonhuman animal can also be used for production of antibodies against a specific antigen by introducing genes encoding such specific antibody, for example by operatively linking the genes to a gene which is expressed in the milk of the animal.

"Treatment" refers to the administration of an effective amount of a therapeutically active compound of the present invention with the purpose of easing, ameliorating, arresting or eradicating (curing) symptoms or disease states.

An "effective amount" or "therapeutically effective amount" refers to an amount effective, at dosages and for periods of time necessary, to achieve a desired therapeutic result. A therapeutically effective amount of a HER2 antibody may vary according to factors such as the disease state, age, sex, and weight of the individual, and the ability of the HER2 antibody to elicit a desired response in the individual. A therapeutically effective amount is also one in which any toxic or detrimental effects of the antibody or antibody portion are outweighed by the therapeutically beneficial effects.

An "anti-idiotypic" antibody is an antibody which recognizes unique determinants generally associated with the antigen-binding site of an antibody.

Further Aspects and Embodiments of the Invention

As described above, the invention relates to a bispecific antibody comprising two different antigen-binding regions, one which has a binding specificity for HER2 and one which has a binding specificity for CD3.

In one aspect, the invention relates to a bispecific molecule comprising a first antigen binding region from a HER2 antibody described herein and a second antigen binding region from a CD3 antibody described herein.

In one embodiment, the HER2 antigen-binding region is from a HER2 antibody which cross-blocks or binds to the same epitope as a reference antibody from cross-block group 1, described herein. In a specific embodiment, the bispecific antibody comprises an antigen-binding region from an antibody of cross-block group 1, as described herein.

In one embodiment, the HER2 antigen-binding region is from a HER2 antibody which cross-blocks or binds to the same epitope as a reference antibody from cross-block group 2, described herein. In a specific embodiment, the bispecific antibody comprises an antigen-binding region from an antibody of cross-block group 2, as described herein.

In one embodiment, the HER2 antigen-binding region is from a HER2 antibody which cross-blocks or binds to the same epitope as a reference antibody from cross-block group 3, described herein. In a specific embodiment, the bispecific antibody comprises an antigen-binding region from an antibody of cross-block group 3, as described herein.

In one embodiment, the HER2 antigen-binding region is from a HER2 antibody which cross-blocks or binds to the same epitope as a reference antibody from cross-block group 4, described herein. In a specific embodiment, the bispecific antibody comprises an antigen-binding region from an antibody of cross-block group 4, as described herein.

In a particular embodiment, the bispecific antibody of any one of the preceding embodiments comprises an antigen-binding region which cross-blocks or binds to the same epitope as a reference CD3 antibody comprising the VH and VL regions of CD3 antibody YTH12.5, HUM291 (also known as visilizumab), huOKT3-C114S-gLC (related to teplizumab), all known in the art, or comprising the VH and VL regions of CD3 antibody huCLB-T3/4, which represents a humanized variant of CLB-T3/4. Further details on these CD3 antibodies are provided in Example 21. In another particular embodiment, the bispecific antibody of any one of the preceding embodiments comprises an antigen-binding region from an antibody selected from YTH12.5, HUM291 huOKT3-C114S-gLC and huCLB-T3/4.

Thus, the bispecific antibody of the present invention may comprise a first antigen-binding region and a second antigen-binding region, which first antigen-binding region binds an epitope on human epidermal growth factor receptor 2 (HER2) and which second antigen-binding region binds an epitope on human CD3.

Antibodies and Antigen-Binding Regions

The bispecific antibody of the present invention comprises two different antigen-binding regions which bind HER2 and CD3, respectively. Furthermore, as described below one method of producing a bispecific antibody of the present invention is based on incubating a first HER2 antibody and a second CD3 antibody under reducing conditions.

Antigen-binding regions binding to HER2 antibodies of the present invention may belong to any of cross-block groups 1, 2, 3 and 4. In the following examples of such antigen-binding regions bind to HER2 belonging to cross-block groups 1, 2, 3, and 4 are given, and reference to "antigen-binding region" in this context is intended to include both an antigen-binding region of a bispecific antibody of the present invention, e.g. a first antigen-binding region, and first HER2 antibody.

In a further or alternative embodiment of the present invention, the bispecific antibody comprises an antigen-binding region of one or more of the human antibodies of cross-blocks 1, 2, 3, or 4, which blocks the binding to HER2.

In a further or alternative embodiment of the present invention, the bispecific antibody comprises an antigen-binding region which blocks the binding to the same epitope on soluble HER2 as one or more of the human antibodies of cross-blocks 1, 2, 3, or 4.

In a further or alternative embodiment of the present invention, the bispecific antibody comprises an antigen-binding region which binds to the same epitope on HER2 as one or more of the human antibodies of cross-blocks 1, 2, 3, or 4.

Thus, the bispecific antibody of the present invention may comprise a first antigen-binding region and a second antigen-binding region, which first and second antigen-binding regions bind different epitopes, and wherein the first antigen-binding region binds an epitope on human epidermal growth factor receptor 2 (HER2).

The first antigen-binding region of the bispecific antibody of the present invention may be an antigen-binding region from any of cross-block groups 1, 2, 3, and 4.

Cross-Block Group 1

In one aspect, the bispecific antibody of the invention comprises an antigen-binding region which blocks the binding to HER2, e.g. soluble HER2, or binds to the same epitope on HER2 as one or more of the human antibodies of cross-block group 1 described herein.

In one embodiment, the antigen-binding region cross-blocks the binding to soluble HER2 of trastuzumab, when determined as described in Example 14.

In one embodiment, the antigen-binding region blocks the binding to HER2, e.g. soluble HER2, or binds to the same epitope as a reference antibody comprising a VH region comprising the sequence of SEQ ID NO:1 and a VL region comprising the sequence of SEQ ID NO:5 (169).

In one embodiment, the antigen-binding region blocks the binding to HER2, e.g. soluble HER2, or binds to the same epitope as a reference antibody comprising a VH region comprising the sequence of SEQ ID NO:8 and a VL region comprising the sequence of SEQ ID NO:12 (050).

In one embodiment, the antigen-binding region blocks the binding to HER2, e.g. soluble HER2, or binds to the same epitope as a reference antibody comprising a VH region comprising the sequence of SEQ ID NO:15 and a VL region comprising the sequence of SEQ ID NO:19 (084).

In one embodiment, the antigen-binding region blocks the binding to HER2, e.g. soluble HER2, or binds to the same epitope as a reference antibody comprising VH and VL regions selected from the group consisting of:

a) a VH region comprising the sequence of SEQ ID NO:77 and a VL region comprising the sequence of SEQ ID NO:78 (049);
b) a VH region comprising the sequence of SEQ ID NO:79 and a VL region comprising the sequence of SEQ ID NO:80 (051);
c) a VH region comprising the sequence of SEQ ID NO:81 and a VL region comprising the sequence of SEQ ID NO:82 (055);
d) a VH region comprising the sequence of SEQ ID NO:83 and a VL region comprising the sequence of SEQ ID NO:84 (123);
e) a VH region comprising the sequence of SEQ ID NO:85 and a VL region comprising the sequence of SEQ ID NO:86 (161); and
f) a VH region comprising the sequence of SEQ ID NO:87 and a VL region comprising the sequence of SEQ ID NO:88 (124).

In another additional or alternative aspect of the bispecific antibody of the invention, one antigen-binding region binds to HER2 and comprises a VH CDR3, VH region and/or VL region sequence similar or identical to such a sequence of an antibody described herein.

In one embodiment, the antigen-binding region comprises a VH CDR3 region having a sequence selected from the group consisting of SEQ ID NO:11 (050, 049, 051, 055), optionally wherein the VH region is derived from the IgHV3-21-1 germline sequence;

SEQ ID No:130, such as the sequence of SEQ ID NO:18 (084), optionally wherein the VH region is derived from the IgHV1-69-04 germline sequence;

SEQ ID NO:133 (169, 123, 161, 124), such as the sequence of SEQ ID NO:4 (169), optionally wherein the VH region is derived from the IgHV1-18-1 germline sequence; or In one embodiment, the antigen-binding region comprises a VH CDR3 region of one of antibodies 123, 161, or 124, as shown in FIG. 1, optionally wherein the VH region is derived from an IgHV1-18-1 germline.

In one embodiment, the bispecific antibody or the first antigen-binding region comprises a VH region selected from the group consisting of a) a VH region comprising the CDR1, CDR2 and CDR3 sequences of SEQ ID NOs:9, 127 and 11, such as the CDR1, CDR2 and CDR3 sequences of SEQ ID NOS: 9, 10 and 11 (050); optionally where the VH region is derived from an IgHV3-23-1 germline;
b) a VH region comprising the CDR1, CDR2 and CDR3 sequences of SEQ ID NOs:128, 129 and 130, such the CDR1, CDR2 and CDR3 sequences of SEQ ID NOs: 16, 17 and 18, respectively (084), optionally where the VH region is derived from an IgHV1-69-04 germline; and
c) a VH region comprising the CDR1, CDR2, and CDR3 sequences of SEQ ID NOs:131, 132, and 133, such as the CDR1, CDR2, and CDR3 sequences of SEQ ID NOs: 2, 3 and 4 (169), respectively, optionally where the VH region is derived from an IgHV1-18-1 germline.

In one embodiment, the bispecific antibody or the first antigen-binding region comprises a VH region selected from the preceding embodiments (a) or (b) and a VL region comprising the CDR1, CDR2, and CDR3 sequences of SEQ ID NO:13, XAS (wherein X is A or V), and SEQ ID No:155, respectively, such as a CDR1 sequence selected from SEQ ID Nos: 13 or 20, a CDR2 which is MS or VAS, and a CDR3 sequence selected from SEQ ID NOs:14 and 21 (050, 084); respectively, optionally where the VL region is derived from an IgKV1-12-01 germline.

In one embodiment, the bispecific antibody or the first antigen-binding region comprises a VH region which is the preceding embodiment (c) and a VL region comprising the CDR1, CDR2, and CDR3 sequences of SEQ ID NO:6, DXS (wherein X=A or T), and SEQ ID NO:156 (169), respectively, optionally wherein the VL region is derived from IgKV3-11-01.

In one embodiment, the bispecific antibody or the first antigen-binding region comprises a VH region comprising the CDR1, CDR2 and CDR3 sequences of SEQ ID NOs:2, 3 and 4, respectively; and, optionally, a VL region comprising the CDR1, CDR2 and CDR3 sequences of SEQ ID NOs:6, DAS, and SEQ ID NO:7, respectively (169).

In one embodiment, the bispecific antibody or the first antigen-binding region comprises a VH region comprising the CDR1, CDR2 and CDR3 sequences of SEQ ID NOs:9, 10 and 11, respectively; and a VL region comprising the CDR1, CDR2 and CDR3 sequences of SEQ ID NOs:13, AAS, and SEQ ID NO:14, respectively (050).

In one embodiment, the bispecific antibody or the first antigen-binding region comprises a VH region comprising the CDR1, CDR2 and CDR3 sequences of SEQ ID NOs:16, 17 and 18, respectively; and a VL region comprising the CDR1, CDR2 and CDR3 sequences of SEQ ID NOs:20, VAS, and SEQ ID NO:21, respectively (084).

In separate embodiments, the bispecific antibody or the first antigen-binding region comprises:

a) a VH region comprising the sequence of SEQ ID NO:1 and, optionally, a VL region comprising the sequence of SEQ ID NO:5 (169);
b) a VH region comprising the sequence of SEQ ID NO:8 and, preferably, a VL region comprising the sequence of SEQ ID NO:12 (050);
c) a VH region comprising the sequence of SEQ ID NO:15 and, preferably, a VL region comprising the sequence of SEQ ID NO:19 (084);
d) a VH region comprising the sequence of SEQ ID NO:77 and, preferably, a VL region comprising the sequence of SEQ ID NO:78 (049);
e) a VH region comprising the sequence of SEQ ID NO:79 and, preferably, a VL region comprising the sequence of SEQ ID NO:80 (051);
f) a VH region comprising the sequence of SEQ ID NO:81 and, preferably, a VL region comprising the sequence of SEQ ID NO:82 (055);
g) a VH region comprising the sequence of SEQ ID NO:83 and, preferably, a VL region comprising the sequence of SEQ ID NO:84 (123);
h) a VH region comprising the sequence of SEQ ID NO:85 and, preferably, a VL region comprising the sequence of SEQ ID NO:86 (161);
i) a VH region comprising the sequence of SEQ ID NO:87 and, preferably, a VL region comprising the sequence of SEQ ID NO:88 (124); and/or
j) a variant of any of said antibodies, wherein said variant preferably has at most 1, 2 or 3 amino-acid modifications, more preferably amino-acid substitutions, such as conservative amino acid substitutions and substitutions where the new amino acid is one at the same position in an aligned sequence in FIG. 1 or 2, particularly at positions indicated by "X" in the corresponding consensus sequence.

Cross-Block Group 2

In one aspect of the antibody of the invention, the bispecific antibody comprises an antigen-binding region which blocks the binding to HER2, e.g. soluble HER2, or binds to the same epitope on HER2 as one or more of the human antibodies of cross-block group 2 described herein.

In one embodiment, the antigen-binding region cross-blocks the binding to soluble HER2 of pertuzumab, when determined as described in Example 14.

In one embodiment, the antigen-binding region blocks the binding to HER2, e.g. soluble HER2, or binds to the same epitope as a reference antibody comprising a VH region comprising the sequence of SEQ ID NO:22 and a VL region comprising the sequence of SEQ ID NO:26 (025).

In one embodiment, the antigen-binding region blocks the binding to HER2, e.g. soluble HER2, or binds to the same epitope as a reference antibody comprising a VH region comprising the sequence of SEQ ID NO:29 and a VL region comprising the sequence of SEQ ID NO:32 (091).

In one embodiment, the antigen-binding region blocks the binding to HER2, e.g. soluble HER2, or binds to the same epitope as a reference antibody comprising a VH region comprising the sequence of SEQ ID NO:35 and a VL region comprising the sequence of SEQ ID NO:39 (129).

In one embodiment, the antigen-binding region blocks the binding to HER2, e.g. soluble HER2, or binds to the same epitope as a reference antibody comprising VH and VL regions selected from the group consisting of:

a) a VH region comprising the sequence of SEQ ID NO:89 and a VL region comprising the sequence of SEQ ID NO:90 (001);
b) a VH region comprising the sequence of SEQ ID NO:91 and a VL region comprising the sequence of SEQ ID NO:92 (143);
c) a VH region comprising the sequence of SEQ ID NO:93 and a VL region comprising the sequence of SEQ ID NO:94 (019);
d) a VH region comprising the sequence of SEQ ID NO:95 and a VL region comprising the sequence of SEQ ID NO:96 (021);
e) a VH region comprising the sequence of SEQ ID NO:97 and a VL region comprising the sequence of SEQ ID NO:98 (027);
f) a VH region comprising the sequence of SEQ ID NO:99 and a VL region comprising the sequence of SEQ ID NO:100 (032)
g) a VH region comprising the sequence of SEQ ID NO:101 and a VL region comprising the sequence of SEQ ID NO:102 (035);
h) a VH region comprising the sequence of SEQ ID NO:103 and a VL region comprising the sequence of SEQ ID NO:104 (036);
i) a VH region comprising the sequence of SEQ ID NO:105 and a VL region comprising the sequence of SEQ ID NO:106 (054); and
j) a VH region comprising the sequence of SEQ ID NO:107 and a VL region comprising the sequence of SEQ ID NO:108 (094).

In another additional or alternative aspect of the bispecific antibody of the invention, the bispecific antibody or the first antigen-binding region comprises a VH CDR3, VH region and/or VL region sequence similar or identical to a sequence of the novel antibodies described herein.

In one embodiment, the bispecific antibody or the first antigen-binding region comprises a VH CDR3 region having a sequence selected from the group consisting of SEQ ID NO:136, such as the sequence of SEQ ID NO:25 (025), optionally wherein the VH region is derived from the IgHV4-34-1 germline sequence;

SEQ ID NO:139, such as the sequence of SEQ ID NO:31 (091), optionally wherein the VH region is derived from the IgHV4-34-01 germline sequence; and SEQ ID NO:142, such as the sequence of SEQ ID NO:38 (129), optionally wherein the VH region is derived from the IgHV3-30-01 germline sequence.

In one embodiment, the bispecific antibody or the first antigen-binding region comprises a VH CDR3 region of one of antibodies 001, 143, 019, 021, 027, 032, 035, 036, 054 or 094 as shown in FIG. 1, optionally wherein the VH region is derived from an IgHV4-34-1 germline.

In one embodiment, the bispecific antibody or the first antigen-binding region comprises a VH region selected from the group consisting of a) a VH region comprising the CDR1, CDR2 and CDR3 sequences of SEQ ID NOs:134, 135 and 136, such as the CDR1, CDR2 and CDR3 sequences of SEQ ID NOS: 23, 24 and 25 (025); optionally where the VH region is derived from an IgHV4-34-1 germline;
b) a VH region comprising the CDR1, CDR2 and CDR3 sequences of SEQ ID NOs:137, 138 and 139, such the CDR1, CDR2 and CDR3 sequences of SEQ ID NOs:

30, 163, and 31, respectively (091), optionally where the VH region is derived from an IgHV4-34-01 germline; and c) a VH region comprising the CDR1, CDR2, and CDR3 sequences of SEQ ID NOs:140, 141 and 142, such as the CDR1, CDR2, and CDR3 sequences of SEQ ID NOs: 36, 37 and 38 (129), respectively, optionally where the VH region is derived from an IgHV3-30-01 germline.

In one embodiment, the bispecific antibody or the first antigen-binding region comprises a VH region selected from the preceding embodiment (a) and a VL region comprising the CDR1, CDR2, and CDR3 sequences of SEQ ID NO:157, MS, and SEQ ID No:164, respectively, such as the CDR1, CDR2, and CDR3 sequences of SEQ ID Nos:27, MS, and SEQ ID NO:28 (025); respectively, optionally where the VL region is derived from an IgKV1D-16-01 germline.

In one embodiment, the bispecific antibody or the first antigen-binding region comprises a VH region selected from the preceding embodiment (b) and a VL region comprising the CDR1, CDR2, and CDR3 sequences of SEQ ID NO:33, $AX_1X_2$ (wherein $X_1$ is A or T, preferably A; and $X_2$ is S or F, preferably S), and SEQ ID No:158, respectively, such as the CDR1, CDR2 and CDR3 sequences of SEQ ID Nos:33, MS, and SEQ ID NO:34 (091); respectively, optionally where the VL region is derived from an IgKV1D-16-01 germline.

In one embodiment, the bispecific antibody or the first antigen-binding region comprises a VH region which is the preceding embodiment (c) and a VL region comprising the CDR1, CDR2, and CDR3 sequences of SEQ ID NO:40, DAS and SEQ ID NO:41 (129), respectively, optionally wherein the VL region is derived from IgKV3-11-01.

In one embodiment, the bispecific antibody or the first antigen-binding region comprises a VH region comprising the CDR1, CDR2 and CDR3 sequences of SEQ ID NOs:23, 24 and 25, respectively; and, optionally, a VL region comprising the CDR1, CDR2 and CDR3 sequences of SEQ ID NOs:27, MS, and SEQ ID NO:28, respectively (025).

In one embodiment, the bispecific antibody comprises a VH region comprising the CDR1, CDR2 and CDR3 sequences of SEQ ID NOs:30, 163 and 31, respectively; and a VL region comprising the CDR1, CDR2 and CDR3 sequences of SEQ ID NOs:33, MS, and SEQ ID NO:34, respectively (091).

In one embodiment, the bispecific antibody or the first antigen-binding region comprises a VH region comprising the CDR1, CDR2 and CDR3 sequences of SEQ ID NOs:36, 37 and 38, respectively; and a VL region comprising the CDR1, CDR2 and CDR3 sequences of SEQ ID NOs:40, DAS, and SEQ ID NO:41, respectively (129).

In separate embodiments, the bispecific antibody or the first antigen-binding region comprises:

a) a VH region comprising the sequence of SEQ ID NO:22 and, optionally, a VL region comprising the sequence of SEQ ID NO:26 (025);

b) a VH region comprising the sequence of SEQ ID NO:29 and, preferably, a VL region comprising the sequence of SEQ ID NO:32 (091);

c) a VH region comprising the sequence of SEQ ID NO:35 and, preferably, a VL region comprising the sequence of SEQ ID NO:39 (129);

d) a VH region comprising the sequence of SEQ ID NO:89 and, preferably, a VL region comprising the sequence of SEQ ID NO:90 (001);

e) a VH region comprising the sequence of SEQ ID NO:91 and, preferably, a VL region comprising the sequence of SEQ ID NO:92 (143);

f) a VH region comprising the sequence of SEQ ID NO:93 and, preferably, a VL region comprising the sequence of SEQ ID NO:94 (019);

g) a VH region comprising the sequence of SEQ ID NO:95 and, preferably, a VL region comprising the sequence of SEQ ID NO:96 (021);

h) a VH region comprising the sequence of SEQ ID NO:97 and, preferably, a VL region comprising the sequence of SEQ ID NO:98 (027);

i) a VH region comprising the sequence of SEQ ID NO:99 and, preferably, a VL region comprising the sequence of SEQ ID NO:100 (032);

j) a VH region comprising the sequence of SEQ ID NO:101 and, preferably, a VL region comprising the sequence of SEQ ID NO:102 (035);

k) a VH region comprising the sequence of SEQ ID NO:103 and, preferably, a VL region comprising the sequence of SEQ ID NO:104 (036);

l) a VH region comprising the sequence of SEQ ID NO:105 and, preferably, a VL region comprising the sequence of SEQ ID NO:106 (054);

m) a VH region comprising the sequence of SEQ ID NO:106 and, preferably, a VL region comprising the sequence of SEQ ID NO:108 (094); and/or n) a variant of any of said antibodies, wherein said variant preferably has at most 1, 2 or 3 amino-acid modifications, more preferably amino-acid substitutions, such as conservative amino acid substitutions and substitutions where the new amino acid is one at the same position in an aligned sequence in FIG. 1 or 2, particularly at positions indicated by "X" in the corresponding consensus sequence.

Cross-Block Group 3

In one aspect of the bispecific antibody of the invention, the bispecific antibody comprises an antigen-binding region which blocks the binding to HER2, e.g. soluble HER2, or binds to the same epitope on HER2 as one or more of the human antibodies of cross-block group 3 described herein.

In one embodiment, the antigen-binding region cross-blocks the binding to soluble HER2 of F5 and/or C1, when determined as described in Example 14.

In one embodiment, the antigen-binding region blocks the binding to HER2, e.g. soluble HER2, or binds to the same epitope as a reference antibody comprising a VH region comprising the sequence of SEQ ID NO:46 and a VL region comprising the sequence of SEQ ID NO:49 (127).

In one embodiment, the antigen-binding region blocks the binding to HER2, e.g. soluble HER2, or binds to the same epitope as a reference antibody comprising a VH region comprising the sequence of SEQ ID NO:49 and a VL region comprising the sequence of SEQ ID NO:53 (159).

In one embodiment, the antigen-binding region blocks the binding to HER2, e.g. soluble HER2, or binds to the same epitope as a reference antibody comprising a VH region comprising the sequence of SEQ ID NO:56 and a VL region comprising the sequence of SEQ ID NO:60 (098).

In one embodiment, the antigen-binding region blocks the binding to HER2, e.g. soluble HER2, or binds to the same epitope as a reference antibody comprising a VH region comprising the sequence of SEQ ID NO:63 and a VL region comprising the sequence of SEQ ID NO:67 (153).

In one embodiment, the antigen-binding region blocks the binding to HER2, e.g. soluble HER2, or binds to the same epitope as a reference antibody comprising a VH region comprising the sequence of SEQ ID NO:70 and a VL region comprising the sequence of SEQ ID NO:74 (132).

In one embodiment, the antigen-binding region blocks the binding to HER2, e.g. soluble HER2, or binds to the same epitope as a reference antibody comprising VH and VL regions selected from the group consisting of:

a) a VH region comprising the sequence of SEQ ID NO:109 and a VL region comprising the sequence of SEQ ID NO:110 (105);
b) a VH region comprising the sequence of SEQ ID NO:111 and a VL region comprising the sequence of SEQ ID NO:112 (100);
c) a VH region comprising the sequence of SEQ ID NO:113 and a VL region comprising the sequence of SEQ ID NO:114 (125);
d) a VH region comprising the sequence of SEQ ID NO:115 and a VL region comprising the sequence of SEQ ID NO:116 (162);
e) a VH region comprising the sequence of SEQ ID NO:117 and a VL region comprising the sequence of SEQ ID NO:118 (033);
f) a VH region comprising the sequence of SEQ ID NO:119 and a VL region comprising the sequence of SEQ ID NO:120 (160)
g) a VH region comprising the sequence of SEQ ID NO:121 and a VL region comprising the sequence of SEQ ID NO:122 (166);
h) a VH region comprising the sequence of SEQ ID NO:123 and a VL region comprising the sequence of SEQ ID NO:124 (152); and
i) a VH region comprising the sequence of SEQ ID NO:125 and a VL region comprising the sequence of SEQ ID NO:126 (167).

In another additional or alternative aspect of the bispecific antibody of the invention, the bispecific antibody or the first antigen-binding region comprises a VH CDR3, VH region and/or VL region sequence similar or identical to a sequence of the novel antibodies described herein.

In one embodiment, the bispecific antibody or the first antigen-binding region comprises a VH CDR3 region having a sequence selected from the group consisting of SEQ ID NO:148, such as the sequence of SEQ ID NO:48 (127), optionally wherein the VH region is derived from the IgHV5-51-01 germline sequence;

SEQ ID NO:52 (159), optionally wherein the VH region is derived from the IgHV5-51-01 germline sequence;

SEQ ID NO:145, such as the sequence of SEQ ID NO:59 (098), optionally wherein the VH region is derived from the IgHV3-23-01 germline sequence;

SEQ ID NO:154, such as the sequence of SEQ ID NO:66 (153), optionally wherein the VH region is derived from the IgHV3-30-03-01 germline sequence; and SEQ ID NO:151, such as the sequence of SEQ ID NO:73 (132), optionally wherein the VH region is derived from the IgHV1-18-01 germline sequence.

In one embodiment, the bispecific antibody or the first antigen-binding region comprises a VH CDR3 region of one of antibodies 105, 100, 125 or 162 as shown in FIG. 1, optionally wherein the VH region is derived from an IgHV3-23-1 germline.

In one embodiment, the bispecific antibody or the first antigen-binding region comprises a VH CDR3 region of one of antibodies 033, 160, 166, 152 or 167 as shown in FIG. 1, optionally wherein the VH region is derived from an IgHV3-30-3-01 germline.

In one embodiment, the bispecific antibody or the first antigen-binding region comprises a VH region selected from the group consisting of a) a VH region comprising the CDR1, CDR2 and CDR3 sequences of SEQ ID NOs:146, 147 and 148, such as the CDR1, CDR2 and CDR3 sequences of SEQ ID NOS: 43, 44 and 45 (127); optionally where the VH region is derived from an IgHV5-51-01 germline;
b) a VH region comprising the CDR1, CDR2 and CDR3 sequences of SEQ ID NOs:149, 51 and 52, such as the CDR1, CDR2 and CDR3 sequences of SEQ ID NOs: 50, 51 and 52, respectively (159), optionally where the VH region is derived from an IgHV5-51-01 germline;
c) a VH region comprising the CDR1, CDR2, and CDR3 sequences of SEQ ID NOs:143, 144 and 145, such as the CDR1, CDR2, and CDR3 sequences of SEQ ID NOs: 57, 58 and 59 (098), respectively, optionally where the VH region is derived from an IgHV3-23-01 germline;
d) a VH region comprising the CDR1, CDR2 and CDR3 sequences of SEQ ID NOs:152, 153 and 154, such as the CDR1, CDR2 and CDR3 sequences of SEQ ID NOs:64, 65 and 66, respectively (153), optionally where the VH region is derived from an IgHV3-30-03-01 germline; and
e) a VH region comprising the CDR1, CDR2, and CDR3 sequences of SEQ ID NOs:71, 150 and 151, such as the CDR1, CDR2, and CDR3 sequences of SEQ ID NOs: 71, 72 and 73 (132), respectively, optionally where the VH region is derived from an IgHV1-18-01 germline.

In one embodiment, the bispecific antibody or the first antigen-binding region comprises a VH region selected from the preceding embodiment (a) and a VL region comprising the CDR1, CDR2, and CDR3 sequences of SEQ ID NO:47, MS and SEQ ID NO:48, respectively (127); respectively, optionally where the VL region is derived from an IgKV1D-8-01 germline.

In one embodiment, the bispecific antibody or the first antigen-binding region comprises a VH region selected from the preceding embodiment (b) and a VL region comprising the CDR1, CDR2, and CDR3 sequences of SEQ ID NO:54, MS, and SEQ ID No:55 (159); respectively, optionally where the VL region is derived from an IgKV1D-16-01 germline.

In one embodiment, the bispecific antibody or the first antigen-binding region comprises a VH region which is the preceding embodiment (c) and a VL region comprising the CDR1, CDR2, and CDR3 sequences of SEQ ID NO:159, MS and SEQ ID NO:160, respectively, such as the VL CDR1, CDR2 and CDR3 sequences of SEQ ID NOS: 61, MS and SEQ ID NO:62 (098), optionally wherein the VL region is derived from IgKV1D-16-01.

In one embodiment, the bispecific antibody or the first antigen-binding region comprises a VH region which is the preceding embodiment (d) and a VL region comprising the CDR1, CDR2, and CDR3 sequences of SEQ ID NO:161, XAS (wherein X=D or A, preferably D), and SEQ ID NO:162 (153), respectively, such as the VL CDR sequences of SEQ ID NO:68, DAS, and 69, optionally wherein the VL region is derived from IgKV1D-16-01.

In one embodiment, the bispecific antibody or the first antigen-binding region comprises a VH region which is the preceding embodiment (e) and a VL region comprising the CDR1, CDR2, and CDR3 sequences of SEQ ID NO:75, DAS and SEQ ID NO:76 (132), respectively, optionally wherein the VL region is derived from IgKV3-11-01.

In one embodiment, the bispecific antibody or the first antigen-binding region comprises a VH region comprising the CDR1, CDR2 and CDR3 sequences of SEQ ID NOs:43, 44 and 45, respectively; and a VL region comprising the CDR1, CDR2 and CDR3 sequences of SEQ ID NOs:47, MS, and SEQ ID NO:48, respectively (127).

In one embodiment, the bispecific antibody or the first antigen-binding region comprises a VH region comprising the CDR1, CDR2 and CDR3 sequences of SEQ ID NOs:50, 51 and 52, respectively; and a VL region comprising the CDR1, CDR2 and CDR3 sequences of SEQ ID NOs:54, MS, and SEQ ID NO:55, respectively (159).

In one embodiment, the bispecific antibody or the first antigen-binding region comprises a VH region comprising the CDR1, CDR2 and CDR3 sequences of SEQ ID NOs:57, 58 and 59, respectively; and a VL region comprising the CDR1, CDR2 and CDR3 sequences of SEQ ID NOs:60, MS, and SEQ ID NO:61, respectively (098).

In one embodiment, the bispecific antibody or the first antigen-binding region comprises a VH region comprising the CDR1, CDR2 and CDR3 sequences of SEQ ID NOs:64, 65 and 66, respectively; and, optionally, a VL region comprising the CDR1, CDR2 and CDR3 sequences of SEQ ID NOs:68, DAS, and SEQ ID NO:69, respectively (153).

In one embodiment, the bispecific antibody or the first antigen-binding region comprises a VH region comprising the CDR1, CDR2 and CDR3 sequences of SEQ ID NOs:71, 72 and 73, respectively; and a VL region comprising the CDR1, CDR2 and CDR3 sequences of SEQ ID NOs:75, DAS, and SEQ ID NO:76, respectively (132).

In separate embodiments, the bispecific antibody or the first antigen-binding region comprises:

a) a VH region comprising the sequence of SEQ ID NO:46 and, preferably, a VL region comprising the sequence of SEQ ID NO:49 (127);
b) a VH region comprising the sequence of SEQ ID NO:49 and, preferably, a VL region comprising the sequence of SEQ ID NO:53 (159);
c) a VH region comprising the sequence of SEQ ID NO:56 and, preferably, a VL region comprising the sequence of SEQ ID NO:60 (098);
d) a VH region comprising the sequence of SEQ ID NO:63 an, optionally, a VL region comprising the sequence of SEQ ID NO:67 (153);
e) a VH region comprising the sequence of SEQ ID NO:70 and, preferably, a VL region comprising the sequence of SEQ ID NO:74 (132);
f) a VH region comprising the sequence of SEQ ID NO:109 and, preferably, a VL region comprising the sequence of SEQ ID NO:110 (105);
g) a VH region comprising the sequence of SEQ ID NO:111 and, preferably, a VL region comprising the sequence of SEQ ID NO:112 (100);
h) a VH region comprising the sequence of SEQ ID NO:113 and, preferably, a VL region comprising the sequence of SEQ ID NO:114 (125);
i) a VH region comprising the sequence of SEQ ID NO:115 and, preferably, a VL region comprising the sequence of SEQ ID NO:116 (162);
j) a VH region comprising the sequence of SEQ ID NO:117 and, preferably, a VL region comprising the sequence of SEQ ID NO:118 (033);
k) a VH region comprising the sequence of SEQ ID NO:119 and, preferably, a VL region comprising the sequence of SEQ ID NO:120 (160)
l) a VH region comprising the sequence of SEQ ID NO:121 and, preferably, a VL region comprising the sequence of SEQ ID NO:122 (166);
m) a VH region comprising the sequence of SEQ ID NO:123 and, preferably, a VL region comprising the sequence of SEQ ID NO:124 (152);
o) a VH region comprising the sequence of SEQ ID NO:125 and, preferably, a VL region comprising the sequence of SEQ ID NO:126 (167); and/or
p) a variant of any of said antibodies, wherein said variant preferably has at most 1, 2 or 3 amino-acid modifications, more preferably amino-acid substitutions, such as conservative amino acid substitutions and substitutions where the new amino acid is one at the same position in an aligned sequence in FIG. 1 or 2, particularly at positions indicated by "X" in the corresponding consensus sequence.

Cross-Block Group 4

In one aspect of the bispecific antibody of the invention, the bispecific antibody comprises an antigen-binding region which binds HER2 but which does not block the binding to soluble HER2 of a second antibody, optionally in immobilized form, comprising the VH and VL sequences of any of trastuzumab, pertuzumab, F5, and C1, when determined as described in Example 14.

In an additional or alternative aspect of the antibody of the invention, the antigen-binding region blocks or cross-blocks the binding to HER2 of one or more of the human antibodies of cross-block group 4.

In one embodiment, the antigen-binding region blocks the binding to HER2 of a reference antibody, optionally immobilized, wherein the reference antibody comprises a VH region comprising the sequence of SEQ ID NO:165 and a VL region comprising the sequence of SEQ ID NO:169 (005), preferably wherein the antibody is fully blocking when determined as described in Example 14.

In one embodiment, the antigen-binding region blocks the binding to HER2 of a reference antibody, optionally immobilized, wherein the reference antibody comprises a VH region comprising the sequence of SEQ ID NO:172 and a VL region comprising the sequence of SEQ ID NO:176 (006), preferably wherein the antibody is fully-blocking when determined as described in Example 14.

In one embodiment, the antigen-binding region blocks the binding to HER2 of a reference antibody, optionally immobilized, wherein the reference antibody comprises a VH region comprising the sequence of SEQ ID NO:179 and a VL region comprising the sequence of SEQ ID NO:183 (059), preferably wherein the antibody is fully-blocking when determined as described in Example 14.

In one embodiment, the antigen-binding region blocks the binding to HER2 of a reference antibody, optionally immobilized, wherein the reference antibody comprises a VH region comprising the sequence of SEQ ID NO:186 and a VL region comprising the sequence of SEQ ID NO:190 (060), preferably wherein the antibody is fully-blocking when determined as described in Example 14.

In one embodiment, the antigen-binding region blocks the binding to HER2 of a reference antibody, optionally immobilized, wherein the reference antibody comprises a VH region comprising the sequence of SEQ ID NO:193 and a VL region comprising the sequence of SEQ ID NO:197 (106), preferably wherein the antibody is fully-blocking when determined as described in Example 14.

In one embodiment, the antigen-binding region blocks the binding to HER2 of a reference antibody, optionally immobilized, wherein the reference antibody comprises a VH region comprising the sequence of SEQ ID NO:200 and a VL region comprising the sequence of SEQ ID NO:204 (111), preferably wherein the antibody is fully-blocking when determined as described in Example 14.

In separate and specific embodiments, the antigen-binding region blocks the binding of two, three, four, five, or six reference antibodies of the preceding embodiment, such as, e.g., antibodies 005 and 111, antibodies 005 and 006; antibodies 059 and 106; antibodies 006 and 059; antibodies 059, 106, 005 and 060; antibodies 006, 59, 060, and 111; or antibodies 059, 106, 005, 060, 111 and 006.

In one embodiment, the antibody, when immobilized, competes for binding to soluble HER2 with all antibodies defined in the preceding embodiment for 25% or more, preferably 50% or more, when determined as described in Example 14.

In one aspect of the antibody of the invention, the antibody binds the same epitope on HER2 as one or more of the novel human antibodies described herein.

In one embodiment, the antigen-binding region binds the same epitope as an antibody comprising a VH region comprising the sequence of SEQ ID NO:165 and, optionally, a VL region comprising the sequence of SEQ ID NO:169 (005).

In one embodiment, the antigen-binding region binds the same epitope as an antibody comprising a VH region comprising the sequence of SEQ ID NO:172 and a VL region comprising the sequence of SEQ ID NO:176 (006).

In one embodiment, the antigen-binding region binds the same epitope as an antibody comprising a VH region comprising the sequence of SEQ ID NO:179 and a VL region comprising the sequence of SEQ ID NO:183 (059).

In one embodiment, the antigen-binding region binds the same epitope as an antibody comprising a VH region comprising the sequence of SEQ ID NO:186 and a VL region comprising the sequence of SEQ ID NO:190 (060).

In one embodiment, the antigen-binding region binds the same epitope as an antibody comprising a VH region comprising the sequence of SEQ ID NO:193 and a VL region comprising the sequence of SEQ ID NO:197 (106).

In one embodiment, the antigen-binding region binds the same epitope as an antibody comprising a VH region comprising the sequence of SEQ ID NO:200 and a VL region comprising the sequence of SEQ ID NO:204 (111).

In one embodiment, the antigen-binding region binds to the same epitope as at least one antibody selected from the group consisting of:

a) an antibody comprising a VH region comprising the sequence of SEQ ID NO:207 and a VL region comprising the sequence of SEQ ID NO:208 (041)

b) an antibody comprising a VH region comprising the sequence of SEQ ID NO:209 and a VL region comprising the sequence of SEQ ID NO:210 (150), and c) an antibody comprising a VH region comprising the sequence of SEQ ID NO:211 and a VL region comprising the sequence of SEQ ID NO:212 (067);

d) an antibody comprising a VH region comprising the sequence of SEQ ID NO:213 and a VL region comprising the sequence of SEQ ID NO:214 (072);

e) an antibody comprising a VH region comprising the sequence of SEQ ID NO:215 and a VL region comprising the sequence of SEQ ID NO:216 (163);

f) an antibody comprising a VH region comprising the sequence of SEQ ID NO:217 and a VL region comprising the sequence of SEQ ID NO:218 (093);

g) an antibody comprising a VH region comprising the sequence of SEQ ID NO:219 and a VL region comprising the sequence of SEQ ID NO:220 (044).

In another additional or alternative aspect of the bispecific antibody of the invention, the bispecific antibody or the first antigen-binding region comprises a VH CDR3, VH region and/or VL region sequence similar or identical to a sequence of the HER2 antibodies described herein.

In one embodiment, the bispecific antibody or the first antigen-binding region comprises a VH CDR3 region having an amino acid sequence selected from the group consisting of SEQ ID No:223, such as the sequence of SEQ ID No:168, 189, 196 (005, 060, 106), optionally wherein the VH region is derived from the IgHV5-51-1 germline;

SEQ ID No:226, such as the sequence of SEQ ID NO:175 (006), optionally wherein the VH region is derived from the IgHV3-23-1 germline sequence;

SEQ ID NO:229, such as the sequence of SEQ ID NO:182 (059), optionally wherein the VH region is derived from the IgHV1-18-1 germline sequence; or SEQ ID NO:231, such as the sequence of SEQ ID NO:203 (111), optionally wherein the VH region is derived from the IgHV1-69-4 germline sequence.

In one embodiment, the bispecific antibody or the first antigen-binding region comprises a VH CDR3 region comprising the amino acid sequence of SEQ ID NO: 223, wherein X1=Q, H, or L; X2=R, A, T, or K; X3=G; X4=D; X5=R or none; X6=G or none; X7=Y or F; X8=Y or D; X9=Y, F, or H; X10=Y, D, S, F, or N; X11=M or L; and X12=V or I; preferably, wherein X1=Q, X2=R or A; X5=X6=none; X7=Y or F; X8=Y; X9=F; X10=Y; and X12=V. In a particular embodiment the antibody comprises a VH CDR3 region comprising the amino acid sequence of SEQ ID NO: 223, wherein X1=Q, X2=R or A; X3=G; X4=D, X5=X6=none; X7=Y or F; X8=Y; X9=F; X10=Y; and X12=V.

In one embodiment the antibody or the first antigen-binding region comprises a VH CDR3 region comprising the amino acid sequence of SEQ ID NO:223, wherein X1=Q, X2=K; X3=G; X4=D, X5=X6=none; X7=F; X8=Y; X9=X10=F; X11=L; and X12=V; or wherein X1=Q, X2=A; X3=G; X4=D, X5=X6=none; X7=X8=Y; X9=Y; X10=N; X11=M; and X12=V; or wherein X1=Q, X2=K; X3=G; X4=D, X5=X6=none; X7=X8=Y; X9=H; X10=Y; X11=L; and X12=V; or wherein X1=Q, X2=K; X3=G; X4=D, X5=X6=none; X7=Y; X8=Y; X9=F; X10=N; X11=L; and X12=V; or wherein X1=Q, X2=R; X3=G; X4=D, X5=X6=none; X7=Y; X8=Y; X9=F; X10=N; X11=L; and X12=V; or wherein X1=Q, X2=R; X3=G; X4=D, X5=X6=none; X7=Y; X8=Y; X9=X10=F; X11=L; and X12=I; or wherein X1=Q, X2=A; X3=G; X4=D, X5=X6=none; X7=X8=Y; X9=Y; X10=N; X11=M; and X12=V.

In one embodiment, the bispecific antibody or the first antigen-binding region comprises a VH CDR3 region of one of antibodies 041, 150, 067, 072, 163, or 093, as shown in FIG. 1, optionally wherein the VH region is derived from an IgHV5-51-1 germline.

In one embodiment, the bispecific antibody or the first antigen-binding region comprises a VH region selected from the group consisting of a) a VH region comprising the CDR1, CDR2 and CDR3 sequences of SEQ ID NOs:221, 222 and 223, such as
   a. a CDR1 sequence selected from SEQ ID NOs:166, 187, and 194; a CDR2 sequence selected from 167, 188, and 195; and a CDR3 sequence selected from 168, 189, and 196 (005, 060, 106), b. the CDR1, CDR2, and CDR3 sequences of SEQ ID NOs:166, 167 and 168, respectively (005), c. the CDR1, CDR2, and CDR3 sequences of SEQ ID NOs:187, 188 and 189, respectively (060), d. the CDR1, CDR2, and CDR3 sequences of SEQ ID NOs:196, 197 and 198, respectively (106), optionally where the VH region is derived from an IgHV5-51-1 germline;

b) a VH region comprising the CDR1, CDR2 and CDR3 sequences of SEQ ID NOs:224, 225 and 226, such the CDR1, CDR2 and CDR3 sequences of SEQ ID NOs: 173, 174, and 175, respectively (006), optionally where the VH region is derived from an IgHV3-23-1 germline; and c) a VH region comprising the CDR1, CDR2, and CDR3 sequences of SEQ ID NOs:227, 228, and 229, such as the CDR1, CDR2, and CDR3 sequences of SEQ ID NOs: 180, 181 and 182 (059), respectively, optionally where the VH region is derived from an IgHV1-18-1 germline; and d) a VH region comprising the CDR1, CDR2, and CDR3 sequences of SEQ ID NOs:230, 202 and 231, such as the CDR1, CDR2, and CDR3 sequences of SEQ ID NOs: 201, 202 and 203 (111), respectively, optionally where the VH region is derived from an IgHV1-69-4 germline.

In one embodiment, the bispecific antibody or the first antigen-binding region comprises a VH region selected from the preceding embodiments (a), (c) or (d) and a VL region comprising the CDR1, CDR2, and CDR3 sequences of SEQ ID NO:232, GAS, and SEQ ID No:233, respectively, such as a CDR1 sequence selected from SEQ ID Nos: 170, 184, 191, 198 and 205, a CDR2 which is GAS, and a CDR3 sequence selected from 171, 85, 192, 199 and 206 (005, 059, 060, 106, 111); respectively, optionally where the VL region is derived from an IgKV3-20-01 germline.

In one embodiment, the bispecific antibody or the first antigen-binding region comprises a VH region which is the preceding embodiment (b) and a VL region comprising the CDR1, CDR2, and CDR3 sequences of SEQ ID NO:177, DAS, and SEQ ID NO:178 (006), respectively, optionally where the VL region is derived from IgKV3-11-01.

In one embodiment, the bispecific antibody or the first antigen-binding region comprises a VH region comprising the CDR1, CDR2 and CDR3 sequences of SEQ ID NOs: 166, 167 and 168, respectively; and, optionally, a VL region comprising the CDR1, CDR2 and CDR3 sequences of SEQ ID NOs:170, GAS, and SEQ ID NO:171, respectively (005).

In one embodiment, the bispecific antibody or the first antigen-binding region comprises a VH region comprising the CDR1, CDR2 and CDR3 sequences of SEQ ID NOs: 173, 174 and 175, respectively; and a VL region comprising the CDR1, CDR2 and CDR3 sequences of SEQ ID NOs: 177, DAS, and SEQ ID NO:178, respectively (006).

In one embodiment, the bispecific antibody or the first antigen-binding region comprises a VH region comprising the CDR1, CDR2 and CDR3 sequences of SEQ ID NOs: 180, 181 and 182, respectively; and a VL region comprising the CDR1, CDR2 and CDR3 sequences of SEQ ID NOs: 184, GAS, and SEQ ID NO:185, respectively (059).

In one embodiment, the bispecific antibody or the first antigen-binding region comprises a VH region comprising the CDR1, CDR2 and CDR3 sequences of SEQ ID NOs: 187, 188 and 189, respectively; and a VL region comprising the CDR1, CDR2 and CDR3 sequences of SEQ ID NOs: 191, GAS, and SEQ ID NO:192, respectively (060).

In one embodiment, the bispecific antibody or the first antigen-binding region comprises a VH region comprising the CDR1, CDR2 and CDR3 sequences of SEQ ID NOs: 194, 195 and 196, respectively; and a VL region comprising the CDR1, CDR2 and CDR3 sequences of SEQ ID NOs: 198, GAS, and SEQ ID NO:199, respectively (106).

In one embodiment, the bispecific antibody or the first antigen-binding region comprises a VH region comprising the CDR1, CDR2 and CDR3 sequences of SEQ ID NOs: 201, 202 and 203, respectively; and a VL region comprising the CDR1, CDR2 and CDR3 sequences of SEQ ID NOs: 205, GAS, and SEQ ID NO:206, respectively (111).

In one embodiment, the bispecific antibody or the first antigen-binding region comprises a VH region comprising the CDR1 sequence of SEQ ID NO:221, wherein X1=S; X2=T and X3=S; the CDR2 sequence of SEQ ID NO:226, wherein X1=Y and X2=H and the CDR3 sequence of SEQ ID NO:227, wherein X1=Q, X2=K; X3=G; X4=D, X5=X6=none; X7=F; X8=Y; X9=X10=F; X11=L; and X12=V; and a VL region comprising the CDR1 sequence of SEQ ID NO:232, wherein X1=X2=S; the CDR2 sequence GAS; and the CDR3 sequence of SEQ ID NO: 233, wherein X1=Q, X2=S, X3=X4=none and X5=L (041).

In one embodiment, the bispecific antibody or the first antigen-binding region comprises a VH region comprising the CDR1 sequence of SEQ ID NO:221, wherein X1=S; X2=T and X3=S; the CDR2 sequence of SEQ ID NO:222, wherein X1=Y and X2=H, and the CDR3 sequence of SEQ ID NO:223, wherein X1=Q, X2=A; X3=G; X4=D, X5=X6=none; X7=X8=Y; X9=Y; X10=N; X11=M; and X12=V; and a VL region comprising the CDR1 sequence of SEQ ID NO:232, wherein X1=X2=S; the CDR2 sequence GAS; and the CDR3 sequence of SEQ ID NO: 233, wherein X1=Q, X2=S, X3=X4=none and X5=L (150).

In one embodiment, the bispecific antibody or the first antigen-binding region comprises a VH region comprising the CDR1 sequence of SEQ ID NO:221, wherein X1=S; X2=T and X3=S; the CDR2 sequence of SEQ ID NO:222, wherein X1=Y and X2=D, and the CDR3 sequence of SEQ ID NO:223, X1=Q, X2=K; X3=G; X4=D, X5=X6=none; X7=X8=Y; X9=H; X10=Y; X11=L; and X12=V; and a VL region comprising the CDR1 sequence of SEQ ID NO:232, wherein X1=X2=S; the CDR2 sequence GAS; and the CDR3 sequence of SEQ ID NO: 233, wherein X1=Q, X2=S, X3=P, X4=R and X5=L (067).

In one embodiment, the bispecific antibody or the first antigen-binding region comprises a VH region comprising the CDR1 sequence of SEQ ID NO:221, wherein X1=S; X2=T and X3=S; the CDR2 sequence of SEQ ID NO:222, wherein X1=Y and X2=D, and the CDR3 sequence of SEQ ID NO:223, wherein X1=Q, X2=K; X3=G; X4=D, X5=X6=none; X7=Y; X8=Y; X9=F; X10=N; X11=L; and X12=V; and a VL region comprising the CDR1 sequence of SEQ ID NO:232, wherein X1=X2=S; the CDR2 sequence GAS; and the CDR3 sequence of SEQ ID NO: 233, wherein X1=Q, X2=S, X3=P, X4=R and X5=L (072).

In one embodiment, the bispecific antibody or the first antigen-binding region comprises a VH region comprising the CDR1 sequence of SEQ ID NO:221, wherein X1=R; X2=I and X3=S; the CDR2 sequence of SEQ ID NO:222, wherein X1=Y and X2=D, and the CDR3 sequence of SEQ ID NO:223, wherein X1=Q, X2=R; X3=G; X4=D, X5=X6=none; X7=Y; X8=Y; X9=F; X10=N; X11=L; and X12=V; and a VL region comprising the CDR1 sequence of SEQ ID NO:232, wherein X1=X2=S; the CDR2 sequence GAS; and the CDR3 sequence of SEQ ID NO: 233, wherein X1=Q, X2=S, X3=X4=none and X5=L (163).

In one embodiment, the bispecific antibody or the first antigen-binding region comprises a VH region comprising the CDR1 sequence of SEQ ID NO:221, wherein X1=S; X2=T and X3=S; the CDR2 sequence of SEQ ID NO:222, wherein X1=Y and X2=D, and the CDR3 sequence of SEQ ID NO:223, wherein X1=Q, X2=R; X3=G; X4=D, X5=X6=none; X7=Y; X8=Y; X9=X10=F; X11=L; and X12=I; and a VL region comprising the CDR1 sequence of SEQ ID NO:232, wherein X1=X2=S; the CDR2 sequence GAS; and the CDR3 sequence of SEQ ID NO: 233, wherein X1=Q, X2=S, X3=X4=none and X5=L (093).

In one embodiment, the bispecific antibody or the first antigen-binding region comprises a VH region comprising the CDR1 sequence of SEQ ID NO:221, wherein X1=R; X2=S and X3=S; the CDR2 sequence of SEQ ID NO:222, wherein X1=F and X2=D, and the CDR3 sequence of SEQ ID NO:223, wherein X1=Q, X2=A; X3=G; X4=D, X5=X6=none; X7=X8=Y; X9=Y; X10=N; X11=M; and X12=V; and a VL region comprising the CDR1 sequence of SEQ ID NO:232, wherein X1=X2=S; the CDR2 sequence GAS; and the CDR3 sequence of SEQ ID NO: 233, wherein X1=Q, X2=S, X3=X4=none and X5=L (044).

In separate embodiments, the bispecific antibody or the first antigen-binding region comprises:

a) a VH region comprising the sequence of SEQ ID NO:165 and, optionally, a VL region comprising the sequence of SEQ ID NO:169 (005)
b) a VH region comprising the sequence of SEQ ID NO:172 and, preferably, a VL region comprising the sequence of SEQ ID NO:176 (006)
c) a VH region comprising the sequence of SEQ ID NO:179 and, preferably, a VL region comprising the sequence of SEQ ID NO:183 (059)
d) a VH region comprising the sequence of SEQ ID NO:186 and, preferably, a VL region comprising the sequence of SEQ ID NO:190 (060)
e) a VH region comprising the sequence of SEQ ID NO:193 and, preferably, a VL region comprising the sequence of SEQ ID NO:197 (106)
f) a VH region comprising the sequence of SEQ ID NO:200 and, preferably, a VL region comprising the sequence of SEQ ID NO:204 (111)
g) a VH region comprising the sequence of SEQ ID NO:297 and, preferably, a VL region comprising the sequence of SEQ ID NO:208 (041)
h) a VH region comprising the sequence of SEQ ID NO:209 and, preferably, a VL region comprising the sequence of SEQ ID NO:210 (150),
i) a VH region comprising the sequence of SEQ ID NO:211 and, preferably, a VL region comprising the sequence of SEQ ID NO:212 (067),
j) a VH region comprising the sequence of SEQ ID NO:213 and, preferably, a VL region comprising the sequence of SEQ ID NO:214 (072),
k) a VH region comprising the sequence of SEQ ID NO:215 and, preferably, a VL region comprising the sequence of SEQ ID NO:216 (163),
l) a VH region comprising the sequence of SEQ ID NO:217 and, preferably, a VL region comprising the sequence of SEQ ID NO:218 (093),
m) a VH region comprising the sequence of SEQ ID NO:219 and, preferably, a VL region comprising the sequence of SEQ ID NO:220 (044), and/or
n) a variant of any of said antibodies, wherein said variant preferably has at most 1, 2 or 3 amino-acid modifications, more preferably amino-acid substitutions, such as conservative amino acid substitutions and substitutions where the new amino acid is one at the same position in an aligned sequence in FIG. 1 or 2, particularly at positions indicated by "X" in the corresponding consensus sequence.

Functional Properties of Antigen-Binding Regions or HERZ Antibodies of Cross-Block Groups 1, 2, 3, and 4

In another aspect of the antibody of the invention, the bispecific antibody comprises an antigen-binding region from a HER2 antibody which binds to the same HER2 epitope as one or more of the novel Group 1, 2, 3 or 4 antibodies described herein, preferably when determined as described in Example 14; and is further characterized by one or more properties determined as described in Examples 12, 13, 15, 16, 17, 18 and 19.

Thus the first antigen-binding region of the bispecific antibody of the present invention may be same as one of the following HER2 antibodies. The first HER2 antibody of the present invention may have one or more of the following characteristics.

In one embodiment, the HER2 antibody has a lower $EC_{50}$ value (half maximal effective concentration) than trastuzumab in binding to A431 cells, preferably an ECK value lower than 0.80 μg/ml, 0.50 μg/ml, or 0.30 μg/ml, when determined as described in Example 12, and preferably binds the same epitope as at least one reference antibody comprising the VH and VL regions selected from the group consisting of a) a VH region comprising the sequence of SEQ ID NO:1 and a VL region comprising the sequence of SEQ ID NO:5 (169);
b) a VH region comprising the sequence of SEQ ID NO:15 and a VL region comprising the sequence of SEQ ID NO:19 (084);
c) a VH region comprising the sequence of SEQ ID NO:22 and a VL region comprising the sequence of SEQ ID NO:26 (025);
d) a VH region comprising the sequence of SEQ ID NO:29 and a VL region comprising the sequence of SEQ ID NO:32 (091);
e) a VH region comprising the sequence of SEQ ID NO:46 and a VL region comprising the sequence of SEQ ID NO:49 (127);
f) a VH region comprising the sequence of SEQ ID NO:49 and a VL region comprising the sequence of SEQ ID NO:53 (159);
g) a VH region comprising the sequence of SEQ ID NO:56 and a VL region comprising the sequence of SEQ ID NO:60 (098);
h) a VH region comprising the sequence of SEQ ID NO:63 and a VL region comprising the sequence of SEQ ID NO:67 (153);
i) a VH region comprising the sequence of SEQ ID NO:70 and a VL region comprising the sequence of SEQ ID NO:74 (132)
j) a VH region comprising the sequence of SEQ ID NO:1 and a VL region comprising the sequence of SEQ ID NO:5 (005);
k) a VH region comprising the sequence of SEQ ID NO:8 and a VL region comprising the sequence of SEQ ID NO:11 (006); and
l) a VH region comprising the sequence of SEQ ID NO:15 and a VL region comprising the sequence of SEQ ID NO:19 (059).

In an additional or alternative embodiment, the HER2 antibody or the first antigen-binding region specifically binds HER2-positive Rhesus monkey epithelial cells, when determined as described in Example 13, and preferably binds the same epitope as at least one reference antibody comprising the VH and VL regions selected from the group consisting of the VH and VL regions of any of antibodies 169, 050, 084, 025, 091, 129, 127, 159, 098, 153 132, 005, 006, 059, 060, 106 and 111.

In an additional or alternative embodiment, the anti-HER2 antibody or the first antigen-binding region efficiently induces ADCC (antibody-dependent cell-mediated cytotoxicity), preferably achieving a specific $^{51}$Cr-release of at least 30%, more preferably at least 40%, when determined as described in Example 15, and preferably binds the same epitope as at least one reference antibody comprising the VH and VL regions selected from the group consisting of:

a) a VH region comprising the sequence of SEQ ID NO:1 and a VL region comprising the sequence of SEQ ID NO:5 (169);
b) a VH region comprising the sequence of SEQ ID NO:8 and a VL region comprising the sequence of SEQ ID NO:12 (050);
c) a VH region comprising the sequence of SEQ ID NO:15 and a VL region comprising the sequence of SEQ ID NO:19 (084);
d) a VH region comprising the sequence of SEQ ID NO:22 and a VL region comprising the sequence of SEQ ID NO:26 (025);
e) a VH region comprising the sequence of SEQ ID NO:29 and a VL region comprising the sequence of SEQ ID NO:32 (091);
f) a VH region comprising the sequence of SEQ ID NO:35 and a VL region comprising the sequence of SEQ ID NO:39 (129); and
g) a VH region comprising the sequence of SEQ ID NO:63 an, preferably, a VL region comprising the sequence of SEQ ID NO:67 (153).

In an additional or alternative embodiment, the anti-HER2 antibody or the first antigen-binding region specifically binds HER2-expressing AU565 cells but promotes ligand-independent proliferation of the cells less than any of F5 and C1 when determined as described in Example 16, and preferably binds the same epitope as at least one reference antibody comprising the VH and VL regions selected from the group consisting of a) a VH region comprising the sequence of SEQ ID NO:1 and a VL region comprising the sequence of SEQ ID NO:5 (169);
b) a VH region comprising the sequence of SEQ ID NO:8 and a VL region comprising the sequence of SEQ ID NO:12 (050);
c) a VH region comprising the sequence of SEQ ID NO:15 and a VL region comprising the sequence of SEQ ID NO:19 (084);
d) a VH region comprising the sequence of SEQ ID NO:22 and a VL region comprising the sequence of SEQ ID NO:26 (025);
e) a VH region comprising the sequence of SEQ ID NO:29 and a VL region comprising the sequence of SEQ ID NO:32 (091);
f) a VH region comprising the sequence of SEQ ID NO:35 and a VL region comprising the sequence of SEQ ID NO:39 (129);
g) a VH region comprising the sequence of SEQ ID NO:46 and a VL region comprising the sequence of SEQ ID NO:49 (127);
h) a VH region comprising the sequence of SEQ ID NO:49 and a VL region comprising the sequence of SEQ ID NO:53 (159);
i) a VH region comprising the sequence of SEQ ID NO:56 and a VL region comprising the sequence of SEQ ID NO:60 (098);
j) a VH region comprising the sequence of SEQ ID NO:63 and a VL region comprising the sequence of SEQ ID NO:67 (153);
k) a VH region comprising the sequence of SEQ ID NO:70 and a VL region comprising the sequence of SEQ ID NO:74 (132)
l) a VH region comprising the sequence of SEQ ID NO:1 and a VL region comprising the sequence of SEQ ID NO:5 (005); and
m) a VH region comprising the sequence of SEQ ID NO:22 and a VL region comprising the sequence of SEQ ID NO:26 (060).

In an additional or alternative embodiment, the anti-HER2 antibody or the/first antigen-binding region specifically binds HER2-expressing AU565 cells and inhibits ligand-independent proliferation of the cells, preferably inhibiting proliferation by at least 20%, more preferably at least 25%, when determined as described in Example 16, and preferably binds the same epitope as at least one reference antibody comprising the VH and VL regions selected from the group consisting of:

a) a VH region comprising the sequence of SEQ ID NO:1 and a VL region comprising the sequence of SEQ ID NO:5 (169); and
b) a VH region comprising the sequence of SEQ ID NO:8 and a VL region comprising the sequence of SEQ ID NO:12 (050).

In an additional or alternative embodiment, the anti-HER2 antibody specifically binds HER2-expressing AU565 cells but has no significant effect on, or does not promote, ligand-induced proliferation of the cells, preferably inhibiting proliferation by no more than 25%, more preferably by no more than 15%, when determined as described in Example 17, and binds the same epitope as at least one reference antibody comprising the VH and VL regions selected from the group consisting of:

a) a VH region comprising the sequence of SEQ ID NO:1 and a VL region comprising the sequence of SEQ ID NO:5 (169);
b) a VH region comprising the sequence of SEQ ID NO:8 and a VL region comprising the sequence of SEQ ID NO:12 (050);
c) a VH region comprising the sequence of SEQ ID NO:15 and a VL region comprising the sequence of SEQ ID NO:19 (084); and
d) a VH region comprising the sequence of SEQ ID NO:56 and a VL region comprising the sequence of SEQ ID NO:60 (098).

In an additional or alternative embodiment, the anti-HER2 antibody specifically binds HER2-expressing MCF-7 cells and inhibits ligand-induced proliferation, e.g. it may completely inhibit the ligand-induced effect or inhibit the total proliferation by 50%, e.g. 60% or 70% or 80%, of the cells when determined as described in Example 17, and binds the same epitope as at least one reference antibody comprising the VH and VL regions selected from the group consisting of:

a) a VH region comprising the sequence of SEQ ID NO:22 and a VL region comprising the sequence of SEQ ID NO:26 (025);

b) a VH region comprising the sequence of SEQ ID NO:29 and a VL region comprising the sequence of SEQ ID NO:32 (091);
c) a VH region comprising the sequence of SEQ ID NO:35 and a VL region comprising the sequence of SEQ ID NO:39 (129); and
d) a VH region comprising the sequence of SEQ ID NO:63 and, preferably, a VL region comprising the sequence of SEQ ID NO:67 (153).

In an additional or alternative embodiment, the first anti-HER2 antibody is internalized by tumor cells expressing HER2, such as AU565 cells, to a higher degree than trastuzumab and pertuzumab, preferably more than twice or three times the amount of internalized trastuzumab, preferably when determined according to Example 18, and binds to the same epitope as an antibody comprising VH and VL regions selected from the group consisting of:
a) a VH region comprising the sequence of SEQ ID NO:46 and a VL region comprising the sequence of SEQ ID NO:49 (127);
b) a VH region comprising the sequence of SEQ ID NO:49 and a VL region comprising the sequence of SEQ ID NO:53 (159);
c) a VH region comprising the sequence of SEQ ID NO:56 and a VL region comprising the sequence of SEQ ID NO:60 (098);
d) a VH region comprising the sequence of SEQ ID NO:63 and a VL region comprising the sequence of SEQ ID NO:67 (153); and
e) a VH region comprising the sequence of SEQ ID NO:70 and a VL region comprising the sequence of SEQ ID NO:74 (132).

Preferably, the antibody binds to the same epitope as an antibody comprising VH and VL regions selected from
a) a VH region comprising the sequence of SEQ ID NO:46 and a VL region comprising the sequence of SEQ ID NO:49 (127) and
b) a VH region comprising the sequence of SEQ ID NO:56 and a VL region comprising the sequence of SEQ ID NO:60 (098).

In a further embodiment, the antibody binds to Domain II or IV of HER2, preferably wherein the antibody does not significantly promote proliferation of HER2 expressing cells, and is more efficiently internalized, or is internalized to a higher degree, than trastuzumab or pertuzumab into HER2-expressing tumor cells, preferably when determined as described in the Examples, e.g. examples 16 and 19, respectively.

In a further embodiment the antibody enhanced HER2 downmodulation more than trastuzumab, e.g. the antibody enhanced HER2 downmodulation by more 30%, such as more than 40% or more than 50% when determined as described in Example 22, preferably wherein the antibody binds to the same epitope as an antibody of cross-block group 3 of the present invention, e.g. an antibody binding to the same epitope as an antibody comprising VH and VL regions selected from the group consisting of:
a) a VH region comprising the sequence of SEQ ID NO:56 and a VL region comprising the sequence of SEQ ID NO:60 (098);
b) a VH region comprising the sequence of SEQ ID NO:63 and a VL region comprising the sequence of SEQ ID NO:67 (153).

In another or alternative embodiment the antibody decreased tumour growth and improved survival in vivo more than trastuzumab, when determined as described in Example 25, preferably wherein the antibody binds to the same epitope as an antibody of cross-block 1 or cross-block 2 of the present invention, e.g. an antibody binding to the same epitope as an antibody comprising VH and VL regions selected from the group consisting of:
a) a VH region comprising the sequence of SEQ ID NO:1 and a VL region comprising the sequence of SEQ ID NO:5 (169);
b) a VH region comprising the sequence of SEQ ID NO:15 and a VL region comprising the sequence of SEQ ID NO:19 (084); and
c) a VH region comprising the sequence of SEQ ID NO:29 and a VL region comprising the sequence of SEQ ID NO:32 (091).

In another or alternative embodiment the antibody decreased tumour growth and improved survival in vivo more than trastuzumab, when determined as described in Example 26, preferably wherein the antibody binds to the same epitope as an antibody of cross-block 2 or cross-block 3 of the present invention, e.g. an antibody binding to the same epitope as an antibody comprising VH and VL regions selected from the group consisting of:
a) a VH region comprising the sequence of SEQ ID NO:22 and a VL region comprising the sequence of SEQ ID NO:26 (025);
b) a VH region comprising the sequence of SEQ ID NO:29 and a VL region comprising the sequence of SEQ ID NO:32 (091);
c) a VH region comprising the sequence of SEQ ID NO:35 and a VL region comprising the sequence of SEQ ID NO:39 (129); and
d) a VH region comprising the sequence of SEQ ID NO:63 and a VL region comprising the sequence of SEQ ID NO:67 (153).

More particularly, wherein the antibody binds to the same epitope as an antibody comprising VH and VL regions selected from the group consisting of:
a) a VH region comprising the sequence of SEQ ID NO:22 and a VL region comprising the sequence of SEQ ID NO:26 (025); and
b) a VH region comprising the sequence of SEQ ID NO:29 and a VL region comprising the sequence of SEQ ID NO:32 (091).

In one embodiment, the conjugated antibody kills at least 60%, preferably at least 70% AU565 cells or A431 cells, when determined as described in Example 18, and cross-blocks at least one antibody selected from
a) an antibody comprising a VH region comprising the sequence of SEQ ID NO:1 and a VL region comprising the sequence of SEQ ID NO:5 (005)
b) an antibody comprising a VH region comprising the sequence of SEQ ID NO:22 and a VL region comprising the sequence of SEQ ID NO:26 (060)
c) an antibody comprising a VH region comprising the sequence of SEQ ID NO:15 and a VL region comprising the sequence of SEQ ID NO:19 (059), and
d) an antibody comprising a VH region comprising the sequence of SEQ ID NO:36 and a VL region comprising the sequence of SEQ ID NO:40 (111).

In separate and specific embodiments, the antibody of the preceding embodiment fully cross-blocks, preferably bind to the same epitope as, antibody 005, 060, 059, 111, or a combination thereof.

In one embodiment, the antibody of the preceding embodiment kills at least 80% of A431 cells when determined as described in Example 18, and cross-blocks at least one antibody selected from a) an antibody comprising a VH region comprising the sequence of SEQ ID NO:1 and a VL region comprising the sequence of SEQ ID NO:5 (005), and
b) an antibody comprising a VH region comprising the sequence of SEQ ID NO:22 and a VL region comprising the sequence of SEQ ID NO:26 (060).

In separate and specific embodiments, the antibody of the preceding embodiment fully cross-blocks, preferably bind to the same epitope as, antibody 005, 060, or a combination thereof.

In an additional or alternative embodiment, the antibody is internalized by tumor cells expressing HER2, such as AU565 cells, more than trastuzumab is, preferably more than twice or three times the amount of internalized trastuzumab, preferably when determined according to Example 19, and cross-blocks at least one antibody selected from the group consisting of:

a) an antibody comprising a VH region comprising the sequence of SEQ ID NO:1 and a VL region comprising the sequence of SEQ ID NO:5 (005)
b) an antibody comprising a VH region comprising the sequence of SEQ ID NO:8 and a VL region comprising the sequence of SEQ ID NO:11 (006)
c) an antibody comprising a VH region comprising the sequence of SEQ ID NO:15 and a VL region comprising the sequence of SEQ ID NO:19 (059)
d) an antibody comprising a VH region comprising the sequence of SEQ ID NO:22 and a VL region comprising the sequence of SEQ ID NO:26 (060)
e) an antibody comprising a VH region comprising the sequence of SEQ ID NO:29 and a VL region comprising the sequence of SEQ ID NO:33 (106)
f) an antibody comprising a VH region comprising the sequence of SEQ ID NO:36 and a VL region comprising the sequence of SEQ ID NO:40 (111).

In separate and specific embodiments, the antibody of the preceding embodiment fully cross-blocks, preferably bind to the same epitope as, antibody 005, 006, 059, 060, 106, 111, or a combination thereof.

Bispecific Antibodies

In one embodiment, the antibody is a bispecific antibody, comprising (i) a first antigen-binding region of a HER2 antibody as defined herein, e.g. an antibody of cross-block 1, 2, 3 or 4, and (ii) a second antibody comprising an antigen-binding region of an antibody which binds to CD3.

First Antigen-Binding Region

In one embodiment the first antigen-binding region comprises a VH region comprising a CDR3 sequence of an antibody of cross-block 1, 2, 3 or 4 as defined herein, such as SEQ ID NO: 4, 25, 66 or 168 (169, 025, 153, or 005). In a particular embodiment, the first antigen-binding region comprises a VH region comprising a CDR3 sequence of SEQ ID NO: 4 (169).

In one embodiment the first antigen-binding region comprises a VH region comprising CDR1, CDR2 and CDR3 sequences of an antibody of cross-block 1, 2, 3 or 4 as defined herein, such as CDR1, CDR2, and CDR3 sequences SEQ ID NOs: 2, 3 and 4 (169), or CDR1, CDR2 and CDR3 sequences of SEQ ID NOs:23, 24 and 25 (025), or CDR1, CDR2 and CDR3 sequences of SEQ ID NOs: 64, 65 and 66 (153), or CDR1, CDR2 CDR3 sequence of SEQ ID NOs: 166, 167 and 168 (005). In a particular embodiment, the first antigen-binding region comprises a VH region comprising CDR1, CDR2 and CDR3 sequences of CDR1, CDR2, and CDR3 sequences SEQ ID NOs: 2, 3 and 4 (169).

In a further or alternative embodiment the first antigen-binding region comprises a VH region comprising a CDR3 sequence of an antibody of cross-block 1, 2, 3 or 4 as defined herein, such as CDR3 sequence an antibody of cross-block 1 of SEQ ID NO: 11 (050), or SEQ ID NO: 18 (084); or a CDR3 sequence of an antibody of cross-block 2 of SEQ ID NO: 31 (091), or SEQ ID NO: 38 (129), or a CDR3 sequence of an antibody of cross-block 3 of SEQ ID NO: 45 (127), or SEQ ID NO:52 (159), or SEQ ID NO:59 (098), or SEQ ID NO:73 (132), or a CDR3 sequence of an antibody of cross-block 4 of SEQ ID NO:175 (006), SEQ ID NO: 182 (059), SEQ ID NO:189 (060), SEQ ID NO:196 (106), or SEQ ID NO:203 (111).

In one embodiment the first antigen-binding region comprises a VH region comprising CDR1, CDR2 and CDR3 sequences of an antibody of cross-block 1, 2 or 3 as defined herein, such as CDR1, CDR2, and CDR3 sequences SEQ ID NOs: 2, 3 and 4 (169), or CDR1, CDR2 and CDR3 sequences of SEQ ID NOs:23, 24 and 25 (025), or CDR1, CDR2 and CDR3 sequences of SEQ ID NOs: 64, 65 and 66 (153), or CDR1, CDR2 CDR3 sequence of SEQ ID NOs: 166, 167 and 168 (005).

In one embodiment the first antigen-binding region comprises a VH region comprising CDR1, CDR2 and CDR3 sequences of an antibody of cross-block 1, 2, 3 or 4 as defined herein, and a VL region comprising CDR1, CDR2 and CDR3 sequences of an antibody of cross-block 1, 2, 3 or 4 as defined herein.

In a further or alternative embodiment the first antigen-binding region comprises a VH region comprising CDR1, CDR2 and CDR3 sequences of an antibody of cross-block 1, 2, 3 or 4 as defined herein, such as CDR1, CDR2, and CDR3 sequences of an antibody of cross-block 1 of SEQ ID NOs: 9, 10 and 11 (050), or SEQ ID NOs: 16, 17 and 18 (084); or CDR1, CDR2, and CDR3 sequences of an antibody of cross-block 2 of SEQ ID NOs: 30, 163 and 31 (091), or SEQ ID NOs: 36, 37 and 38 (129), or CDR1, CDR2, and CDR3 sequences of an antibody of cross-block 3 SEQ ID NOs: 43, 44 and 45 (127), or SEQ ID NOs:50, 51 and 52 (159), or SEQ ID NOs:57, 58 and 59 (098), or SEQ ID NOs:71, 72 and 73 (132), or CDR1, CDR2 and CDR3 sequences of an antibody of cross-block 4 such as SEQ ID NOS: 173, 174, and 175 (006), SEQ ID NOS: 180, 181, and 182 (059), SEQ ID NOS:187, 188, and 189 (060), SEQ ID NOS:194, 195, and 196 (106), or SEQ ID NOS:201, 202, and 203 (111).

In one embodiment the first antigen-binding region comprises a VH region and a VL region selected from the group consisting of:

a) a VH region comprising the CDR1, CDR2, and CDR3 sequences of SEQ ID NOs: 2, 3 and 4; and a VL region comprising the CDR1, CDR2 and CDR3 sequences of SEQ ID: 6, DAS and SEQ ID NO:7, respectively (169);
b) a VH region comprising the CDR1, CDR2, and CDR3 sequences of SEQ ID NOs: 23, 24 and 25; and a VL region comprising the CDR1, CDR2 and CDR3 sequences of SEQ ID NO: 27, MS and SEQ ID NO:28, respectively (025);
c) a VH region comprising the CDR1, CDR2 and CDR3 sequences of SEQ ID NOs:64, 65 and 66; and a VL region comprising the CDR1, CDR2 and CDR3 sequences of SEQ ID NO: 68, DAS and SEQ ID NO:69 (153); and
d) a VH region comprising the CDR1, CDR2 and CDR3 sequences of SEQ ID NOs:166, 167 and 168; and a VL region comprising the CDR1, CDR2 and CDR3 sequences of SEQ ID NO: 170, GAS and SEQ ID NO:171 (005).

In a particular embodiment, the VH region comprises the CDR1, CDR2, and CDR3 sequences of SEQ ID NOs: 2, 3 and 4 the VL region comprises the CDR1, CDR2 and CDR3 sequences of SEQ ID: 6, DAS and SEQ ID NO:7, respectively (169).

In a further or alternative embodiment the first antigen-binding region comprises a VH region and a VL region selected from the group consisting of:

a) a VH region comprising the CDR1, CDR2 and CDR3 sequences of SEQ ID NOs:9, 127 and 11, such as the CDR1, CDR2 and CDR3 sequences of SEQ ID NOS: 9, 10 and 11 (050); optionally where the VH region is derived from an IgHV3-23-1 germline;

b) a VH region comprising the CDR1, CDR2 and CDR3 sequences of SEQ ID NOs:128, 129 and 130, such the CDR1, CDR2 and CDR3 sequences of SEQ ID NOs: 16, 17 and 18, respectively (084), optionally where the VH region is derived from an IgHV1-69-04 germline; and c) a VH region comprising the CDR1, CDR2 and CDR3 sequences of SEQ ID NOs:137, 138 and 139, such the CDR1, CDR2 and CDR3 sequences of SEQ ID NOs: 30, 163, and 31, respectively (091), optionally where the VH region is derived from an IgHV4-34-01 germline; and d) a VH region comprising the CDR1, CDR2, and CDR3 sequences of SEQ ID NOs:140, 141 and 142, such as the CDR1, CDR2, and CDR3 sequences of SEQ ID NOs: 36, 37 and 38 (129), respectively, optionally where the VH region is derived from an IgHV3-30-01 germline.

e) a VH region comprising the CDR1, CDR2 and CDR3 sequences of SEQ ID NOs:146, 147 and 148, such as the CDR1, CDR2 and CDR3 sequences of SEQ ID NOS: 43, 44 and 45 (127); optionally where the VH region is derived from an IgHV5-51-01 germline;

f) a VH region comprising the CDR1, CDR2 and CDR3 sequences of SEQ ID NOs:149, 51 and 52, such as the CDR1, CDR2 and CDR3 sequences of SEQ ID NOs: 50, 51 and 52, respectively (159), optionally where the VH region is derived from an IgHV5-51-01 germline;

g) a VH region comprising the CDR1, CDR2, and CDR3 sequences of SEQ ID NOs:143, 144 and 145, such as the CDR1, CDR2, and CDR3 sequences of SEQ ID NOs: 57, 58 and 59 (098), respectively, optionally where the VH region is derived from an IgHV3-23-01 germline;

h) a VH region comprising the CDR1, CDR2, and CDR3 sequences of SEQ ID NOs:71, 150 and 151, such as the CDR1, CDR2, and CDR3 sequences of SEQ ID NOs: 71, 72 and 73 (132), respectively, optionally where the VH region is derived from an IgHV1-18-01 germline;

i) a VH region comprising the CDR1, CDR2 and CDR3 sequences of SEQ ID NOs:221, 222 and 223, such as the CDR1, CDR2, and CDR3 sequences of SEQ ID NOs:187, 188 and 189, respectively (060), optionally where the VH region is derived from an IgHV5-51-1 germline;

j) A VH region comprising the CDR1, CDR2, and CDR3 sequences of SEQ ID NOs:194, 195 and 196, respectively (106), optionally where the VH region is derived from an IgHV5-51-1 germline;

k) a VH region comprising the CDR1, CDR2 and CDR3 sequences of SEQ ID NOs:224, 225 and 226, such the CDR1, CDR2 and CDR3 sequences of SEQ ID NOs: 173, 174, and 175, respectively (006), optionally where the VH region is derived from an IgHV3-23-1 germline;

l) a VH region comprising the CDR1, CDR2, and CDR3 sequences of SEQ ID NOs:227, 228, and 229, such as the CDR1, CDR2, and CDR3 sequences of SEQ ID NOs: 180, 181 and 182 (059), respectively, optionally where the VH region is derived from an IgHV1-18-1 germline; and m) a VH region comprising the CDR1, CDR2, and CDR3 sequences of SEQ ID NOs:230, 202 and 231, such as the CDR1, CDR2, and CDR3 sequences of SEQ ID NOs: 201, 202 and 203 (111), respectively, optionally where the VH region is derived from an IgHV1-69-4 germline.

Second Antigen-Binding Region

In any one of the preceding embodiments, the second antigen-binding region can be derived from a CD3 antibody.

In one embodiment, the second antigen-binding region is derived from a CD3 antibody comprising the VH CDR3 sequence of SEQ ID NO: 244 (huCLB-T3/4).

In a further embodiment, the second antigen-binding region is derived from a CD3 antibody comprising the VL CDR3 sequence of SEQ ID NO: 246 (huCLB-T3/4).

In further embodiment, the second antigen-binding region is derived from a CD3 antibody is an antibody comprising a VH region selected from the group consisting of:

a) a VH region comprising the CDR1, CDR2 and CDR3 sequences of SEQ ID NOS:242, 243 and 244, respectively (huCLB-T3/4);

b) a VH region comprising the CDR1, CDR2 and CDR3 sequences of SEQ ID NO:234 (YTH12.5);

c) a VH region comprising the CDR1, CDR2 and CDR3 sequences of SEQ ID NO:238 (huOKT3-C114S-gLC); and d) a VH region comprising the CDR1, CDR2 and CDR3 sequences of SEQ ID NO:236 (HUM291).

In a further embodiment, the second antigen-binding region is derived from a CD3 antibody comprising a VH region comprising the VH CDR1, CDR2 and CDR3 sequences of SEQ ID NO:234 and a VL region comprising the VLCDR1, CDR2 and CDR3 sequences of SEQ ID NO:235 (YTH12.5).

In a specific embodiment, the second antigen-binding region is derived from a CD3 antibody comprising a VH region comprising the sequence of SEQ ID NO: 234 (YTH12.5) and VL region comprising the sequence of SEQ ID NO:235 (YTH12.5).

In one embodiment, the second antigen-binding region is derived from a CD3 antibody comprising a VH region comprising the VH CDR1, CDR2 and CDR3 sequences of SEQ ID NOS:242, 243 and 244, respectively, and, optionally, a VL region comprising the VL CDR1, CDR2 and CDR3 sequences of SEQ ID NOS:245, DTS and 246, respectively (huCLB-T3/4).

In a specific embodiment, the second antigen-binding region is derived from a CD3 antibody comprising a VH region comprising the sequence of SEQ ID NO: 240 (huCLB-T3/4) and, optionally, VL region comprising the sequence of SEQ ID NO:241 (huCLB-T3/4).

In one embodiment, the second antigen-binding region is derived from a CD3 antibody comprising a VH region comprising the VH CDR1, CDR2 and CDR3 sequences of SEQ ID NO:238 and a VL region comprising the VL CDR1, CDR2 and CDR3 sequences of SEQ ID NO:239 (huOKT3-C114S-gLC).

In a specific embodiment, the second antigen-binding region is derived from a CD3 antibody comprising a VH region comprising the sequence of SEQ ID NO: 238 and VL region comprising the sequence of SEQ ID NO:239 (huOKT3-C114S-gLC).

In one embodiment, the second antigen-binding region is derived from a CD3 antibody comprising a VH region comprising the VH CDR1, CDR2 and CDR3 sequences of SEQ ID NO:236 and a VL region comprising the VL CDR1, CDR2 and CDR3 sequences of SEQ ID NO:237 (HUM291).

In a specific embodiment, the second antigen-binding region is derived from a CD3 antibody comprising a VH region comprising the sequence of SEQ ID NO:236 and VL region comprising the sequence of SEQ ID NO:237 (HUM291).

Specific Combinations of Bispecific Antibodies

One embodiment of the present invention relates to a bispecific antibody having a second antigen-binding region comprising a VH region comprising a CDR3 sequence of a CD3 antibody according to SEQ ID NO: 244 (huCLB-T3/4), and a first antigen-binding region comprising a VH region comprising a CDR3 sequence of a HER2 antibody of cross-block 1, 2, 3, or 4 as defined herein, such as SEQ ID NOs: 4, 25, 66, or 168 (169, 025, 153, or 005).

Another embodiment of the present invention relates to a bispecific antibody having a second antigen-binding region comprising a VH region comprising a CDR3 sequence of a CD3 antibody according to SEQ ID NO: 244 (huCLB-T3/4) and a VL region comprising a CDR3 sequence of a CD3 antibody according to SEQ ID NO: 246 (huCLB-T3/4), and a first antigen-binding region comprising a VH region comprising a CDR3 sequence of a HER2 antibody of cross-block 1, 2, 3, or 4 as defined herein, such as SEQ ID NOs: 4, 25, 66, or 168 (169, 025, 153, or 005) and a VL region comprising a CDR3 sequence of a HER2 antibody of cross-block 1, 2, 3, or 4 as defined herein, such as SEQ ID NOs: 7, 28, 69, or 171 (169, 025, 153, or 005).

Another embodiment of the present invention relates to a bispecific antibody having a second antigen-binding region comprising a VH region comprising CDR1, CDR2, and CDR3 sequences of a CD3 antibody according to SEQ ID NOs: 242, 243, and 244 (huCLB-T3/4), and a first antigen-binding region comprises a VH region comprising CDR1, CDR2, and CDR3 sequences of a HER2 antibody of cross-block 1, 2, 3, or 4 as defined herein, such as SEQ ID NOs: 2, 3, and 4 (169), SEQ ID NOs: 23, 24, and 25 (025), SEQ ID NOs: 64, 65, and 66 (153), or SEQ ID NOs: 166, 167, and 168 (005).

Another embodiment of the present invention relates to a bispecific antibody having a second antigen-binding region comprising a VH region comprising CDR1, CDR2, and CDR3 sequences of a CD3 antibody according to SEQ ID NOs: 242, 243, and 244 (huCLB-T3/4) and a VL region comprising CDR1, CDR2, and CDR3 sequences of a CD3 antibody according to SEQ ID NOs: 245, DTS, and 246 (huCLB-T3/4), and a first antigen-binding region comprising a VH region comprising CDR1, CDR2, and CDR3 sequences of a HER2 antibody of cross-block 1, 2, 3, or 4 as defined herein and a VL region comprising CDR1, CDR2, and CDR3 sequences of a HER2 antibody of cross-block 1, 2, 3, or 4 as defined herein, such as SEQ ID NOs: 2, 3, 4, 6, DAS, and 7 (169), SEQ ID NOs: 23, 24, 25, 27, MS, and 28 (025), SEQ ID NOs: 64, 65, 66, 68, DAS, and 69 (153), or SEQ ID NOs: 166, 167, 168, 170, GAS, and 171 (005).

Another embodiment of the present invention relates to a bispecific antibody having a second antigen-binding region comprising a VH region of a CD3 antibody according to SEQ ID NO: 240 (huCLB-T3/4), and a first antigen-binding region comprising a VH region of a HER2 antibody of cross-block 1, 2, 3, or 4 as defined herein, such as SEQ ID NOs: 1, 22, 63, or 165 (169, 025, 153, or 005).

Another embodiment of the present invention relates to a bispecific antibody having a second antigen-binding region comprising a VH region and a VL region of a CD3 antibody according to SEQ ID NOs: 240 and 241 (huCLB-T3/4), and a first antigen-binding region comprising a VH region and a VL region of a HER2 antibody of cross-block 1, 2, 3, or 4 as defined herein, such as SEQ ID NOs: 1 and 5 (169), 22 and 26 (025), 63 and 67 (153), or 165 and 169 (005).

One embodiment of the present invention relates to a bispecific antibody having a second antigen-binding region comprising a VH region comprising a VH CDR3 sequence of a CD3 antibody according to SEQ ID NO: 234 (YTH12.5), and a first antigen-binding region comprising a VH region of a HER2 antibody of cross-block 1, 2, 3, or 4 as defined herein, such as SEQ ID NOs: 4, 25, 66, or 168 (169, 025, 153, or 005).

Another embodiment of the present invention relates to a bispecific antibody having a second antigen-binding region comprising a VH region comprising a CDR3 sequence of a CD3 antibody according to SEQ ID NO: 234 (YTH12.5) and a VL region comprising a CDR3 sequence of a CD3 antibody according to SEQ ID NO: 235 (YTH12.5), and a first antigen-binding region comprising a VH region comprising a CDR3 sequence of a HER2 antibody of cross-block 1, 2, 3, or 4 as defined herein, such as SEQ ID NOs: 4, 25, 66, or 168 (169, 025, 153, or 005) and a VL region comprising a CDR3 sequence of a HER2 antibody of cross-block 1, 2, 3, or 4 as defined herein, such as SEQ ID NOs: 7, 28, 69, or 171 (169, 025, 153, or 005).

Another embodiment of the present invention relates to a bispecific antibody having a second antigen-binding region comprising a VH region comprising a VH CDR1, CDR2, and CDR3 sequence according to SEQ ID NO: 234 (YTH12.5), and a first antigen-binding region of a HER2 antibody of cross-block 1, 2, 3, or 4 as defined herein, such as SEQ ID NOs: 2, 3, and 4 (169), SEQ ID NOs: 23, 24, and 25 (025), SEQ ID NOs: 64, 65, and 66 (153), or SEQ ID NOs: 166, 167, and 168 (005).

Another embodiment of the present invention relates to a bispecific antibody having a second antigen-binding region comprising a VH region comprising CDR1, CDR2, and CDR3 sequences of a CD3 antibody according to SEQ ID NO: 234 (YTH12.5) and a VL region comprising CDR1, CDR2, and CDR3 sequences of a CD3 antibody according to SEQ ID NO: 235 (YTH12.5), and a first antigen-binding region comprising a VH region comprising CDR1, CDR2, and CDR3 sequences of a HER2 antibody of cross-block 1, 2, 3, or 4 as defined herein and a VL region comprising CDR1, CDR2, and CDR3 sequences of a HER2 antibody of cross-block 1, 2, 3, or 4 as defined herein, such as SEQ ID NOs: 2, 3, 4, 6, DAS, and 7 (169), SEQ ID NOs: 23, 24, 25, 27, MS, and 28 (025), SEQ ID NOs: 64, 65, 66, 68, DAS, and 69 (153), or SEQ ID NOs: 166, 167, 168, 170, GAS, and 171 (005).

Another embodiment of the present invention relates to a bispecific antibody having a second antigen-binding region comprising a VH region of a CD3 antibody according to SEQ ID NO: 234 (YTH12.5), and a first antigen-binding region of a HER2 antibody of cross-block 1, 2, 3, or 4, such as SEQ ID NOs: 1, 22, 63, or 165 (169, 025, 153, or 005).

Another embodiment of the present invention relates to a bispecific antibody having a second antigen-binding region comprising a VH region and a VL region of a CD3 antibody according to SEQ ID NOs: 234 and 235 (YTH12.5), and a first antigen-binding region comprising a VH region and a VL region of a HER2 antibody of cross-block 1, 2, 3, or 4 as defined herein, such as SEQ ID NOs: 1 and 5 (169), 22 and 26 (025), 63 and 67 (153), or 165 and 169 (005).

One embodiment of the present invention relates to a bispecific antibody having a second antigen-binding region comprising a VH region comprising a VH CDR3 sequence of a CD3 antibody according to SEQ ID NO: 236 (HUM291), and a first antigen-binding region comprising a VH region of a HER2 antibody of cross-block 1, 2, 3, or 4 as defined herein, such as SEQ ID NOs: 4, 25, 66, or 168 (169, 025, 153, or 005).

Another embodiment of the present invention relates to a bispecific antibody having a second antigen-binding region comprising a VH region comprising a CDR3 sequence of a CD3 antibody according to SEQ ID NO: 236 (HUM291) and a VL region comprising a CDR3 sequence of a CD3 antibody according to SEQ ID NO: 237 (HUM291), and a first antigen-binding region comprising a VH region comprising a CDR3 sequence of a HER2 antibody of cross-block 1, 2, 3, or 4 as defined herein, such as SEQ ID NOs: 4, 25, 66, or 168 (169, 025, 153, or 005) and a VL region comprising a CDR3 sequence of a HER2 antibody of cross-block 1, 2, 3, or 4 as defined herein, such as SEQ ID NOs: 7, 28, 69, or 171 (169, 025, 153, or 005).

Another embodiment of the present invention relates to a bispecific antibody having a second antigen-binding region comprising a VH region comprising a VH CDR1, CDR2, and CDR3 sequence according to SEQ ID NO: 236 (HUM291), and a first antigen-binding region of a HER2 antibody of cross-block 1, 2, 3, or 4 as defined herein, such as SEQ ID NOs: 2, 3, and 4 (169), SEQ ID NOs: 23, 24, and 25 (025), SEQ ID NOs: 64, 65, and 66 (153), or SEQ ID NOs: 166, 167, and 168 (005).

Another embodiment of the present invention relates to a bispecific antibody having a second antigen-binding region comprising a VH region comprising CDR1, CDR2, and CDR3 sequences of a CD3 antibody according to SEQ ID NO: 236 (HUM291) and a VL region comprising CDR1, CDR2, and CDR3 sequences of a CD3 antibody according to SEQ ID NO: 237 (HUM2915), and a first antigen-binding region comprising a VH region comprising CDR1, CDR2, and CDR3 sequences of a HER2 antibody of cross-block 1, 2, 3, or 4 as defined herein and a VL region comprising CDR1, CDR2, and CDR3 sequences of a HER2 antibody of cross-block 1, 2, 3, or 4 as defined herein, such as SEQ ID NOs: 2, 3, 4, 6, DAS, and 7 (169), SEQ ID NOs: 23, 24, 25, 27, MS, and 28 (025), SEQ ID NOs: 64, 65, 66, 68, DAS, and 69 (153), or SEQ ID NOs: 166, 167, 168, 170, GAS, and 171 (005).

Another embodiment of the present invention relates to a bispecific antibody having a second antigen-binding region comprising a VH region of a CD3 antibody according to SEQ ID NO: 236 (HUM291), and a first antigen-binding region of a HER2 antibody of cross-block 1, 2, 3, or 4, such as SEQ ID NOs: 1, 22, 63, or 165 (169, 025, 153, or 005).

Another embodiment of the present invention relates to a bispecific antibody having a second antigen-binding region comprising a VH region and a VL region of a CD3 antibody according to SEQ ID NOs: 236 and 237 (HUM291), and a first antigen-binding region comprising a VH region and a VL region of a HER2 antibody of cross-block 1, 2, 3, or 4 as defined herein, such as SEQ ID NOs: 1 and 5 (169), 22 and 26 (025), 63 and 67 (153), or 165 and 169 (005).

One embodiment of the present invention relates to a bispecific antibody having a second antigen-binding region comprising a VH region comprising a VH CDR3 sequence of a CD3 antibody according to SEQ ID NO: 238 (huOKT3-C114S-gLC), and a first antigen-binding region comprising a VH region of a HER2 antibody of cross-block 1, 2, 3, or 4 as defined herein, such as SEQ ID NOs: 4, 25, 66, or 168 (169, 025, 153, or 005).

Another embodiment of the present invention relates to a bispecific antibody having a second antigen-binding region comprising a VH region comprising a CDR3 sequence of a CD3 antibody according to SEQ ID NO: 238 (huOKT3-C114S-gLC) and a VL region comprising a CDR3 sequence of a CD3 antibody according to SEQ ID NO: 239 (huOKT3-C114S-gLC), and a first antigen-binding region comprising a VH region comprising a CDR3 sequence of a HER2 antibody of cross-block 1, 2, 3, or 4 as defined herein, such as SEQ ID NOs: 4, 25, 66, or 168 (169, 025, 153, or 005) and a VL region comprising a CDR3 sequence of a HER2 antibody of cross-block 1, 2, 3, or 4 as defined herein, such as SEQ ID NOs: 7, 28, 69, or 171 (169, 025, 153, or 005).

Another embodiment of the present invention relates to a bispecific antibody having a second antigen-binding region comprising a VH region comprising a VH CDR1, CDR2, and CDR3 sequence according to SEQ ID NO: 238 (huOKT3-C114S-gLC), and a first antigen-binding region of a HER2 antibody of cross-block 1, 2, 3, or 4 as defined herein, such as SEQ ID NOs: 2, 3, and 4 (169), SEQ ID NOs: 23, 24, and 25 (025), SEQ ID NOs: 64, 65, and 66 (153), or SEQ ID NOs: 166, 167, and 168 (005).

Another embodiment of the present invention relates to a bispecific antibody having a second antigen-binding region comprising a VH region comprising CDR1, CDR2, and CDR3 sequences of a CD3 antibody according to SEQ ID NO: 238 (huOKT3-C114S-gLC) and a VL region comprising CDR1, CDR2, and CDR3 sequences of a CD3 antibody according to SEQ ID NO: 239 (huOKT3-C114S-gLC), and a first antigen-binding region comprising a VH region comprising CDR1, CDR2, and CDR3 sequences of a HER2 antibody of cross-block 1, 2, 3, or 4 as defined herein and a VL region comprising CDR1, CDR2, and CDR3 sequences of a HER2 antibody of cross-block 1, 2, 3, or 4 as defined herein, such as SEQ ID NOs: 2, 3, 4, 6, DAS, and 7 (169), SEQ ID NOs: 23, 24, 25, 27, MS, and 28 (025), SEQ ID NOs: 64, 65, 66, 68, DAS, and 69 (153), or SEQ ID NOs: 166, 167, 168, 170, GAS, and 171 (005).

Another embodiment of the present invention relates to a bispecific antibody having a second antigen-binding region comprising a VH region of a CD3 antibody according to SEQ ID NO: 238 (huOKT3-C114S-gLC), and a first antigen-binding region of a HER2 antibody of cross-block 1, 2, 3, or 4, such as SEQ ID NOs: 1, 22, 63, or 165 (169, 025, 153, or 005).

Another embodiment of the present invention relates to a bispecific antibody having a second antigen-binding region comprising a VH region and a VL region of a CD3 antibody according to SEQ ID NOs: 238 and 239 (huOKT3-C114S-gLC), and a first antigen-binding region comprising a VH region and a VL region of a HER2 antibody of cross-block 1, 2, 3, or 4 as defined herein, such as SEQ ID NOs: 1 and 5 (169), 22 and 26 (025), 63 and 67 (153), or 165 and 169 (005).

In an additional or alternative embodiment the bispecific antibody is a HER2×CD3 bispecific antibody induce T cell mediated cytotoxicity of AU565 as described in Example 21, and binds the same epitopes as at least one of the bispecific antibodies selected from the group consisting of huCLB-T3/4×HER2-169, huCLB-T3/4×HER2 153, and huCLB-T3/4×HER2 005 described in Example 21.

In a further embodiment, the first and second antigen-binding regions of the bispecific antibody according to the invention comprise human antibody VH sequences and, optionally, human antibody VL sequences.

In a further embodiment, the first and second antigen-binding regions of the bispecific antibody according to the invention the first and second antigen-binding regions are from heavy-chain antibodies.

In a further embodiment, the first and second antigen-binding regions of the bispecific antibody according to the invention the first and second antigen-binding regions comprise a first and second light chain.

In a further embodiment, the first and second antigen-binding regions of the bispecific antibody according to the invention wherein said first and second light chains are different.

Fc Regions

In one aspect of the present invention, the bispecific HER2×CD3 antibody according to the present invention further comprises a first Fc region and a second Fc region which may be comprised in a first and a second Fab-arm which respectively further comprise the first and second antigen-binding regions described above (or vice versa).

In another aspect of the present invention, the bispecific HER2×CD3 antibody comprises a first and a second Fab-arm comprising a first and a second antigen-binding region, respectively. Typically, the first and second antigen-binding region is the HER2 binding domain and the CD3 binding domain, respectively. The bispecific HER2×CD3 antibody further comprises a first and a second Fc region, typically comprising a first and a second heavy chain polypeptide, respectively.

In the one aspect of the present invention, the bispecific HER2×CD3 antibody comprises the first Fab-arm comprising the first antigen-binding region and the first Fc region, and the second Fab-arm comprising the second antigen-binding region and the second Fc region.

In another aspect of the present invention, the bispecific HER2×CD3 antibody comprises the second Fab-arm comprising the second antigen-binding region and the first Fc region, and the first Fab-arm comprising the first antigen-binding region and the second Fc region.

The first and second Fc-regions may each be of any isotype, including, but not limited to, IgG1, IgG2, IgG3 and IgG4, and may comprise one or more mutations or modifications. In one embodiment, each of the first and second Fc regions is of the IgG4 isotype or derived therefrom, optionally with one or more mutations or modifications. In one embodiment, each of the first and second Fc regions is of the IgG1 isotype or derived therefrom, optionally with one or more mutations or modifications. In another embodiment, one of the Fc regions is of the IgG1 isotype and the other of the IgG4 isotype, or is derived from such respective isotype, optionally with one or more mutations or modifications.

In one embodiment, one or both Fc-regions are effector-function-deficient. For example, the Fc-region(s) may be of an IgG4 isotype, or a non-IgG4 type, e.g. IgG1, IgG2 or IgG3, which has been mutated such that the ability to mediate effector functions, such as ADCC, has been reduced or even eliminated. Such mutations have e.g. been described in Dall'Acqua W F et al., J Immunol. 177(2):1129-1138 (2006) and Hezareh M, J Virol.; 75(24):12161-12168 (2001). Other exemplary modifications are described in the Examples, e.g., in Example 27.

In one embodiment, one or both Fc-regions comprise an IgG1 wildtype sequence (SEQ ID NO:247, see Example 21).

In one embodiment, one or both of the Fc regions comprise a mutation removing the acceptor site for Asn-linked glycosylation or is otherwise manipulated to change the glycosylation properties. For example, in an IgG1 Fc-region, an N297Q mutation can be used to remove an Asn-linked glycosylation site. Accordingly, in a specific embodiment, one or both Fc-regions comprise an IgG1 wildtype sequence with an N297Q mutation (SEQ ID NO:250, see Example 21).

In a further embodiment, one or both of the Fc regions are glyco-engineered to reduce fucose and thus enhance ADCC, e.g. by addition of compounds to the culture media during antibody production as described in US2009317869 or as described in van Berkel et al. (2010) Biotechnol. Bioeng. 105:350 or by using FUT8 knockout cells, e.g. as described in Yamane-Ohnuki eta/(2004) Biotechnol. Bioeng 87:614. ADCC may alternatively be optimized using the method described by Umaãa et al. (1999) Nature Biotech 17:176. In a further embodiment, one or both of the Fc-regions have been engineered to enhance complement activation, e.g. as described in Natsume et al. (2009) Cancer Sci. 100:2411.

In one embodiment of the invention, the first or second antigen-binding regions or a part thereof, e.g. one or more CDRs, are of a species in the family Camelidae, see WO2010001251, or a species of cartilaginous fish, such as the nurse shark. In one embodiment, the first and second antigen-binding regions or heavy chains are from heavy-chain antibodies.

In one embodiment, the first and/or second Fc-region is conjugated to a drug, a prodrug or a toxin or contains an acceptor group for the same. Such acceptor group may e.g. be an unnatural amino acid.

In one aspect, the bispecific antibody of the invention comprises a first Fc-region comprising a first CH3 region, and a second Fc-region comprising a second CH3 region, wherein the sequences of the first and second CH3 regions are different and are such that the heterodimeric interaction between said first and second CH3 regions is stronger than each of the homodimeric interactions of said first and second CH3 regions. More details on these interactions and how they can be achieved are provided in PCT/EP2011/056388, published as WO 2011131746 (Genmab), which is hereby incorporated by reference in its entirety.

As described further herein and in the Examples, a stable bispecific HER2×CD3 molecule can be obtained at high yield using a particular method on the basis of one homodimeric starting HER2 antibody and one homodimeric starting CD3 antibody containing only a few, fairly conservative, asymmetrical mutations in the CH3 regions. Asymmetrical mutations mean that the sequences of said first and second CH3 regions contain amino acid substitutions at non-identical positions.

In one embodiment, the first Fc-region has an amino acid substitution at a position selected from the group consisting of: 366, 368, 370, 399, 405, 407 and 409, and the second Fc-region has an amino acid substitution at a position selected from the group consisting of: 366, 368, 370, 399, 405, 407 and 409, and wherein the first and second Fc-regions are not substituted in the same positions.

In one embodiment, the first Fc-region has an amino acid substitution at position 366, and said second Fc-region has an amino acid substitution at a position selected from the group consisting of: 368, 370, 399, 405, 407 and 409. In one embodiment the amino acid at position 366 is selected from Ala, Asp, Glu, His, Asn, Val, or Gln.

In one embodiment, the first Fc-region has an amino acid substitution at position 368, and said second Fc-region has an amino acid substitution at a position selected from the group consisting of: 366, 370, 399, 405, 407 and 409.

In one embodiment, the first Fc-region has an amino acid substitution at position 370, and said second Fc-region has an amino acid substitution at a position selected from the group consisting of: 366, 368, 399, 405, 407 and 409.

In one embodiment, the first Fc-region has an amino acid substitution at position 399, and said second Fc-region has an amino acid substitution at a position selected from the group consisting of: 366, 368, 370, 405, 407 and 409.

In one embodiment, the first Fc-region has an amino acid substitution at position 405, and said second Fc-region has an amino acid substitution at a position selected from the group consisting of: 366, 368, 370, 399, 407 and 409.

In one embodiment, the first Fc-region has an amino acid substitution at position 407, and said second Fc-region has an amino acid substitution at a position selected from the group consisting of: 366, 368, 370, 399, 405, and 409.

In one embodiment, the first Fc-region has an amino acid substitution at position 409, and said second Fc-region has an amino acid substitution at a position selected from the group consisting of: 366, 368, 370, 399, 405, and 407.

Accordingly, in one embodiment, the sequences of said first and second CH3 regions contain asymmetrical mutations, i.e. mutations at different positions in the two CH3 regions, e.g. a mutation at position 405 in one of the CH3 regions and a mutation at position 409 in the other CH3 region.

In one embodiment, the first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino-acid substitution at a position selected from the group consisting of: 366, 368, 370, 399, 405 and 407. In one such embodiment, said first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino acid other than Phe, e.g. Gly, Ala, Val, Ile, Ser, Thr, Lys, Arg, His, Asp, Asn, Glu, Gln, Pro, Trp, Tyr, Cys, Lys, or Leu, at position 405. In a further embodiment hereof, said first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino acid other than Phe, Arg or Gly, e.g. Leu, Ala, Val, Ile, Ser, Thr, Met, Lys, His, Asp, Asn, Glu, Gln, Pro, Trp, Tyr, or Cys, at position 405.

In another embodiment, said first Fc-region comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises an amino acid other than Phe, e.g. Gly, Ala, Val, Ile, Ser, Thr, Lys, Arg, His, Asp, Asn, Glu, Gln, Pro, Trp, Tyr, Leu, Met, or Cys, at position 405 and a Lys at position 409. In a further embodiment hereof, said first Fc-region comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises an amino acid other than Phe, Arg or Gly, e.g. Leu, Ala, Val, Ile, Ser, Thr, Met, Lys, His, Asp, Asn, Glu, Gln, Pro, Trp, Tyr, or Cys, at position 405 and a Lys at position 409.

In another embodiment, said first Fc-region comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises a Leu at position 405 and a Lys at position 409. In a further embodiment hereof, said first Fc-region comprises a Phe at position 405 and an Arg at position 409 and said second Fc-region comprises an amino acid other than Phe, Arg or Gly, e.g. Leu, Ala, Val, Ile, Ser, Thr, Lys, Met, His, Asp, Asn, Glu, Gln, Pro, Trp, Tyr, or Cys, at position 405 and a Lys at position 409. In another embodiment, said first Fc-region comprises Phe at position 405 and an Arg at position 409 and said second Fc-region comprises a Leu at position 405 and a Lys at position 409.

In a further embodiment, said first Fc-region comprises an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises a Lys at position 409, a Thr at position 370 and a Leu at position 405. In a further embodiment, said first Fc-region comprises an Arg at position 409 and said second Fc-region comprises a Lys at position 409, a Thr at position 370 and a Leu at position 405.

In an even further embodiment, said first Fc-region comprises a Lys at position 370, a Phe at position 405 and an Arg at position 409 and said second Fc-region comprises a Lys at position 409, a Thr at position 370 and a Leu at position 405.

In another embodiment, said first Fc-region comprises an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises a Lys at position 409 and: a) an Ile at position 350 and a Leu at position 405, or b) a Thr at position 370 and a Leu at position 405.

In another embodiment, said first Fc-region comprises an Arg at position 409 and said second HER2 antibody comprises a Lys at position 409 and: a) an Ile at position 350 and a Leu at position 405, or b) a Thr at position 370 and a Leu at position 405.

In another embodiment, said first Fc-region comprises a Thr at position 350, a Lys at position 370, a Phe at position 405 and an Arg at position 409 and said second HER2 antibody comprises a Lys at position 409 and: a) an Ile at position 350 and a Leu at position 405, or b) a Thr at position 370 and a Leu at position 405.

In another embodiment, said first Fc-region comprises a Thr at position 350, a Lys at position 370, a Phe at position 405 and an Arg at position 409 and said second Fc-region comprises an Ile at position 350, a Thr at position 370, a Leu at position 405 and a Lys at position 409.

In another embodiment, said first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino acid other than Tyr, Asp, Glu, Phe, Lys, Gln, Arg, Ser or Thr, e.g. Leu, Met, Gly, Ala, Val, Ile, His, Asn, Pro, Trp, or Cys, at position 407. In another embodiment, said first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an Ala, Gly, His, Ile, Leu, Met, Asn, Val or Trp at position 407.

In another embodiment, said first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has a Gly, Leu, Met, Asn or Trp at position 407.

In another embodiment, said first Fc-region has a Tyr at position 407 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino acid other than Tyr, Asp, Glu, Phe, Lys, Gln, Arg, Ser or Thr, e.g. Leu, Met, Gly, Ala, Val, Ile, His, Asn, Pro, Trp, or Cys, at position 407 and a Lys at position 409.

In another embodiment, said first Fc-region has a Tyr at position 407 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an Ala, Gly, His, Ile, Leu, Met, Asn, Val or Trp at position 407 and a Lys at position 409.

In another embodiment, said first Fc-region has a Tyr at position 407 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has a Gly, Leu, Met, Asn or Trp at position 407 and a Lys at position 409.

In another embodiment, said first Fc-region has a Tyr at position 407 and an Arg at position 409 and said second Fc-region has an amino acid other than Tyr, Asp, Glu, Phe, Lys, Gln, Arg, Ser or Thr, e.g. Leu, Met, Gly, Ala, Val, Ile, His, Asn, Pro, Trp, or Cys, at position 407 and a Lys at position 409.

In another embodiment, said first Fc-region has a Tyr at position 407 and an Arg at position 409 and said second Fc-region has an Ala, Gly, His, Ile, Leu, Met, Asn, Val or Trp at position 407 and a Lys at position 409.

In another embodiment, said first Fc-region has a Tyr at position 407 and an Arg at position 409 and said second Fc-region has a Gly, Leu, Met, Asn or Trp at position 407 and a Lys at position 409.

In one embodiment, the first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409, and the second Fc-region has (i) an amino acid other than Phe, Leu and Met, e.g. Gly, Ala, Val, Ile, Ser, Thr, Lys, Arg, His, Asp, Asn, Glu, Gln, Pro, Trp, Tyr, or Cys, at position 368, or
(ii) a Trp at position 370, or
(iii) an amino acid other than Asp, Cys, Pro, Glu or Gln, e.g. Phe, Leu, Met, Gly, Ala, Val, Ile, Ser, Thr, Lys, Arg, His, Asn, Trp, Tyr, or Cys, at position 399 or
(iv) an amino acid other than Lys, Arg, Ser, Thr, or Trp, e.g. Phe, Leu, Met, Ala, Val, Gly, Ile, Asn, His, Asp, Glu, Gln, Pro, Tyr, or Cys, at position 366.

In one embodiment, the first Fc-region has an Arg, Ala, His or Gly at position 409, and the second homodimeric protein has (i) a Lys, Gln, Ala, Asp, Glu, Gly, His, Ile, Asn, Arg, Ser, Thr, Val, or Trp at position 368, or
(ii) a Trp at position 370, or
(iii) an Ala, Gly, Ile, Leu, Met, Asn, Ser, Thr, Trp, Phe, His, Lys, Arg or Tyr at position 399, or
(iv) an Ala, Asp, Glu, His, Asn, Val, Gln, Phe, Gly, Ile, Leu, Met, or Tyr at position 366.

In one embodiment, the first Fc-region has an Arg at position 409, and the second homodimeric protein has (i) an Asp, Glu, Gly, Asn, Arg, Ser, Thr, Val, or Trp at position 368, or
(ii) a Trp at position 370, or
(iii) a Phe, His, Lys, Arg or Tyr at position 399, or
(iv) an Ala, Asp, Glu, His, Asn, Val, Gln at position 366.

In addition to the above-specified amino-acid substitutions, said first and second homodimeric protein may contain further amino-acid substitutions, deletion or insertions relative to wild-type Fc sequences.

In a further embodiment, said first and second Fab-arms (or heavy-chain constant domains) comprising the first and second Fc regions comprise, except for the specified mutations, a sequence independently selected from the following:

```
(IgG1m(a)):
                                        (SEQ ID NO: 247)
GQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKS
LSLSPGK

(IgG1m(f)):
                                        (SEQ ID NO: 257)
GQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKS
LSLSPGK,
and

(IgG1m(ax)):
                                        (SEQ ID NO: 258)
GQPREPQVYTLPPSRDELTKNQVSLTCLVKGFYPSDIAVEWESNGQPENN
YKTTPPVLDSDGSFFLYSKLTVDKSRWQQGNVFSCSVMHEGLHNHYTQKS
LSLSPGK.
```

In one embodiment, neither said first nor said second Fc-region comprises a Cys-Pro-Ser-Cys sequence in the (core) hinge region.

In a further embodiment, both said first and said second Fc-region comprise a Cys-Pro-Pro-Cys sequence in the (core) hinge region.

In separate and specific embodiments, one or both Fab arms comprise a heavy-chain constant region sequence independently selected from SEQ ID NO: 247, 248, 249, 250, 251, 252, 253, 254, and 255 (see Example 21).

In one particular example, the CD3 antibody is an antibody with a VH region comprising the sequence of SEQ ID NO:234 (VH YTH12.5) and VL region comprising the sequence of SEQ ID NO:235 (VL YTH12.5). Another example is a CD3 antibody with a VH region comprising the sequence of SEQ ID NO:240 (VH huCLB-T3/4) and VL region comprising the sequence of SEQ ID NO:241 (VL huCLB-T3/4).

In one embodiment, the bispecific antibody comprises (i) a first Fab-arm comprising an Fc region and VH and VL sequences, wherein the VH region comprises the amino acid sequence of SEQ ID NO:63, and the VL region comprises the amino acid sequence of SEQ ID NO:67 (153), optionally wherein the first Fab-arm comprises an IgG1,K Fc region having Arg at position 409, or Gln at position 297, or Arg at position 409 and Gln at position 297; and (ii) a second Fab-arm having an Fc region and VH and VL sequences, wherein the VH region comprises the amino acid sequence of SEQ ID NO:171 and the VL region comprises the amino acid sequence of SEQ ID NO:172 (YTH12.5), optionally wherein the second Fab-arm comprises an IgG1,κ Fc region having an Gln at position 297, or Leu at position 405, or Gln at position 297 and Leu at position 405.

In one embodiment, the bispecific antibody comprises (i) a first Fab-arm having an Fc region and VH and VL sequences, wherein the VH region comprises the amino acid sequence of SEQ ID NO:1, and the VL region comprises the amino acid sequence of SEQ ID NO:5 (169), optionally wherein the first Fab-arm comprises an IgG1,κ Fc region having Arg at position 409; and (ii) a second Fab-arm having an Fc region and VH and VL sequences, wherein the VH region comprises the amino acid sequence of SEQ ID NO:171 and the VL region comprises the amino acid sequence of SEQ ID NO:172 (YTH12.5), optionally wherein the second Fab-arm comprises an IgG1,κ Fc region having an Gln at position 297, or Leu at position 405, or Gln at position 297 and Leu at position 405.

In one embodiment, the bispecific antibody comprises (i) a first Fab-arm having an Fc region and VH and VL sequences, wherein the VH region comprises the amino acid sequence of SEQ ID NO:63, and the VL region comprises the amino acid sequence of SEQ ID NO:67 (153), optionally wherein the first Fab-arm comprises an IgG1,κ Fc region having Arg at position 409, or Gln at position 297, or Arg at position 409 and Gln at position 297; and (ii) a second Fab-arm having an Fc region and VH and VL sequences, wherein the VH region comprises the amino acid sequence of SEQ ID NO:173 and the VL region comprises the amino acid sequence of SEQ ID NO:174 (huCLB-T3/4), optionally wherein the second Fab-arm comprises an IgG1,κ Fc region having an Gln at position 297, or Leu at position 405, or Gln at position 297 and Leu at position 405.

In one embodiment, the bispecific antibody comprises (i) a first Fab-arm having an Fc region and VH and VL sequences, wherein the VH region comprises the amino acid sequence of SEQ ID NO:1, and the VL region comprises the amino acid sequence of SEQ ID NO:5 (169), optionally wherein the first Fab-arm comprises an IgG1,κ Fc region having Arg at position 409; and (ii) a second Fab-arm having an Fc region and VH and VL sequences, wherein the VH region comprises the amino acid sequence of SEQ ID NO:173 and the VL region comprises the amino acid sequence of SEQ ID NO:174 (huCLB-T3/4), optionally wherein the second Fab-arm comprises an IgG1,κ Fc region having an Gln at position 297, or Leu at position 405, or Gln at position 297 and Leu at position 405.

In any of the above embodiments, the first and/or second Fab-arm may further comprise CH1 and/or CL sequences.

In one embodiment the bispecific antibody is selected from the group consisting of: IgG1-HER2-153-K409R×IgG1-YTH12.5-F405L, IgG1-HER2-153-K409R×IgG1-YTH12.5-N297Q-F405L, IgG1-HER2-153-K409R×IgG1-hu-CLB-T3/4-F405L, IgG1-HER2-153-K409R×IgG1-hu-CLB-T3/4-N297Q-F405L, IgG1-HER2-153-N297Q-K409R×IgG1-YTH12.5-F405L, IgG1-HER2-153-N297Q-K409R×IgG1-YTH12.5-N297Q-F405L, IgG1-HER2-153-N297Q-K409R×IgG1-hu-CLB-T3/4-F405L, IgG1-HER2-153-N297Q-K409R×IgG1-hu-CLB-T3/4-N297Q-F405L, IgG1-HER2-169-K409R×IgG1-hu-CLB-T3/4-F405L, IgG1-HER2-169-K409R×IgG1-hu-CLB-T3/4-N297Q-F405L, IgG1-HER2-169-K409R×IgG1-YTH12.5-F405L and IgG1-HER2-169-K409R×IgG1-YTH12.5-N297Q-F405L, wherein ITL means IgG1,κ having Ile at position 350, Thr at position 370, and Leu at position 405, K409R means IgG1,κ having an Arg at position 409, and F405L means IgG1,κ having a Leu at position 405, N297Q means a Gln at position 297, and wherein the bold numbers refer to antibodies described herein with the VH and VL regions comprising the sequences described in Table 1 and Example 21.

In an additional embodiment, the bispecific antibody induces dose-dependent killing of AU565, NIH-3T3, A431 and A549 cells when determined as described in Example 29, and binds the same epitopes as the bispecific antibody IgG1-HER2-169×IgG1-CLBT3/4.

Bispecific Antibody Formats

The present invention provides bispecific HER2×CD3 antibodies which efficiently promote T cell-mediated killing of HER2-expressing tumor cells. Depending on the desired functional properties for a particular use, particular antigen-binding regions can be selected from the set of antibodies or antigen-binding regions provided by the present invention or from those antibodies or antigen-binding regions sharing, e.g., an epitope or cross-blocking region with the antibodies or antigen-binding regions provided by the present invention. Many different formats and uses of bispecific antibodies are known in the art, and were recently been reviewed by Chames and Baty (2009) Curr Opin Drug Disc Dev 12: 276.

Exemplary bispecific antibody molecules of the invention comprise (i) a single antibody that has two arms comprising different antigen-binding regions, one with a specificity to a HER2 epitope and one with a specificity to CD3, (ii) a single antibody that has one antigen-binding region or arm specific to a HER2 epitope and a second antigen-binding region or arm specific to a CD3 epitope, (iii) a single chain antibody that has a first specificity to a HER2 epitope and a second specificity to a CD3 epitope, e.g., via two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific $(Fab')_2$ fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody.

In one embodiment, the bispecific antibody of the present invention is a diabody, a cross-body, or a bispecific antibody obtained via a controlled Fab arm exchange as those described in the present invention.

Examples of different classes of bispecific antibodies include but are not limited to

- IgG-like molecules with complementary CH3 domains to force heterodimerisation
- recombinant IgG-like dual targeting molecules, wherein the two sides of the molecule each contain the Fab fragment or part of the Fab fragment of at least two different antibodies;
- IgG fusion molecules, wherein full length IgG antibodies are fused to extra Fab fragment or parts of Fab fragment;
- Fc fusion molecules, wherein single chain Fv molecules or stabilized diabodies are fused to heavy-chain constant-domains, Fc-regions or parts thereof;
- Fab fusion molecules, wherein different Fab-fragments are fused together;
- ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

Examples of IgG-like molecules with complementary CH3 domains molecules include but are not limited to the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody)(EMD Serono), the Biclonic (Merus) and the DuoBody (Genmab A/S).

Examples of recombinant IgG-like dual targeting molecules include but are not limited to Dual Targeting (DT)-Ig (GSK/Domantis), Two-in-one Antibody (Genentech), Cross-linked Mabs (Karmanos Cancer Center), $mAb^2$ (F-Star) and CovX-body (CovX/Pfizer).

Examples of IgG fusion molecules include but are not limited to Dual Variable Domain (DVD)-Ig (Abbott), IgG-like Bispecific (ImClone/Eli Lilly), Ts2Ab (MedImmune/AZ) and BsAb (Zymogenetics), HERCULES (Biogen Idec) and TvAb (Roche).

Examples of Fc fusion molecules include but are not limited to ScFv/Fc Fusions (Academic Institution), SCORPION (Emergent BioSolutions/Trubion, Zymogenetics/BMS), Dual Affinity Retargeting Technology (Fc-DART) (MacroGenics) and $Dual(ScFv)_2$-Fab (National Research Center for Antibody Medicine—China).

Examples of Fab fusion bispecific antibodies include but are not limited to $F(ab)_2$ (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech).

Examples of ScFv-, diabody-based and domain antibodies include but are not limited to Bispecific T Cell Engager (BITE) (Micromet, Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Methods of Preparing Bispecific Antibodies Methods of preparing bispecific antibodies of the present invention include those described in WO 2008119353 (Genmab), WO 2011131746 (Genmab) and reported by van der Neut-Kolfschoten et al. (Science. 2007 Sep. 14; 317(5844):1554-7). Examples of other platforms useful for preparing bispecific antibodies include but are not limited to BITE (Micromet), DART (MacroGenics), Fcab and $Mab^2$ (F-star), Fc-engineered IgG1 (Xencor) or DuoBody (based on Fab arm exchange, Genmab, this application, described below and in, e.g., Example 20).

Traditional methods such as the hybrid hybridoma and chemical conjugation methods (Marvin and Zhu (2005) Acta Pharmacol Sin 26:649) can also be used. Co-expression in a host cell of two antibodies, consisting of different heavy and light chains, leads to a mixture of possible antibody products in addition to the desired bispecific antibody, which can then be isolated by, e.g., affinity chromatography or similar methods.

Strategies favoring the formation of a functional bispecific, product, upon co-expression of different antibody constructs can also be used, e.g., the method described by Lindhofer et al. (1995 J Immunol 155:219). Fusion of rat and mouse hydridomas producing different antibodies leads to a limited number of heterodimeric proteins because of preferential species-restricted heavy/light chain pairing. Another strategy to promote formation of heterodimers over homodimers is a "knob-into-hole" strategy in which a protuberance is introduced on a first heavy-chain polypeptide and a corresponding cavity in a second heavy-chain polypeptide, such that the protuberance can be positioned in the cavity at the interface of these two heavy chains so as to promote heterodimer formation and hinder homodimer formation. "Protuberances" are constructed by replacing small amino-acid side-chains from the interface of the first polypeptide with larger side chains. Compensatory "cavities" of identical or similar size to the protuberances are created in the interface of the second polypeptide by replacing large amino-acid side-chains with smaller ones (U.S. Pat. No. 5,731,168). EP1870459 (Chugai) and WO 2009089004 (Amgen) describe other strategies for favoring heterodimer formation upon co-expression of different antibody domains in a host cell. In these methods, one or more residues that make up the CH3-CH3 interface in both CH3 domains are replaced with a charged amino acid such that homodimer formation is electrostatically unfavorable and heterodimerization is electrostatically favorable. WO2007110205 (Merck) describe yet another strategy, wherein differences between IgA and IgG CH3 domains are exploited to promote heterodimerization.

Another in vitro method for producing bispecific antibodies has been described in WO 2008119353 (Genmab), wherein a bispecific antibody is formed by "Fab-arm" or "half-molecule" exchange (swapping of a heavy chain and attached light chain) between two monospecific IgG4- or IgG4-like antibodies upon incubation under reducing conditions. The resulting product is a bispecific antibody having two Fab arms which may comprise different sequences.

A preferred method for preparing bispecific HER2×CD3 antibodies of the present invention includes the method described in WO 2011131746 (Genmab) comprising the following steps:

a) providing a first antibody comprising an Fc region, said Fc region comprising a first CH3 region;

b) providing a second antibody comprising a second Fc region, said Fc region comprising a second CH3 region, wherein the first antibody is a HER2 antibody and the second antibody is a CD3 antibody, or vice versa;

wherein the sequences of said first and second CH3 regions are different and are such that the heterodimeric interaction between said first and second CH3 regions is stronger than each of the homodimeric interactions of said first and second CH3 regions;

c) incubating said first antibody together with said second antibody under reducing conditions; and d) obtaining said bispecific HER2×CD3 antibody.

Without being limited to theory, in step c), the heavy-chain disulfide bonds in the hinge regions of the parent antibodies are reduced and the resulting cysteines are then able to form inter heavy-chain disulfide bond with cysteine residues of another parent antibody molecule (originally with a different specificity). In one embodiment of this method, the reducing conditions in step c) comprise the addition of a reducing agent, e.g. a reducing agent selected from the group consisting of: 2-mercaptoethylamine (2-MEA), dithiothreitol (DTT), dithioerythritol (DTE), glutathione, tris(2-carboxyethyl)phosphine (TCEP), L-cysteine and beta-mercapto-ethanol, preferably a reducing agent selected from the group consisting of: 2-mercaptoethylamine, dithiothreitol and tris(2-carboxyethyl)phosphine. In a further embodiment, step c) comprises restoring the conditions to become non-reducing or less reducing, for example by removal of a reducing agent, e.g. by desalting.

Typically, in this method, the first and second antibodies are a HER2 and CD3 antibody binding to epitopes of HER2 and CD3, respectively, and/or comprising different antigen-binding sequences of HER2 and CD3, respectively.

For this method any of the HER2 and CD3 antibodies described above may be used including first and second HER2 and CD3 antibodies, respectively, comprising a first and/or second Fc regions. Examples of such first and second Fc regions, including combination of such first and second Fc regions may include any of those described above. In a particular embodiment the first and second HER2 and CD3 antibodies, respectively, may be chosen so as to obtain a bispecific antibody as described herein.

In one embodiment of this method, said first and/or second antibodies are full-length antibodies.

The Fc regions of the first and second antibodies may be of any isotype, including, but not limited to, IgG1, IgG2, IgG3 or IgG4. In one embodiment of this method, the Fc regions of both said first and said second antibodies are of the IgG1 isotype. In another embodiment, one of the Fc regions of said antibodies is of the IgG1 isotype and the other of the IgG4 isotype. In the latter embodiment, the resulting bispecific antibody comprises an Fc region of an IgG1 and an Fc region of IgG4 and may thus have interesting intermediate properties with respect to activation of effector functions. A similar product can be obtained if said first and/or said second antibody comprises a mutation removing the acceptor site for Asn-linked glycosylation or is otherwise manipulated to change the glycosylation properties.

In a further embodiment of this method, one or both of the antibodies is glyco-engineered to reduce fucose and thus enhance ADCC, e.g. by addition of compounds to the culture media during antibody production as described in US2009317869 or as described in van Berkel et al. (2010) Biotechnol. Bioeng. 105:350 or by using FUT8 knockout cells, e.g. as described in Yamane-Ohnuki eta/(2004) Biotechnol. Bioeng 87:614. ADCC may alternatively be optimized using the method described by Umaña et al. (1999) Nature Biotech 17:176. In a further embodiment, one or both of the antibodies have been engineered to enhance complement activation, e.g. as described in Natsume et al. (2009) Cancer Sci. 100:2411.

In a further embodiment of this method, one or both of the antibodies have been engineered to reduce or increase the binding to the neonatal Fc receptor (FcRn) in order to manipulate the serum half-life of the heterodimeric protein. In a further embodiment, one of the antibody starting proteins has been engineered to not bind Protein A, thus allowing to separate the heterodimeric protein from said homodimeric starting protein by passing the product over a protein A column.

In a particular embodiment of this method, the antibody or a part thereof, e.g. one or more CDRs, is of a species in the family Camelidae, see WO2010001251, or a species of cartilaginous fish, such as the nurse shark, or is a heavy-chain or domain antibody.

In one embodiment, the first and/or second HER2 antibody is conjugated to a drug, a prodrug or a toxin or contains an acceptor group for the same. Such acceptor group may e.g. be an unnatural amino acid.

As described above, the sequences of the first and second CH3 regions of the homodimeric starting antibodies are different and are such that the heterodimeric interaction between said first and second CH3 regions is stronger than each of the homodimeric interactions of said first and second CH3 regions. More details on these interactions and how they can be achieved are provided in PCT/EP2011/056388, published as WO 2011131746 (Genmab), which is hereby incorporated by reference in its entirety.

In particular, a stable bispecific HER2×CD3 molecule can be obtained at high yield using the above method of the invention on the basis of two homodimeric starting antibodies which bind HER2 and CD3, respectively, and contain only a few, fairly conservative, asymmetrical mutations in the CH3 regions. Asymmetrical mutations mean that the sequences of said first and second CH3 regions contain amino acid substitutions at non-identical positions.

In one embodiment of this method, the first antibody has an amino acid substitution at a position selected from the group consisting of: 366, 368, 370, 399, 405, 407 and 409, and the second antibody has an amino acid substitution at a position selected from the group consisting of: 366, 368, 370, 399, 405, 407 and 409, and wherein the first and second antibodies are not substituted in the same positions.

In one embodiment of this method, the first antibody has an amino acid substitution at position 366, and said second antibody has an amino acid substitution at a position selected from the group consisting of: 368, 370, 399, 405, 407 and 409. In one embodiment the amino acid at position 366 is selected from Ala, Asp, Glu, His, Asn, Val, or Gln.

In one embodiment of this method, the first antibody protein has an amino acid substitution at position 368, and said second antibody has an amino acid substitution at a position selected from the group consisting of: 366, 370, 399, 405, 407 and 409.

In one embodiment of this method, the first antibody has an amino acid substitution at position 370, and said second antibody has an amino acid substitution at a position selected from the group consisting of: 366, 368, 399, 405, 407 and 409.

In one embodiment of this method, the first antibody has an amino acid substitution at position 399, and said second antibody has an amino acid substitution at a position selected from the group consisting of: 366, 368, 370, 405, 407 and 409.

In one embodiment of this method, the first antibody has an amino acid substitution at position 405, and said second antibody has an amino acid substitution at a position selected from the group consisting of: 366, 368, 370, 399, 407 and 409.

In one embodiment of this method, the first antibody has an amino acid substitution at position 407, and said second antibody has an amino acid substitution at a position selected from the group consisting of: 366, 368, 370, 399, 405, and 409.

In one embodiment of this method, the first antibody has an amino acid substitution at position 409, and said second antibody has an amino acid substitution at a position selected from the group consisting of: 366, 368, 370, 399, 405, and 407.

Accordingly, in one embodiment of this method, the sequences of said first and second CH3 regions contain asymmetrical mutations, i.e. mutations at different positions in the two CH3 regions, e.g. a mutation at position 405 in one of the CH3 regions and a mutation at position 409 in the other CH3 region.

In one embodiment of this method, the first antibody has an amino acid other than Lys, Leu or Met at position 409 and said second antibody has an amino-acid substitution at a position selected from the group consisting of: 366, 368, 370, 399, 405 and 407. In one such embodiment, said first antibody has an amino acid other than Lys, Leu or Met at position 409 and said second antibody has an amino acid other than Phe at position 405. In a further embodiment hereof, said first antibody has an amino acid other than Lys, Leu or Met at position 409 and said second antibody has an amino acid other than Phe, Arg or Gly at position 405.

In another embodiment of this method, said first antibody comprises a Phe at position 405 and an amino acid other than Lys, Leu or Met at position 409 and said second antibody comprises an amino acid other than Phe at position 405 and a Lys at position 409. In a further embodiment hereof, said first antibody comprises a Phe at position 405 and an amino acid other than Lys, Leu or Met at position 409 and said second antibody comprises an amino acid other than Phe, Arg or Gly at position 405 and a Lys at position 409.

In another embodiment of this method, said first antibody comprises a Phe at position 405 and an amino acid other than Lys, Leu or Met at position 409 and said second antibody comprises a Leu at position 405 and a Lys at position 409. In a further embodiment hereof, said first antibody comprises a Phe at position 405 and an Arg at position 409 and said second antibody comprises an amino acid other than Phe, Arg or Gly at position 405 and a Lys at position 409. In another embodiment, said first antibody comprises Phe at position 405 and an Arg at position 409 and said second antibody comprises a Leu at position 405 and a Lys at position 409.

In a further embodiment of this method, said first antibody comprises an amino acid other than Lys, Leu or Met at position 409 and said second homodimeric protein comprises a Lys at position 409, a Thr at position 370 and a Leu at position 405. In a further embodiment, said first homodimeric protein comprises an Arg at position 409 and said second homodimeric protein comprises a Lys at position 409, a Thr at position 370 and a Leu at position 405.

In an even further embodiment of this method, said first antibody comprises a Lys at position 370, a Phe at position 405 and an Arg at position 409 and said second antibody comprises a Lys at position 409, a Thr at position 370 and a Leu at position 405.

In another embodiment of this method, said first antibody comprises an amino acid other than Lys, Leu or Met at position 409 and said second antibody comprises a Lys at position 409 and: a) an Ile at position 350 and a Leu at position 405, or b) a Thr at position 370 and a Leu at position 405.

In another embodiment of this method, said first antibody comprises an Arg at position 409 and said second antibody comprises a Lys at position 409 and: a) an Ile at position 350 and a Leu at position 405, or b) a Thr at position 370 and a Leu at position 405.

In another embodiment of this method, said first antibody comprises a Thr at position 350, a Lys at position 370, a Phe at position 405 and an Arg at position 409 and said second antibody comprises a Lys at position 409 and: a) an Ile at position 350 and a Leu at position 405, or b) a Thr at position 370 and a Leu at position 405.

In another embodiment of this method, said first antibody comprises a Thr at position 350, a Lys at position 370, a Phe at position 405 and an Arg at position 409 and said second comprises an Ile at position 350, a Thr at position 370, a Leu at position 405 and a Lys at position 409.

In another embodiment of this method, said first antibody has an amino acid other than Lys, Leu or Met at position 409 and said second antibody has an amino acid other than Tyr, Asp, Glu, Phe, Lys, Gln, Arg, Ser or Thr at position 407. In another embodiment, said first antibody has an amino acid other than Lys, Leu or Met at position 409 and said second antibody has an Ala, Gly, His, Ile, Leu, Met, Asn, Val or Trp at position 407.

In another embodiment of this method, said first antibody has an amino acid other than Lys, Leu or Met at position 409 and said second antibody has a Gly, Leu, Met, Asn or Trp at position 407.

In another embodiment of this method, said first antibody has a Tyr at position 407 and an amino acid other than Lys, Leu or Met at position 409 and said second antibody has an amino acid other than Tyr, Asp, Glu, Phe, Lys, Gln, Arg, Ser or Thr at position 407 and a Lys at position 409.

In another embodiment of this method, said first antibody has a Tyr at position 407 and an amino acid other than Lys, Leu or Met at position 409 and said second antibody has an Ala, Gly, His, Ile, Leu, Met, Asn, Val or Trp at position 407 and a Lys at position 409.

In another embodiment of this method, said first antibody has a Tyr at position 407 and an amino acid other than Lys, Leu or Met at position 409 and said second antibody has a Gly, Leu, Met, Asn or Trp at position 407 and a Lys at position 409.

In another embodiment of this method, said first antibody has a Tyr at position 407 and an Arg at position 409 and said second antibody has an amino acid other than Tyr, Asp, Glu, Phe, Lys, Gln, Arg, Ser or Thr at position 407 and a Lys at position 409.

In another embodiment of this method, said first antibody has a Tyr at position 407 and an Arg at position 409 and said second antibody has an Ala, Gly, His, Ile, Leu, Met, Asn, Val or Trp at position 407 and a Lys at position 409.

In another embodiment of this method, said first antibody has a Tyr at position 407 and an Arg at position 409 and said second antibody has a Gly, Leu, Met, Asn or Trp at position 407 and a Lys at position 409.

In one embodiment of this method, the first antibody has an amino acid other than Lys, Leu or Met at position 409, and the second antibody has (i) an amino acid other than Phe, Leu and Met at position 368, or
(ii) a Trp at position 370, or
(iii) an amino acid other than Asp, Cys, Pro, Glu or Gln at position 399, or
(iv) an amino acid other than Lys, Arg, Ser, Thr, or Trp at position 366.

In one embodiment of this method, the first homodimeric protein has an Arg, Ala, His or Gly at position 409, and the second homodimeric protein has (i) a Lys, Gln, Ala, Asp, Glu, Gly, His, Ile, Asn, Arg, Ser, Thr, Val, or Trp at position 368, or
(ii) a Trp at position 370, or
(iii) an Ala, Gly, Ile, Leu, Met, Asn, Ser, Thr, Trp, Phe, His, Lys, Arg or Tyr at position 399, or
(iv) an Ala, Asp, Glu, His, Asn, Val, Gln, Phe, Gly, Ile, Leu, Met, or Tyr at position 366.

In one embodiment of this method, the first homodimeric protein has an Arg at position 409, and the second homodimeric protein has (i) an Asp, Glu, Gly, Asn, Arg, Ser, Thr, Val, or Trp at position 368, or
(ii) a Trp at position 370, or
(iii) a Phe, His, Lys, Arg or Tyr at position 399, or
(iv) an Ala, Asp, Glu, His, Asn, Val, Gln at position 366.

In addition to the above-specified amino-acid substitutions, said first and second homodimeric protein may contain further amino-acid substitutions, deletion or insertions relative to wild-type Fc sequences.

In a further embodiment, said first and second CH3 regions, except for the specified mutations, comprise the sequences of IgG1m(a) (SEQ ID NO:256), IgG1m(f) (SEQ ID NO:257), or IgG1m(ax) (SEQ ID NO:258).

Thus, in one embodiment, neither said first nor said second antibody comprises a Cys-Pro-Ser-Cys sequence in the (core) hinge region.

In a further embodiment, both said first and said second antibody comprise a Cys-Pro-Pro-Cys sequence in the (core) hinge region.

The bispecific antibodies of the invention may also be obtained by co-expression of constructs encoding the first and second polypeptides in a single cell. Thus, in a further aspect, the invention relates to a method for producing a bispecific antibody, said method comprising the following steps:

a) providing a first nucleic-acid construct encoding a first polypeptide comprising a first Fc region and a first antigen-binding region of a first antibody heavy chain, said first Fc region comprising a first CH3 region, b) providing a second nucleic-acid construct encoding a second polypeptide comprising a second Fc region and a second antigen-binding region of a second antibody heavy chain, said second Fc region comprising a first CH3 region, wherein the sequences of said first and second CH3 regions are different and are such that the heterodimeric interaction between said first and second CH3 regions is stronger than each of the homodimeric interactions of said first and second CH3 regions, and wherein said first homodimeric protein has an amino acid other than Lys, Leu or Met at position 409 and said second homodimeric protein has an amino-acid substitution at a position selected from the group consisting of: 366, 368, 370, 399, 405 and 407, optionally wherein said first and second nucleic acid constructs encode light chain sequences of said first and second antibodies c) co-expressing said first and second nucleic-acid constructs in a host cell, and d) obtaining said heterodimeric protein from the cell culture.

Thus, the present invention also relates to a recombinant eukaryotic or prokaryotic host cell which produces a bispecific antibody of the present invention.

In one embodiment of the present invention, the bispecific antibody is obtained by any of the methods according to the present invention.

Suitable expression vectors, including promoters, enhancers, etc., and suitable host cells for the production of antibodies are well-known in the art. Examples of host cells include yeast, bacterial and mammalian cells, such as CHO or HEK cells.

In one embodiment of this method, said first CH3 region has an amino acid other than Lys, Leu or Met at position 409 and said second CH3 region has an amino acid other than Phe at position 405.

In another embodiment of this method, said first CH3 region has an amino acid other than Lys, Leu or Met at position 409 and said second CH3 region has an amino acid other than Phe at position 405, such as other than Phe, Arg or Gly at position 405; or said first CH3 region has an amino acid other than Lys, Leu or Met at position 409 and said second CH3 region has an amino acid other than Tyr, Asp, Glu, Phe, Lys, Gln, Arg, Ser or Thr at position 407.

In some embodiments, said first and second polypeptides are full-length heavy chains of two antibodies that bind different epitopes (i.e. said first and second nucleic-acid constructs encode full-length heavy chains of two antibodies that bind different epitopes), and thus the heterodimeric protein is a bispecific antibody. This bispecific antibody can be a heavy-chain antibody, or said host cell may further express one or more nucleic-acid constructs encoding a light-chain. If only one light-chain construct is co-expressed with the heavy chain constructs, then a functional bispecific antibody is only formed if the light chain sequence is such that it can form a functional antigen-binding domain with each of the heavy chains. If two or more different light-chain constructs are co-expressed with the heavy chain, multiple products will be formed.

In further embodiments, the co-expression method according to the invention comprises any of the further features described under the in vitro method above.

In a further aspect, the invention relates to an expression vector comprising the first and second nucleic-acid constructs specified herein above. In a further embodiment, the expression vector further comprises a nucleotide sequence encoding the constant region of a light chain, a heavy chain or both light and heavy chains of an antibody, e.g. a human antibody.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a HER2 antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a CaP04-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

Exemplary expression vectors for the antibodies of the invention are also described in Examples 2 and 3.

In one embodiment, the vector is suitable for expression of the HER2 antibody in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

An expression vector may also or alternatively be a vector suitable for expression in mammalian cells, e.g. a vector comprising glutamine synthetase as a selectable marker, such as the vectors described in Bebbington (1992) Biotechnology (NY) 10:169-175.

A nucleic acid and/or vector may also comprises a nucleic acid sequence encoding a secretion/localization sequence, which can target a polypeptide, such as a nascent polypeptide chain, to the periplasmic space or into cell culture media. Such sequences are known in the art, and include secretion leader or signal peptides.

The expression vector may comprise or be associated with any suitable promoter, enhancer, and other expression-facilitating elements. Examples of such elements include strong expression promoters (e. g., human CMV IE promoter/enhancer as well as RSV, SV40, SL3-3, MMTV, and HIV LTR promoters), effective poly (A) termination sequences, an origin of replication for plasmid product in E. coli, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the HER2 antibody-encoding expression vector may be positioned in and/or delivered to the host cell or host animal via a viral vector.

In an even further aspect, the invention relates to a host cell comprising the first and second nucleic-acid constructs specified herein above.

Thus the present invention also relates to a recombinant eukaryotic or prokaryotic host cell which produces a bispecific antibody of the present invention, such as a transfectoma.

The first HER2 antibody may be expressed in a recombinant eukaryotic or prokaryotic host cell, such as a transfectoma, Examples of host cells include yeast, bacterial, and mammalian cells, such as CHO or HEK cells. For example, in one embodiment, the host cell may comprise a first and second nucleic acid construct stably integrated into the cellular genome. In another embodiment, the present invention provides a cell comprising a non-integrated nucleic acid, such as a plasmid, cosmid, phagemid, or linear expression element, which comprises a first and second nucleic acid construct as specified above. In an even further aspect, the invention relates to a transgenic non-human animal or plant comprising nucleic acids encoding one or two sets of a human heavy chain and a human light chain, wherein the animal or plant produces an bispecific antibody of the invention of the invention.

In a further aspect, the invention relates to a hybridoma which produces an antibody of the invention as defined herein. In an even further aspect, the invention relates to a transgenic non-human animal or plant comprising nucleic acids encoding one or two sets of a human heavy chain and a human light chain, wherein the animal or plant produces an bispecific antibody of the invention of the invention.

In a further aspect, the invention relates to a method for producing a HER2×CD3 antibody of the invention, said method comprising the steps of a) culturing a host cell of the invention as described herein above, and
b) purifying the antibody of the invention from the culture media.

Preparation of HERZ and CD3 Antibodies

Depending on the method for production of a bispecific antibody according to the present invention, it may be relevant to first produce bivalent, monospecific antibodies. This may for example be relevant if the bispecific antibody is produced as described above which methods are based on the mixing of two bivalent monospecific antibodies under reducing conditions.

Monoclonal antibodies, such as the HER2 antibody, for use in the present invention, for example to provide an antigen-binding region sharing an epitope or cross-blocking region with an antibody of cross-block groups 1, 2, 3 or 4 may be produced, e.g., by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody is a human antibody. Human monoclonal antibodies directed against HER2 or CD3 may be generated using transgenic or transchromosomal mice carrying parts of the human immune system rather than the mouse system. Such transgenic and transchromosomic mice include mice referred to herein as HuMAb® mice and KM mice, respectively, and are collectively referred to herein as "transgenic mice".

The HuMAb® mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or K and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the Hco7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-Balb/C mice can be generated by crossing HCo12 to KCo5[J/K](Balb) as described in w0/2009/097006.

Splenocytes from these transgenic mice may be used to generate hybridomas that secrete human monoclonal antibodies according to well known techniques.

Further, HER2 antigen-binding regions may be obtained from human antibodies or antibodies from other species identified through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

The bispecific antibody of the invention can be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. The effector function of the antibodies of the present invention may be changed by isotype switching to, e.g., an IgG1, IgG2, IgG3, IgG4, IgD, IgA, IgE, or IgM antibody for various therapeutic uses. In one embodiment, both Fc-regions of an antibody of the present invention are of the IgG1 isotype, for instance an IgG1,κ. In one embodiment, the two Fc-regions of a bispecific antibody are of the IgG1 and IgG4 isotypes, respectively. Optionally, the Fc-region may be modified in the hinge and/or CH3 region as described elsewhere herein.

In one embodiment, the bispecific antibody of the invention is a full-length antibody, preferably an IgG1 antibody, in particular an IgG1,κ antibody or a variant thereof. In another embodiment, the bispecific antibody of the invention comprises an antibody fragment or a single-chain antibody. Antibody fragments may e.g. be obtained by fragmentation using conventional techniques, and the fragments screened for utility in the same manner as described herein for whole antibodies. For example, $F(ab')_2$ fragments may be generated by treating an antibody with pepsin. The resulting $F(ab')_2$ fragment may be treated to reduce disulfide bridges with a reducing agent, such as dithiothreitol, to produce Fab' fragments. Fab fragments may be obtained by treating an antibody with papain. A $F(ab')_2$ fragment may also be produced by binding Fab' fragments via a thioether bond or a disulfide bond. Antibody fragments may also be generated by expression of nucleic acids encoding such fragments in recombinant cells (see for instance Evans et al., J. Immunol. Meth. 184, 123-38 (1995)). For example, a chimeric gene encoding a portion of an $F(ab')_2$ fragment could include DNA sequences encoding the $C_H1$ domain and hinge region of the H chain, followed by a translational stop codon to yield such a truncated antibody fragment molecule.

Bispecific HER2×CD3 antibodies of the invention may also be prepared from single chain antibodies. Single chain antibodies are peptides in which the heavy and light chain Fv regions are connected. In one embodiment, the bispecific antibody of the present invention comprises a single-chain Fv (scFv) wherein the heavy and light chains in the Fv of a HER2 antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). A bispecific antibody can then be formed from two VH and VL from a single-chain HER2 antibody and a single-chain CD3 antibody, or a polyvalent antibody formed from more than two VH and VL chains.

In one embodiment, one or both Fc-regions of the HER2 and CD3 mAbs for producing a bispecific antibody of the invention are effector-function-deficient. In one embodiment, the effector-function-deficient antibody is a human stabilized IgG4 antibody, which has been modified to prevent Fab-arm exchange (van der Neut Kolfschoten et al. (2007) Science 317(5844):1554-7). Examples of suitable human stabilized IgG4 antibodies are antibodies, wherein arginine at position 409 in a heavy chain constant region of human IgG4, which is indicated in the EU index described in Kabat et al., is substituted with lysine, threonine, methionine, or leucine, preferably lysine (described in WO2006033386 (Kirin)) and/or wherein the hinge region has been modified to comprise a Cys-Pro-Pro-Cys sequence.

In one embodiment, the stabilized IgG4 antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions, but does not comprise a Cys-Pro-Pro-Cys sequence in the hinge region. Preferably, said antibody comprises a Lys or Ala residue at the position corresponding to 409 or the CH3 region of the antibody has been replaced by the CH3 region of human IgG1, of human IgG2 or of human IgG3. See also WO2008145142 (Genmab) and WO 211131746 (Genmab).

In an even further embodiment, the stabilized IgG4 antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions and wherein said antibody comprises a Cys-Pro-Pro-Cys sequence in the hinge region. Preferably, said antibody comprises a Lys or Ala residue at the position corresponding to 409 or the CH3 region of the antibody has been replaced by the CH3 region of human IgG1, of human IgG2 or of human IgG3.

In a further embodiment, the effector-function-deficient antibody is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J Immunol. 177(2):1129-1138 (2006) and Hezareh M, J Virol.; 75(24):12161-12168 (2001).

Conjugates

In a further aspect, the present invention provides a bispecific HER2×CD3 antibody linked or conjugated to one or more therapeutic moieties, such as a cytotoxin, a chemotherapeutic drug, a cytokine, an immunosuppressant, and/or a radioisotope. Such conjugates are referred to herein as "immunoconjugates" or "drug conjugates". Immunoconjugates which include one or more cytotoxins are referred to as "immunotoxins".

Compositions

In a further main aspect, the invention relates to a pharmaceutical composition comprising:

a bispecific HER2×CD3 antibody as defined herein, and a pharmaceutically-acceptable carrier.

The pharmaceutical composition of the present invention may contain one bispecific antibody of the present invention or a combination of different bispecific antibodies of the present invention.

The pharmaceutical compositions may be formulated in accordance with conventional techniques such as those disclosed in Remington: The Science and Practice of Pharmacy, 19th Edition, Gennaro, Ed., Mack Publishing Co., Easton, Pa., 1995. A pharmaceutical composition of the present invention may e.g. include diluents, fillers, salts, buffers, detergents (e.g., a nonionic detergent, such as Tween-20 or Tween-80), stabilizers (e. g., sugars or protein-free amino acids), preservatives, tissue fixatives, solubilizers, and/or other materials suitable for inclusion in a pharmaceutical composition.

Pharmaceutically acceptable carriers include any and all suitable solvents, dispersion media, coatings, antibacterial and antifungal agents, isotonicity agents, antioxidants and absorption delaying agents, and the like that are physiologically compatible with a bispecific antibody of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, carboxymethyl cellulose colloidal solutions, tragacanth gum and injectable organic esters, such as ethyl oleate, and/or various buffers. Pharmaceutically acceptable carriers include sterile aqueous solutions or dispersions and sterile powders for the extemporaneous preparation of sterile injectable solutions or dispersion. Proper fluidity may be maintained, for example, by the use of coating materials, such as lecithin, by the maintenance of the required particle size in the case of dispersions, and by the use of surfactants.

Pharmaceutical bispecific antibodies of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole, butylated hydroxytoluene, lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical bispecific antibodies of the present invention may also comprise isotonicity agents, such as sugars, polyalcohols, such as mannitol, sorbitol, glycerol or sodium chloride in the compositions.

The pharmaceutical bispecific antibodies of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The bispecific antibodies of the present invention may be prepared with carriers that will protect the bispecific antibody against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

The actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. In one embodiment, a pharmaceutical composition of the present invention is administered parenterally. "Administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

Uses

In a further main aspect, the invention relates to a bispecific HER2×CD3 antibody of the invention for use as a medicament.

The bispecific antibodies of the invention may be used for a number of purposes. In particular, the antibodies of the invention may be used for the treatment of various forms of cancer, including metastatic cancer and refractory cancer.

In one embodiment, the bispecific antibodies of the invention are used for the treatment of breast cancer, including primary, metastatic, and refractory breast cancer.

In one embodiment, the bispecific antibodies of the invention are used for the treatment of a form of cancer selected from the group consisting of prostate cancer, non-small cell lung cancer, bladder cancer, ovarian cancer, gastric cancer, colorectal cancer, esophageal cancer, squamous cell carcinoma of the head & neck, cervical cancer, pancreatic cancer, testis cancer, malignant melanoma and a soft-tissue cancer (e.g. synovial sarcoma).

Similarly, the invention relates to a method for killing a tumor cell expressing HER2, comprising administration, to an individual in need thereof, of an effective amount of an antibody of the invention, such as an antibody drug-conjugate (ADC).

The present invention also relates to a method for inhibiting growth and/or proliferation of one or more tumor cells expressing HER2, comprising administration, to an individual in need thereof, of a bispecific antibody of the present invention.

The present invention alto relates to a method for treating cancer, comprising a) selecting a subject suffering from a cancer comprising rumor cells co-expressing HER2, and
b) administering to the subject the bispecific antibody of the present invention or a pharmaceutical composition of the present invention.

In one embodiment, said tumor cell is involved in a form of cancer selected from the group consisting of: breast cancer, prostate cancer, non-small cell lung cancer, bladder cancer, ovarian cancer, gastric cancer, colorectal cancer, esophageal cancer and squamous cell carcinoma of the head & neck, cervical cancer, pancreatic cancer, testis cancer, malignant melanoma, and a soft-tissue cancer (e.g., synovial sarcoma).

In one embodiment, the tumor cell is one that co-expresses HER2, and is a tumor cell involved in breast cancer, colorectal cancer, endometrial/cervical cancer, lung cancer, malignant melanoma, ovarian cancer, pancreatic cancer, prostate cancer, testis cancer, a soft-tissue tumor (e.g., synovial sarcoma), or bladder cancer.

In one aspect, the invention relates to a method for treating cancer in a subject, comprising selecting a subject suffering from a cancer comprising tumor cells expressing HER2, and administering to the subject a bispecific antibody of the invention. In one embodiment, the subject suffers from a cancer selected from the group consisting of breast cancer, colorectal cancer, endometrial/cervical cancer, lung cancer, malignant melanoma, ovarian cancer, pancreatic cancer, prostate cancer, testis cancer, a soft-tissue tumor (e.g., synovial sarcoma), or bladder cancer.

Also, the invention relates to the use of a bispecific antibody that binds to human HER2 and human CD3 for the preparation of a medicament for the treatment of cancer, such as one of the specific cancer indications mentioned above.

The invention further relates to a bispecific antibody for use in the treatment of cancer, such as one of the cancer indications mentioned above.

In a further embodiment of the methods of treatment of the present invention, the efficacy of the treatment is being monitored during the therapy, e.g. at predefined points in time, by determining tumor burden or HER2 expression levels on the relevant tumor cells.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the bispecific antibodies depend on the disease or condition to be treated and may be determined by the persons skilled in the art. An exemplary, non-limiting range for a therapeutically effective amount of a compound of the present invention is about 0.001-10 mg/kg, such as about 0.001-5 mg/kg, for example about 0.001-2 mg/kg, such as about 0.001-1 mg/kg, for instance about 0.001, about 0.01, about 0.1, about 1 or about 10 mg/kg.

A physician or veterinarian having ordinary skill in the art may readily determine and prescribe the effective amount of the pharmaceutical composition required. For example, the physician or veterinarian could start doses of the bispecific antibody employed in the pharmaceutical composition at levels lower than that required in order to achieve the desired therapeutic effect and gradually increase the dosage until the desired effect is achieved. In general, a suitable daily dose of a bispecific antibody of the present invention will be that amount of the compound which is the lowest dose effective to produce a therapeutic effect. Administration may e.g. be parenteral, such as intravenous, intramuscular or subcutaneous. In one embodiment, the bispecific antibodies may be administered by infusion in a weekly dosage of calculated by $mg/m^2$. Such dosages can, for example, be based on the mg/kg dosages provided above according to the following: dose (mg/kg)×70: 1.8. Such administration may be repeated, e.g., 1 to 8 times, such as 3 to 5 times. The administration may be performed by continuous infusion over a period of from 2 to 24 hours, such as of from 2 to 12 hours. In one embodiment, the bispecific antibodies may be administered by slow continuous infusion over a long period, such as more than 24 hours, in order to reduce toxic side effects.

In one embodiment the bispecific antibodies may be administered in a weekly dosage of calculated as a fixed dose for up to 8 times, such as from 4 to 6 times when given once a week. Such regimen may be repeated one or more times as necessary, for example, after 6 months or 12 months. Such fixed dosages can, for example, be based on the mg/kg dosages provided above, with a body weight estimate of 70 kg. The dosage may be determined or adjusted by measuring the amount of bispecific antibody of the present invention in the blood upon administration by for instance taking out a biological sample and using anti-idiotypic antibodies which target the HER2 antigen binding region of the bispecific antibodies of the present invention.

In one embodiment, the bispecific antibodies may be administered by maintenance therapy, such as, e.g., once a week for a period of 6 months or more.

A bispecific antibody may also be administered prophylactically in order to reduce the risk of developing cancer, delay the onset of the occurrence of an event in cancer progression, and/or reduce the risk of recurrence when a cancer is in remission.

The bispecific antibodies of the invention may also be administered in combination therapy, i.e., combined with other therapeutic agents relevant for the disease or condition to be treated. Accordingly, in one embodiment, the antibody-containing medicament is for combination with one or more further therapeutic agent, such as a cytotoxic, chemotherapeutic or anti-angiogenic agent.

Such combined administration may be simultaneous, separate or sequential. For simultaneous administration the agents may be administered as one composition or as separate compositions, as appropriate. The present invention thus also provides methods for treating a disorder involving cells expressing HER2 as described above, which methods comprise administration of a bispecific antibody of the present invention combined with one or more additional therapeutic agents as described below.

In one embodiment, the present invention provides a method for treating a disorder involving cells expressing HER2 in a subject, which method comprises administration of a therapeutically effective amount of a bispecific antibody of the present invention, and optionally at least one additional therapeutic agent, or an antibody binding to a different HER2 epitope than said antibody, to a subject in need thereof.

In one embodiment, the present invention provides a method for treating or preventing cancer, which method comprises administration of a therapeutically effective amount of a bispecific antibody of the present invention and at least one additional therapeutic agent to a subject in need thereof.

In one embodiment, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In another embodiment, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In another embodiment, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In another embodiment, such an additional therapeutic agent may be selected from a topoisomerase inhibitor, such as topotecan or irinotecan, or a cytostatic drug, such as etoposide and teniposide.

In another embodiment, such an additional therapeutic agent may be selected from a growth factor inhibitor, such as an inhibitor of ErbB1 (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM1 or pertuzumab) or an inhibitor of both EGFR and HER2, such as lapatinib).

In another embodiment, such an additional therapeutic agent may be selected from a tyrosine kinase inhibitor, such as imatinib (Glivec, Gleevec STI571) or lapatinib, PTK787/ZK222584.

In another embodiment, the present invention provides a method for treating a disorder involving cells expressing HER2 in a subject, which method comprises administration of a therapeutically effective amount of a bispecific antibody of the present invention and at least one inhibitor of angiogenesis, neovascularization, and/or other vascularization to a subject in need thereof.

Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF (e.g. bevacizumab), bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2).

Other examples of such inhibitors of angiogenesis, neovascularization, and/or other vascularization are anti-angiogenic heparin derivatives (e.g., heperinase III), temozolomide, NK4, macrophage migration inhibitory factor, cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other targets, such as anti-alpha-v/beta-3 integrin and anti-kininostatin antibodies.

In one embodiment, a therapeutic agent for use in combination with a bispecific antibody for treating the disorders as described above may be an anti-cancer immunogen, such as a cancer antigen/tumor-associated antigen (e.g., epithelial cell adhesion molecule (EpCAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines) or tumor-derived heat shock proteins, In one embodiment, a therapeutic agent for use in combination with a bispecific antibody for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFa2b), IFNβ, GM-CSF, CD4OL, Flt3 ligand, stem cell factor, ancestim, and TNFα. Suitable chemokines may include Glu-Leu-Arg (ELR)-negative chemokines such as IP-10, MCP-3, MIG, and SDF-1a from the human CXC and C—C chemokine families. Suitable cytokines include cytokine derivatives, cytokine variants, cytokine fragments, and cytokine fusion proteins.

In one embodiment, a therapeutic agent for use in combination with a bispecific antibody for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs,□ and anti-sense Bcl-2.

In one embodiment, a therapeutic agent for use in combination with a bispecific antibody for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In one embodiment, a therapeutic agent for use in combination with a bispecific antibody for treating the disorders as described above may be an anti-anergic agent, such asmolecules that block the activity of CTLA-4, e.g. ipilimumab.

In one embodiment, a therapeutic agent for use in combination with a bispecific antibody for treating the disorders as described above may be an anti-cancer nucleic acid or an anti-cancer inhibitory RNA molecule.

Examples of other anti-cancer agents, which may be relevant as therapeutic agents for use in combination with a bispecific antibody according to the invention for treating the disorders as described above are differentiation inducing agents, retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRa, PDGFRbeta, Flk2, Flt4, FGFR1, FGFR2, FGFR3, FGFR4, TRKA, TRKC, RON (such as an anti-RON antibody), Sea, Tie, Tie2, Eph, Ret, Ros, Alk, LTK, PTK7 and similar agents.

Examples of other anti-cancer agents, which may be relevant as therapeutic agents for use in combination with a bispecific antibody according to the invention for treating the disorders as described above are estramustine and epirubicin.

Examples of other anti-cancer agents, which may be relevant as therapeutic agents for use in combination with a bispecific antibody according to the invention for treating the disorders as described above are a HSP90 inhibitor like 17-allyl amino geld-anamycin, antibodies directed against a tumor antigen such as PSA, CA125, KSA, integrins, e.g. integrin β1, or inhibitors of VCAM. Examples of other anti-cancer agents, which may be relevant as therapeutic agents for use in combination with a bispecific antibody for treating the disorders as described above are calcineurin-inhibitors (such as valspodar, PSC 833 and other MDR-1 or p-glycoprotein inhibitors), TOR-inhibitors (such as sirolimus, everolimus and rapamcyin), and inhibitors of "lymphocyte homing" mechanisms (such as FTY720), and agents with effects on cell signaling such as adhesion molecule inhibitors (for instance anti-LFA).

In one embodiment, the bispecific antibody of the invention is for use in combination with one or more other therapeutic antibodies, such as ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva) and/or rituximab.

In another embodiment, two or more different antibodies of the invention as described herein are used in combination for the treatment of disease. Particularly interesting combinations include two or more non-blocking antibodies. Such combination therapy may lead to binding of an increased number of antibody molecules per cell, which may give increase efficacy, e.g. via activation of complement-mediated lysis.

In addition to the above, other embodiments of combination therapies of the invention include the following:

For the treatment of breast cancer, a bispecific antibody or a therapeutic conjugate thereof, in combination with methotrexate, paclitaxel, doxorubicin, carboplatin, cyclophosphamide, daunorubicin, epirubicin, 5-fluorouracil, gemcitabine, ixabepilone, mutamycin, mitoxantrone, vinorelbine, docetaxel, thiotepa, vincristine, capecitabine, an EGFR antibody (e.g. zalutumumab, cetuximab, panitumumab or nimotuzumab) or other EGFR inhibitor (such as gefitinib or erlotinib), another HER2 antibody or—conjugate (such as, e.g., trastuzumab, trastuzumab-DM1 or pertuzumab), an inhibitor of both EGFR and HER2 (such as lapatinib), and/or in combination with a HER3 inhibitor.

For the treatment of non-small-cell lung cancer, a bispecific antibody of the invention in combination with EGFR inhibitors, such as an EGFR antibody, e.g. zalutumumab, cetuximab, panitumumab or nimotuzumab or other EGFR inhibitors (such as gefitinib or erlotinib), or in combination with an another HER2 agent (such as a HER2 antibody, e.g. trastuzumab, trastuzumab-DM1 or pertuzumab) or in combination with an inhibitor of both EGFR and HER2, such as lapatinib, or in combination with a HER3 inhibitor.

For the treatment of colorectal cancer, a bispecific antibody of the invention in combination with one or more compounds selected from: gemcitabine, bevacizumab, FOLFOX, FOLFIRI, XELOX, IFL, oxaliplatin, irinotecan, 5-FU/LV, Capecitabine, UFT, EGFR targeting agents, such as cetuximab, panitumumab, zalutumumab; VEGF inhibitors, or tyrosine kinase inhibitors such as sunitinib.

For the treatment of prostate cancer, a bispecific antibody in combination with one or more compounds selected from: hormonal/antihormonal therapies; such as antiandrogens, Luteinizing hormone releasing hormone (LHRH) agonists, and chemotherapeutics such as taxanes, mitoxantrone, estramustine, 5FU, vinblastine, and ixabepilone.

Radiotherapy—Surgery

In one embodiment, the present invention provides a method for treating a disorder involving cells expressing HER2 in a subject, which method comprises administration of a therapeutically effective amount of a bispecific antibody, such as a HER2×CD3 antibody of the present invention, and radiotherapy to a subject in need thereof.

In one embodiment, the present invention provides a method for treating or preventing cancer, which method comprises administration of a therapeutically effective amount of a bispecific antibody, such as a HER2×CD3 antibody of the present invention, and radiotherapy to a subject in need thereof.

In one embodiment, the present invention provides the use of a bispecific antibody of the present invention, for the preparation of a pharmaceutical composition for treating cancer to be administered in combination with radiotherapy.

Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In a further embodiment, the present invention provides a method for treating or preventing cancer, which method comprises administration to a subject in need thereof of a therapeutically effective amount of a bispecific antibody of the present invention, in combination with surgery.

Diagnostic Uses

The bispecific antibodies of the invention may also be used for diagnostic purposes. Thus, in a further aspect, the invention relates to a diagnostic composition comprising a bispecific HER2×CD3 antibody as defined herein, and to its use. In one embodiment, the present invention provides a kit for diagnosis of cancer comprising a container comprising a bispecific HER2×CD3 antibody, and one or more reagents for detecting binding of the antibody to HER2. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized.

The present invention is further illustrated by the following examples, which should not be construed as limiting the scope of the invention.

EXAMPLES

Example 1

Expression Constructs for HER2 and HER2 Variants

Fully codon-optimized constructs for expression of full length HER2 (1255 aa, Swissprot P04626), the extracellular domain (ECD) of HER2 (Her2-ECDHis, aa 1-653 with a C-terminal His6 tag), the naturally occurring HER2 splice variant (Her2-delex16, resulting from exon 16 deletion and lacking aa 633-648) and a truncated form of the HER2 receptor (Her2-stumpy, aa 648-1256), were generated. The construct contained suitable restriction sites for cloning and an optimal Kozak sequence (Kozak, M., Gene 1999; 234 (2):187-208.). The constructs were cloned in the mammalian expression vector pEE13.4 (Lonza Biologics; Bebbington, C. R., et al., Biotechnology (N Y) 1992; 10(2):169-75) and fully sequenced to confirm the correctness of the construct.

Example 2

Expression Constructs for Pertuzumab, C1 and F5

Fully codon-optimized constructs for expression of the heavy chain (HC) and the light chain (LC) of the IgG1 antibodies pertuzumab, Cl and F5 in HEK cells, were generated. The variable regions encoded by these constructs are identical to those described in U.S. Pat. No. 6,949,245 for pertuzumab heavy chain and light chain and U.S. Pat. No. 7,244,826 for C1 and F5 heavy and light chain. For C1 and F5, the mammalian expression vectors p33G1f and p33K or p33L (pcDNA3.3 (Invitrogen)) containing the fully codon optimized constant region for the human IgG1 heavy chain (allotype f), the human kappa light chain or the human lambda light chain, respectively, were used. For pertuzumab, the mammalian expression vectors pG1f (pEE12.4 (Lonza Biologics) and pKappa (pEE6.4 (Lonza Biologics), containing the fully codon-optimized constant region for the human IgG1 heavy chain (allotype f) and the human kappa light chain, respectively, were used.

Trastuzumab (Herceptin®) can be produced in the same manner, using the heavy and light chain sequences described in, e.g., U.S. Pat. No. 7,632,924.

The sequence disclosures of U.S. Pat. Nos. 6,949,245; 7,244,826 and 7,632,924 are hereby incorporated by reference in their entireties.

Example 3

Transient Expression in HEK-293 or CHO Cells

Freestyle™ 293-F (a HEK-293 subclone adapted to suspension growth and chemically defined Freestyle medium, (HEK-293F)) cells were obtained from Invitrogen and transfected with the appropriate plasmid DNA, using 293fectin (Invitrogen) according to the manufacturer's instructions. In the case of antibody expression, the appropriate heavy chain and light chain expression vectors were co-expressed.

pEE13.4Her2, pEE13.4Her2-delex16 and pEE13.4Her2-stumpy were transiently transfected in the Freestyle™ CHO—S (Invitrogen) cell line using Freestyle MAX transfection reagent (Invitrogen). Expression of HER2 and Her2-delex16 was tested by means of FACS analysis as described below.

Example 4

Stable Polyclonal Pool Expression in NS0 pEE13.4Her2, pEE13.4Her2-delex16 and pEE13.4Her2-stumpy were stably transfected in NS0 cells by nucleofection (Amaxa). A pool of stably transfected cells was established after selection on glutamine dependent growth, based on the integrated glutamine synthetase selection marker (Barnes, L. M., et al., Cytotechnology 2000; 32(2):109-123).

Example 5

Purification of His-Tagged HER2

Her2ECDHis was expressed in HEK-293F cells. The His-tag in Her2ECDHis enabled purification with immobilized metal affinity chromatography, since the His-tagged protein binds strongly to the resin beads, while other proteins present in the culture supernatant do not bind strongly. In this process, a chelator fixed onto the chromatographic resin was charged with $Co^{2+}$ cations. Her2ECDHis containing supernatant was incubated with the resin in batch mode (i.e. solution). After incubation, the beads were retrieved from the supernatant and packed into a column. The column was washed in order to remove weakly bound proteins. The strongly bound Her2ECDHis proteins were then eluted with a buffer containing imidazole, which competes with the binding of His to $Co^{2+}$. The eluent was removed from the protein by buffer exchange on a desalting column.

Example 6

Immunization Procedure of Transgenic Mice

Antibodies 001, 019, 021, 025, 027, 032, 033, 035, 036, 049, 050, 051, 054, 055, 084, 091, 094, 098, 100, 105, 123 and 124 were derived from the following immunization: three female HCo12 mice, one male and two female HCo12-Balb/C mice, one male HCo17 mouse and one male HCo20 mouse (Medarex, San José, Calif., USA) were immunized alternating with $5\times10^6$ NS0 cells stably transfected with Her2ECD intraperitoneal (IP) and 20 μg Her2ECDHis protein coupled to the hapten Keyhole Limpet Hemocyanin (KLH) subcutaneous (SC) at the tail base, with an interval of fourteen days. A maximum of eight immunizations was performed per mouse (four IP and four SC immunizations). The first immunization with cells was done in complete Freunds' adjuvant (CFA; Difco Laboratories, Detroit, Mich., USA). For all other immunizations, cells were injected IP in PBS and KLH coupled Her2ECDHis was injected SC using incomplete Freunds' adjuvant (IFA; Difco Laboratories, Detroit, Mich., USA).

Antibodies 125, 127, 129, 132, 152, 153 and 159 were derived from the following immunization: one male and two female HCo12-Balb/C mice, one female HCo20 mouse, and one female HCo12 mouse (Medarex) were immunized alternating with $5\times10^6$ NS0 cells stably transfected with Her2delex16 IP and 20 μg Her2ECDHis protein coupled to the hapten Keyhole Limpet Hemocyanin (KLH) SC at the tail base, with an interval of fourteen days. A maximum of eight immunizations was performed per mouse (four IP and four SC immunizations). The first immunization with cells was done in complete Freunds' adjuvant (CFA; Difco Laboratories, Detroit, Mich., USA). For all other immunizations, cells were injected IP in PBS and KLH coupled Her2ECD was injected SC using incomplete Freunds' adjuvant (IFA; Difco Laboratories, Detroit, Mich., USA).

Antibody 143, 160, 161, 162, 166 and 169 were derived from the following immunization: one female and one male Hco12 mouse, one female Hco12-Balb/C mouse, one male HCo17 mouse and one male HCo20 mouse (Medarex) were immunized alternating with 20 μg Her2ECDHis protein coupled to the hapten Keyhole Limpet Hemocyanin (KLH), alternating IP and SC at the tail base with an interval of fourteen days. A maximum of eight immunizations was performed per mouse (four IP and four SC immunizations). The first immunization was done IP in complete Freunds' adjuvant (CFA; Difco Laboratories, Detroit, Mich., USA). The other immunizations were injected using incomplete Freunds' adjuvant (IFA; Difco Laboratories, Detroit, Mich., USA).

Antibodies 005, 006, 041, 044, 059, 060, 067, 072, 093, 106 and 111 were derived from the following immunization procedure: two female HCo12 mice, one female and one male HCo12-Balb/C mouse, one female and one male HCo17 mouse, and two male HCo20 mice (Medarex, San José, Calif., USA) were immunized every fortnight, alternating between $5\times10^6$ NS0 cells stably transfected with Her2ECDHis intraperitoneal (IP) and 20 μg Her2ECDHis protein coupled to the hapten Keyhole Limpet Hemocyanin (KLH) subcutaneous (SC) at the tail base. A maximum of eight immunizations was performed per mouse (four IP and four SC immunizations). The first immunization with cells was done in complete Freunds' adjuvant (CFA; Difco Laboratories, Detroit, Mich., USA). For all other immunizations, cells were injected IP in PBS and KLH coupled Her2ECD was injected SC using incomplete Freunds' adjuvant (IFA; Difco Laboratories, Detroit, Mich., USA).

Antibody 150 was derived from immunization of one female HCo17 mouse (Medarex) alternating with $5\times10^6$ NS0 cells stably transfected with Her2delex16 IP and 20 μg Her2ECDHis protein coupled to the hapten Keyhole Limpet Hemocyanin (KLH) SC at the tail base, with an interval of fourteen days. A maximum of eight immunizations was performed (four IP and four SC immunizations). The first immunization with cells was done in complete Freunds' adjuvant (CFA; Difco Laboratories, Detroit, Mich., USA). For all other immunizations, cells were injected IP in PBS and KLH coupled Her2ECD was injected SC using incomplete Freunds' adjuvant (IFA; Difco Laboratories, Detroit, Mich., USA).

Antibody 163 was derived from immunization of one male HCo20 mouse (Medarex) with 20 μg Her2ECDHis protein coupled to the hapten Keyhole Limpet Hemocyanin (KLH), alternating IP and SC at the tailbase with an interval of fourteen days. A maximum of eight immunizations was performed (four IP and four SC immunizations). The first immunization was done IP in complete Freunds' adjuvant (CFA; Difco Laboratories, Detroit, Mich., USA). The other immunizations were injected using incomplete Freunds' adjuvant (IFA; Difco Laboratories, Detroit, Mich., USA).

Mice with at least two sequential titers against TC1014-Her2, TC1014-Her2delex16 or TC1014-Her2stumpy in the antigen specific FMAT screening assay (as described in Example 7), were considered positive and fused.

Example 7

Homogeneous Antigen Specific Screening Assay

The presence of HER2 antibodies in sera of immunized mice or HuMab (human monoclonal antibody) hybridoma or transfectoma culture supernatant was determined by homogeneous antigen specific screening assays (four quadrant) using Fluorometric Micro volume Assay Technology (FMAT; Applied Biosystems, Foster City, Calif., USA). For this, a combination of 4 cell based assays was used. Binding to TC1014-Her2 (CHO—S cells transiently expressing the HER2 receptor; produced as described above), TC1014-Her2delex16 (CHO—S cells transiently expressing the extracellular domain of Her2-delex (a 16 amino acid deletion mutant of the HER2 receptor; produced as described above) and TC1014-Her2stumpy (CHO—S cells transiently expressing the extracellular stumpy domain of the HER2 receptor; produced as described above) as well as CHO—S wild type cells (negative control cells which do not express HER2) was determined. Samples were added to the cells to allow binding to HER2. Subsequently, binding of HuMab was detected using a fluorescent conjugate (Goat anti-Human IgG-Cy5; Jackson ImmunoResearch). TH1014-Pertuzumab (produced in HEK-293F cells) was used as a positive control and HuMab®-mouse pooled serum and HuMab-KLH were used as negative controls. The samples were scanned using an Applied Biosystems 8200 Cellular Detection System (8200 CDS) and 'counts×fluorescence' was used as read-out. Samples were stated positive when counts were higher than 50 and counts×fluorescence were at least three times higher than the negative control.

Example 8

HuMab Hybridoma Generation

HuMab mice with sufficient antigen-specific titer development (defined as above) were sacrificed and the spleen and lymph nodes flanking the abdominal aorta and vena cava were collected. Fusion of splenocytes and lymph node cells to a mouse myeloma cell line was done by electrofusion using a CEEF 50 Electrofusion System (Cyto Pulse Sciences, Glen Burnie, Md., USA), essentially according to the manufacturer's instructions. Next, the primary wells were sub cloned using the ClonePix system (Genetix, Hampshire, UK). To this end specific primary well hybridoma's were seeded in semisolid medium made from 40% CloneMedia (Genetix, Hampshire, UK) and 60% HyQ 2× complete media (Hyclone, Waltham, USA). The sub clones were retested in the antigen-specific binding assay as described in Example 7 and IgG levels were measured using an Octet (Fortebio, Menlo Park, USA) in order to select the most specific and best producing clone per primary well for further expansion. Further expansion and culturing of the resulting HuMab hybridomas were done based upon standard protocols (e.g. as described in Coligan J. E., Bierer, B. E., Margulies, D. H., Shevach, E. M. and Strober, W., eds. Current Protocols in Immunology, John Wiley & Sons, Inc., 2006). Clones derived by this process were designated PC1014.

Example 9

Mass Spectrometry of Purified Antibodies

Small aliquots of 0.8 mL antibody containing supernatant from 6-well or Hyperflask stage were purified using PhyTip columns containing Protein G resin (PhyNexus Inc., San Jose, USA) on a Sciclone ALH 3000 workstation (Caliper Lifesciences, Hopkinton, USA). The PhyTip columns were used according to manufacturer's instructions, although buffers were replaced by: Binding Buffer PBS (B. Braun, Medical B. V., Oss, Netherlands) and Elution Buffer 0.1M Glycine-HCl pH 2.7 (Fluka Riedel-de Haën, Buchs, Germany). After purification, samples were neutralized with 2M Tris-HCl, pH 9.0 (Sigma-Aldrich, Zwijndrecht, Netherlands). Alternatively, in some cases larger volumes of culture supernatant were purified using MabSelect SuRe columns (GE Health Care).

After purification, the samples were placed in a 384-well plate (Waters, 100 μl square well plate, part #186002631). Samples were deglycosylated overnight at 37° C. with N-glycosidase F (Roche cat no 11365177001. DTT (15 mg/mL) was added (1 μL/well) and incubated for 1 h at 37° C. Samples (5 or 6 μL) were desalted on an Acquity UPLC™ (Waters, Milford, USA) with a BEH300 C18, 1.7 μm, 2.1×50 mm column at 60° C. MQ water and LC-MS grade acetonitrile (Biosolve, cat no 01204101, Valkenswaard, The Netherlands) with both 0.1% formic acid (Fluka, cat no 56302, Buchs, Germany), were used as Eluens A and B, respectively. Time-of-flight electrospray ionization mass spectra were recorded on-line on a micrOTOF™ mass spectrometer (Bruker, Bremen, Germany) operating in the positive ion mode. Prior to analysis, a 900-3000 m/z scale was calibrated with ES tuning mix (Agilent Technologies, Santa Clara, USA). Mass spectra were deconvoluted with DataAnalysis™ software v. 3.4 (Bruker) using the Maximal Entropy algorithm searching for molecular weights between 5 and 80 kDa.

After deconvolution, the resulting heavy and light chain masses for all samples were compared in order to find duplicate antibodies. This was sometimes due to the presence of an extra light chain, but in the comparison of the heavy chains, the possible presence of C-terminal lysine variants was also taken into account. This resulted in a list of unique antibodies, i.e., a unique combination of specific heavy and light chains. In case duplicate antibodies were found, one unique antibody was selected based on results from other tests.

Example 10

Sequence Analysis of the HER2 Antibody Variable Domains and Cloning in Expression Vectors Total RNA of the HER2 HuMabs was prepared from $5\times10^6$ hybridoma cells and 5'-RACE-Complementary DNA (cDNA) was prepared from 100 ng total RNA, using the SMART RACE cDNA Amplification kit (Clontech), according to the manufacturer's instructions. VH and VL coding regions were amplified by PCR and cloned directly, in frame, in the pG1f and pKappa expression vectors, by ligation independent cloning (Aslanidis, C. and P. J. de Jong, Nucleic Acids Res 1990; 18(20): 6069-74). The appropriate heacy chain and light chain vectors were transiently co-expressed in Freestyle™ 293-F cells using 293fectin. Clones derived by this process were designated TH1014 (TH stands for transient HEK cells). For each antibody, 16 VL clones and 8 VH clones were sequenced. Clones with predicted heavy and light chain mass in agreement with the mass of the hybridoma derived material of the same antibody (as determined by mass spectrometry) were selected for further study and expression.

The resulting sequences are shown in FIGS. 1 and 2 and in the Sequence Listing. Selected sequences are also described in more detail below. CDR sequences were defined according to IMGT (Lefranc M P. et al., Nucleic Acids Research, 27, 209-212, 1999 and Brochet X. Nucl. Acids Res. 36, W503-508 (2008)). Table 1, Table 2 and Table 3 give an overview of antibody sequence information or germline sequences, and Table 4 shows consensus sequences.

TABLE 1A and 1B

| Heavy chain variable region (VH), light chain variable region (VL) and CDR sequences of HuMabs 169, 050, 084, 025, 091, 129, 127, 159, 098, 153, and 132 (Table 1A) and HuMabs 005, 006, 059, 060, 106, and 111 (Table 18). | | |
|---|---|---|
| 1A: | | |
| SEQ ID No: 1 | VH 169 | QVQLVQSGAEVKKPGASVKVSCKASGYTFTNYGISWVRQAP GQGLEWMGWLSAYSGNTIYAQKLQGRVTMTTDTSTTTAY MELRSLRSDDTAVYYCARDRIVVRPDYFDYWGQGTLVTVSS |
| SEQ ID No: 2 | VH 169, CDR1 | GYTFTNYG |
| SEQ ID No: 3 | VH 169, CDR2 | LSAYSGNT |
| SEQ ID No: 4 | VH 169, CDR3 | ARDRIVVRPDYFDY |
| SEQ ID No: 5 | VL 169 | EIVLTQSPATLSLSPGERATLSCRASQSVSSYLAWYQQKPGQ APRLLIYDASNRATGIPARFSGSGSGTDFTLTISSLEPEDFAV YYCQQRSNWPRTFGQGTKVEIK |
| SEQ ID No: 6 | VL 169, CDR1 | QSVSSY |
| | VL 169, CDR2 | DAS |
| SEQ ID No: 7 | VL 169, CDR3 | QQRSNWPRT |
| SEQ ID No: 8 | VH 050 | EVQLLESGGGLVQPGGSLRLSCAASGFTFSSYAMNWVRQAP GKGLEWVSAISGRGGTTYYADSVKGRFTISRDNSKNTLYLQ MSSLRAEDTAVYYCAKARANWDYFDYWGQGTLVTVSS |
| SEQ ID No: 9 | VH 050, CDR1 | GFTFSSYA |
| SEQ ID No: 10 | VH 050, CDR2 | ISGRGGTT |
| SEQ ID No: 11 | VH 050, CDR3 | AKARANWDYFDY |
| SEQ ID No: 12 | VL 050 | DIQMTQSPSSVSASVGDRVTITCRASQGISSWLAWYQHKPG KAPKLLIYAASILQSGVPSRFSGSGSGTDFTLTISSLQPEDFAT YYCQQANSFPITFGQGTRLEIK |
| SEQ ID No: 13 | VL 050, CDR1 | QGISSW |
| | VL 050, CDR2 | MS |
| SEQ ID No: 14 | VL 050, CDR3 | QQANSFPIT |
| SEQ ID No: 15 | VH 084 | QVQLVQSGAEVKKPGSSVKVSCKASGGTFRTYAINWVRQAP GQGLEWMGRINTVLGIVNHAQKFQGRVTITADKSTNTAYM ELNSLRSEDTAVYYCAREKGVDYYYGIEVWGQGTTVTVSS |
| SEQ ID No: 16 | VH 084, CDR1 | GGTFRTYA |
| SEQ ID No: 17 | VH 084, CDR2 | INTVLGIV |
| SEQ ID No: 18 | VH 084, CDR3 | AREKGVDYYYGIEV |
| SEQ ID No: 19 | VL 084 | DIQMTQSPSSVSASVGDRVTITCRASQGISSWLAWYQHKPG KAPKLLIYVASTLQSGVPSRFSGSGSGTDFTLTISSLQPEDFA TYYCQQANSFPLTFGGGTKVEIK |
| SEQ ID No: 20 | VL 084, CDR1 | QGISSW |
| | VL 084, CDR2 | VAS |
| SEQ ID No: 21 | VL 084, CDR3 | QQANSFPLT |
| SEQ ID No: 22 | VH 025 | QVQLQQWGAGLLKPSETLSLTCAVYGGSFSDYYWNWIRQP PGKGLEWIGEIHHSGSTNYNPSLKSRVTISVDTSKNQFSLKL SSVTAADTAVYYCARGYYDSGVYYFDYWAQGTLVTVSS |
| SEQ ID No: 23 | VH 025, CDR1 | GGSFSDYY |
| SEQ ID No: 24 | VH 025, CDR2 | IHHSGST |
| SEQ ID No: 25 | VH 025, CDR3 | ARGYYDSGVYYFDY |
| SEQ ID No: 26 | VL 025 | DIQMTQSPSSLSASVGDRVTITCRASQGISRWLAWYQQKPE KAPKSLIYAASSLRSGVPSRFSGSGSGTDFTLTISSLQPEDFA TYYCQQYNSYPITFGQGTRLEIK |

TABLE 1A and 1B-continued

Heavy chain variable region (VH), light chain variable region (VL) and CDR sequences of HuMabs 169, 050, 084, 025, 091, 129, 127, 159, 098, 153, and 132 (Table 1A) and HuMabs 005, 006, 059, 060, 106, and 111 (Table 18).

| | | |
|---|---|---|
| SEQ ID No: 27 | VL 025, CDR1 | QGISRW |
| | VL 025, CDR2 | MS |
| SEQ ID No: 28 | VL 025, CDR3 | QQYNSYPIT |
| SEQ ID No: 29 | VH 091 | QVQLQQWGAGLLKPSETLSLTCAVSGGSFSGYYWTWIRQP PGKGLEWIGEIYHSGDTNYNPSLKSRVTISVDTSKNQFSLKL YSVTAADTAVYYCARLYFGSGIYYLDYWGQGTLVTVSS |
| SEQ ID No: 30 | VH 091, CDR1 | GGSFSGYY |
| SEQ ID No: 163 | VH 091, CDR2 | IYHSGDT |
| SEQ ID No: 31 | VH 091, CDR3 | ARLYFGSGIYYLDY |
| SEQ ID No: 32 | VL 091 | DIQMTQSPSSLSASVGDRVTITCRASQGISSWLVWYQQKPE KAPKSLIYAASSLQSGVPSRFSGSGSGTDFTLTISSLQPEDFA TYYCQQYNSFPPTFGQGTKVEIK |
| SEQ ID No: 33 | VL 091, CDR1 | QGISSW |
| | VL 091, CDR2 | MS |
| SEQ ID No: 34 | VL 091, CDR3 | QQYNSFPPT |
| SEQ ID No: 35 | VH 129 | QVQLVESGGGVVQPGRSLRLSCAASGFTFSTFAIHWVRQAP GKGLEWVAVISYDGGHKFYADSVKGRFTISRDNSKNTLYLQ MNSLRAEDTAMYYCARGLGVWGAFDYWGQGTLVTVSS |
| SEQ ID No: 36 | VH 129, CDR1 | GFTFSTFA |
| SEQ ID No: 37 | VH 129, CDR2 | ISYDGGHK |
| SEQ ID No: 38 | VH 129, CDR3 | ARGLGVWGAFDY |
| SEQ ID No: 39 | VL 129 | EIVLTQSPATLSLSPGERATLSCRASQSVSSYLAWYQQKPGQ APRLLIYDASNRATGIPARFSGSGSGTDFTLTISSLEPEDFAV YYCQQRSNWWTFGQGTKVEIK |
| SEQ ID No: 40 | VL 129, CDR1 | QSVSSY |
| | VL 129, CDR2 | DAS |
| SEQ ID No: 41 | VL 129, CDR3 | QQRSNWWT |
| SEQ ID No: 42 | VH 127 | EVQLVQSGAEVKKPGESLTISCKGSGYSFSIYWIGWVRQMP GKGLEWMGIIFPGDSDIRYSPSFQGQVTISADKSISTAYLQW SSLKASDTAMYYCARQPGDWSPRHWYFDLWGRGTLVTVSS |
| SEQ ID No: 43 | VH 127, CDR1 | GYSFSIYW |
| SEQ ID No: 44 | VH 127, CDR2 | IFPGDSDI |
| SEQ ID No: 45 | VH 127, CDR3 | ARQPGDWSPRHWYFDL |
| SEQ ID No: 46 | VL 127 | VIWMTQSPSLLSASTGDRVTISCRMSQGISSYLAWYQQKPG KAPELLIYAASTLQSGVPSRFSGSGSGTDFTLTISYLQSEDFA TYYCQQYYSFPLTFGGGTKVEIK |
| SEQ ID No: 47 | VL 127, CDR1 | QGISSY |
| | VL 127, CDR2 | MS |
| SEQ ID No: 48 | VL 127, CDR3 | QQYYSFPLT |
| SEQ ID No: 49 | VH 159 | EVQLVQSGAEVKKPGESLKISCKGSGYNFTSYWIGWVRQMP GKGLEWMGIIYPGDSDTRYSPSFQGQVTISADKSISTAYLQ WSSLKASDTAMYYCARWGTYYDILTGYFNWFDPWGQGTLV TVSS |
| SEQ ID No: 50 | VH 159, CDR1 | GYNFTSYW |
| SEQ ID No: 51 | VH 159, CDR2 | IYPGDSDT |
| SEQ ID No: 52 | VH 159, CDR3 | ARWGTYYDILTGYFN |

TABLE 1A and 1B-continued

| Heavy chain variable region (VH), light chain variable region (VL) and CDR sequences of HuMabs 169, 050, 084, 025, 091, 129, 127, 159, 098, 153, and 132 (Table 1A) and HuMabs 005, 006, 059, 060, 106, and 111 (Table 18). | | |
|---|---|---|
| SEQ ID No: 53 | VL 159 | DIQMTQSPSSLSASVGDRVTITCRASQGISSWLAWYQQKPE KAPKSLIYAASSLQSGVPSRFSGSGSGTDFTLTISSLQPEDFA TYYCQQYYTYPWTFGQGTKVEIK |
| SEQ ID No: 54 | VL 159, CDR1 | QGISSW |
| | VL 159, CDR2 | MS |
| SEQ ID No: 55 | VL 159, CDR3 | QQYYIYPWT |
| SEQ ID No: 56 | VH 098 | EVQLLESGGGLVQPGGSLRLSCAASGFTFSNYGMSWVRQAP GKGLEWVSAISGSAYSTYYADSVKGRFTISRDNSKNTLWLQ MNSLRADTAVYYCAKAHYHGSGSYYTLFDYWGQGTLVTVS S |
| SEQ ID No: 57 | VH 098, CDR1 | GFTFSNYG |
| SEQ ID No: 58 | VH 098, CDR2 | ISGSAYST |
| SEQ ID No: 59 | VH 098, CDR3 | AKAHYHGSGSYYTLFDY |
| SEQ ID No: 60 | VL 098 | DIQMTQSPSSLSASVGDRVTITCRASQGISSWLAWYQQKPE KAPKSLIYAASSLQSGVPSRFSGSGSGTDFTLTISSLQPEDFA TYYCQQYNSYPYTFGQGTKLEIK |
| SEQ ID No: 61 | VL 098, CDR1 | QGISSW |
| | VL 098, CDR2 | MS |
| SEQ ID No: 62 | VL 098, CDR3 | QQYNSYPYT |
| SEQ ID No: 63 | VH 153 | QVQLVESGGGVVQPGRSLRLSCAASGFTFSDYVIHWVRQAP GKGLEWVTVISYDGSNKYYADSVKGRFTISRDNSKNTLYLQ MNSLSAEDTAMYYCARGGITGTTGVFDYWGQGTLVTVSS |
| SEQ ID No: 64 | VH 153, CDR1 | GFTFSDYV |
| SEQ ID No: 65 | VH 153, CDR2 | ISYDGSNK |
| SEQ ID No: 66 | VH 153, CDR3 | ARGGITGTTGVFDY |
| SEQ ID No: 67 | VL 153 | DIQMTQSPSSLSASVGDRVTITCRASQGISSWLAWYQQKPE KAPKSLIYDASSLQSGVPSRFSGSGYGTDFSLTISSLQPEDFA IYYCQQYKSYPITFGQGTRLEIK |
| SEQ ID No: 68 | VL 153, CDR1 | QGISSW |
| | VL 153, CDR2 | DAS |
| SEQ ID No: 69 | VL 153, CDR3 | QQYKSYPIT |
| SEQ ID No: 70 | VH 132 | QVQLVQSGAEVKKPGASVKVSCKASGYTFTSYGISWVRQAP GQGLEWMGWISAYNGNSNYVQKFQGRVTMTTDTTTSTAY MELRSLTSDDTAVYYCAREYSYDSGTYFYYGMDVWGQGTT VTVSS |
| SEQ ID No: 71 | VH 132, CDR1 | GYTFTSYG |
| SEQ ID No: 72 | VH 132, CDR2 | ISAYNGNS |
| SEQ ID No: 73 | VH 132, CDR3 | AREYSYDSGTYFYYGMDV |
| SEQ ID No: 74 | VL 132 | EIVLTQSPATLSLSPGERATLSCRASQSVSSYLAWYQQKPGQ APRLLIYDASNRATGIPARFSGSGSGTDFTLTISSLEPEDFAV YYCQQRSNWPMYTFGQGTKLEIK |
| SEQ ID No: 75 | VL 132, CDR1 | QSVSSY |
| | VL 132, CDR2 | DAS |
| SEQ ID No: 76 | VL 132, CDR3 | QQRSNWPMYT |

TABLE 1A and 1B-continued

Heavy chain variable region (VH), light chain variable region (VL) and CDR sequences of HuMabs 169, 050, 084, 025, 091, 129, 127, 159, 098, 153, and 132 (Table 1A) and HuMabs 005, 006, 059, 060, 106, and 111 (Table 18).

| 1B) | | | |
|---|---|---|---|
| SEQ ID No: | 165 | VH 005 | EVQLVQSGAEVKKPGESLKISCKASGYSFHFYWIGWVRQMP GKGLEWMGSIYPGDSDTRYRPSFQGQVTISADKSISTAYLQ VVTSLKASDTAIYYCARQRGDYYYFYGMDVWGQGTTVTVSS |
| SEQ ID No: | 166 | VH 005, CDR1 | GYSFHFYW |
| SEQ ID No: | 167 | VH 005, CDR2 | IYPGDSDT |
| SEQ ID No: | 168 | VH 005, CDR3 | ARQRGDYYYFYGMDV |
| SEQ ID No: | 169 | VL 005 | EIVLTQSPGTLSLSPGERATLSCRASQSVSSSYLAWYQQKPG QVPRLLIYGASSRATGIPDRFSGSGSGTDFTLTISRLEPEDFA VYYCQQYGSS-LTFGGGTKVEIK |
| SEQ ID No: | 170 | VL 005, CDR1 | QSVSSSY |
| | | VL 005, CDR2 | GAS |
| SEQ ID No: | 171 | VL 005, CDR3 | QQYGSSLT |
| SEQ ID No: | 172 | VH 006 | EVQLLESGGGLVQPGGSLRLSCAASGFTFSNYALIWVRQAPG KGLEWVSIIRGGAGSTYYADSVKGRFTISRDNSKNTLYLQM NSLRAEDTAVYYCAKARIWGPLFDYWGQGTLVTVSS |
| SEQ ID No: | 173 | VH 006, CDR1 | GFTFSNYA |
| SEQ ID No: | 174 | VH 006, CDR2 | IRGGAGST |
| SEQ ID No: | 175 | VH 006, CDR3 | AKARIWGPLFDY |
| SEQ ID No: | 176 | VL 006 | EIVLTQSPATLSLSPGERATLSCRASQSVSSYLAWYQQKPGQ APRLLIYDASNRATGIPARFSGSGSGTDFTLTISSLEPEDFAV YYCQQRSNWPPLTFGGGTKVEIK |
| SEQ ID No: | 177 | VL 006, CDR1 | QSVSSY |
| | | VL 006, CDR2 | DAS |
| SEQ ID No: | 178 | VL 006, CDR3 | QQRSNWPPLT |
| SEQ ID No: | 179 | VH 059 | QVQLVQSGAEVKKPGASVRVPCKASGYTFTRYGISWVRQAP GQGLEWMGWISAYNGKTYYAQKLQGRVTMTTDTSTSTAY MELRSLRSDDTAVYYCARSPLLWFEELYFDYWGQGTLVTVS S |
| SEQ ID No: | 180 | VH 059, CDR1 | GYTFTRYG |
| SEQ ID No: | 181 | VH 059, CDR2 | ISAYNGKT |
| SEQ ID No: | 182 | VH 059, CDR3 | ARSPLLWFEELYFDY |
| SEQ ID No: | 183 | VL 059 | EIVLTQSPGTLSLSPGERATLSCRASQSVSSTYLAWYQQKPG QAPRLLIYGASSRATGIPDRFSGSGSGTDFTLTISRLEPEDFA VYYCQQYGTSLFTFGPGTKVDIK |
| SEQ ID No: | 184 | VL 059, CDR1 | QSVSSTY |
| | | VL 059, CDR2 | GAS |
| SEQ ID No: | 185 | VL 059, CDR3 | QQYGTSLFT |
| SEQ ID No: | 186 | VH 060 | EVQLVQSGAEVKKPGESLKISCKGSGYRFTSYWIGWVRQMP GKGLEWMGSIYPGDSYTRNSPSFQGQVTISADKSIATAYLQ WNSLKASDTAMYYCARHAGDFYYFDGLDVWGQGTTVTVSS |
| SEQ ID No: | 187 | VH 060, CDR1 | GYRFTTSYW |
| SEQ ID No: | 188 | VH 060, CDR2 | IYPGDSYT |
| SEQ ID No: | 189 | VH 060, CDR3 | ARHAGDFYYFDGLDV |
| SEQ ID No: | 190 | VL 060 | EIVLTQSPGTLSLSPGERATLSCRASQSVSSSYLAWYQQKPG QAPRLLIYGASSRATGIPDRFSGSGSGTDFTLTISRLEPEDFA VYYCQQYGSSPPITFGQGTRLEIK |

TABLE 1A and 1B-continued

Heavy chain variable region (VH), light chain variable region (VL) and CDR sequences of HuMabs 169, 050, 084, 025, 091, 129, 127, 159, 098, 153, and 132 (Table 1A) and HuMabs 005, 006, 059, 060, 106, and 111 (Table 18).

| | | |
|---|---|---|
| SEQ ID No: 191 | VL 060, CDR1 | QSVSSSY |
| | VL 060, CDR2 | GAS |
| SEQ ID No: 192 | VL 060, CDR3 | QQYGSSPPIT |
| SEQ ID No: 193 | VH 106 | EVQLVQSGAEVKKPGESLKISCKGSGYSFTRYWIGWVRQMP GKGLEWMGIIYPGDSDTRYSPSFQGQVTISADKSISTAYLQ WSSLIKASDTAMYYCARLTGDRGFDYYSGMDVWGQGTTVT VSS |
| SEQ ID No: 194 | VH 106, CDR1 | GYSFTRYW |
| SEQ ID No: 195 | VH 106, CDR2 | IYPGDSDT |
| SEQ ID No: 196 | VH 106, CDR3 | ARLTGDRGFDYYSGMDV |
| SEQ ID No: 197 | VL 106 | EIVLTQSPGTLSLSPGERATLSCRASQSVSSSYLAWYQQKPG QAPRLLIYGASSRATGIPDRFSGSGSGTDFTLTISRLEPEDFA VYYCQQYGSS-FTFGPGTKVDIK |
| SEQ ID No: 198 | VL 106, CDR1 | QSVSSSY |
| | VL 106, CDR2 | GAS |
| SEQ ID No: 199 | VL 106, CDR3 | QQYGSSFT |
| SEQ ID No: 200 | VH 111 | QVQLVQSGAEVKKPGSSVKVSCKASGGTFSSYGISWVRQAP GPGLEWMGRIIPILGIANYAQKFQGRVTITADKSTNTAYMEL SSLRSEDTAVYYCARDQEYSSNWYYWGQGTLVTVSS |
| SEQ ID No: 201 | VH 111, CDR1 | GGTFSSYG |
| SEQ ID No: 202 | VH 111, CDR2 | IIPILGIA |
| SEQ ID No: 203 | VH 111, CDR3 | ARDQEYSSNWYY |
| SEQ ID No: 204 | VL 111 | EIVLTQSPGTLSLSPGERATLSCRASQSVRSSYLAWYQQKPG QAPRLLIYGASSRATGIPDRFSGSGSGTDFTLTISRLEPEDFA VYYCQLYGSSPTFGPGTKVDIK |
| SEQ ID No: 205 | VL 111, CDR1 | QSVRSSY |
| | VL 111, CDR2 | GAS |
| SEQ ID No: 206 | VL 111, CDR3 | QLYGSSPT |

TABLE 2

Mouse origin and heavy and light chain sequence homologies of selected HuMabs.

| HuMab: | Mouse: | Strain: | Germline VH: | Germline VL: |
|---|---|---|---|---|
| 169 | 361494 | HCo20 | IgHV1-18-01 | IgKV3-11-01 |
| 050 | 350633 | HCo12 | IgHV3-23-01 | IgKV1-12-01 |
| 084 | 350615 | HCo12-BalbC | IgHV1-69-04 | IgKV1-12-01 |
| 025 | 350631 | HCo12 | IgHV4-34-01 | IgKV1D-16-01 |
| 091 | 350630 | HCo12 | IgHV4-34-01 | IgKV1D-16-01 |
| 129 | 359783 | HCo12-BalbC | IgHV3-30-3-01 | IgKV3-11-01 |
| 127 | 359783 | HCo12-BalbC | IgHV5-51-01 | IgKV1D-8-01 |
| 159 | 363503 | HCo12 | IgHV5-51-01 | IgKV1D-16-01 |
| 098 | 350659 | HCo17 | IgHV3-23-01 | IgKV1D-16-01 |
| 153 | 359785 | HCo12-BalbC | IgHV3-30-3-01 | IgKV1D-16-01 |

TABLE 2-continued

Mouse origin and heavy and light chain sequence homologies of selected HuMabs.

| HuMab: | Mouse: | Strain: | Germline VH: | Germline VL: |
|---|---|---|---|---|
| 132 | 361487 | HCo20 | IgHV1-18-01 | IgKV3-11-01 |
| 005 | 350611 | HCo12-BalbC | IgHV5-51-1 | IgKV3-20-01 |
| 006 | 350611 | HCo12-BalbC | IgHV3-23-1 | IgKV3-11-01 |
| 059 | 350654 | HCo17 | IgHV1-18-1 | IgKV3-20-01 |
| 060 | 350654 | HCo17 | IgHV5-51-1 | IgKV3-20-01 |
| 106 | 350660 | HCo17 | IgHV5-51-1 | IgKV3-20-01 |
| 111 | 350660 | HCo17 | IgHV1-69-4 | IgKV3-20-01 |

TABLE 3A and 3B

Heavy chain variable region (VH), light chain variable region (VL) sequences of HuMabs 049, 051, 055, 123, 161, 124, 001, 143, 019, 021, 027, 032, 035, 036, 054, 094 (3A) and HuMabs 041, 150, 067, 072, 163, 093, and 044 (3B). The respective CDRs correspond to those underlined in FIGS. 1 and 2, for VH and VL sequences, respectively.

| | | |
|---|---|---|
| 3A: | | |
| SEQ ID No: 77 | VH 049 | EVQLLESGGDLVQPGGSLRLSCAASGFTFSSYAMSWVRQAPGKGLEWV<br>SAISGRGGTMADSVKGRFTISRDNSKSTLCLQMNSLRAEDTAVYYCA<br>KARANWDYFDYWGQGTLVTVSS |
| SEQ ID No: 78 | VL 049 | DIQMTQSPSSVSASVGDRVTITCRASQGISSWLAWYQHKPGKAPKLLIY<br>AASILQSGVPSRFSGSGSGTDFTLTISSLRPEDFAMCQQANSFPITFG<br>QGTRLEIK |
| SEQ ID No: 79 | VH 051 | EVQLLESGGDLVQPGGSLRLSCAASGFTFSSYAMSWVRQAPGKGLEWV<br>SAISGRGGTMADSVKGRFTISRDNSKSTLCLQMNSLRAEDTAVYYCA<br>KARANWDYFDYWGQGTLVTVSS |
| SEQ ID No: 80 | VL 051 | DIQMTQSPSSVSASVGDRVTITCRASQGISSWLAWYQHKPGKAPKLLIY<br>AASILQSGVPSRFSGSGSGTDFTLTISSLRPEDFAMCQQANSFPITFG<br>QGTRLEIK |
| SEQ ID No: 81 | VH 055 | EVQLLESGGGLVQPGGSLRLSCAASGFTFSSYAMNWVRQAPGKGLEWV<br>SAISGRGGTMADSVKGRFTISRDNSKSTLCLQMNSLRAEDTAVYYCA<br>KARANWDYFDYWGQGTLVTVSS |
| SEQ ID No: 82 | VL 055 | DIQMTQSPSSVSASVGDRVTITCRASQGISSWLAWYQHKPGKAPKLLIY<br>AASILQSGVPSRFSGSGSGTDFTLTISSLRPEDFAMCQQANSFPITFG<br>QGTRLEIK |
| SEQ ID No: 83 | VH 123 | QVQLVQSGAEVKKPGASVKVSCKAAGYTFTNYGISWVRQAPGQALEW<br>MGWITTYSSNTIYAQKLQGRVTMTTDTSTSTAYMELRSLRSDDTAVYY<br>CARDRVVVRPDYFDYWGQGTLVTVSS |
| SEQ ID No: 84 | VL 123 | EIVLTQSPATLSLSPGERATLSCRASQSVSSYLAWYQQKPGQAPRLLIYD<br>TSNRATGIPARFSGSGSGTDFTLTISSLEPEDFAVYYCQQRSHWPRTFG<br>QGTKVEIK |
| SEQ ID No: 85 | VH 161 | QVQLVQSGAEVKKPGASVKVSCKASGYTFTNYGISWVRQAPGQGLEW<br>MGWLSAYSGNTIYAQKLQGRVTMTTDTSTTTAYMELRSLRSDDTAVYY<br>CARDRIVVRPDYFDYWGQGTLVTVSS |
| SEQ ID No: 86 | VL 161 | EIVLTQSPATLSLSPGERATLSCRASQSVSSYLAWYQQKPGQAPRLLIYD<br>ASNRATGIPARFSGSGSGTDFTLTISSLEPEDFAVYYCQQRSNWPRTFG<br>QGTKVEIK |
| SEQ ID No: 87 | VH 124 | QVQLVQSGAEVKKPGASVKVSCKAAGYTFTNYGISWVRQAPGQGLEW<br>MGWIITYNGNTIYAQRFQDRVTMTIDTSTSTAYMELRSLRSDDTAVYY<br>CARDRIIVRPDYFDYWGQGTLVTVSS |
| SEQ ID No: 88 | VL 124 | EIVLTQSPATLSLSPGERATLSCRASQSVSSYLAWYQQKPGQAPRLLIYD<br>ASNRATGIPARFSGSGSGTDFTLTISSLEPEDFAVYYCQQRSNWPRTFG<br>QGTKVEIK |
| SEQ ID No: 89 | VH 001 | QVQLQQWGAGLLKPSETLSLTCAVYGGSFSGYYWNWIRQPPGKGLEWI<br>GEINHSGSTNYNPSLKSRVTISVDTSKNQFSLKLSSVTAADTAVYYCARG<br>NYGSGYYYFDLWGRGTQVTVSS |
| SEQ ID No: 90 | VL 001 | DIQMTQSPSSLSASVGDRVTITCRASQGISSWLAWYQQKPEKAPKSLIF<br>AASSLQSGVPSRFSGSGSGTDFTLTISSLQPEDFAMCQQYISFPITFGQ<br>GTRLEIK |
| SEQ ID No: 91 | VH 143 | QVQLQQWGAGLLKPSETLSLTCAVYGGSFSGYYWNWIRQPPGKGLEWI<br>GEIHHSGSANYNPSLMSRVTISVDTSKNQFSLQLSSVTAADTAVYYCAR<br>GYYGSGYYYFDYWGQGTLVTVSS |
| SEQ ID No: 92 | VL 143 | DIQMTQSPSSLSASVGDRVTITCRASQGISSWLAWYQQKPEKAPKSLIY<br>AASRLQSGVPSRFSGSGSGTDFTLTISSLQPEDFAMCQQYNSYPITFG<br>QGTRLEIK |
| SEQ ID No: 93 | VH 019 | QVQLQQWGAGLLKPSETLSLTCAVYGGSFSDYYWNWIRQPPGKGLEWI<br>GEIHHVGSTNYNPSLKSRVTISVDTSKSQFSLKLSSVTAADTAVYYCARG<br>YYDSGVYYFDYWAQGTLVTVSS |
| SEQ ID No: 94 | VL 019 | DIQMTQSPSSLSASVGDRVTITCRASQGISRWLAWYQQKPEKAPKSLIY<br>AASSLRSGVPSRFSGSGSGTDFTLTISSLQPEDFATYYCQQYNSYPITFG<br>QGTRLEIK |

TABLE 3A and 3B-continued

Heavy chain variable region (VH), light chain variable region (VL) sequences of HuMabs 049, 051, 055, 123, 161, 124, 001, 143, 019, 021, 027, 032, 035, 036, 054, 094 (3A) and HuMabs 041, 150, 067, 072, 163, 093, and 044 (3B). The respective CDRs correspond to those underlined in FIGS. 1 and 2, for VH and VL sequences, respectively.

| | | |
|---|---|---|
| SEQ ID No: 95 | VH 021 | QVQLQQWGAGLLKPSETLSLTCAVYGGSFSDYYWNWIRQPPGKGLEWI GEIHHSGSTNYNPSLKSRVTISVDTSKNQFSLKLSSVTAADTAVYYCARG YYASGVYYFDYWGQGTLVTVSS |
| SEQ ID No: 96 | VL 021 | DIQMTQSPSSLSASVGDRVTITCRASQGISSWLAWYQQKPEKAPKSLIY AASSLQSGVPSRFSGSGSGTDFTLTISSLQPEDFAMCQQYNSYPITFG QGTRLEIK |
| SEQ ID No: 97 | VH 027 | QVQLQQWGAGLLKPSETLSLTCAVYGGSFSDYFWNWIRQPPGKGLEWI GEIHHSGSTNYNPSLKSRVTISVDTSKNQFSLNLSSVTAADTAVYYCARG LIGSGYYYFDYWDQGTLVTVSS |
| SEQ ID No: 98 | VL 027 | DIQMTQSPSSLSASVGDRVTITCRASQGISSWLAWYQQKPEKAPKSLIY AASSLQSGVPSRFSGSGSGTDFTLTISSLQPEDFAMCQQYNSYPITFG QGTRLEIK |
| SEQ ID No: 99 | VH 032 | QVQLQQWGAGLLKPSETLSLTCAVYGGSFSGYYWSWIRQPPGKGLEWI GEINHSGDTNYNPSLTSRVTISVDTSKNQFSLKLSSVTAADTAVYYCARL FYGSGIYYFDYWGQGTLVTVSS |
| SEQ ID No: 100 | VL 032 | DIQMTQSPSSLSASVGDRVTITCRASQGISSWLAWYQQKPEKAPKSLIY ATFRLQSGVPSRFSGSGSGTDFTLTISSLQPEDFATYYCQQYNSFPPTFG QGTKVEIK |
| SEQ ID No: 101 | VH 035 | QVQLQQWGAGLLKPSETLSLTCAIYGGSFSGYYWSWIRQPPGKGLEWI GEINHSGDTNYNPSLTSRVTISVDTSKNQFSLKLSSVTAADTAVYYCARL FYGSGIYYFDYWGQGTLVTVSS |
| SEQ ID No: 102 | VL 035 | DIQMTQSPSSLSASVGDRVTITCRASQGISSWLAWYQQKPEKAPKSLIY ATFRLQSGVPSRFSGSGSGTDFTLTISSLQPEDFATYYCQQYNSFPPTFG QGTKVEIK |
| SEQ ID No: 103 | VH 036 | QVQLQQWGAGLLKPSETLSLTCAVYGGSFSDYYWSWIRQPPGKGLEWI GEINHSGSTNYNPSLKSRVTISVDTSKNQFSLKLSSVTAADTAVYYCARL YYGSGTYYFDYWGQGTLVTVSS |
| SEQ ID No: 104 | VL 036 | DIQMTQSPSSLSASVGDRVTITCRASQGISSWLTWYQQKPEKAPKSLIY AASRLQSGVPSRFSGSGSGTDFTLTISSLQPEDFATYYCQQYNSFPPTFG QGTKVEIK |
| SEQ ID No: 105 | VH 054 | QVQLQQWGAGLLKPSETLSLTCAVYGGSFSGYYWSWIRQPPGKGLEWI GEIHHSGSTNYNPSLKSRVTISVDTSKNQFSLKLSSVTAADTAVYYCARL WYGSGSYYFDYWGQGTLVTVSS |
| SEQ ID No: 106 | VL 054 | DIQMTQSPSSLSASVGDRVTITCRASQGISSWLAWYQQKPEKAPKSLIY AASSLQSGVPSRFSGSGSGTDFTLTISSLQPEDFATYYCQQYNSFPPTFG GGTKVEIK |
| SEQ ID No: 107 | VH 094 | QVQLQQWGAGLLKPSETLSLTCAVSGGSFSGYYWTWIRQPPGKGLEWI GEIYHSGDTNYNPSLKSRVTISVDTSKNQFSLKLYSVTAADTAVYYCARL YFGSGIYYLDYWGQGTLVTVSS |
| SEQ ID No: 108 | VL 094 | DIQMTQSPSSLSASVGDRVTITCRASQGISSWLVWYQQKPEKAPKSLIY AASSLQSGVPSRFSGSGSGTDFTLTISSLQPEDFATYYCQQYNSFPPTFG QGTKVEIK |
| SEQ ID No: 109 | VH 105 | EVQLLESGGGLVQPGGSLRLSCAASGFTFSNYGMSWVRQAPGKGLEWV SAISGSAYSTYYADSVKGRFTISRDNSKNTLWLQMNSLRAEDTAVYYCA KAHYHGSGSYYTLFDYWGQGTLVTVSS |
| SEQ ID No: 110 | VL 105 | DIQMTQSPSSLSASVGDRVTITCRASQGISSWLAWYQQKPEKAPKSLIY AASSLQSGVPSRFSGSGSGTDFTLTISSLQPEDFATYYCQQYNSYPYTFG QGTKLEIK |
| SEQ ID No: 111 | VH 100 | EVQLLESGGGLVQPGGSLRLSCAASGFTFNNYGMNWVRQAPGKGLEW VSAISGTGYSTYYADSVKGRFTISRDNSKNTLYLQMNSLRAEDTAVYYC AKAHYFGSGSYYTLFDYWGQGTLVTVSS |
| SEQ ID No: 112 | VL 100 | DIQMTQSPSSLSASVGDRVTITCRASQGISSWLAWYQQKPEKAPKSLIY AASSLQSGVPSRFSGSGSGTDFTLTISSLQPEDFATYYCQQYNSYPYTFG QGTKLEIK |

TABLE 3A and 3B-continued

Heavy chain variable region (VH), light chain variable region (VL) sequences of HuMabs 049, 051, 055, 123, 161, 124, 001, 143, 019, 021, 027, 032, 035, 036, 054, 094 (3A) and HuMabs 041, 150, 067, 072, 163, 093, and 044 (38). The respective CDRs correspond to those underlined in FIGS. 1 and 2, for VH and VL sequences, respectively.

| | | |
|---|---|---|
| SEQ ID No: 113 | VH 125 | EVQLLESGGGLVQPGGSLRLSCAASGFTFTDYAMNWVRQAPGKGLEWV STISGSGYATYYADSVKGRFTISRDNSKTTLYLQMNSLRAEDTAVYYCAK GHTLGSGSYYTLFDYWGQGTLVTVSS |
| SEQ ID No: 114 | VL 125 | DIQMTQSPSSLSASVGDRVTITCRASQGINSWLAWYQQKPEKAPKSLIY AASSLQSGVPSRFSGSGSGTDFTLTISSLQPEDFATYYCQQYNSYPYTFG QGTKLEIK |
| SEQ ID No: 115 | VH 162 | EVQLWESGGGSVQPGGSLRLSCAASGFTFSSYGMSWVRQAPGKGLEW VSGISGSGYSTYYADSVKGRFTISRDNSKNTLYLQMNSLRAEDTAVYYC AKGYYHGSGSYYTSFDYWGQGTLVTVSS |
| SEQ ID No: 116 | VL 162 | DIQMTQSPSSLSASVGDRVTITCRASQGISSWLAWYQQKPEKAPKSLIY AASSLQSGVPSRFSGSGSGTDFTLTISSLQPEDFATYYCQQYNSYPLTFG GGTKVEIK |
| SEQ ID No: 117 | VH 033 | QVQLVESGGGVVQTGRSLRLSCAASGFTFSSHAMHWVRQAPGKGLEW VAAISYDGSNKYYADSVKGRFTISRDNSKNTLYLQMNSLRAEDTAVYYC ARGDYISSSGVFDYWGQGTLVTVSS |
| SEQ ID No: 118 | VL 033 | DIQMTQSPSSLSASVGDRVTITCRASQGISSWLAWYQQKPEKAPKSLIY AASSLQSGVPSRFSGSGSGTDFTLTISSLQPEDFATYYCQQYNSYPITFG QGTRLEIK |
| SEQ ID No: 119 | VH 160 | QVQLVESGGGVVQPGRSLRLSCAASGFTFSSHAMHWVRQAPGKGLEW VAAISYDGSNKYYADSVKGRFTISRDNSKNTMYLQMNSLRAEDTAMCY CARGSITGSTGVFDYWGQGTLVTVSS |
| SEQ ID No: 120 | VL 160 | DIQMTQSPSSLSASVGDRVTITCRASQDISSWLAWYQQKPEKAPKSLIY AASSLQSGVPSRFSGSGSGTDFTLTISSLQPEDFATYYCQQYNSYPITFG QGTRLEIK |
| SEQ ID No: 121 | VH 166 | QVQLVESGGGVVQPGRSLRLSCAASGFTFSSYAMHWVRQAPGKGLEW VAVISYDGSNEYYADSVKGRFTISRDNSKNTLYLQMNSLRAEDTAVYYC ARGSIIGSTGVFDYWGQGTLVTVSS |
| SEQ ID No: 122 | VL 166 | DIQMTQSPSSLSASVGDRVTITCRASQGISNWLAWYQQKPEKAPKSLIY DASSLQSGVPSRFSGSGSGTDFTLTISSLQPEDFATYYCQQYNSYPITFG QGTRLEIK |
| SEQ ID No: 123 | VH 152 | QVQVVESGGGVVQPGRSLRLSCAASGFTFSSYAMHWVRQAPGKGLEW VAVISYDGSYKYYADSVKGRFTISRDNSKNTLYLQMNSLRAEDTAVYYC ARGSITGSTGVFDYWGQGTLVTVSS |
| SEQ ID No: 124 | VL 152 | DIQMTQSPSSLSASVGDRVTITCRASQGINSWLAWYQQKPEKAPKSLIY DASSLQSGVPSRFSGSGSGTDFTLTISSLQPENFATYYCQQYNSYPITFG QGTRLEIK |
| SEQ ID No: 125 | VH 167 | QVQLVESGGGVVQPGRSLRLSCAASGFTFSSYAIHWVRQAPGKGLEWV AVISYDGSNKYYADSVKGRFTISRDNSKNTLYLQMNSLRAEDTAVYYCA RGSITGSTGVFDYWGQGTLVTVSS |
| SEQ ID No: 126 | VL 167 | DIQMTQSPSSLSASVGDRVTITCRASQGISNWLAWYQQKPEKAPKSLIY DASSLQSGVPSRFSGSGSGTDFTLTISSLQPEDFATYYCQQYNSYPITFG QGTRLEIK |
| | 3B: | |
| SEQ ID No: 207 | VH 041 | EVQLVQSGAEVKKPGESLKISCKGSGYSFTSYWIGWVRQMPGKGLEWM GSIYPGDSHTRYRPSFQGQVTISADKSISTAYLQWSSLKASDTAMYYCA RQKGDFYYFFGLDVWGQGTAITVSS |
| SEQ ID No: 208 | VL 041 | EIVLTQSPGTLSLSPGERATLSCRASQSVSSSYLAWYQQKPGQAPRLLIY GASSRATGIPDRFSGSGSGTDFTLTISRLEPEDFAVYYCQQYGSSLTFGG GTKVEIK |
| SEQ ID No: 209 | VH 150 | EVQLVQSGAEVKKPGESLKISCKGSGYSFTSYWIGWVRQMPGKGLEWM GSIYPGDSHTRYRPSFQGQVTISADKSISTAYLQWSSLKASDTAMYYCA RQAGDYYYYNGDVWGQGTTVTVSS |
| SEQ ID No: 210 | VL 150 | EIVLTQSPGTLSLSPGERATLSCRASQSVSSSYLTWYQQKPGQAPRLLIY GASSRATGIPDRFSGSGSGTDFTLTISRLEPEDFAVYYCQQYGSSLTFGG GTKVEIK |

TABLE 3A and 3B-continued

| Heavy chain variable region (VH), light chain variable region (VL) sequences of HuMabs 049, 051, 055, 123, 161, 124, 001, 143, 019, 021, 027, 032, 035, 036, 054, 094 (3A) and HuMabs 041, 150, 067, 072, 163, 093, and 044 (38). The respective CDRs correspond to those underlined in FIGS. 1 and 2, for VH and VL sequences, respectively. | | |
|---|---|---|
| SEQ ID No: 211 | VH 067 | EVQLVQSGAEVKKPGESLKISCKGSGYSFTSYWIGWVRQMPGKGLEWM GIIYPGDSDTRYSPSFQGQVTISVDKSISTAYLQWSSLKASDTAMYYCAR QKGDYYYHYGLDVWGQGTTVTVSS |
| SEQ ID No: 212 | VL 067 | EIVLTQSPGTLSLSPGERATLSCRASQSVSSSYLAWYQQKPGQAPRLLIY GASSRATGIPDRFSGSGSGTDFTLTISRLEPEDFAVYYCQQYGSSPRLTF GGGTKVEIK |
| SEQ ID No: 213 | VH 072 | EVQLVQSGAEVKKPGESLKISCKGSGYSFTSYWIGWVRQMPGKGLEWM GIIYPGDSDTRYSPSFQGQVTISADKSISTAYLQWSSLKASDTAMYYCAR QKGDYYYFNGLDVWGQGTTVTVSS |
| SEQ ID No: 214 | VL 072 | EIVLTQSPGTLSLSPGERATLSCRASQSVSSSYLAWYQQKPGQAPRLLIY GASSRATGIPDRFSGSGSGTDFTLTISRLEPEDFAVYYCQQYGSSPRLTF GGGTKVEIK |
| SEQ ID No: 215 | VH 163 | EVQLVQSGAEVKKPGESLKISCQGSGYRFISYWIGWVRQMPGKGLEWM GRIYPGDSDTRYSPSFQGQVTISVDKSISTAYLQWSSLKASDTAMYYCA RQRGDYYYFNGLDVWGQGTTVTVSS |
| SEQ ID No: 216 | VL 163 | EIVLTQSPGTLSLSPGERATLSCRASQSVSSSYLAWYQQKPGQAPRLLIY GASSRATGIPDRFSGSGSGTDFTLTISRLEPEDFAVYYCQQYGSSLTFGG GTKVEIK |
| SEQ ID No: 217 | VH 093 | EVQLVQSGAEVKKPGESLKISCKGSGYSFTSYWIGWVRQMPGKGLEWM GRIYPGDSDTRYSPSFQGQVTISADKSITTAYLQWSSLRASDTAMYYCA RQRGDYYYFFGLDIWGQGTTVTVSL |
| SEQ ID No: 218 | VL 093 | EIVLTQSPGTLSLSPGERATLSCRASQSVSSSYLAWYQQKPGQAPRLLIY GASSRATGIPDRFSGSGSGTDFTLTISRLEPEDFAVYYCQQYGSSLTFGG GTKVEIK |
| SEQ ID No: 219 | VH 044 | EVQLVQSGAEVKKPGESLKISCKGSGYRFSSYWIGWVRQMPGKGLEWM GSIFPGDSDTRYSPSFQGQVTISADKSITTAYLQWSSLKASDTAMYYCA RQAGDYYYYNGMDVWGQGTTVTVSS |
| SEQ ID No: 220 | VL 044 | EIVLTQSPGTLSLSPGERATLSCRASQSVSSSYLAWYQQKPGQAPRLLIY GASSRATGIPDRFSGSGSGTDFTLTISRLEPEDFAVYYCQQYGSSLTFGG GTKVEIK |

TABLE 4

| Consensus CDRs based on sequence alignments shown in FIGS. 1 and 2. | | | | |
|---|---|---|---|---|
| SEQ ID No: 9 050-049-051-055 | IgHV3-23-1 | VH CDR1 | GFTFSSYA | |
| SEQ ID No: 127 050-049-051-055 | IgHV3-23-1 | VH CDR2 | ISGX1GGX2T | Wherein X1 = R or S, and X2 = T or S; preferably, wherein X1 = R and X2 = T |
| SEQ ID No: 11 050-049-051-055 | IgHV3-23-1 | VH CDR3 | AKARANWDYFDY | |
| SEQ ID No: 128 084 | IgHV1-69-04 | VH CDR1 | GGTFX1X2YA | Wherein X1 = R or S, and X2 = T or S; preferably, wherein X1 = R and X2 = T |
| SEQ ID No: 129 084 | IgHV1-69-04 | VH CDR2 | IX1X2X3LGIX4 | Wherein X1 = N or I, X2 = T or P, X3 = V or I, and X4 = V or A, preferably, wherein X1 = N, X2 = T, X3 = V, and X4 = V |
| SEQ ID No: 130 084 | IgHV1-69-04 | VH CDR3 | AREKGVDYYYGX1 X2 | Wherein X1 = I or M, X2 = E or D; preferably, wherein X1 = I, X2 = E |
| SEQ ID No: 131 169-123-161-124 | IgHV1-18-1 | VH CDR1 | GYTFTXYG | Wherein X = N or S, preferably N |
| SEQ ID No: 132 169-123-161-124 | IgHV1-18-1 | VH CDR2 | IX1X2YX3GNT | Wherein X1 = S, T, or I; X2 = A or T; X3 = S or N; preferably, wherein X1 = S, X2 = A, and X3 = S |

TABLE 4-continued

| Consensus CDRs based on sequence alignments shown in FIGS. 1 and 2. | | | | |
|---|---|---|---|---|
| SEQ ID No: 133 169-123-161-124 | IgHV1-18-1 | VH CDR3 | ARDRX1X2VRPDY FDY | Wherein X1 = I or V, X2 = V or I; preferably, wherein X1 = I and X2 = V |
| SEQ ID No: 134 025-001-143-019-021-027 | IgHV4-34-01 | VH CDR1 | GGSFSX1YX2 | Wherein X1 = D or G and X2 = Y or F; preferably, wherein X1 = D and X2 = Y |
| SEQ ID No: 135 025-001-143-019-021-027 | IgHV4-34-01 | VH CDR2 | IX1HX2GSX3 | Wherein X1 = H or N, X2 = S or V, and X3 = T or A; preferably, wherein X1 = H, X2 = S, and X3 = T |
| SEQ ID No:136 025-001-143-019-021-027 | IgHV4-34-01 | VH CDR3 | ARGX1X2X3SGX4 YYFDX5 | Wherein X1 = Y, N or L; X2 = Y or I, X3 = D, G or A; X4 = V or Y; and X5 = Y or L; preferably, wherein X1 = Y, X2 = Y, X3 = D, X4 = V, and X5 = Y |
| SEQ ID No: 137 091-032-035-036-054-094 | IgHV4-34-01 | VH CDR1 | GGSFSX1YY | Wherein X1 = G or D, preferably G |
| SEQ ID No: 138 091-032-035-036-054-094 | IgHV4-34-01 | VH CDR2 | IX1HSGX2T | Wherein X1 = Y, N or H; and X2 = D or S; preferably, wherein X1 = Y and X2 = D |
| SEQ ID No: 139 091-032-035-036-054-094 | IgHV4-34-01 | VH CDR3 | ARLX1X2GSGX3Y YX4DY | Wherein X1 = Y, F or W; X2 = F or Y; X3 = I, T or S; and X4 = L or F; preferably, wherein X1 = Y, X2 = F, X3 = I, and X4 = L |
| SEQ ID No: 140 129 | IgHV3-30-01 | VH CDR1 | GFTFSX1X2A | Wherein X1 = T or F, X2 = F or Y; preferably, wherein X1 = T and X2 = F |
| SEQ ID No: 141 129 | IgHV3-30-01 | VH CDR2 | ISYDGX1X2K | Wherein X1 = G or S, X2 = H or N; preferably, wherein X1 = G and X2 = H |
| SEQ ID No: 142 129 | IgHV3-30-01 | VH CDR3 | ARGLGVWGX1FD Y | Wherein X1 = A or Y, preferably A |
| SEQ ID No: 143 098-105-100-125-162 | IgHV3-23-01 | VH CDR1 | GFTFX1X2YX3 | Wherein X1 = S, N or T; X2 = N, D or S; and X3 = G or A; preferably, wherein X1 = S, X2 = N and X3 = G |
| SEQ ID No: 144 098-105-100-125-162 | IgHV3-23-01 | VH CDR2 | ISGX1X2X3X4T | Wherein X1 = S or T, X2 = A or G, X3 = Y or G, X4 = S or A; preferably, wherein X1 = S, X2 = A, X3 = Y, X4 = S |
| SEQ ID No: 145 098-105-100-125-162 | IgHV3-23-01 | VH CDR3 | AKX1X2X3X4GSG SYYTX5FDY | Wherein X1 = A or G; X2 = H or Y; X3 = Y or T; X4 = H, F or L; X5 = L or S; preferably, wherein X1 = A; X2 = H; X3 = Y; X4 = H; X5 = L |
| SEQ ID No: 146 127 | IgHV5-51-01 | VH CDR1 | GYSFX1X2YW | Wherein X1 = S or T, X2 = I or S; preferably, wherein X1 = S, X2 = I |
| SEQ ID No: 147 127 | IgHV5-51-01 | VH CDR2 | IX1PGDSDX2 | Wherein X1 = F or Y, X2 = I or T; preferably, wherein X1 = F, X2 = I |
| SEQ ID No: 148 127 | IgHV5-51-01 | VH CDR3 | ARQPGDWSPRH WYFDL | |
| SEQ ID No: 149 159 | IgHV5-51-01 | VH CDR1 | GYXFTSYW | Wherein X = N or S, preferably N |
| SEQ ID No: 51 159 | IgHV5-51-01 | VH CDR2 | IYPGDSDT | |
| SEQ ID No: 52 159 | IgHV5-51-01 | VH CDR3 | ARWGTYYDILTGY FN | |
| SEQ ID No: 71 132 | IgHV1-18-01 | VH CDR1 | GYTFTSYG | |
| SEQ ID No: 150 132 | IgHV1-18-01 | VH CDR2 | ISAYNGNX | Wherein X = S or T, preferably S |

TABLE 4-continued

| Consensus CDRs based on sequence alignments shown in FIGS. 1 and 2. | | | | |
|---|---|---|---|---|
| SEQ ID No: 151 132 | IgHV1-18-01 | VH CDR3 | AREYSYDSGTYFY YGMDV | |
| SEQ ID No: 152 153-033-160-166-152-167 | IgHV3-30-03-01 | VH CDR1 | GFTFSX1X2X3 | Wherein X1 = D or S, X2 = Y or H, X3 = V or A; preferably, wherein X1 = D, X2 = Y, X3 = V |
| SEQ ID No: 153 153-033-160-166-152-167 | IgHV3-30-03-01 | VH CDR2 | ISYDGSX1X2 | Wherein X1 = N or Y, X2 = K or E, preferably wherein X1 = N and X2 = K |
| SEQ ID No: 154 153-033-160-166-152-167 | IgHV3-30-03-01 | VH CDR3 | ARGX1X2X3X4X5 X6GX7FDY | Wherein X1 = G, D or S; X2 = I or Y; X3 = T or I; X4 = G or S; X5 = T or S; X6 = T or S; X7 = Y or V; preferably, wherein X1 = G; X2 = I; X3 = T; X4 = G; X5 = T; X6 = T; and X7 = V |
| SEQ ID No: 13 050-084-049-051-055 | IgKV1-12-01 | VL CDR1 | QGISSW | |
| 050-084-049-051-055 | IgKV1-12-01 | VL CDR2 | XAS | Wherein X = A or V |
| SEQ ID No: 155 050-084-049-051-055 | IgKV1-12-01 | VL CDR3 | QQANSFPXT | Wherein X = I or L |
| SEQ ID No: 6 169-124-161-123 | IgKV3-11-01 | VL CDR1 | QSVSSY | |
| 169-124-161-123 | IgKV3-11-01 | VL CDR2 | DXS | Wherein X = A or T, preferably A |
| SEQ ID No: 156 169-124-161-123 | IgKV3-11-01 | VL CDR3 | QQRSXWPRT | Wherein X = N or H, preferably N |
| SEQ ID No: 157 025-001-019-143-021-027 | IgKV1D-16-01 | VL CDR1 | QGISXW | Wherein X = R or S, preferably R |
| 025-001-019-143-021-027 | IgKV1D-16-01 | VL CDR2 | AAS | |
| SEQ ID No: 164 025-001-019-143-021-027 | IgKV1D-16-01 | VL CDR3 | QQYNSXPIT | Wherein X = Y or F, preferably Y |
| SEQ ID No: 33 091-032-035-036-054-094 | IgKV1D-16-01 | VL CDR1 | QGISSW | |
| 091-032-035-036-054-094 | IgKV1D-16-01 | VL CDR2 | AX1X2 | Wherein X1 = A or T, and X2 = S or F; preferably, wherein X1 = A and X2 = S |
| SEQ ID No: 158 091-032-035-036-054-094 | IgKV1D-16-01 | VL CDR3 | QQYNSFPPT | |
| SEQ ID No: 159 098-100-105-125-162 | IgKV1D-16-01 | VL CDR1 | QGIXSW | Wherein X = S or N, preferably S |
| 098-100-105-125-162 | IgKV1D-16-01 | VL CDR2 | AAS | |
| SEQ ID No: 160 098-100-105-125-162 | IgKV1D-16-01 | VL CDR3 | QQYNSYPXT | Wherein X = Y or L, preferably Y |
| SEQ ID No: 161 153-152-166-167-160-033 | IgKV1D-16-01 | VL CDR1 | QGIX1X2W | Wherein X1 = S or N; X2 = S or N; preferably, wherein X1 = X2 = S |
| 153-152-166-167-160-033 | IgKV1D-16-01 | VL CDR2 | XAS | Wherein X = D or A, preferably D |

TABLE 4-continued

| Consensus CDRs based on sequence alignments shown in FIGS. 1 and 2. | | | | |
|---|---|---|---|---|
| SEQ ID No: 162 153-152-166-167-160-033 | IgKV1D-16-01 | VL CDR3 | QQYXSYPIT | Wherein X = K or N, preferably K |
| SEQ ID No: 221 005-060-106-041-150-067-072-163-093-044 | IgHV5-51-1 | VH CDR1 | GYX1FX2X3YW | wherein X1 = S or R; X2 = S, T, H, or I; and X3 = S, R, or F; preferably, wherein X2 = H or T |
| SEQ ID No: 222 005-060-106-041-150-067-072-163-093-044 | IgHV5-51-1 | VH CDR2 | IX1PGDSX2T | wherein X1 = Y or F; X2 = D, Y, or H preferably, wherein X2 = D or Y |
| SEQ ID No: 223 005-060-106-041-150-067-072-163-093-044 | IgHV5-51-1 | VH CDR3 | ARX1X2X3X4X5X6X7X8YX9X10GX11DX12 | wherein X1 = Q, H, or L; X2 = R, A, T, or K; X3 = G; X4 = D; X5 = R or none; X6 = G or none; X7 = Y or F; X8 = Y or D; X9 = Y, F, or H; X10 = Y, D, S, F, or N; X11 = M or L; and X12 = V or I; preferably, wherein X1 = Q, X2 = R or A; X5 = X6 = none; X7 = Y or F; X8 = Y; X9 = F; X10 = Y; and X12 = V |
| SEQ ID No: 224 006 | IgHV3-23-1 | VH CDR1 | GFTFSXYA | wherein X = N or S, preferably N |
| SEQ ID No: 225 006 | IgHV3-23-1 | VH CDR2 | IX1GX2X3GST | wherein X1 = R or S; X2 = G or S; and X3 = A or G, preferably wherein X1 = R; X2 = G; and X3 = A |
| SEQ ID No: 226 006 | IgHV3-23-1 | VH CDR3 | AKRIWGPXFDY | wherein X = L or Y, preferably L |
| SEQ ID No: 227 059 | IgHV1-18-1 | VH CDR1 | GYTFTXYG | wherein X = R or S. preferably R |
| SEQ ID No: 228 059 | IgHV1-18-1 | VH CDR2 | ISAYNGXT | wherein X = K or N, preferably K |
| SEQ ID No: 229 059 | IgHV1-18-1 | VH CDR3 | ARSPLLWFEELYFDY | |
| SEQ ID No:230 111 | IgHV1-69-4 | VH CDR1 | GGTFSSYX | wherein X = G or A, preferably G |
| SEQ ID No: 202 111 | IgHV1-69-4 | VH CDR2 | IIPILGIA | |
| SEQ ID No: 231 111 | IgHV1-69-4 | VH CDR3 | ARDQEYSSX1X2X3 | wherein X1 = N or Y; X2 = W or F; and X3 = Y or D, preferably wherein X1 = N; X2 = W; and X3 = Y |
| SEQ ID No: 232 005-059-060-106-111-041-150-067-072-163-093-044 | IgKV3-20-01 | VL CDR1 | QSVX1SX2Y | wherein X1 = S or R and X2 = S or T |
| 005-059-060-106-111-041-150-067-072-163-093-044 | IgKV3-20-01 | VL CDR2 | GAS | |
| SEQ ID No: 233 005-059-060-106-111-041-150-067-072-163-093-044 | IgKV3-20-01 | VL CDR3 | QX1YGX2SX3X4X5T | wherein X1 = Q or L; X2 = S or T; X3 = P or none; X4 = P, L, R, or none; and X5 = L, F, I, or none; preferably, wherein X4 = P, L, or none |
| SEQ ID No: 177 006 | IgKV3-11-01 | VL CDR1 | QSVSSY | |
| 006 | IgKV3-11-01 | VL CDR2 | DAS | |
| SEQ ID No: 178 006 | IgKV3-11-01 | VL CDR3 | QQRSNWPPLT | |

Example 11

Purification of Antibodies

Culture supernatant was filtered over 0.2 μm dead-end filters, loaded on 5 mL MabSelect SuRe columns (GE Health Care) and eluted with 0.1 M sodium citrate-NaOH, pH 3. The eluate was immediately neutralized with 2M Tris-HCl, pH 9 and dialyzed overnight to 12.6 mM NaH2PO4, 140 mM NaCl, pH 7.4 (B. Braun). Alternatively, subsequent to purification, the eluate was loaded on a HiPrep Desalting column and the antibody was exchanged into 12.6 mM NaH2PO4, 140 mM NaCl, pH 7.4 (B. Braun) buffer. After dialysis or exchange of buffer, samples were sterile filtered over 0.2 μm dead-end filters. Purity was determined by SDS-PAGE and concentration was measured by nephelometry and absorbance at 280 nm. Purified antibodies were stored at 4° C. Mass spectrometry was performed to identify the molecular mass of the antibody heavy and light chains expressed by the hybridomas as described in Example 9.

Example 12

Binding of HER2 Clones to Tumor Cells Expressing Membrane-Bound HER2 Measured by Means of FACS Analysis The binding of HER2 antibodies to AU565 cells (purchased at ATCC, CRL-2351) and A431 cells (purchased at ATCC, CRL-1555), was tested using flow cytometry (FACS Canto II, BD Biosciences). Qifi analysis (Dako, Glostrup, Denmark) revealed that AU565 cells expressed on average 1,000,000 copies of HER2 protein per cell, whereas A431 cells expressed on average 15,000 copies per cell. Binding of HER2 antibodies was detected using a Phycoerythrin (PE)-conjugated goat-anti-human IgG antibody (Jackson). Trastuzumab (clinical-grade Herceptin®) was used as positive control antibody, and an isotype control antibody was used as negative control antibody. $EC_{50}$ values were determined by means of non-linear regression (sigmoidal dose-response with variable slope) using GraphPad Prism V4.03 software (GraphPad Software, San Diego, Calif., USA).

Figure 3E:
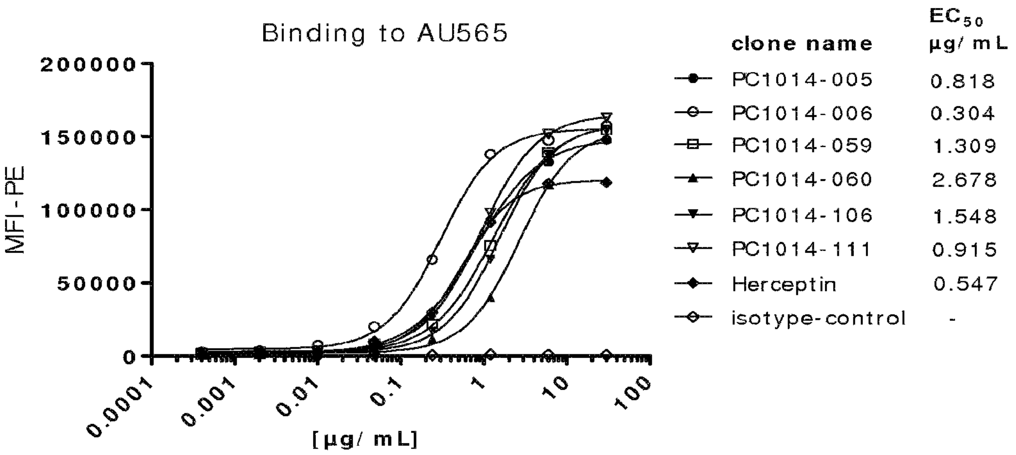
Figure 3F:
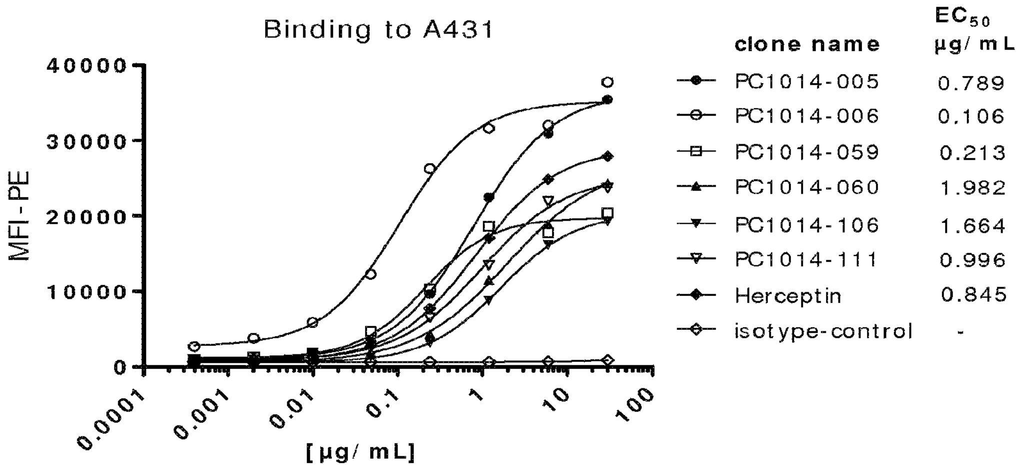

All tested HER2 antibodies bound to HER2 expressed on both AU565 and A431 cells in a dose-dependent manner. For antibodies of cross-block groups 1, 2 and 3, the $EC_{50}$ values for binding varied between 0.336-2.290 μg/mL for AU565 cells and 0.068-1.135 μg/mL for A431 cells (FIG. 3A-D). For antibodies of cross-block group 4, the $EC_{50}$ values for binding varied between 0.304-2.678 μg/mL for AU565 cells and 0.106-1.982 μg/mL for A431 cells (FIGS. 3E and F). Especially on A431 cells, large differences in $EC_{50}$ values were observed between the tested antibodies. However, antibody 098 had the best (i.e., lowest) $EC_{50}$ value on both types of cells. Also some differences in maximum binding levels were observed between different antibodies, on both AU565 and A431 cells. Of the tested cross-block groups 1-3 antibodies, antibody 098 also had the highest maximum binding level on AU565 cells, whereas antibody 025 had the highest maximum binding level on A431 cells. For antibodies of cross-block group 4, antibodies 005 and 006 demonstrated higher maximum binding levels on A431 as compared to other HER2 antibodies.

Example 13

Binding of HER2 Antibodies to Membrane-Bound HER2 Expressed on Rhesus Epithelial Cells Measured by Means of FACS Analysis To determine cross-reactivity with Rhesus HER2, the binding of HER2 antibodies to HER2-positive Rhesus epithelial cells (4MBr-5 purchased at ATCC) was tested using flow cytometry (FACS Canto II, BD Biosciences). A Phycoerythrin-conjugated goat-anti-human IgG antibody (Jackson) was used as a secondary conjugate. An isotype control antibody was used as negative control antibody.

Figure 4A:
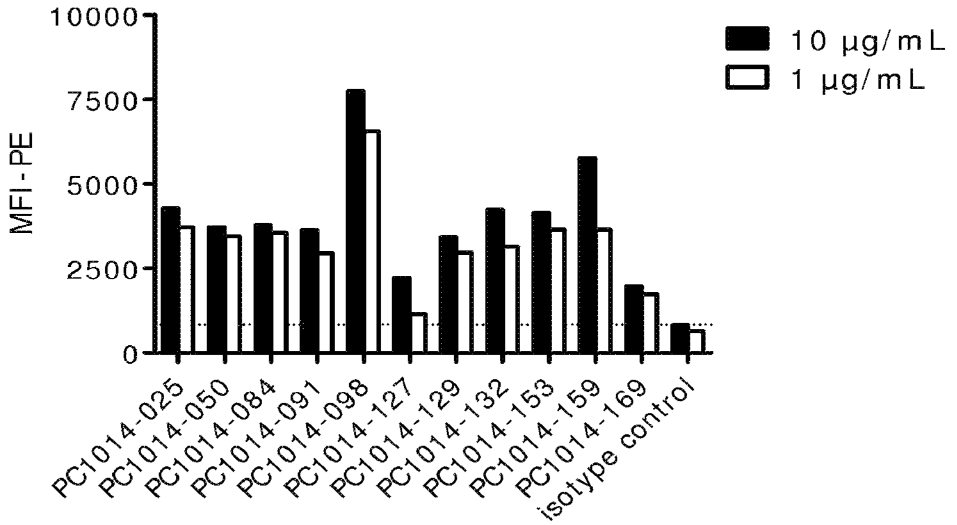
FIGS. 4A and 4B: Binding of HER2 antibodies to HER2 expressed on monkey Rhesus epithelial cells. Data shown are mean fluorescence intensities (MFI) of one experiment, described in Example 13.
Figure 4B:
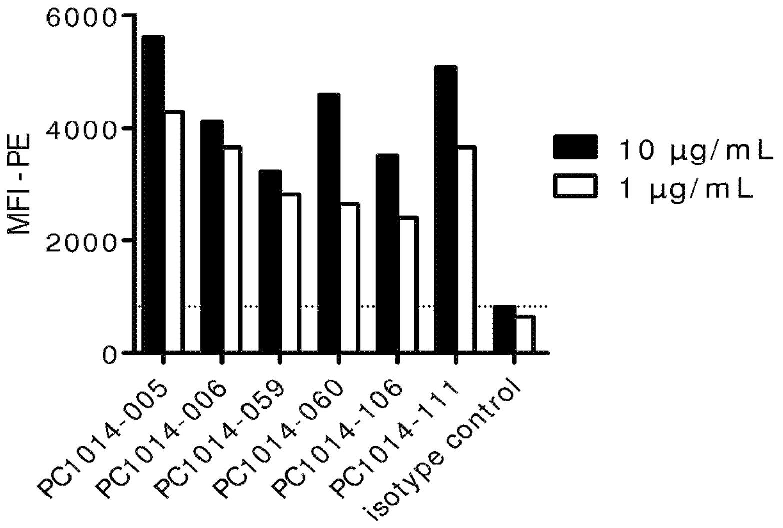

All tested HER2 antibodies were cross-reactive with Rhesus monkey HER2 (FIGS. 4A and B). At both tested concentrations (1 μg/mL and 10 μg/mL), the HER2 antibodies were able to bind specifically to Rhesus monkey HER2. Antibody 127 demonstrated poor binding at 1 μg/mL concentration, but showed good binding at 10 μg/mL concentration. Antibody 098 had the highest binding level at both antibody concentrations. No binding was observed with the isotype control antibody.

Example 14

Competition of HER2 Antibodies for Binding to Soluble Her2ECDHis Measured in Sandwich-ELISA The optimal coating concentrations of the tested HER2 antibodies and optimal Her2ECDHis concentration were determined in the following manner: ELISA wells were coated overnight at 4° C. with HER2 HuMabs serially diluted in PBS (0.125-8 μg/mL in 2-fold dilutions). Next, the ELISA wells were washed with PBST (PBS supplemented with 0.05% Tween-20 [Sigma-Aldrich, Zwijndrecht, The Netherlands]) and blocked for one hour at room temperature (RT) with PBSTC (PBST supplemented 2% [v/v] chicken serum [Gibco, Paisley, Scotland]). The ELISA wells were then washed with PBST and incubated for one hour at RT with Her2ECDHis serially diluted in PBSTC (0.25-2 μg/mL in 2-fold dilutions). Unbound Her2ECDHis was washed away with PBST, and bound Her2ECDHis was incubated for one hour at RT with 0.25 μg/mL biotinylated rabbit-anti-6× his-biot (Abcam, Cambridge, UK). The plate was thereafter washed with PBST and incubated for one hour with 0.1 μg/mL Streptavidin-poly-HRP (Sanquin, Amsterdam, The Netherlands) diluted in PBST. After washing, the reaction was visualized through a 15 minutes incubation with 2,2'-azino-bis (3-ethylbenzothiazoline-6-sulfonic acid) (ABTS: one ABTS tablet diluted in 50 mL ABTS buffer (Roche Diagnostics, Almere, The Netherlands)) at RT protected from light. The colorization was stopped by adding an equal volume of oxalic acid (Sigma-Aldrich, Zwijndrecht, The Netherlands). Fluorescence at 405 nm was measured on a microtiter plate reader (Biotek Instruments, Winooski, USA). The antibody concentrations that resulted in sub-optimal binding of each antibody were determined and used for the following cross-block experiments.

Each HER2 antibody was coated to the ELISA wells at the sub-optimal dose that was determined as described above. After blocking of the ELISA wells, the wells were incubated with the predetermined concentration of 1 μg/mL biotinylated Her2ECDHis in the presence or absence of an excess of a second (competitor) HER2 antibody. The ELISA was then performed as described above. Residual binding of Her2ECDHis to the coated antibody was expressed as a percentage relative to the binding observed in the absence of competitor antibody. Percentage competition was then determined as 100 minus the percentage of inhibition. 75% competition was considered as complete cross-block, whereas 25-74% competition was considered as partial cross-block, and 0-24% competition was considered non-blocking.

Cross-Block Groups 1, 2 and 3:

As shown in Table 5A, all HER2 antibodies of these groups were found to be able to block binding to Her2ECDHis, at least partially, for themselves. After dividing the antibodies into 3 major cross-block groups, all antibodies were tested for competition with at least one representative antibody from each group.

The first group comprised trastuzumab and antibodies 169, 050 and 084, which blocked each other for binding to Her2ECDHis, but did not cross-block antibodies from other groups.

The second group comprised pertuzumab and antibodies 025, 091 and 129, which blocked each other for binding to Her2ECDHis, except for antibodies 129 and 091 which both cross-blocked pertuzumab and 025, but not each other. None of the antibodies of group 2 blocked antibodies from other groups.

A third group comprised antibodies C1, F5, 127, 098, 132, 153 and 159, which did not cross-block any antibody from the other groups. Within this group 3, some variation was observed. Antibody 127 was the only antibody that was able to cross-block all other antibodies in this group for binding to Her2ECDHis; antibody 159 cross-blocked all other antibodies within this group, except 132; clone 098 cross-blocked all antibodies of group 3, except 132 and 153; antibody 153 cross-blocked 127, 132 and 159 for binding to Her2ECDHis, but not 098, C1 or F5; clone 132 cross-blocked 127, 132 and 153. When added as competitor antibodies, F5 and C1 only demonstrated cross-blocking of each other. However, the reverse reaction also revealed competition with antibodies 127, 098 and 159, but not 153 and 132. Possibly, these differences may have resulted from lower affinities of antibodies Cl and F5 for Her2ECDHis.

Values higher than 100% can be explained by avidity effects and the formation of antibody-Her2ECDHis complexes containing two non-competing antibodies.

Cross-Block Group 4:

As shown in Table 5, all HER2 antibodies of this group competed for binding to Her2ECDHis, at least partially, with themselves. Trastuzumab (clinical grade Herceptin®) and pertuzumab (TH1014-pert, transiently produced in HEK-293 cells) could only compete with themselves, and not with any of the other listed HER2 antibodies of cross-block group 4. C1 and F5 (both transiently produced in HEK-293 cells) competed with each other for binding to Her2ECDHis, but did not compete with other HER2 antibodies of cross-block group 4.

Antibodies 005, 006, 059, 060, 106 and 111 all competed with each other for binding to Her2ECDHis, but did not cross-block with trastuzumab, pertuzumab, C1 or F5. Clones 005, 059, 060 and 106 only blocked 006 when 006 was the competitor antibody. In the reverse reaction where 006 was immobilized, no blocking was found with 005, 059, 060 or 106. This was possibly a result of the higher apparent affinity of clone 006 compared to 005, 059, 060, 106 and 111, shown in FIGS. 3A and 3B. Values higher than 100% can be explained by avidity effects and the formation of antibody-Her2ECDHis complexes containing two non-blocking antibodies.

TABLE 5

Competition and cross-blocking of HER2 antibodies for binding to Her2ECDHis

5A:

| Immobilized mAb | Competing mAb: tras | 169 | 050 | 084 | pert | 025 | 091 | 129 | C1 | F5 | 127 | 159 | 098 | 153 | 132 |
|---|---|---|---|---|---|---|---|---|---|---|---|---|---|---|---|
| Trastuzumab | 6 | 15 | 6 | 51 | 100 | 107 | 100 | 85 | 103 | 99 | 115 | 90 | 101 | 101 | 101 |
| TH1014-169 | 19 | 45 | 21 | 73 | 101 | 98 | 105 | 106 | ND | ND | ND | ND | 105 | 102 | ND |
| TH1014-050 | 13 | 30 | 12 | 74 | 95 | 104 | 98 | 110 | ND | ND | ND | ND | 102 | 104 | ND |
| TH1014-084 | 74 | 73 | 76 | 20 | 101 | 106 | 104 | 104 | ND | ND | ND | ND | 109 | 98 | ND |
| TH1014-pert | 104 | 100 | 94 | 95 | 9 | 20 | 19 | 39 | 106 | 125 | 116 | 81 | 103 | 100 | 109 |
| TH1014-025 | 98 | 98 | 100 | 104 | 8 | 18 | 21 | 15 | ND | ND | ND | ND | 102 | 99 | ND |
| TH1014-091 | 99 | 99 | 95 | 100 | 5 | 13 | 15 | 78 | ND | ND | ND | ND | 98 | 98 | ND |
| TH1014-129 | 93 | 99 | 97 | 92 | 22 | 55 | 76 | 12 | ND | ND | ND | ND | 106 | 98 | ND |
| TH1014-C1 | 89 | ND | ND | ND | ND | ND | ND | ND | 65 | 58 | 73 | 53 | 58 | 77 | 90 |
| TH1014-F5 | 197 | ND | ND | ND | ND | ND | ND | ND | 70 | 21 | 62 | 15 | 16 | 80 | 125 |
| TH1014-127 | 102 | ND | ND | ND | ND | ND | ND | ND | 112 | 88 | 11 | 8 | 58 | 21 | 44 |
| TH1014-159 | 111 | ND | ND | ND | 112 | ND | ND | ND | 96 | 86 | 15 | 6 | 11 | 40 | 79 |
| TH1014-098 | 107 | 102 | 100 | 103 | 104 | 108 | 104 | 107 | 125 | 96 | 21 | 9 | 17 | 110 | 142 |
| TH1014-153 | 134 | 111 | 103 | 107 | 121 | 97 | 102 | 106 | 257 | 96 | 27 | 23 | 115 | 28 | 33 |
| TH1014-132 | 353 | ND | ND | ND | 288 | ND | ND | ND | 422 | 379 | 30 | 131 | 309 | 41 | 32 |
| Cross-block group | 1 | 1 | 1 | 1 | 2 | 2 | 2 | 2b | 3a | 3a | 3a | 3a | 3a | 3b | 3b |

5B:

| Immobilized mAb | Competing mAb: Tras | Pert | C1 | F5 | 106 | 111 | 005 | 006 | 059 | 060 |
|---|---|---|---|---|---|---|---|---|---|---|
| Trastuzumab | 6 | 100 | 103 | 99 | 114 | 166 | 137 | 110 | 120 | 119 |
| TH1014-pert | 104 | 9 | 106 | 125 | 115 | 145 | 151 | 125 | 132 | 118 |
| TH1014-C1 | 89 | 85 | 65 | 58 | 84 | 86 | 98 | 99 | 89 | 93 |
| TH1014-F5 | 197 | 178 | 70 | 21 | 129 | 183 | 178 | 192 | 165 | 185 |

TABLE 5-continued

| Competition and cross-blocking of HER2 antibodies for binding to Her2ECDHis | | | | | | | | | | |
|---|---|---|---|---|---|---|---|---|---|---|
| PC1014-106 | 323 | 275 | 471 | 495 | 26 | 21 | 25 | 25 | 25 | 23 |
| PC1014-111 | 110 | 102 | 122 | 119 | 75 | 14 | 51 | 10 | 65 | 36 |
| PC1014-005 | 126 | 115 | 157 | 227 | 54 | 32 | 18 | 15 | 22 | 12 |
| PC1014-006 | 163 | 136 | 136 | 153 | 127 | 47 | 148 | 20 | 129 | 125 |
| PC1014-059 | 117 | 107 | 78 | 128 | 23 | 12 | 13 | 11 | 12 | 11 |
| PC1014-060 | 106 | 99 | 108 | 126 | 37 | 35 | 30 | 6 | 14 | 19 |
| Cross-block group | 1 | 2 | 3 | 3 | 4 | 4 | 4 | 4 | 4 | 4 |

Depicted values are mean percentages of binding relative to the binding observed in the absence of competitor antibody, of two independent experiments. Competition experiments with HEK produced TH1014-C1 and TH1014-F5 were performed once. Trastuzumab (clinical grade Herceptin®) and HEK-produced pertuzumab (TH1014-pert) were also tested.

Example 15

Antibody-Dependent Cell-Mediated Cytotoxicity (ADCC)

SK-BR-3 cells (purchased at ATCC, HTB-30) were harvested ($5\times10^6$ cells), washed (twice in PBS, 1500 rpm, 5 min) and collected in 1 mL RPMI 1640 medium supplemented with 10% cosmic calf serum (CCS) (HyClone, Logan, Utah, USA), to which 200 μCi $^{51}$Cr (Chromium-51; Amersham Biosciences Europe GmbH, Roosendaal, The Netherlands) was added. The mixture was incubated in a shaking water bath for 1.5 hours at 37° C. After washing of the cells (twice in PBS, 1500 rpm, 5 min), the cells were resuspended in RPMI 1640 medium supplemented with 10% CCS, counted by trypan blue exclusion and diluted to a concentration of $1\times10^5$ cells/mL.

Meanwhile, peripheral blood mononuclear cells (PBMCs) were isolated from fresh buffy coats (Sanquin, Amsterdam, The Netherlands) using standard Ficoll density centrifugation according to the manufacturer's instructions (lymphocyte separation medium; Lonza, Verviers, France). After resuspension of cells in RPMI 1640 medium supplemented with 10% CCS, cells were counted by trypan blue exclusion and concentrated to $1\times10^7$ cells/mL.

Trastuzumab was produced in CHO cells resulting in an (increased) non-core fucosylation grade of 12.4%, whereas the other HER2 antibodies were produced in HEK cells, resulting on average in 4% non-core fucosylation.

For the ADCC experiment, 50 μL $^{51}$Cr-labeled SK-BR-3 cells (5.000 cells) were pre-incubated with 15 μg/mL HER2 antibody (IgG1,κ) in a total volume of 100 μL RPMI medium supplemented with 10% CCS in a 96-well microtiter plate. After 15 min at RT, 50 μL PBMCs (500,000 cells) were added, resulting in an effector to target ratio of 100:1. The maximum amount of cell lysis was determined by incubating 50 μL $^{51}$Cr-labeled SK-BR-3 cells (5,000 cells) with 100 μL 5% Triton-X100. The amount of spontaneous lysis was determined by incubating 5000 $^{51}$Cr-labeled SK-BR-3 cells in 150 μL medium, without any antibody or effector cells. The level of antibody-independent cell lysis was determined by incubating 5,000 SK-BR-3 cells with 500,000 PBMCs without antibody. Subsequently, the cells were incubated 4 hr at 37° C., 5% $CO_2$. To determine the amount of cell lysis, the cells were centrifuged (1,200 rpm, 3 min) and 75 μL of supernatant was transferred to micronic tubes, after which the released $^{51}$Cr was counted using a gamma counter. The measured counts per minute (cpm) were used to calculate the percentage of antibody-mediated lysis as follows:

$$(\text{cpm sample} - \text{cpm Ab-independent lysis})/(\text{cpm max. lysis} - \text{cpm spontaneous lysis})\times100\%$$

Figure 5A:
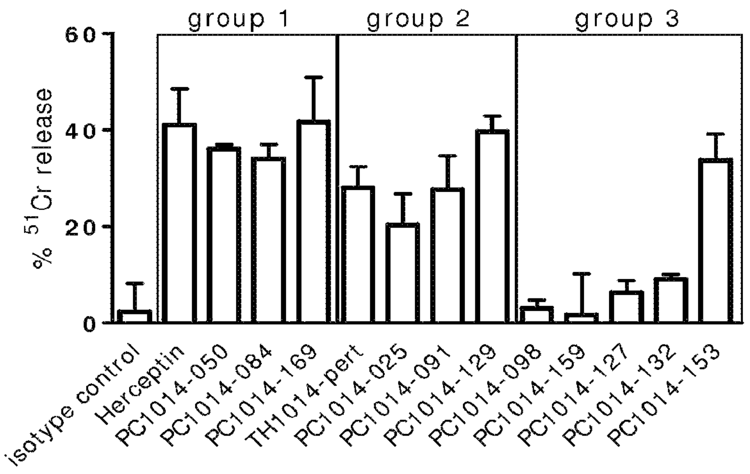
FIGS. 5A and 5B: Chromium-release (ADCC) assay of HER2 antibodies, showing PBMC-mediated lysis of $^{51}$Cr-labeled SK-BR-3 cells after incubation with HER2 antibody. Values depicted are the mean maximum percentages $^{51}$Cr-release±the standard deviation from one representative in vitro ADCC experiment with SK-BR-3 cells. See Example 15 for details.
Figure 5B:
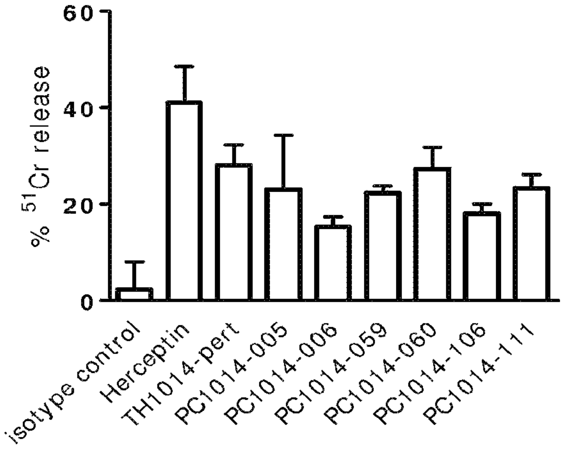

HER2 antibodies from cross-block groups 1 and 2 induced efficient lysis of SK-BR-3 cells through ADCC (FIG. 5A). From group 3, antibody 153 was the only antibody that induced efficient ADCC, antibody 132 induced about 10% ADCC, and clones 098, 159 and 127 did not induce ADCC. See FIG. 5. All HER2 antibodies from cross-block group 4 induced efficient lysis of SK-BR-3 cells through ADCC (FIG. 5B). The average percentage lysis by the different antibodies of cross-block group 4 varied between 15% and 28%, in contrast to trastuzumab (Herceptin®), which showed on average 41% lysis. Without being bound by theory, the higher percentage lysis by trastuzumab possibly resulted from an increased non-core fucosylation grade (12.4%) due to its CHO production, compared to ~4% non-core fucosylation on the other HEK-produced HER2 antibodies, or by recognizing an epitope that induces less internalization of the HER2 receptor-antibody complexes.

Example 16

Inhibition of Ligand-Independent Proliferation of AU565 Cells

HER2 antibodies were tested for their ability to inhibit proliferation of AU565 cells in vitro. Due to the high HER2 expression levels on AU565 cells (~1,000,000 copies per cell as described in Example 12), HER2 is constitutively active in these cells and thus not dependent on ligand-induced heterodimerization.

In a 96-well tissue culture plate (Greiner bio-one, Frickenhausen, Germany), 9,000 AU565 cells were seeded per well in the presence of 10 μg/mL HER2 antibody in serum-free cell culture medium. As a control, cells were seeded in serum-free medium without antibody. After 3 days, the amount of viable cells was quantified with Alamarblue (BioSource International, San Francisco, US) according to the manufacturer's instructions. Fluorescence was monitored using the EnVision 2101 Multilabel reader (PerkinElmer, Turku, Finland) with standard Alamarblue settings. The Alamarblue signal of antibody-treated cells was plotted as a percentage relative to untreated cells. Dunnett's test was applied for statistical analysis.

Figure 6:
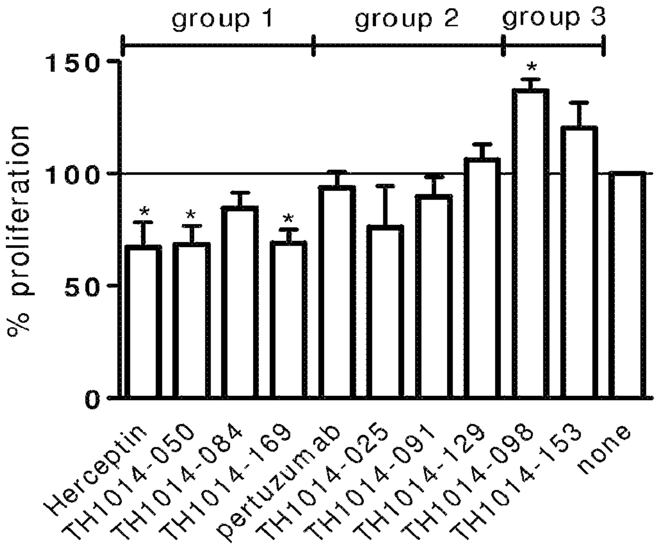
FIG. 6: Effect of HER2 antibodies on the proliferation of AU565 cells, as compared to untreated cells (set to 100%). Data shown are percentages proliferation of AU565 cells compared to untreated cells measured in three independent experiments±the standard deviation. * Significant ($P<0.05$). See Example 16 for details.

The percentage proliferation of AU565 cells after HER2 antibody treatment was compared to untreated cells, which was set to 100%. Of the tested Group 1 antibodies, trastuzumab, 050 and 169 demonstrated significant inhibition of AU565 cell proliferation ($P<0.05$), whereas 084 had no effect. None of the tested antibodies from group 2 (Pertuzumab, 025, 092 and 129) was able to inhibit AU565 cell proliferation. The tested antibodies from group 3 (098 and 153) did not inhibit AU565 proliferation. In contrast, both antibodies induced enhanced proliferation of AU565 cells compared to untreated cells (098 more than 153). See FIG. 6. For trastuzumab and pertuzumab, this was in accordance with the results described by Juntilla et al. (Cancer Cell 2009; 15(5):353-355).

From cross-block group 4, TH1014-F5 significantly enhanced proliferation of AU565 cells indicating that this is an agonistic antibody, whereas none of the other antibodies of cross-block group 4 tested (005, 060 and pertuzumab) had a substantial effect on AU565 proliferation (data not shown). Enhancing proliferation can be an advantage in some therapeutic applications of ADC-conjugates, e.g., where the cytotoxic action of the drug relies on, or is enhanced by, cell proliferation.

Example 17

Inhibition of Ligand-Induced Proliferation of MCF-7 Cells

Since HER2 is an orphan receptor, its signaling is mainly dependent on activation of other ErbB-family members such as EGFR and Her3. Upon ligand binding, these two receptors can bind to and activate the HER2 receptor, resulting in e.g. proliferation. Various publications describe that pertuzumab efficiently inhibits Heregulin-β1-induced proliferation (Franklin M C. Cancer Cell 2004/Landgraf R. BCR 2007). For trastuzumab, it has been described that it has little effect on Heregulin-β1-induced HER2/HER3 heterodimerization and proliferation (Larsen S S., et al., Breast Cancer Res Treat 2000; 58:41-56; Agus D B., et al., Cancer Cell 2002; 2:127-137; Wehrman et al. (2006), supra).

To investigate the ability of the present human HER2 antibodies to interfere with Heregulin-β1-induced HER2/HER3 heterodimers, a Heregulin-β1-induced proliferation assay was performed. Therefore, MCF7 cells (purchased at ATCC, HTB-22) expressing ~20.000 HER2 molecules per cell, were seeded in a 96-wells tissue culture plate (Greiner bio-one) (2.500 cells/well) in complete cell culture medium. After 4 hours, the cell culture medium was replaced with starvation medium containing 1% Cosmic Calf Serum (CCS) and 10 μg/mL HER2 antibody. Next, Heregulin-β1 (PeproTech, Princeton Business Park, US) diluted in 1% CCS containing starvation medium was added to the wells to a final concentration of 1.5 ng/mL. After 4 days incubation, the amount of viable cells was quantified with Alamarblue (BioSource International) according to the manufacturer's instructions. Fluorescence was monitored using the EnVision 2101 Multilabel reader (PerkinElmer) with standard Alamarblue settings. The Alamarblue signal of HER2 antibody-treated ligand-induced cells was plotted as a percentage signal compared to ligand-induced cells incubated without HER2 antibody. Dunnett's test was applied for statistical analysis.

Figure 7:
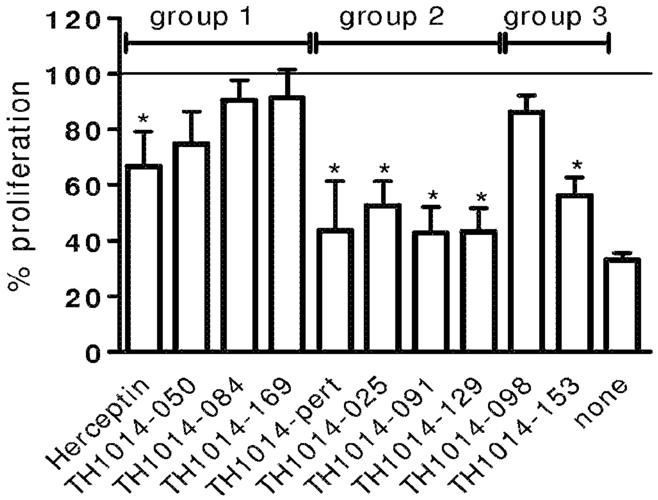
FIG. 7: Percentage of viable MCF7 cells stimulated with Heregulin-β1 and treated with the indicated HER2 antibodies, relative to cells stimulated with Heregulin-β1 only. As a control, the percentage proliferation of unstimulated cells is shown (none). Data was obtained from three independent experiments±the stdev. * Significant inhibition of Heregulin-β1-induced proliferation ($P<0.05$). See Example 17 for details.

The percentage of viable MCF7 cells stimulated with Heregulin-β1 and treated with the indicated HER2 antibody, relative to the viable cells after stimulation with Heregulin-β1 in the absence of HER2 antibody, was calculated. There was no MCF-7 proliferation in absence of both Heregulin-β1 and antibody. Antibodies 025, 091, 129, 153 and pertuzumab (TH1014-pert) demonstrated significant inhibition of Heregulin-β1-induced MCF-7 proliferation ($P<0.05$). Also trastuzumab showed some inhibition of Heregulin-β1-induced proliferation of MCF-7 cells, although not as efficient as the other tested HER2 antibodies. It has been reported that domain IV of HER2 is involved in the stabilization of EGFR/HER2 heterodimers, but without details on its contribution to HER2/HER3 heterodimers (Wehrman et al., supra). Antibodies 050, 084, 169 and 098 had no statistically significant effect on Heregulin-β1-induced proliferation of MCF-7 cells. See FIG. 7. Without being limited to theory, this suggests that these antibodies do not inhibit ligand-induced HER2/HER3 heterodimerization.

Example 18

Anti-Kappa-ETA' Assay

To investigate the suitability of HER2 antibodies for an antibody-drug conjugate approach, a generic in vitro cell-based killing assay using kappa-directed pseudomonas-exotoxin A (anti-kappa-ETA') was developed. The assay makes use of a high affinity anti-kappa domain antibody conjugated to a truncated form of the pseudomonas-exotoxin A. Upon internalization, the anti-kappa-ETA' domain antibody undergoes proteolysis and disulfide-bond reduction, separating the catalytic from the binding domain. The catalytic domain is transported from the Golgi to the endoplasmic reticulum via the KDEL retention motif, and subsequently translocated to the cytosol where it inhibits protein synthesis and induces apoptosis (ref. Kreitman R J. BioDrugs 2009; 23(1):1-13). In this assay, to identify HER2 antibodies that enable internalization and killing through the toxin, HER2 antibodies are preconjugated with the anti-kappa-ETA' before incubation with HER2-positive cells.

First, the optimal concentration of anti-kappa-ETA' was determined for each cell line, i.e. the maximally tolerated dose that does not lead to induction of non-specific cell death. AU565 cells (7,500 cells/well) and A431 cells (2500 cells/well) were seeded in normal cell culture medium in 96-wells tissue culture plate (Greiner bio-one) and allowed to adhere for at least 4 hours. Next, cells were incubated with 100, 10, 1, 0.1, 0.01, 0.001 and 0 μg/mL anti-kappa-ETA' dilutions in normal cell culture medium. After 3 days, the amount of viable cells was quantified with Alamarblue (BioSource International, San Francisco, US) according to the manufacturer's instruction. Fluorescence was monitored using the EnVision 2101 Multilabel reader (PerkinElmer, Turku, Finland) with standard Alamarblue settings. The highest concentration anti-kappa-ETA' that did not kill the cells by itself was used for following experiments (0.5 μg/mL for AU565 and 1 μg/mL for A431).

Next, antibody-mediated internalization and killing by the toxin was tested for different HER2 antibodies. Cells were seeded as described above. Dilution-series of HER2 antibodies were pre-incubated for 30 minutes with the predetermined concentration anti-kappa-ETA' before adding them to the cells. After 3 days of incubation, the amount of viable cells was quantified as described above. The Alamarblue signal of cells treated with anti-kappa-ETA' conjugated antibodies was plotted compared to cells treated with antibody alone. 23.4 μg/mL Staurosporin was used as positive control for cell killing. An isotype control antibody was used as negative control.

Figure 8A:
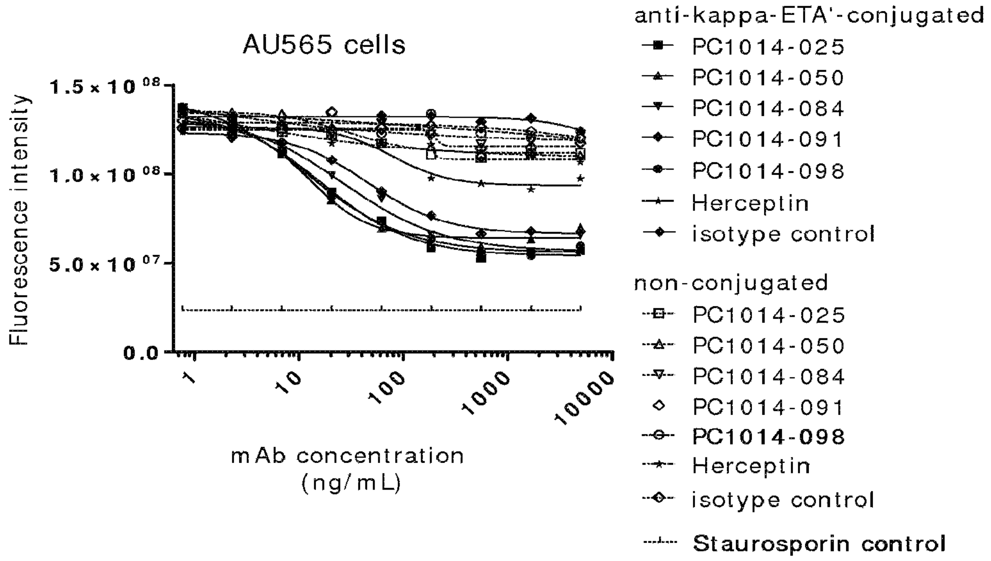
FIGS. 8A-8D: ADC assay, showing killing of AU565 cells (FIG. 8A, FIG. 8B) or A431 cells (FIG. 8C, FIG. 8D) via anti-kappa-ETA'-conjugated HER2 antibodies.
Figure 8B:
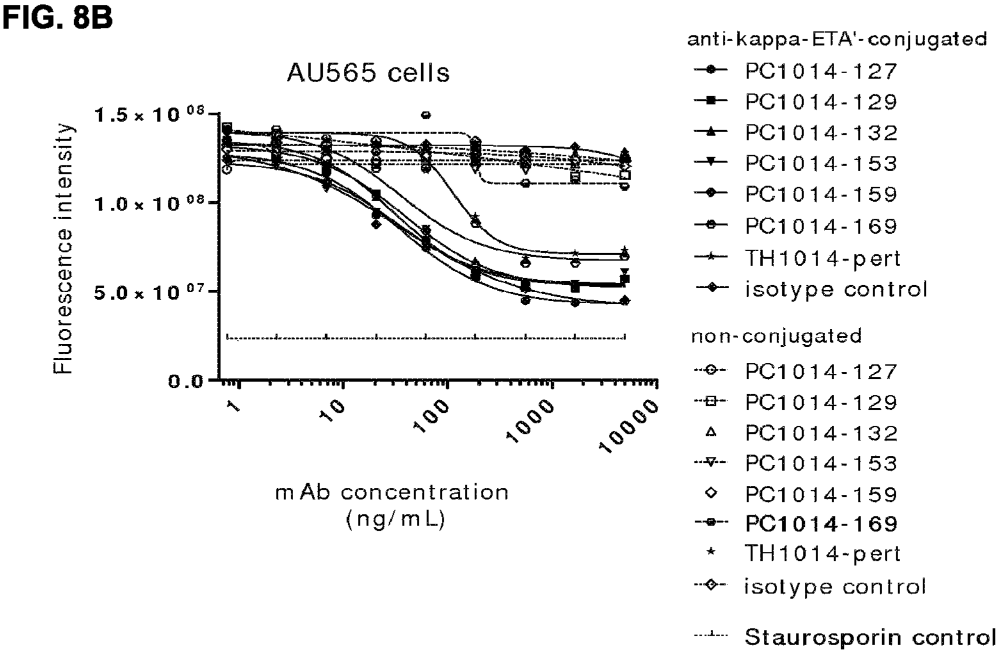

Cross-Block Groups 1, 2 and 3:

As shown in FIG. 8A/B and Table 6A, all anti-kappa-ETA'-conjugated HER2 antibodies were able to kill AU565 cells in a dose-dependent manner. All tested anti-kappa-ETA'-conjugated HER2 antibodies demonstrated better killing of AU565 cells (70.3-49.9%) compared to both antikappa-ETA'-conjugated trastuzumab (31.9%) and anti-kappa-ETA'-conjugated pertuzumab (TH1014-pert) (47.51%). and the $EC_{50}$ values were increased. 12.12-46.49 ng/mL compared to 78.49 ng/mL for anti-kappa-ETA'-conjugated trastuzumab and 117.8 ng/mL for anti-kappa-ETA'-conjugated pertuzumab. Antibody 159 had the highest percentage of cell-kill, and 098 the lowest $EC_{50}$.

Figure 8C:
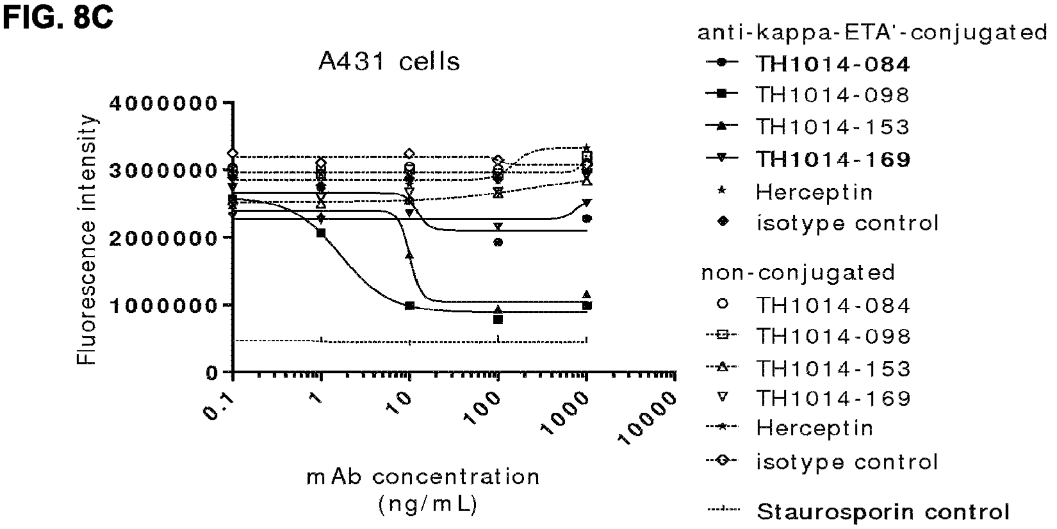
Figure 8D:
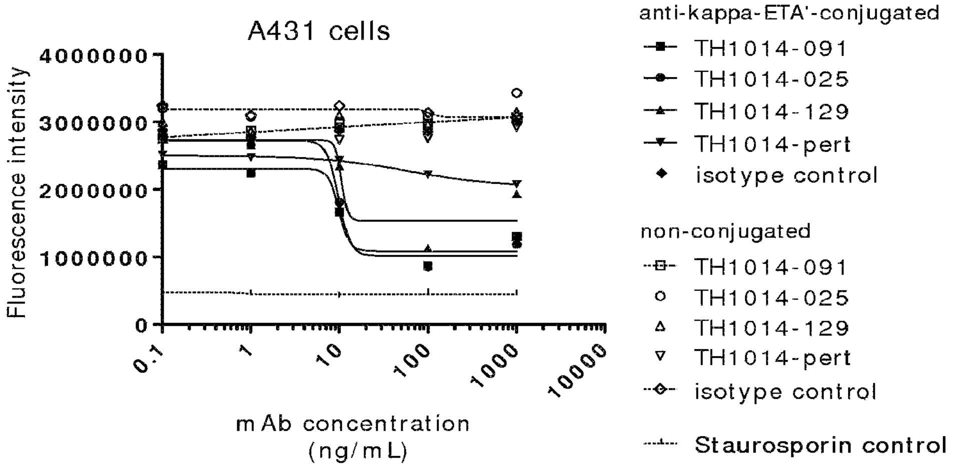
Figure 9A:
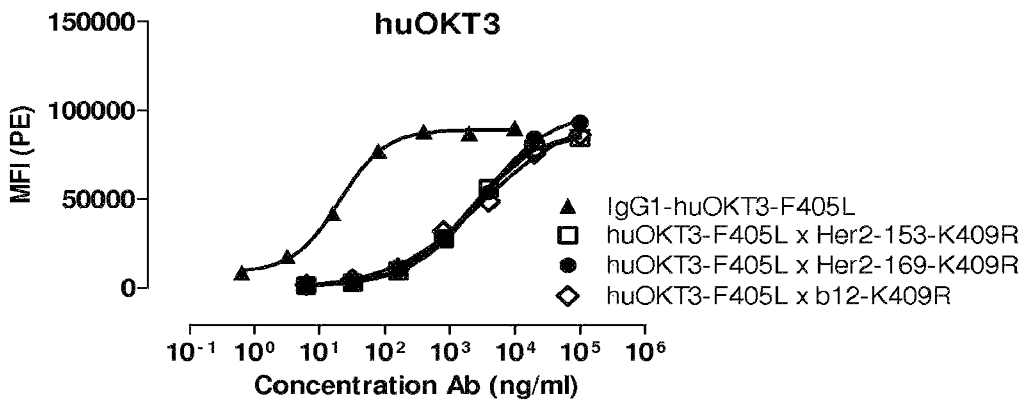
FIGS. 9A-9D: Binding of bispecific HER2×CD3 antibodies to Jurkat cells. All generated bispecific antibodies show binding to Jurkat, albeit with a lower apparent affinity than the monospecific parental antibodies (nomenclature=CD3 clone×HER2 clone).
Figure 9B:
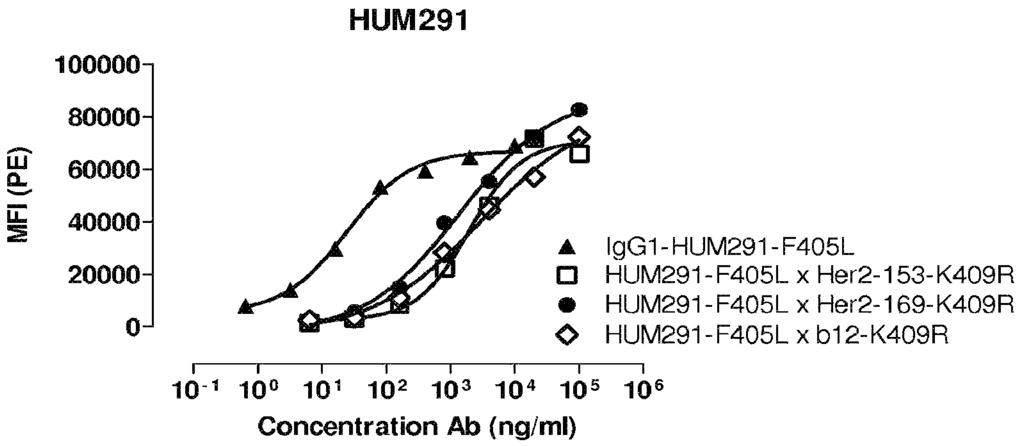
Figure 9C:
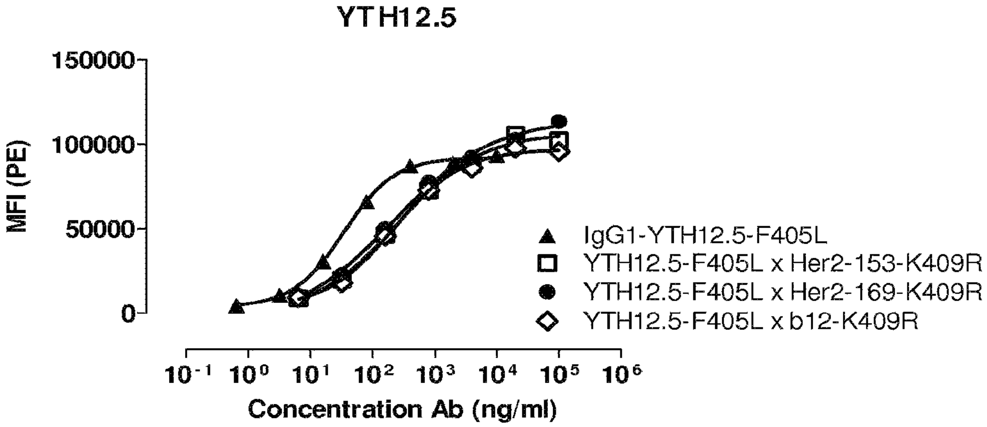
Figure 9D:
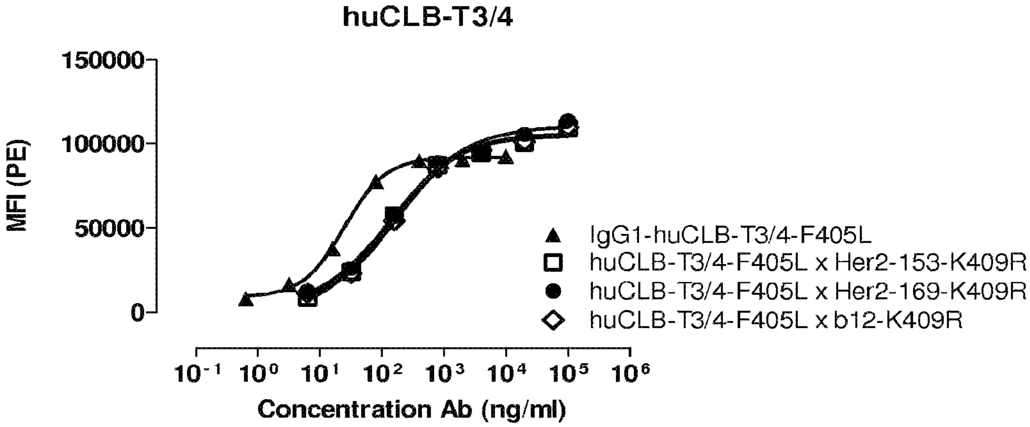

As shown in FIGS. 8C,D and Table 7A, antibodies 025, 091, 098, 129 and 153 were able to induce effective killing of A431 cells (≥75%). The highest percentage of cell-kill, and lowest $EC_{50}$ was shown by antibody 098. When conjugated to anti-kappa-ETA', trastuzumab and isotype control antibody did not induce killing of A431 cells. Antibodies 169, 084 and pertuzumab induced percentages of cell kill of no more than about 50%. No cell kill was observed with non-conjugated HER2 antibodies.

Cross-Block Group 4:

As shown in Table 6B, all anti-kappa-ETA'-conjugated HER2 antibodies of cross-block group 4 were able to kill AU565 cells in a dose-dependent manner. (50-72% cell killing). Antibodies 005 and 111 demonstrated more than three times improved $EC_{50}$ values (resp. 15.13 and 24.20 ng/mL) compared to trastuzumab (78.49 ng/mL). Non-conjugated HER2 antibodies of cross-block group 4 did not induce killing of AU565 cells at the concentrations tested.

As shown in Table 7B, antibodies 005 and 060 were able to induce effective killing of A431 cells (≥85%) when conjugated to anti-kappa-ETA' Antibodies 005 and 111 demonstrated killing of A431 cells already at low antibody concentrations (10 ng/mL) with $EC_{50}$ values of ~10 ng/mL. No cell kill was observed with non-conjugated HER2 antibodies of cross-block 4.

TABLE 6

Data shown are $EC_{50}$ values and maximal percentage cell kill of AU565 cells treated with anti-kappa-ETA'-conjugated HER2 antibodies (A, cross-block groups 1, 2, and 3; b, cross-block group 4), measured in one representative experiment. Cell-kill induced by Staurosporin was set as 100% and MFI of untreated cells was set as 0%.

| antibody | % cells killed | $EC_{50}$ ng/mL |
|---|---|---|
| | A: | |
| PC1014-159 | 70.3 | 34.93 |
| PC1014-127 | 69.0 | 34.46 |
| PC1014-132 | 61.6 | 39.35 |
| PC1014-129 | 60.8 | 30.85 |
| PC1014-153 | 60.3 | 32.26 |
| PC1014-025 | 60.0 | 16.71 |
| PC1014-098 | 58.7 | 12.12 |
| PC1014-084 | 58.1 | 26.97 |
| PC1014-050 | 52.4 | 12.71 |
| PC1014-091 | 50.6 | 46.49 |
| PC1014-169 | 49.9 | 35.62 |
| TH1014-pert | 47.5 | 117.8 |
| trastuzumab | 31.9 | 78.49 |
| isotype control | Ndet | Ndet |
| | B: | |
| P01014-111 | 72.0 | 24.2 |
| P01014-005 | 69.7 | 15.13 |
| P01014-059 | 67.0 | 67.65 |
| P01014-060 | 64.3 | 79.38 |
| P01014-106 | 59.1 | 107.9 |
| P01014-006 | 50.4 | 45.14 |
| Trastuzumab | 31.9 | 78.49 |
| isotype control | Ndet | Ndet |

Ndet = not detected.

TABLE 7

Data shown are $EC_{50}$ values and maximal percentage cell kill of A431 cells treated with anti-kappa-ETA'-conjugated HER2 antibodies (A, cross-block groups 1, 2, and 3; b, cross-block group 4), measured in one representative experiment. Cell-kill induced by Staurosporin was set as 100% and MFI of untreated cells was set as 0%.

| antibody | % cells killed | $EC_{50}$ ng/mL |
|---|---|---|
| | A: | |
| PC1014-025 | 86.7 | ~9.77 |
| PC1014-084 | 50.5 | ND |
| PC1014-091 | 83.3 | ~9.86 |
| PC1014-098 | 87.2 | 1.65 |
| PC1014-129 | 75.9 | ~10.60 |
| PC1014-153 | 82.4 | ~10.11 |
| PC1014-169 | 34.0 | ND |
| TH1014-pert | 37.0 | 61.58 |
| trastuzumab | Ndet | Ndet |
| isotype control | NDet | NDet |
| | B: | |
| P01014-005 | 88.5 | ~10.07 |
| P01014-060 | 85.0 | ~10.03 |
| Trastuzumab | NDet | NDet |
| isotype control | NDet | NDet |

"NDet" means not detected.

Example 19

Internalization of HER2 Antibodies Measured with an FMAT-Based Fab-CypHer5E Assay To investigate whether the enhanced killing of AU565 cells by the described HER2 antibodies compared to Trastuzumab (Herceptin®) and pertuzumab in the kappa-toxin-ETA' assay described in the previous Example correlated with enhanced internalization of HER2 antibodies, a fab-CypHer5E-based internalization assay was performed. CypHer5E is a pH-sensitive dye which is non-fluorescent at basic pH (extracellular: culture medium) and fluorescent at acidic pH (intracellular: lysosomes), with an acid dissociation constant (pKa) of 7.3.

AU565 cells were seeded in 384-well tissue culture plates (Greiner bio-one), at a density of 3,000 cells/well in normal cell culture medium supplemented with 240 ng/mL fab-CypHer5E (conjugation of Goat-fab-anti-Human IgG [Jackson] with CypHer5E [GE Healthcare, Eindhoven, The Netherlands] was made according to manufacturer's instructions). Next, HER2 antibodies were serially diluted in normal cell culture medium, added to the cells and left at room temperature for 9 hours. Mean fluorescent intensities (MFI) of intracellular CypHer5E were measured using the 8200 FMAT (Applied Biosystems, Nieuwerkerk A/D IJssel, The Netherlands) and 'counts×fluorescence' was used as read-out. An isotype control antibody was used as negative control antibody. $EC_{50}$ values and maximal MFI were determined by means of non-linear regression (sigmoidal dose-response with variable slope) using GraphPad Prism V4.03 software (GraphPad Software, San Diego, Calif., USA).

Cross-Block Groups 1, 2 and 3:

The results are shown in Table 8A, depicting the $EC_{50}$ and maximal MFI values for all tested HER2 antibodies of cross-block groups 1, 2, and 3 in the CypHer5E internalization assay with AU565 cells. The maximal MFI values indicate how many HER2 receptors are internalized upon antibody binding. All HER2 antibodies showed higher maximal MFI values (137,904-38,801) compared to trastuzumab (35,000) and pertuzumab (TH1014-pert) (32,366), indicating that the tested HER2 antibodies induced enhanced receptor internalization. Notably, antibodies that did not compete for HER2 binding with trastuzumab (Herceptin®) or TH1014-pert induced more receptor internalization compared to antibodies that did compete with trastuzumab and TH1014-pert, with the highest MFI achieved by antibodies 098 and 127. Without being limited to theory, this might be inherent to an inability to inhibit HER2 heterodimerization.

Cross-Block Group 4:

The results are shown in Table 8B, depicting the $EC_{50}$ values and maximal MFI for all tested HER2 antibodies of cross-block group 4 in the CypHer5E internalization assay with AU565 cells. The maximal MFI values reflect how many HER2 antibodies were internalized upon binding. All tested human HER2 antibodies of cross-block group 4 showed higher maximal MFI values (130.529-57.428) than trastuzumab (Herceptin®) (35.000) and TH1014-pert (35.323), indicating that these antibodies induced enhanced receptor internalization. The enhanced internalization of TH1014-F5 may be a result from its agonistic activity and the induction of HER2-HER2 dimerization (see Example 16).

TABLE 8

Cypher-5-based internalization assay of HER2 antibodies. Data shown are MFI and $EC_{50}$ values of one representative experiment of two experiments with AU565 cells treated with fab-CypHer5E-labeled HER2 antibodies. Some $EC_{50}$ values could not be calculated (ND).

| A: Cypher 5 | | |
|---|---|---|
| Antibody | $EC_{50}$ ng/mL | Maximal MFI |
| PC1014-025 | 30.05 | 63428 |
| PC1014-091 | 32.99 | 50711 |
| PC1014-129 | 7.15 | 60302 |
| TH1014-pert | 530 | 32366 |
| PC1014-169 | ND | 38801 |
| PC1014-084 | 30.51 | 71059 |
| trastuzumab | 21.70 | 35000 |
| PC1014-098 | 13.77 | 134575 |
| PC1014-127 | ~9.68 | 137904 |
| PC1014-159 | ND | 92427 |
| TH1014-F5 | 22.65 | 113116 |
| PC1014-132 | 11.42 | 112270 |
| PC1014-153 | ~14.91 | 87531 |

| B: Cypher 5 | | |
|---|---|---|
| Antibody | $EC_{50}$ ng/mL | Maximal MFI |
| PC1014-006 | 23.08 | 130829 |
| PC1014-005 | 21.37 | 95117 |
| PC1014-111 | 35.22 | 81680 |
| PC1014-059 | 14.77 | 77123 |
| PC1014-060 | 36.16 | 68184 |
| PC1014-106 | 68.60 | 57428 |
| TH1014-F5 | 22.65 | 113116 |
| TH1014-pert | ~1041 | 35323 |
| Trastuzumab | 21.70 | 35000 |

mAbs that compete with Herceptin mAbs that compete with TH1014-pert mAbs that compete with TH1014-F5

Non-competing mAbs

Example 20

Generation of Bispecific Antibodies by 2-MEA-Induced Fab-Arm Exchange

An in vitro method for producing bispecific antibodies is described in WO 2008119353 (Genmab) and reported by van der Neut-Kolfschoten et al. (Science. 2007 Sep. 14; 317(5844):1554-7). Herein, a bispecific antibody was formed by "Fab-arm" or "half-molecule" exchange (swapping of a heavy chain and attached light chain) between two monospecific IgG4- or IgG4-like antibodies upon incubation under mildly reducing conditions. Without being limited to theory, this Fab-arm exchange reaction was the result of a disulfide-bond isomerization reaction wherein the inter heavy-chain disulfide bonds in the hinge regions of monospecific antibodies were reduced and the resulting free cysteines form a new inter heavy-chain disulfide bond with cysteine residues of another antibody molecule with a different specificity. The resulting product was a bispecific antibody having two Fab arms with different sequences.

The knowledge of this natural IgG4 Fab-arm exchange was adapted to generate a method to produce stable IgG1-based bispecific antibodies (WO 2011131746 (Genmab)). The bispecific antibody product generated by this method described below will no longer participate in IgG4 Fab-arm exchange. The basis for this method was the use of complimentary CH3 domains, which promote the formation of heterodimers under specific assay conditions. To enable the production of bispecific antibodies by this method, IgG1 molecules carrying certain mutations in the CH3 domain were generated: in one of the parental IgG1 antibody T350I, K370T and F405L mutations (or minimally F405L) in the other parental IgG1 antibody the K409R mutation.

To generate bispecific antibodies, these two parental antibodies, each antibody at a final concentration of 0.5 mg/mL (equimolar concentration), were incubated with 25 mM 2-mercaptoethylamine-HCl (2-MEA) in a total volume of 100 μL TE at 37° C. for 90 min. The reduction reaction is stopped when the reducing agent 2-MEA is removed by using spin columns (Microcon centrifugal filters, 30k, Millipore) according to the manufacturer's protocol.

Example 21

HER2×CD3 Bispecific Antibodies Tested in an in Vitro Cytotoxicity Assay

CD3 is a protein complex that is associated with the T cell receptor α and β chain expressed on mature T cells. Combination of a CD3 specific antibody Fab-arm with a tumor antigen specific antibody Fab-arm in a bispecific antibody would result in the specific targeting of T cells to tumor cells, leading to T cell mediated tumor cell lysis. Likewise, CD3 positive T cells could be targeted to other derailed cells in the body, to infected cells or directly to pathogens.

Various HER2×CD3 bispecific antibodies were generated, combining different HER2 and public domain CD3 antibody sequences. Furthermore b12, a gp120 specific antibody (Barbas, C F. J Mol Biol. 1993 Apr. 5; 230(3):812-23) was used as a negative control. Heavy and light chain variable region sequences for the HER2-specific Fab-arm for antibody 153 were SEQ ID NO:63 and 67, respectively, and VH and VL sequences for the HER2-specific Fab-arm of antibody 169 were SEQ ID NO:1 and 5, respectively. The following heavy and light chain variable region sequences for the CD3 specific Fab-arm were used:

YTH12.5 (Routledge et al., Eur J Immunol. 1991, 21(11): 2717-25, hereby incorporated by reference in its entirety, including sequence disclosures)

| | | |
|---|---|---|
| SEQ ID NO: 234 | VH YTH12.5 | EVQLLESGGGLVQPGGSLRLSCAASGFTFS **SFP**MAWVRQAPGKGLEWVSTISTSGGRTYY RDSVKGRFTISRDNSKNTLYLQMNSLRAED TAVYYCAK*FRQYSGGFDY*WGQGTLVTVSS |

-continued

| | | |
|---|---|---|
| SEQ ID NO: 235 | VL YTH12.5 | DIQLTQPNSVSTSLGSTVKLSCTLS**SGNIE**NNYVHWYQLYEGRSPTTMIYDDDKRPDGVPDRFSGSIDRSSNSAFLTIHNVAIEDEAIYFC*HSYVSSFNV*FGGGTKLIVL |

Sequences highlighted by bold represent the CDR1 domains, sequences highlighted by underline represent the CDR2 domains, and sequences highlighted by italic represent the CDR3 domains.

HUM291 (humanized antibody visilizumab, sequences retrieved from the NCBI protein database under GenBank accession No.: AAC28464.1, hereby incorporated by reference in its entirety)

| | | |
|---|---|---|
| SEQ ID NO: 236 | VH HUM291 | QVQLVQSGAEVKKPGASVKVSCKASGYTF**ISYT**MHWVRQAPGQGLEWMGYINPRSGYTHYNQKLKDKATLTADKSASTAYMELSSLRSEDTAVYYCAR*SAYYDYDGFAY*WGQGTLVIVSS |
| SEQ ID NO: 237 | VL HUM291 | DIQMTQSPSSLSASVGDRVTITCSAS**SSVSY**MNWYQQKPGKAPKRLIYDTSKLASGVPSRFSGSGSGTDFTLTISSLQPEDFATYYC*QQWSSNPPT*FGGGTWEIK |

Sequences highlighted by bold represent the CDR1 domains, sequences highlighted by underline represent the CDR2 domains, and sequences highlighted by italic represent the CDR3 domains.

huOKT3-C114S-gLC (used in teplizumab, with an additional C114S mutation in VH; Adair, J. et al. 1994. Hum Antibodies Hybridomas 5:41-47, hereby incorporated by reference in its entirety, including sequence disclosures).

| | | |
|---|---|---|
| SEQ ID NO: 238 | VH huOKT3-C114S-gLC | QVQLVQSGGGVVQPGRSLRLSCKASGYTFT**RYT**MHWVRQAPGKGLEWIGYINPSRGYTNYNQKVKDRFTISRDNSKNTAFLQMDSLRPEDTGVYFCAR*YYDDHYSLDY*WGQGTPVTVSS |
| SEQ ID NO: 239 | VL huOKT3-C114S-gLC | DIQMTQSPSSLSASVGDRVTITCSAS**SSVSY**MNWYQQTPGKAPKRWIYDTSKLASGVPSRFSGSGSGTDYTFTISSLQPEDIATYYC*QQWSSNPFT*FGQGTKLQIT |

Sequences highlighted by bold represent the CDR1 domains, sequences highlighted by underline represent the CDR2 domains, and sequences highlighted by italic represent the CDR3 domains.

huCLB-T3/4 is a humanized version of murine antibody CLB-T3/4 (Parren et al., Res Immunol. 1991, 142(9):749-63, hereby incorporated by reference in its entirety, including sequence disclosures. Briefly, the CLB-T3/4 murine VH and VL sequences as published in Parren et al. (1991) were aligned to the human VH and VL repertoires using the IMGT's V-QUEST. The closest human germlines that were found were IGHV3-21*01 for the VH gene and IGKV3-11*01(+IGKJ4*02) for the VL gene. All amino acid residues in the murine VH and VL sequences that differed were replaced by the human equivalent, except for those within the CDR regions of CLB-T3/4. As no related J-region was found for the VH sequence, the common WGQGTLVTVSS sequence was used for the FR4 region of the heavy chain. Both sequences were cloned into the relevant expression vectors and expressed by cotransfection in HEK293F cells.

| | | |
|---|---|---|
| SEQ ID NO: 240 | VH huCLB-T3/4 | EVQLVESGGGLVKPGGSLRLSCAASGFTFSSYGMFWVRQAPGKGLEWVATISRYSRYIYYPDSVKGRFTISRDNAKNSLYLQMNSLRAEDTAVYYCARRPLYGSSPDYWGQGTLVTVSS |
| SEQ ID NO: 241 | VL huCLB-T3/4 | EIVLTQSPATLSLSPGERATLSCSASSSVTYVHWYQQKPGQAPRLLIYDTSKLASGIPARFSGSGSGTDFTLTISSLEPEDFAVYYCFQGSGYPLTFGSGTKLEMR |
| SEQ ID NO: 242 | VH CDR1 | GFTFSSYG |
| SEQ ID NO: 243 | VH CDR2 | ISRYSRYI |
| SEQ ID NO: 244 | VH CDR3 | ARRPLYGSSPDY |
| SEQ ID NO: 245 | VL CDR1 | SSVTY |
| | VL CDR2 | DTS |
| SEQ ID NO: 246 | VL CDR3 | FQGSGYPLT |

All antibodies were expressed as IgG1,κ being modified in their Fc regions as follows: IgG1-HER2-153-K409R, IgG1-HER2-169-K409R, IgG1-b12-K409R, IgG1-hu-CLB-T3/4-F405L, IgG1-YTH12.5-F405L, IgG1-HUM291-F405L and IgG1-huOKT3-F405L.

Also, for subsequent experiments, N297Q mutants of the same antibodies were generated to make the Fc-domain of the antibodies inert. An inert Fc-domain prevents the antibody to interact with Fc-receptors present on monocytes, since it removes a glycosylation site; glycosylation at this site is critical for IgG-Fcgamma receptor interactions (Bolt S et al., *Eur J Immunol* 1993, 23:403-411). Alternatively to the N297Q mutation, residual Fc activity was further removed by combining three sets of mutations from the public domain in one antibody Fc domain. The mutations L234F, L235E, P331S (Oganesyan, Acta Cryst. (2008). D64, 700-704), D265A (Shields JBC (2001) 276(9) 6591-6604) and N297Q were introduced in the K409R and F405L IgG1 backbone. The combinations of these five mutations, designated LFLEDANQPS (SEQ ID NO:251) is used in some of the examples as well. The following Fc sequences for the different Fc-variants were used (mutations are highlighted by underlined letters:

IgG1 heavy chain constant region-WT
(SEQ ID NO: 247)
ASTKGPSVFPLAPSSKSTSGGTAALGCLVKDYFPEPVWSWNSGALTSGVH

TFPAVLQSSGLYSLSSVVTVPSSSLGTQTYICNVNHKPSNTKVDKRVEPK

SCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK

IgG1 heavy chain constant region-F405L
(SEQ ID NO: 248)
>ASTKGPSVFPLAPSSKSTSGGTAALGCLVKDYFPEPVWSWNSGALTSGV

HTFPAVLQSSGLYSLSSVVTVPSSSLGTQTYICNVNHKPSNTKVDKRVEP

-continued

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFLLYSKLTVDKSRW

QQGNVFSCSVMHEALHNHYTQKSLSLSPGK

IgG1 heavy chain constant region-K409R
(SEQ ID NO: 249)
>ASTKGPSVFPLAPSSKSTSGGTAALGCLVKDYFPEPVWSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSRLTVDKSRW

QQGNVFSCSVMHEALHNHYTQKSLSLSPGK

IgG1 heavy chain constant region-N297Q
(SEQ ID NO: 250)
>ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRVE

PKSCDKTHTCPPCPAPELLGGPSVFLFPPKPKDTLMISRTPEVTCVVVDV

SHEDPEVKFNWYVDGVEVHNAKTKPREEQYQSTYRVVSVLTVLHQDWLNG

KEYKCKVSNKALPAPIEKTISKAKGQPREPQVYTLPPSREEMTKNQVSLT

CLVKGFYPSDIAVEWESNGQPENNYKTTPPVLDSDGSFFLYSKLTVDKSR

WQQGNVFSCSVMHEALHNHYTQKSLSLSPGK

IgG1 heavy chain constant region-LFLEDANQPS mut
(SEQ ID NO: 251)
>ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRVE

PKSCDKTHTCPPCPAPEFEGGPSVFLFPPKPKDTLMISRTPEVTCVVVAV

SHEDPEVKFNWYVDGVEVHNAKTKPREEQYQSTYRVVSVLTVLHQDWLNG

KEYKCKVSNKALPASIEKTISKAKGQPREPQVYTLPPSREEMTKNQVSLT

CLVKGFYPSDIAVEWESNGQPENNYKTTPPVLDSDGSFFLYSKLTVDKSR

WQQGNVFSCSVMHEALHNHYTQKSLSLSPGK

IgG1 heavy chain constant region-F405L N297Q
(SEQ ID NO: 252)
>ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRVE

PKSCDKTHTCPPCPAPELLGGPSVFLFPPKPKDTLMISRTPEVTCVVVDV

SHEDPEVKFNWYVDGVEVHNAKTKPREEQYQSTYRVVSVLTVLHQDWLNG

KEYKCKVSNKALPAPIEKTISKAKGQPREPQVYTLPPSREEMTKNQVSLT

CLVKGFYPSDIAVEWESNGQPENNYKTTPPVLDSDGSFLLYSKLTVDKSR

WQQGNVFSCSVMHEALHNHYTQKSLSLSPGK

IgG1 heavy chain constant region-K409R N297Q
(SEQ ID NO: 253)
>ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRVE

-continued

PKSCDKTHTCPPCPAPELLGGPSVFLFPPKPKDTLMISRTPEVTCVVVDV

SHEDPEVKFNWYVDGVEVHNAKTKPREEQYQSTYRVVSVLTVLHQDWLNG

KEYKCKVSNKALPAPIEKTISKAKGQPREPQVYTLPPSREEMTKNQVSLT

CLVKGFYPSDIAVEWESNGQPENNYKTTPPVLDSDGSFFLYSRLTVDKSR

WQQGNVFSCSVMHEALHNHYTQKSLSLSPGK

IgG1 heavy chain constant region-F405L LFLEDANQPS
(SEQ ID NO: 254)
>ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRVE

PKSCDKTHTCPPCPAPEFEGGPSVFLFPPKPKDTLMISRTPEVTCVVVAV

SHEDPEVKFNWYVDGVEVHNAKTKPREEQYQSTYRVVSVLTVLHQDWLNG

KEYKCKVSNKALPASIEKTISKAKGQPREPQVYTLPPSREEMTKNQVSLT

CLVKGFYPSDIAVEWESNGQPENNYKTTPPVLDSDGSFLLYSKLTVDKSR

WQQGNVFSCSVMHEALHNHYTQKSLSLSPGK

IgG1 heavy chain constant region-K409R LFLEDANQPS
(SEQ ID NO: 255)
>ASTKGPSVFPLAPSSKSTSGGTAALGCLVKDYFPEPVWSWNSGALTSGV

HTFPAVLQSSGLYSLSSVVTVPSSSLGTQTYICNVNHKPSNTKVDKRVEP

KSCDKTHTCPPCPAPEFEGGPSVFLFPPKPKDTLMISRTPEVTCVVVAVS

HEDPEVKFNWYVDGVEVHNAKTKPREEQYQSTYRVVSVLTVLHQDWLNGK

EYKCKVSNKALPASIEKTISKAKGQPREPQVYTLPPSREEMTKNQVSLTC

LVKGFYPSDIAVEWESNGQPENNYKTTPPVLDSDGSFFLYSRLTVDKSRW

QQGNVFSCSVMHEALHNHYTQKSLSLSPGK

The following heavy and light chain variable region sequences for the b12, HIV gp120 specific Fab-arm were used (sequence as described by: Barbas, CF. J Mol Biol. 1993 Apr. 5; 230(3):812-23.)

VH b12
(SEQ ID NO: 256)
>QVQLVQSGAEVKKPGASVKVSCQASGYRFSNFVIHWVRQAPGQRFEWMG
WINPYNGNKEFSAKFQDRVTFTADTSANTAYMELRSLRSADTAVYYCARVG
PYSWDDSPQDNYYMDVWGKGTTVTVSS

VL b12
(SEQ ID NO: 257)
>EIVLTQSPGTLSLSPGERATFSCRSSHSIRSRRVAWYQHKPGQAPRLVIH
GVSNRASGISDRFSGSGSGTDFTLTITRVEPEDFALYYCQVYGASSYTFGQ
GTKLERK

Bispecific antibodies from these HER2 and CD3 specific antibodies were generated as described in Example 20.

Specificity for human CD3 was verified by binding of the bispecific HER2×CD3 antibodies to Jurkat (CD3 expressing T cell line) cells using flow cytometry. Bivalent binding of parental IgG1 anti-CD3 antibodies was compared to binding by monospecific parental antibodies. All generated bispecific batches showed good binding to both Jurkat cells albeit with a lower affinity than monospecific bivalent CD3 antibodies (FIG. 9A-D).

Simultaneous binding of the bispecific antibody huCLB-T3/4-N297Q-F405L×HER2-169-N297Q-K409R was shown by co-incubating two cell populations labeled with different fluorescent dyes in the presence of bispecific antibodies or control antibodies. HER2 positive AU565 cells were labeled with CFSE (FITC/FL-1) and CD3 expressing Jurkat cells were labeled with PKH26 (PE/FL-2), according to manufacturer's instructions. Both cell types were then co-incubated for 30 min at 4° C., in the presence of bispecific HER2×CD3 antibodies. Samples were analyzed by flow cytometry on FACS Cantoll. A quadrant analysis was performed to detect CSFE/PKH26 double-positive cells.

Figure 10A:
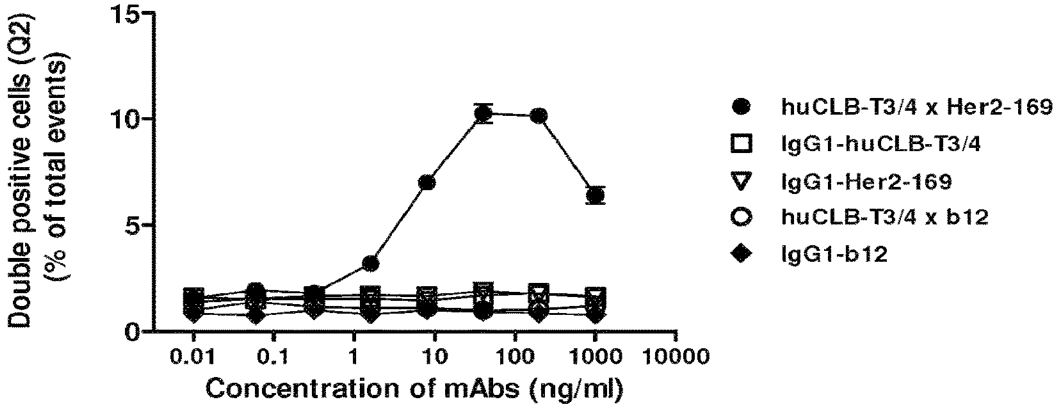
FIGS. 10A and 10B (FIG. 10A) Dose-dependent simultaneous binding of HER2×3 antibodies (HER2 169×LB-T3/
Figure 10B:
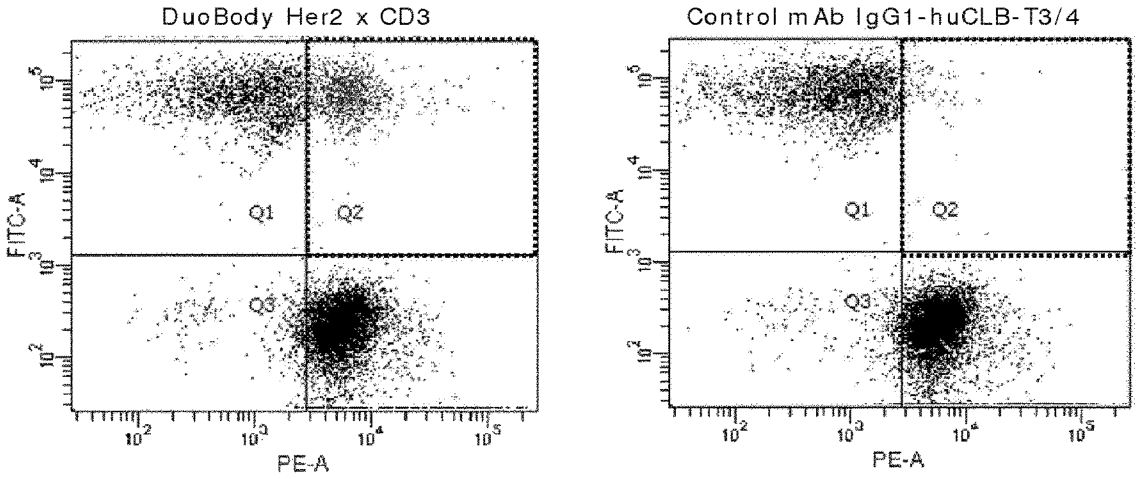
Figure 11A:
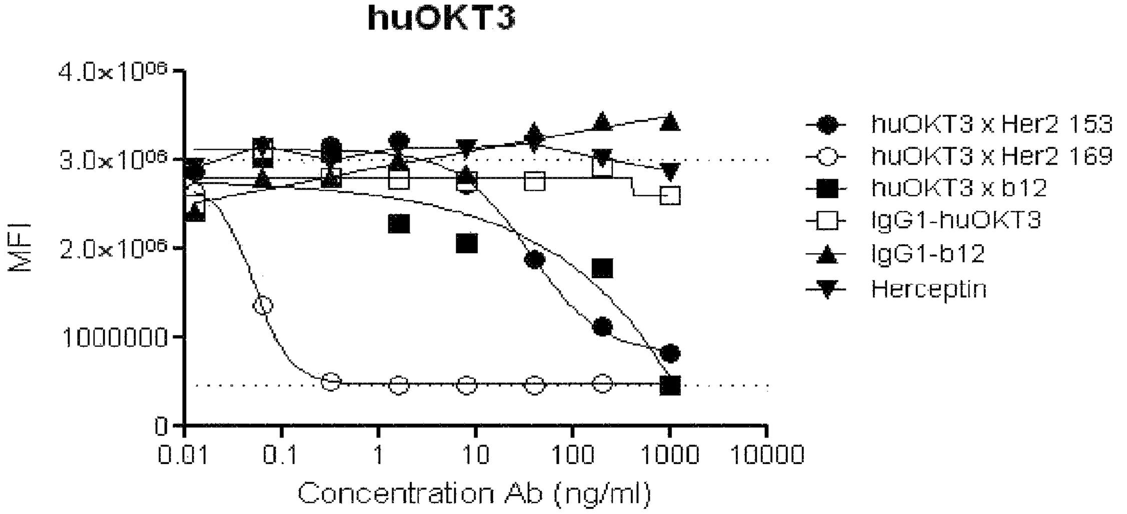
FIGS. 11A-11D: Dose dependent killing of AU565 cells by bispecific HER2×CD3 antibodies. Bispecific antibodies were generated from 4 different CD3 antibodies combined with two different HER2 antibodies (169 and 153) or control antibody IgG1 b12.
Figure 11B:
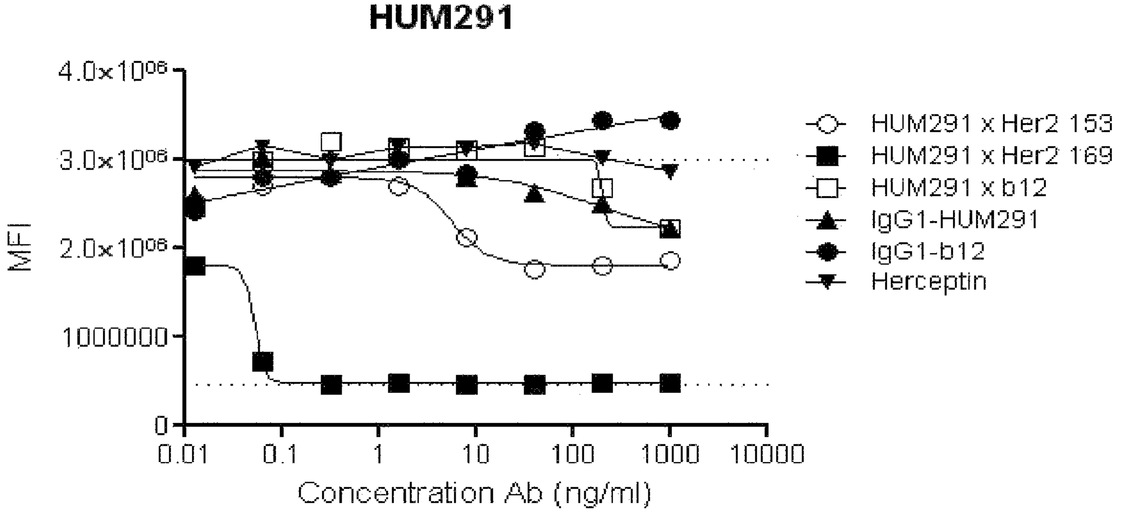
Figure 11C:
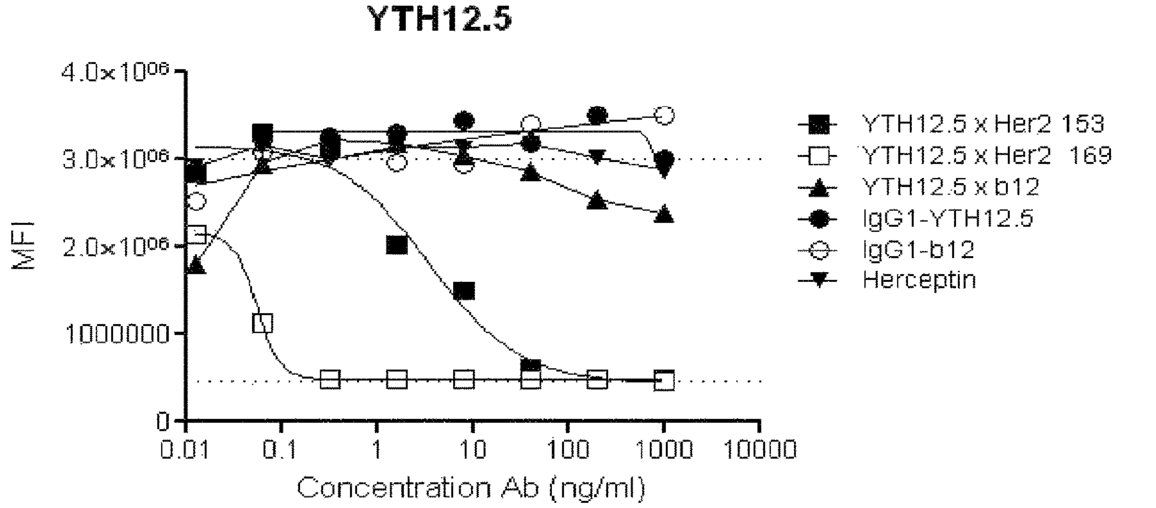
Figure 11D:
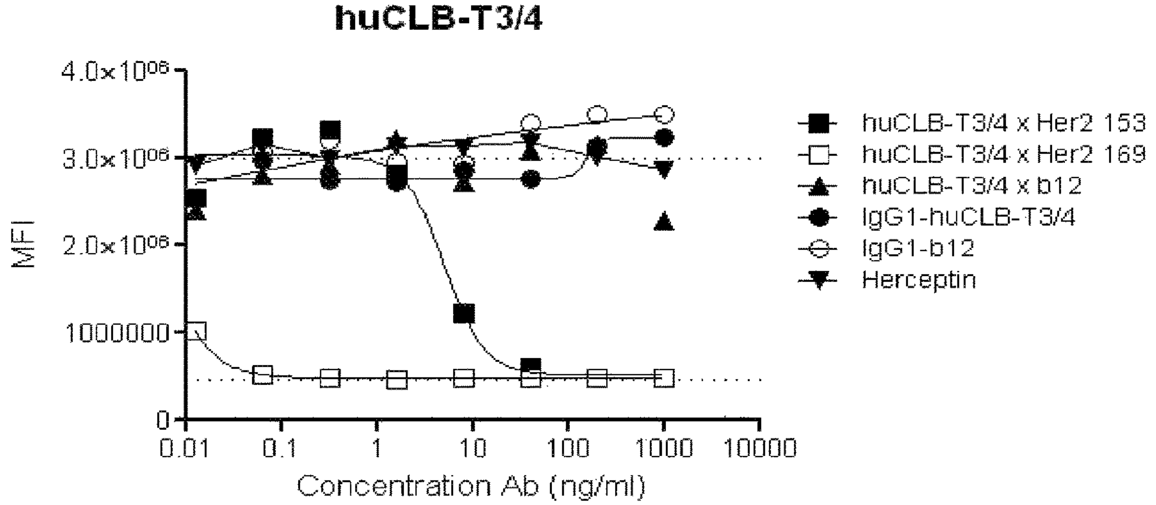

Only in the presence of bispecific antibody, a population of double-positive cells (doublets) was observed, indicating that these antibodies can bind two cell types simultaneously. Data are summarized in FIG. 10A and representative examples of cells treated with bispecific HER2×CD3 (169×CLB-T3/4) and a monospecific control antibody are shown in FIG. 10B.

The HER2×CD3 antibodies were then tested in an in vitro cytotoxicity assay using AU565 cells with either isolated T cells alone or PBMCs as effector cells. AU565 cells were cultured to near confluency. Cells were washed twice with PBS, and trypsinized for 5 minutes at 37° C. 12 mL culture medium was added to inactivate trypsin and cells were spun down for 5 min, 800 rpm. Cells were resuspended in 10 mL culture medium and a single cell suspension was made by passing the cells through a cellstrainer. 100 μL of a $5\times10^5$ cells/mL suspension was added to each well of a 96-well culture plate, and cells were incubated at least 3 hrs at 37° C., 5% CO2 to allow adherence to the plate.

Peripheral blood mononuclear cells (PBMC) were isolated from blood from healthy volunteers using Leucosep 30 mL tubes, according to the manufacturer's protocol (Greiner Bio-one). T cells were isolated from PBMC preparations by negative selection using the Untouched Human T-cells Dynabead kit (Dynal). Isolated cells were resuspended in culture medium to a final concentration op $7\times10^6$ cells/mL.

Culture medium was removed from the adhered AU565 cells, and replaced with 50 μL/well 2× concentrated antibody-dilution and 50 μL/well $7\times10^6$ T cells/mL (ratio effector:target=7:1). Plates were incubated for 3 days at 37° C., 5% $CO_2$. Supernatants were removed and plates were washed twice with PBS. To each well 150 μL culture medium and 15 μL Alamar blue was added. Plates were incubate for 4 hours at 37° C., 5% $CO_2$, and absorbance was measured (Envision, Perkin Elmer).

FIG. 11 shows that all bispecific HER2×CD3 antibodies induced dose-dependent killing of AU565 cells in an in vitro cytotoxicity assay with isolated T cells. Killing was critically dependent on the presence of a tumor-targeting Fab-arm (both clone 169 and 153), whereas control antibodies (CD3 monospecific IgG1-YTH12.5, IgG1-huCLB-T3/4, IgG1-Hum291 and IgG1-OKT3 and irrelevant antigen-specific IgG1-b12, and CD3xb12) did not induce T cell cytotoxicity. Bispecific antibodies containing HER2-169 were more potent than those containing HER2-153.

Figure 17:
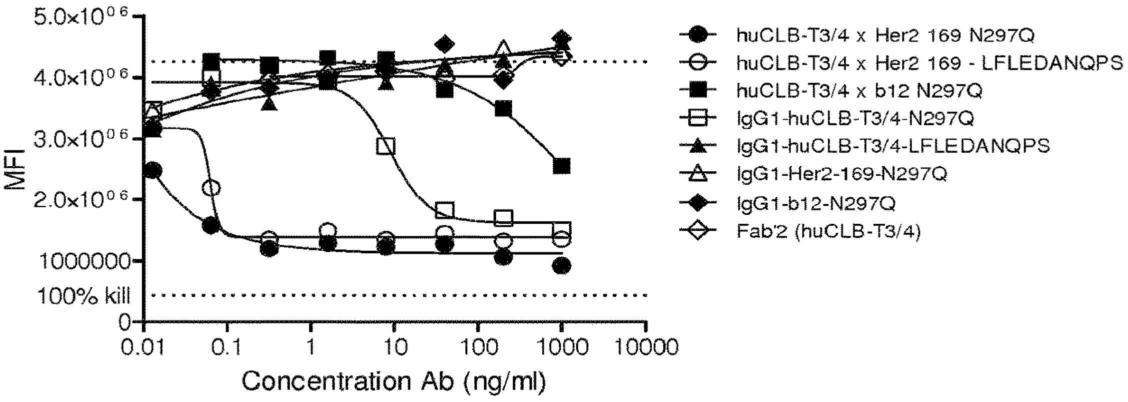
FIG. 17: Non-specific Fc-mediated killing in a cytotoxic assay with PBMCs can be further reduced using antibodies with a modified Fc region (LFLEDANQPS), whereas non-glycosylation via N297Q alone does not completely remove this activity. These mutations do no compromise the specific killing activity of bispecific HER2×CD3 antibody. See Example 27 for details.

As shown in FIG. 17 of Example 27, the N297Q mutation and therefore absence of Fc glycosylation of HER2×CD3 bispecific antibody huCLB-T3/4×HER2-169 did not impact the potential to induce dose dependent cytotoxicity of AU565 cells with PBMC.

Example 22

HER2 Downmodulation

To investigate if enhanced HER2 internalization induced by Group 3 antibodies 098 and 153 and Group 4 antibody 005 also results in enhanced receptor downmodulation, AU565 cells were incubated with HER2 antibodies for 3 days, and analyzed for presence of HER2. AU565 cells were seeded in a 24-wells tissue culture plate (100.000 cells/well) in normal cell culture medium and cultured for 3 days at 37° C. in the presence of 10 μg/mL HER2 antibody. After washing with PBS, cells were lysed by incubating 30 min at room temperature with 25 μL Surefire Lysis buffer (Perkin Elmer, Turku, Finland). Total protein levels were quantified using bicinchoninic acid (BCA) protein assay reagent (Pierce) according to the manufacturer's protocol. HER2 protein levels in the lysates were analyzed using a HER2-specific sandwich ELISA. Rabbit-anti-human HER2 intracellular domain antibody (Cell Signaling) was used to capture HER2 and biotinylated goat-anti-human HER2 polyclonal antibody (R&D), followed by streptavidin-poly-HRP, were used to detect bound HER2. The reaction was visualized using 2,2'-azino-bis 3-ethylbenzothiazoline-6-sulfonic acid (ABTS: dilute one ABTS tablet in 50 mL ABTS buffer [Roche Diagnostics, Almere, The Netherlands]) and stopped with oxalic acid (Sigma-Aldrich, Zwijndrecht, The Netherlands). Fluorescence at 405 nm was measured on a microtiter plate reader (Biotek Instruments, Winooski, USA) and the amount of HER2 was expressed as a percentage relative to untreated cells.

Figure 12:
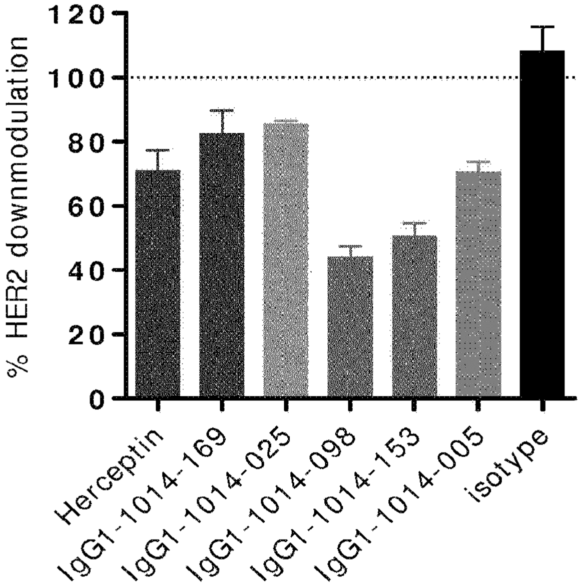
FIG. 12: Antibody induced downmodulation of HER2. Relative percentage of HER2 expressed in AU565 cell lysate after 3 days incubation with 10 μg/mL antibody. The amount of HER2 was quantified using a HER2-specific capture ELISA and plotted as a percentage relative to untreated cells. Data shown are mean of three experiments±standard deviation.

The results shown in FIG. 12 and Table 10 demonstrate that both tested Group 3 antibodies (098 and 153) induced more than 50% HER2 downmodulation. In contrast, antibodies 025, 169 and Trastuzumab (Herceptin®) barely induced downmodulation (approximately 20% of untreated cells) while antibody 005 induced moderate downmodulation (approximately 30% of untreated cells). This was in line with enhanced internalization observed by antibodies 098, 153, and 005.

TABLE 10

Antibody induced downmodulation of HER2 depicted as percentage HER2 compared to untreated cells

| antibody | % HER2 compared to untreated cells |
|---|---|
| Herceptin | 80 |
| IgG1-1014-169 | 82 |
| IgG1-1014-025 | 85 |
| IgG1-1014-098 | 44 |
| IgG1-1014-153 | 50 |
| IgG1-1014-005 | 70 |
| isotype control | 108 |

Example 23

Colocalization of HER2 Antibodies with Lysosomal Marker LAMP1 Analyzed by Confocal Microscopy The HER2 downmodulation assay as described in Example 21 and the CypHer-5E based internalization assay as described in Example 19 indicated that HER2 antibodies from groups 3 and 4 were more efficiently internalized and targeted towards lysosomes compared to antibodies from Groups 1 and 2. To confirm the enhanced lysosomal transport of antibodies from groups 3 and 4, AU565 cells were cultured on glass coverslips and treated for 18 hours with the indicated antibodies. Cells were fixed, permeabilized and stained with FITC-conjugated goat anti-human IgG1 to visualize antibody and mouse anti-human CD107a (LAMP1) followed by goat anti-mouse IgG-Cy5 to identify lysosomes.

However, in these experiments the confocal imaging was done with settings that allowed discriminating between monospecific and bispecific antibodies but not between different monospecific antibodies, in fact, with these settings monospecific antibodies could hardly be detected. To be able to compare between the different monospecific antibodies, the confocal slides were measured again with increased gain settings, to enhance fluorescence intensity. All other steps of the procedure were the same as described in Example 23.

Figure 13:
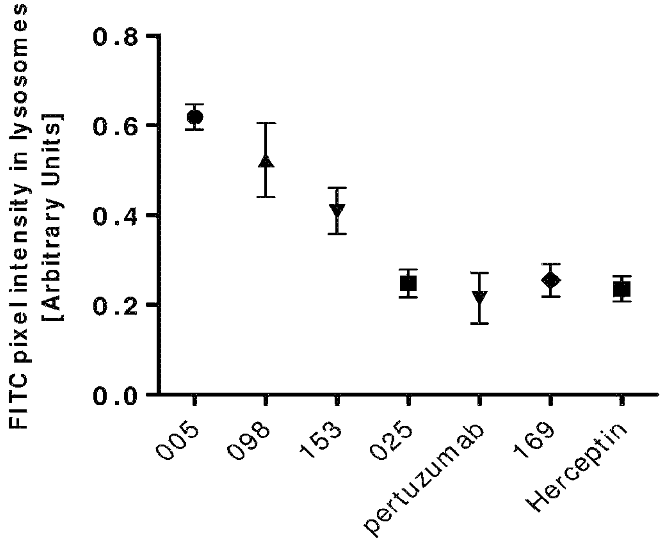
FIG. 13: Colocalization analysis of HER2 antibodies (FITC) with lysosomal marker LAMP1 (Cy5). FITC pixel intensity overlapping with Cy5 for various monospecific HER2 antibodies. FITC pixel intensity in LAMP1/Cy5 positive pixels of three different images is plotted for each antibody. Group 3 antibodies 098 and 153 show higher FITC pixel intensities in the LAMP1/Cy5 positive compartments compared to antibodies 025 and pertuzumab from Group 2 and 169 and Herceptin® from Group 1.

The results are depicted in FIG. 13 and Table 11, and show that the FITC pixel intensity overlapping with Cy5 for various monospecific HER2 antibodies. From each slide three different images were analyzed containing ~1, 3 or >5 cells. Significant variation was observed between the different images within each slide. Still, it was evident that antibodies 005, 098 and 153 were more efficiently targeted towards lysosomal compartments, compared to 025, pertuzumab, 169 and Trastuzumab) (Herceptin®). This correlated well with the enhanced internalization and receptor degradation induced by these antibodies.

TABLE 11

Mean FITC pixel intensities overlapping with Cy5 depicted as arbitrary units.

| antibody | FITC pixel intensity in lysosomes [arbitrary units] |
|---|---|
| TH1014-005 | 0.619 |
| TH1014-098 | 0.522 |
| TH1014-153 | 0.409 |
| TH1014-025 | 0.248 |
| TH1014-pert | 0.214 |
| TH1014-169 | 0.255 |
| Herceptin | 0.236 |

Example 24

HER2 Extracellular Domain Shuffle Human-to-Chicken

To further define the HER2 binding regions recognized by antibodies from the four different cross-competition groups described in Example 14, a HER2 extracellular domain shuffle experiment was performed. To this end, a small gene-synthesis library with five constructs was generated, swapping the sequences of domain I, II, III or IV of the extracellular domain of human HER2 to the corresponding sequence of chicken HER2 (Gallus gallus isoform B NCBI: NP_001038126.1): 1) fully human HER2 (Uniprot P04626) hereafter named hu-HER2, 2) hu-HER2 with chicken domain I (replacing amino acids (aa) 1-203 of the human HER2 with the corresponding chicken HER2 region) hereafter named hu-HER2-ch(I), 3) hu-HER2 with chicken domain II (replacing amino acids (aa) 204-330 of the human HER2 with the corresponding chicken HER2 region) hereafter named hu-HER2-ch(II), 4) hu-HER2 with chicken domain III (replacing aa 331-507 of the human HER2 with the corresponding chicken HER2 region) hereafter named hu-HER2-ch(III) and 5) hu-HER2 with chicken domain IV (replacing aa 508-651 of the human HER2 with the corresponding chicken HER2 region) hereafter named hu-HER2-ch(IV). The human and chicken HER2 orthologs show 67% homology in their extracellular domain with 62% homology in domain I, 72% homology in domain II, 63% homology in domain III and 68% homology in domain IV. The constructs were transiently transfected in the Freestyle™ CHO—S (Invitrogen) cell line using Freestyle MAX transfection reagent (Invitrogen) according to the instructions of the manufacturer, and transfected cells were cultured for 20 hours. HER2 antibody binding to the transfected cells was analyzed by means of flow cytometry: The transfected CHO—S cells were harvested, washed with FACS buffer and incubated with 10 μg/mL HER2 antibody (30 minutes on ice). Binding of HER2 antibodies was detected using a Phycoerythrin (PE)-conjugated goat-anti-human IgG antibody (Jackson). To check if expression between different batches was the same, cells were fixed and permeabilized using Cytofix/Cytoperm solution (BD) according manufacturer's instruction and stained with a rabbit-anti-human intracellular HER2 antibody (DAKO) in combination with a secondary PE-conjugated goat-anti-rabbit antibody (Jackson). An isotype control antibody was used as negative control. Fluorescence was measured on a FACSCanto-II (BD) and binding curves were made by means of non-linear regression (sigmoidal dose-response with variable slope) using GraphPad Prism V4.03 software (GraphPad Software, San Diego, Calif., USA). Loss of binding was used as read out to identify which HER2 domains were recognized by the different antibodies.

Figure 14:
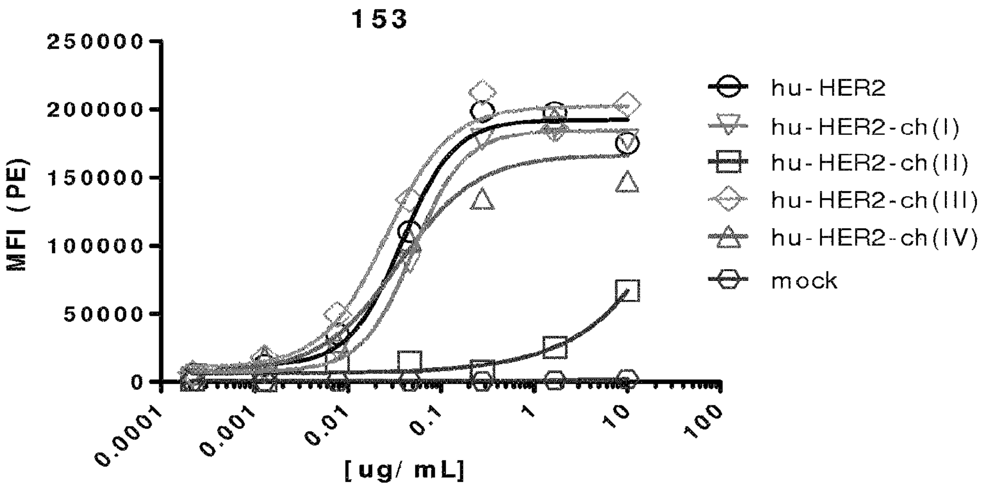
FIG. 14: HER2 antibody binding to CHO—S cells transfected with different HER2 ECD construct analyzed by means of flow cytometry. Hu-HER2=fully human HER2, Hu-HER2-ch(I) CR1=hu-HER2 with chicken domain I, Hu-HER2-ch(II)=hu-HER2 with chicken domain II, hu-HER2-ch(III)=hu-HER2 with chicken domain III and Hu-HER2-ch(IV)=hu-HER2 with chicken domain IV. Data shown are mean fluorescence intensities (MFI) of one representative antibody, TH1014-153. See Example 24 for details.
Figure 15A:
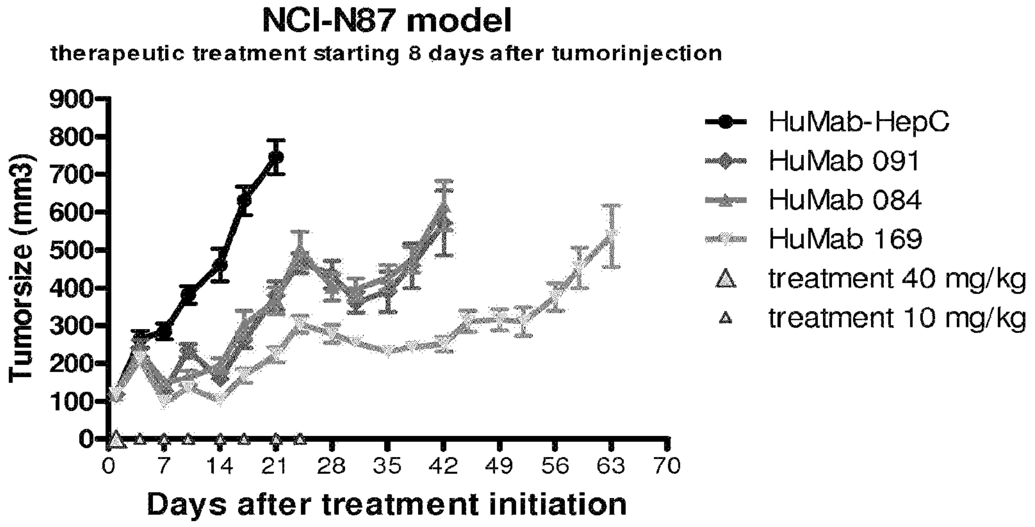
FIGS. 15A-15D: In vivo effect of HER2-HuMabs in the NCI-N87 human gastric carcinoma xenograft model in female CB.17 severe combined immunodeficiency (SCID) mice. Data shown are mean tumorsize S.E.M. per group (n=10 mice per group) (FIG. 15A, FIG. 15C) and survival (FIG. 15B, FIG. 15D). See Example 25 for details.
Figure 15B:
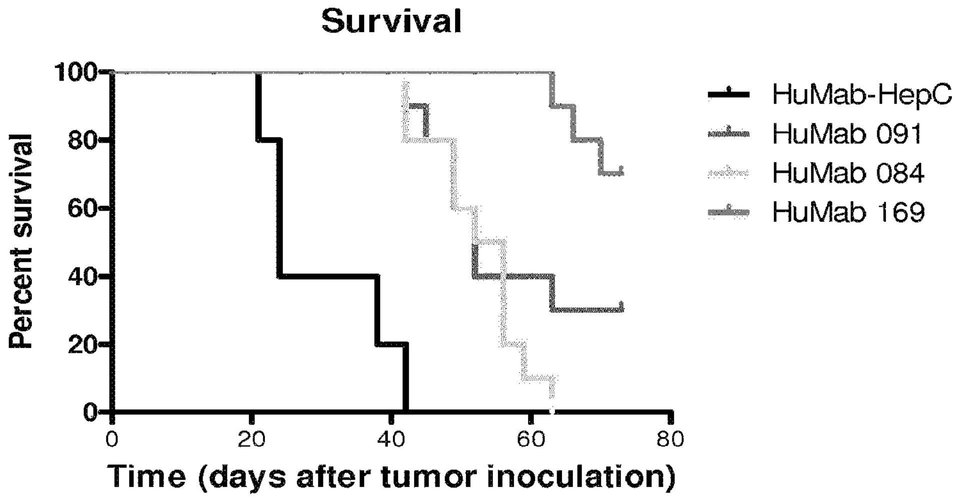
Figure 15C:
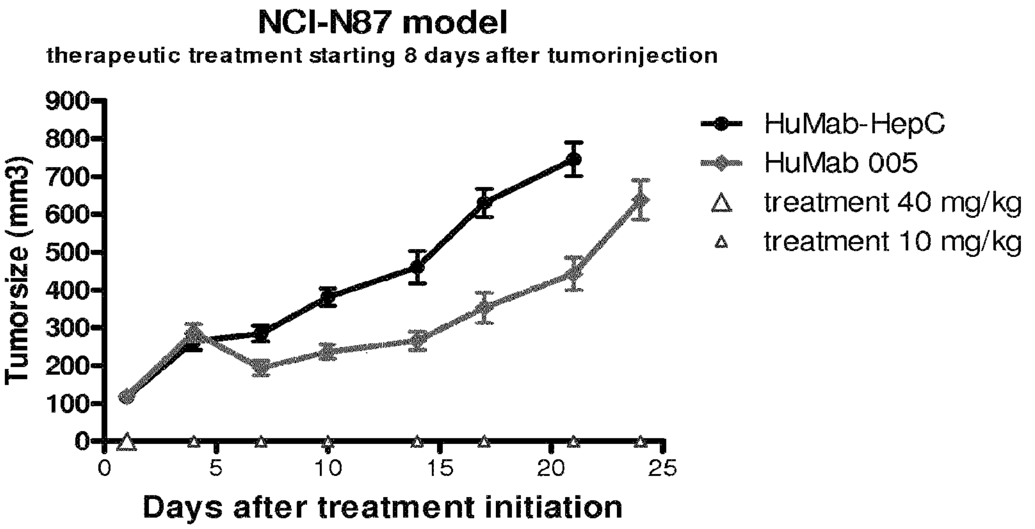
Figure 15D:
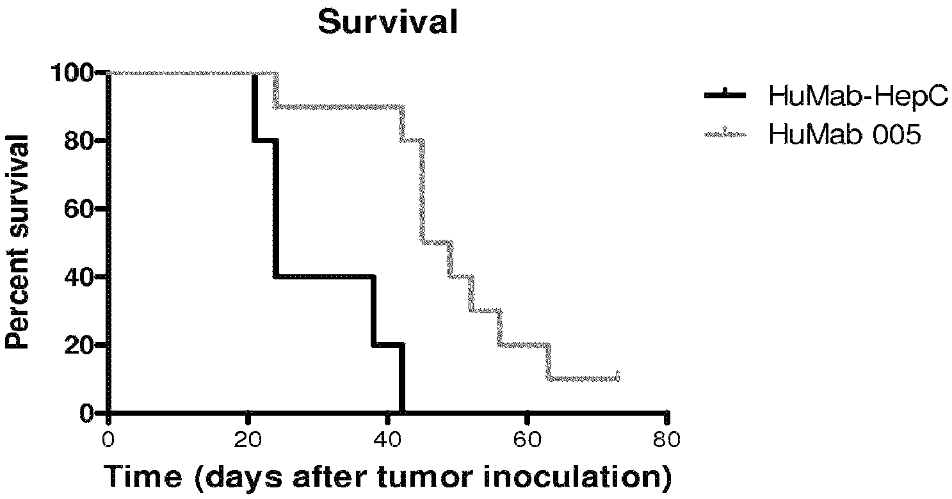

Exemplary binding curves for antibody 153 are shown in FIG. 14. All binding results are shown in Table 12. Group 1 HER2 antibodies 050, 084, 169 and Trastuzumab (Herceptin®) showed loss of binding to Hu-HER2-ch(IV), but not to the proteins with one of the remaining domains shuffled, demonstrating that the epitopes of Group 1 mAbs reside in HER2 domain IV. Group 2 antibodies 025, 091, 129 and pertuzumab showed only loss of binding to Hu-HER2-ch (II), indicating that the epitope resides in HER2 domain II. Antibodies 098 and 153 were both defined to Group 3 in cross-competition assays (not shown) but showed some variation in the shuffle experiment. Antibody 098 clearly showed loss of binding to Hu-HER2-ch(I) and a minor decrease in binding to Hu-HER2-ch(II), while 153 showed only loss of binding to Hu-HER2-ch(II). These data suggest that Group 3 mAbs 098 and 153 can also bind, at least partially, to the HER2 domain II, with epitopes that possibly extend into HER2 domain I, as is the case for 098. Antibodies 005, 006, 060 and 111 showed loss of binding upon substitution of HER2 domain III, which demonstrated that the epitope resides in HER2 domain III. Interestingly, antibodies 059 and 106 demonstrated loss of binding to both hu-HER2-ch(III) and hu-HER2-ch(I), implying that antibodies 059 and 106 recognize a conformational epitope within these two domains.

TABLE 12

Summary of HER2 antibody binding to different HER2ECD receptor constructs. FL; hu-HER2, I; hu-HER2-ch(I), II; hu-HER2-ch(II), III; hu-HER2-ch(III), IV; hu-HER2-ch(IV). +++ indicates normal binding, ++ indicates reduced $EC_{50}$ but the similar maximal binding compared to binding observed to hu-HER2, + indicates reduced $EC_{50}$ and reduced maximal binding detected compared to binding observed to hu-HER2, – indicates no binding.

| | | HER2-domain shuffled | | | | |
|---|---|---|---|---|---|---|
| Antibody | Group | FL | I | II | III | IV |
| Herceptin ® | 1 | +++ | +++ | +++ | +++ | |
| 050 | 1 | +++ | +++ | +++ | +++ | |
| 084 | 1 | +++ | +++ | +++ | +++ | |
| 169 | 1 | +++ | +++ | +++ | +++ | + |
| Pertuzumab | 2 | +++ | +++ | + | +++ | +++ |
| 025 | 2 | +++ | +++ | | +++ | +++ |
| 091 | 2 | +++ | +++ | | +++ | +++ |
| 129 | 2 | +++ | +++ | | +++ | +++ |
| 153 | 3 | +++ | +++ | | +++ | +++ |
| 098 | 3 | +++ | | ++ | +++ | +++ |
| 005 | 4 | +++ | +++ | +++ | | +++ |
| 006 | 4 | +++ | +++ | +++ | | +++ |

TABLE 12-continued

Summary of HER2 antibody binding to different HER2ECD receptor constructs. FL; hu-HER2, I; hu-HER2-ch(I), II; hu-HER2-ch(II), III; hu-HER2-ch(III), IV; hu-HER2-ch(IV). +++ indicates normal binding, ++ indicates reduced $EC_{50}$ but the similar maximal binding compared to binding observed to hu-HER2, + indicates reduced $EC_{50}$ and reduced maximal binding detected compared to binding observed to hu-HER2, – indicates no binding.

| | | HER2-domain shuffled | | | | |
|---|---|---|---|---|---|---|
| Antibody | Group | FL | I | II | III | IV |
| 059 | 4 | +++ | | +++ | | +++ |
| 060 | 4 | +++ | +++ | +++ | | +++ |
| 106 | 4 | +++ | | +++ | | +++ |
| 111 | 4 | +++ | +++ | +++ | | +++ |

Example 25

In Vivo Efficacy of HER2 HuMabs 005, 091, 084 and 169 in NCI-N87 Human Gastric Carcinoma Xenografts in SCID Mice The in vivo effect of HER2-HuMabs 091 (cross-competition Group 2), 084 and 169 (both cross-competition Group 1), and 005 (cross-block Group 4) on tumor growth and survival in a NCI-N87 human gastric carcinoma xenograft model in female CB.17 severe combined immunodeficiency (SCID) mice was determined. $10\times10^6$ NCI-N87 tumor cells in 50% matrigel were injected s.c. in female SCID mice, 10 mice per group. Eight days after tumor inoculation, intravenous treatment with HER2-HuMabs 005, 091, 084, and 169 or control antibody HuMab-HepC was started. In FIGS. 15 (A) and (C), this is indicated as day 1, day of treatment initiation. The first dose was at 40 mg/kg, followed by 10 mg/kg on days 4, 8, 11, 15, 18, 22, and 25 after treatment initiation. Tumor volume was determined at least 2 times per week. Volumes ($mm^3$) were calculated from caliper (PLEXX) measurements as ($width^2\times length$)/2.

The results are depicted in FIGS. 15A, 15B, 15C and 15D, which show that the mice administered with HuMab 005, 084, 169 and 091 demonstrated slower tumor growth (A) and better survival (B) than the mice that received negative control antibody HuMab-HepC. All treatments were well-tolerated.

Example 26

Therapeutic Treatment of BT-474 Breast Tumor Xenografts in Balb/C Nude Mice

The effect of therapeutic treatment of five different HER2 HuMabs on human subcutaneous BT-474 breast tumor xenografts in Balb/C nude mice was determined. BT-474 tumor cells were injected 24 to 72 hours after a whole body irradiation with a γ-source (1.8 Gy, Co60, BioMep, France). $2\times10^7$ BT-474 cells in 200 μl of RPMI 1640 containing matrigel (50:50, v:v; BD Biosciences) were injected subcutaneously into the right flank of female Balb/C nude mice. Body weight and tumor volume of the mice was recorded twice a week. Tumor volumes ($mm^3$) were calculated from caliper (PLEXX) measurements as: ($width^2\times length$)/2.

Treatment with HER2 HuMabs was started when the tumors reached a mean volume of 100-200 mm3. Tumor bearing mice were randomized into groups of 8 mice. One group received twice weekly intravenous (i.v.) injections of the control mAb HuMab-HepC. Four other groups received twice weekly i.v. injections of HER2 HuMab 025, 129, 153 and 091, with a first dose of 20 mg/kg and following 9 doses of 5 mg/kg.

Figure 16A:
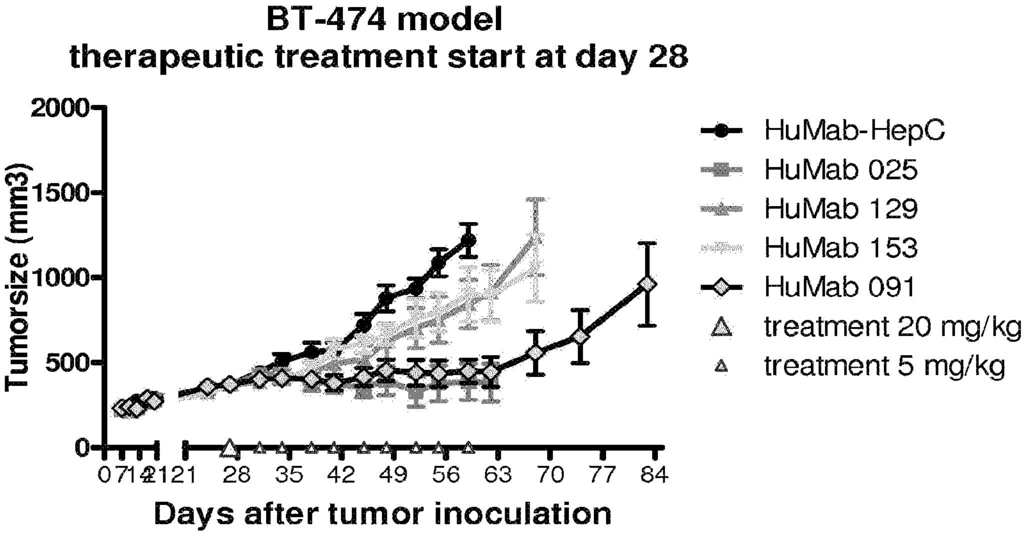
FIGS. 16A and 16B: In vivo effect of HER2 HuMabs in BT-474 breast tumor xenografts in Balb/C nude mice. Data shown are mean tumorsize±S.E.M. per group (n=8 mice per group) (FIG. 16A) and survival (FIG. 16B). See Example 26 for details.
Figure 16B:
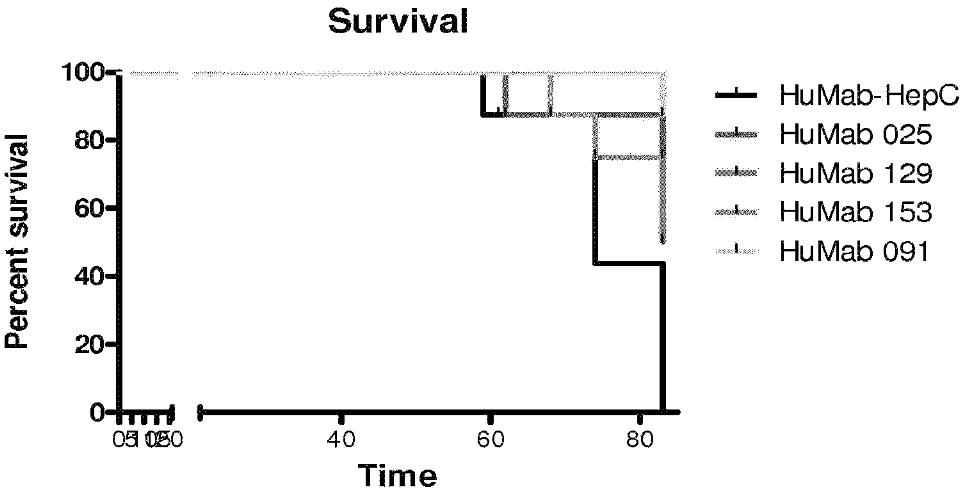

The results are depicted in FIGS. 16A and 16B and show that BT-474 tumor growth was partially inhibited with HuMab 129 and HuMab 153 treatment (about 30 and 50% of inhibition compared to HuMab-HepC control treatment). HuMab-025 and HuMab-091 strongly inhibited the BT-474 tumor growth and the time to reach a tumor volume of 800 $mm^3$ was significantly delayed by these antibodies. Survival was also improved in the HER2 HuMab receiving mice.

Example 27

Removing Fc-Mediated T Cell Activation by Means of Fc Mutations

Monocytes, which are present in PBMCs, express Fc-receptors which can interact with the Fc-domains in the IgG monospecific and bispecific antibodies. In case monospecific CD3 antibodies are used, it is known that such active Fc-domain can cause activation of T-cells. Importantly, if purified T-cells are used as effector cells this Fc-mediated effect is absent due to the absence of monocytes.

In order to remove this activity, a strategy was set up to create antibodies without such Fc-mediated activity. Deglycosylation of antibodies, either post-translational via N-glycanase or genetically via N297Q mutation has been described to result in an inert antibody format (Tao M H et al., Immunol 1989, 143; 2595-2601). These Fc modified antibodies were generated to determine the contribution of Fc-mediated activation of T cells. A panel of (bispecific) antibodies with either a N297Q mutation in the Fc-domain or chemically deglycosylated were compared to antibodies with WT Fc regions in a cytotoxity assay with PBMCs (E:T ratio 5:1). The cytotoxicity assay was performed as described in Example 21, however human PBMC were used instead of purified T-cells. Deglycosylation did not compromise the activity of the HER2×CD3 bispecific antibodies in the cytotoxicity assay whereas the Fc-mediated activity of monospecific huCLB-T3/4 was strongly but not completely removed under the tested conditions (FIG. 17).

To completely remove the residual Fc activity three sets of mutations from the public domain were combined in one mutant. The mutations L234F, L235E, P331S (Oganesyan Acta Cryst. (2008). D64, 700-704), D265A (Shields JBC (2001) 276(9) 6591-6604) and N297Q were introduced in the K409R and F405L IgG1 backbone. This mutant, designated LFLEDANQPS, did not show any residual Fc-mediated activation of T cells in a cytotoxity assay (same protocol as above) with PBMCs (FIG. 17).

Example 28

Effect of HER2 Epitope on HER2×CD3 Efficacy

The effect of the binding site on the tumor target (epitope) was determined by generating three bispecific antibodies recognizing different HER2 epitopes combined with a CD3 antibody that was proven to be effective in a bispecific format (Examples 21 and 27). The HER2-clones 005, 153 and 169 are three non-crossblocking antibodies recognizing a spatially segregated part of HER2 as shown in Example 24. These three HER2-clones were combined with CD3 antibody clone huCLB-T3/4, which recognizes human CD3 as a bispecific molecule and tested in a cytotoxicity assay with either human PBMCs or purified human T cells. The assay was performed as described in example 21. An E:T ratio of 1:1 was used for the T-cells assay, a 2:1 ratio was used for the PBMC assay.

Figure 18A:
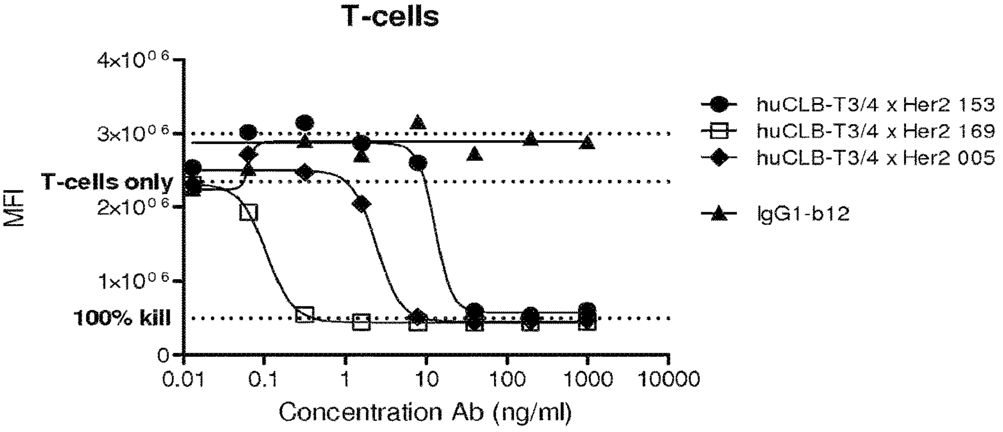
FIGS. 18A and 18B: Location of HER2 epitope has a strong effect on the efficacy of the HER2×CD3 antibodies as shown by comparison studies of three mAbs combined with the same anti-CD3 antibody (huCLB-T3/4) in cytoxicity assays with either T-cells (FIG. 18A) or PBMCs (FIG. 18B) as effector cells.
Figure 18B:
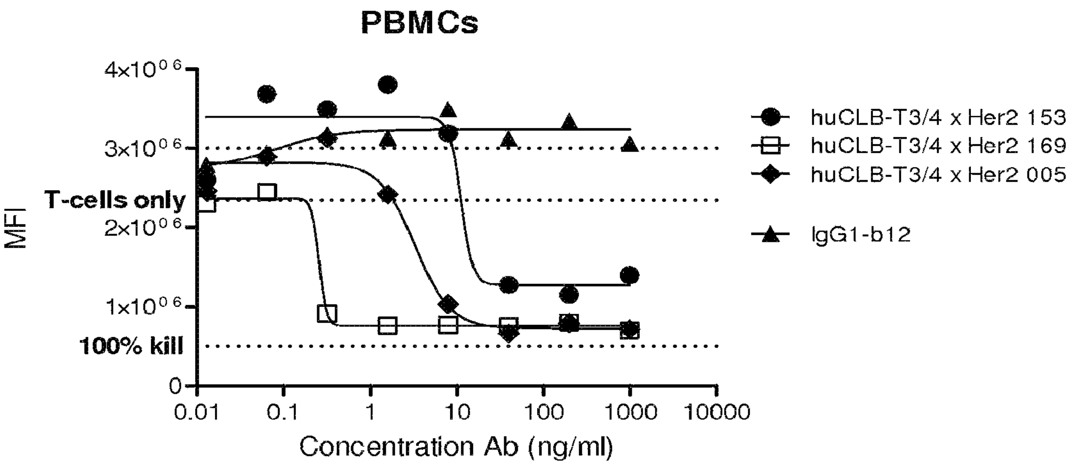

As shown in FIG. 18, all three bispecific antibodies are able to induce killing of AU565 target cells, albeit with different efficacy. These data show an important effect of the location of the target epitope on the cytotoxic potential of a HER2×CD3 bispecific antibody.

Example 29

Efficacy of T Cell Mediated Killing Depends on HER2 Expression Levels

Cell lines with different HER2 expression levels were used to study the effect of target density on the efficacy of bispecific HER2×CD3 antibodies. Bispecific antibody 169×huCLB-T3/4-N297Q was tested in a cytotoxicity assay using A549, A431, 3T3 and AU565 cells. HER2 expression was determined using QIFIKIT® analysis, using the mouse anti-human HER2 (R&D Systems, Cat. MAB1129, Lot IBD0207061) and isotype control antibody (BD, Cat. 555740 Lot 3280) at a concentration of 10 μg/mL. The expression levels are summarized in Table 13.

For the cytotoxity assay the different HER2 expressing cell lines were co-cultured with freshly isolated human T cells with an E:T ratio of 10:1, using the protocol described in Example 21.

Figure 19:
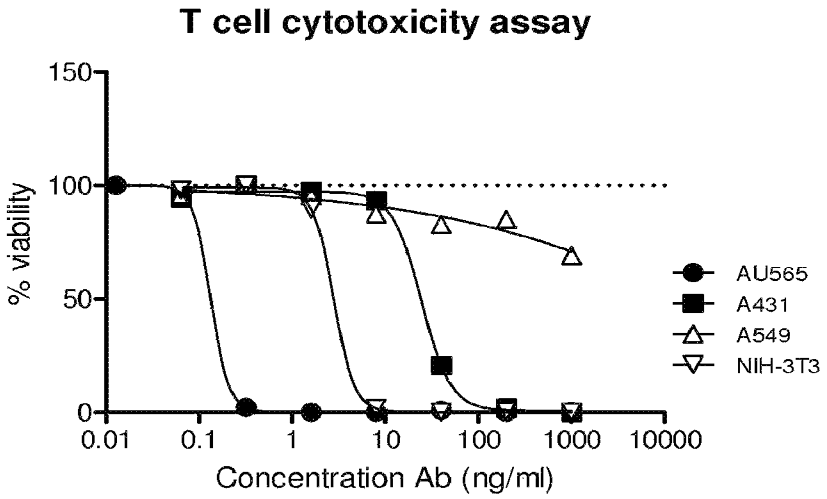
FIG. 19: T cell cytotoxicity assay using target cell lines with various HER2 expression levels. Shown is the percentage of viable cells after three days incubation with T cells in the presence of HER2×CD3 bispecific antibody. The efficacy positively correlated with the expression levels, as the cells with the highest expression were killed at the lowest antibody concentrations.

The cytotoxic efficacy of 169×CLB-T3/4 was correlated with the HER2 expression of the target cell line (FIG. 19). AU565 cells were killed at already very low concentrations of antibody whereas the cells with lowest expression (A549) could hardly be killed in this experimental set up.

TABLE 13

HER2 expression levels of cell lines used in cytotoxity assay.

| Cell line | HER2 expression (molecules per cell) |
|---|---|
| AU565 | 4 × 10e5 |
| NIH-3T3 | 7 × 10e4 |
| A431 | 1.4 × 10e4 |
| A549 | 1 × 10e4 |

Example 30

Characterization of HER2×CD3 Bispecific Antibody Induced T Cell Activation

Figure 20:
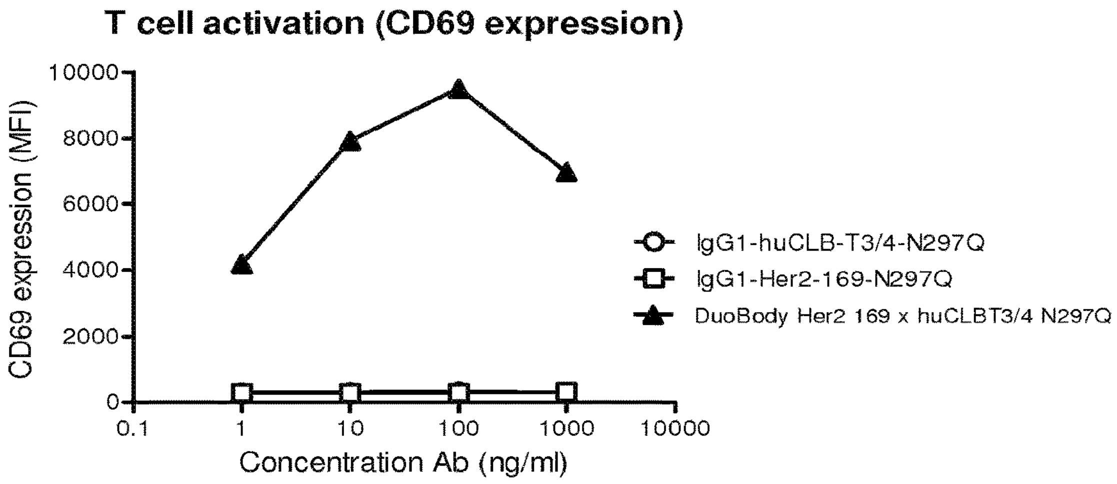
FIG. 20: CD69 expression of T cells co-cultured with AU565 tumor cells in the presence of bispecific HER2×CD3 antibody and monospecific controls.

As shown in previous examples effective killing of various HER2 expressing tumor cell lines was accomplished by using bispecific HER2×CD3 antibodies. The expression of CD69, a well characterized activation marker of cytotoxic T cells, was monitored in T cells co-cultured with AU565 tumor cells in the presence of bispecific HER2×CD3 antibody for 16 h at 37° C. A dose dependent activation of the T cells as measured by CD69 expression was observed (FIG. 20) which correlates with the observed cytotoxicity data shown in Example 21.

Figure 21:
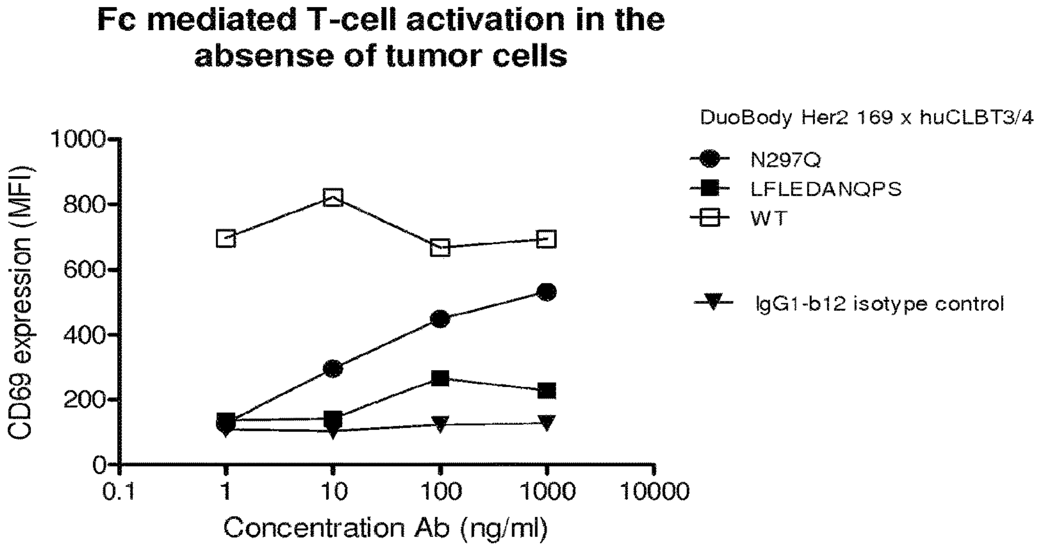
FIG. 21: CD69 expression of T cells in PBMC pool treated with different Fc variants of DuoBody HER2 169× huCLBT3/4 in the absence of tumor cells.

In agreement with the cytotoxicity data shown in Example 27, in vitro characterization of the T cell response revealed that also in the absence of tumor cells, an Fc-mediated T cell activation could be observed when PBMCs were used as effector cells (FIG. 21). This effect was most prominent when a variant with an unmodified Fc of DuoBody HER2 169×huCLBT3/4 was used and could be reduced by introduction of the N297Q mutation. The Fc mediated activation by monospecific CD3 antibodies could be further reduced by using an LFLEDANQPS Fc-mutant (FIG. 21).

An in vitro cytotoxicity assay was performed as described in Example 21. Th1/Th2 cytokine detection in the medium of the different wells was performed by collecting supernatant samples of a cytotoxicity assay to measure cytokine release. Undiluted samples were analysed on FACS using the human Th1/Th2 Cytokine detection kit (BD Biosciences, cat #551809), according to manufacturer's instructions. Cytokine concentration of IL-2, IL-4, IL-6, IL-10, IFN-γ and TNF-α in the samples were calculated based on standard curves of these cytokines. Data was analyzed using Graphpad Prism 5.0 and Excel 2003 software. Three groups of cytokines were analyzed (1) Pro-inflammatory cytokines TNF-α, INF-γ and IL-2 (2) Pro and anti-inflammatory cytokine IL6 and (3) Anti-inflammatory cytokines IL4 and IL10. Cytokine profiles at day 3 generated by T-cells or PBMCs in in vitro cytotoxicity assay with DuoBody huCLB-T3/4×HER2-169 N297Q and all appropriate controls are summarized in Table 14.

Cytokines are upregulated when tumor cells and T-cells were incubated together with DuoBody huCLB-T3/4×HER2-169 N297Q in contrast to the control antibodies and control treatments (medium and T-cells only).

Incubation of tumor cells and PBMC with DuoBody huCLB-T3/4×HER2-169 N297Q also resulted in upregulation of the measured cytokines when compared to control antibody IgG1-1014-169 N297Q and IgG1-Herceptin® and control situations (medium and T-cells only). However, incubation of target cells and PBMCs with control antibody DuoBody huCLB-T3/4-N297Qxb12-N297Q and monospecific huCLB-T3/4-N297Q also resulted in upregulation of most cytokines compared to control situations (medium and T-cells only).

Figure 22:
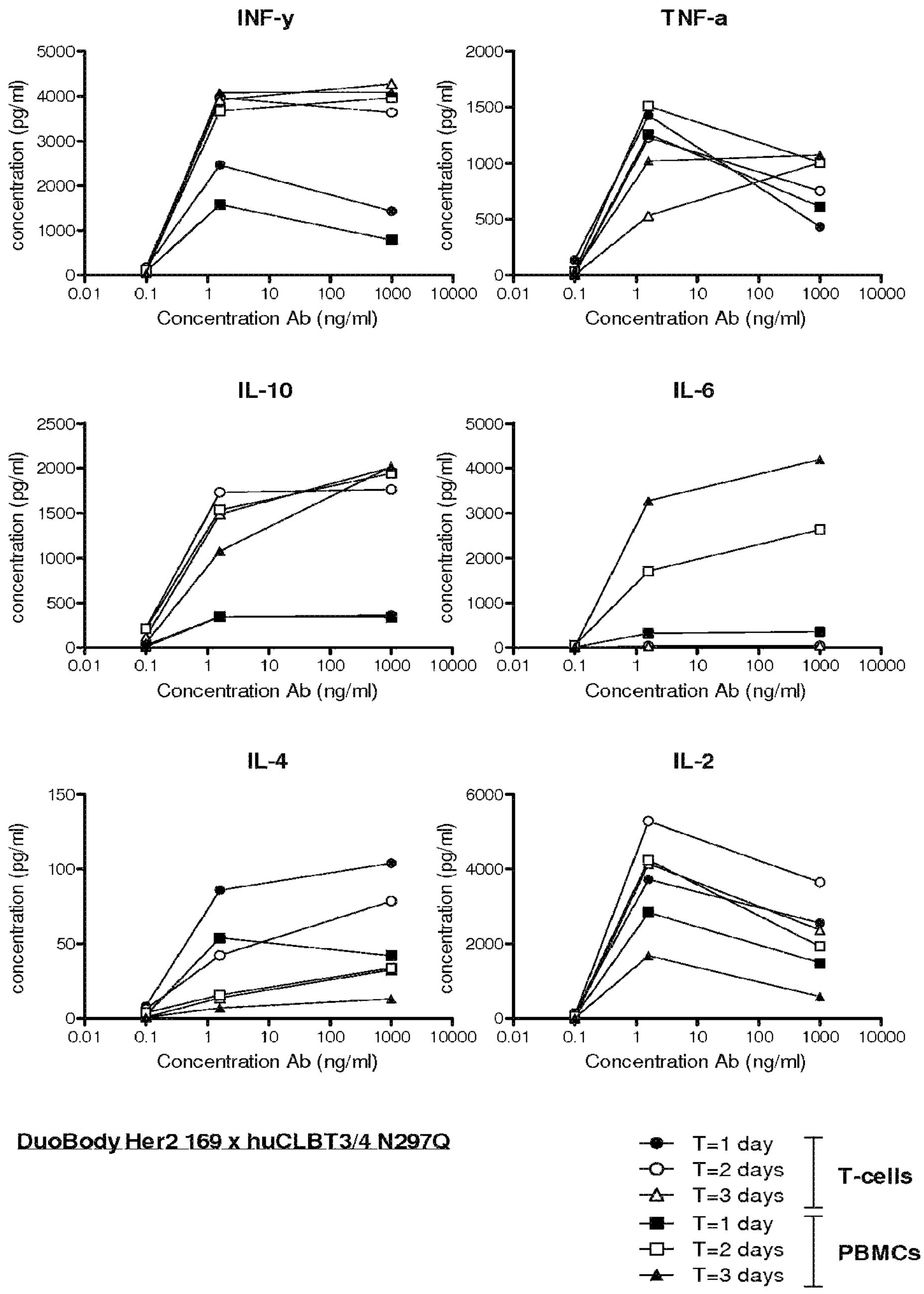
FIG. 22: Cytokine profile resulting from incubation of PBMCs or T-cells with DuoBody huCLB T3/4-Q×HER2-169-Q (CD3-Q/169Q) antibodies and HER2 positive tumor cells.

Cytokine expression was also followed over time. Cytokine profiles at day 1, 2 and 3 generated by T-cells or PBMCs in in vitro cytotoxicity assay with DuoBody™ huCLB-T3/4-N297QxHER2-169-N297Q are depicted in FIG. 22. In general, the pro-inflammatory cytokines, TNF-α, INF-γ and IL-2, were pronounced present in experiments were lower antibody concentrations were used (3 ng/mL). In experiments where antibody concentrations were increased with a factor 300, most pro-inflammatory cytokines were present at lower concentrations. IL-6, the cytokine with pro and anti-inflammatory activity, is hardly secreted by T-cells, but highly secreted by PBMCs upon incubation with tumor cells and DuoBody huCLB-T3/4×HER2-169 N297Q. Some cytokines are secreted at higher levels at day 1 and/or day 2 and decrease at day 3, whereas others are secreted at lower levels at day 1 and show increased expression at day 2 and or 3.

Additionally the release of GM-CSF as a measure for T cell activation was measured. This cytokine is not consumed during the activation of T cells and is therefore better suited for the measurement of cytokines levels in long term experiments. To investigate the observed cytokine release in the control samples as described above Fc mutants were compared to WT antibodies. Hereto T cells samples from co-cultures of PBMCs with AU565 tumor cells in the presence of bispecific antibodies were analyzed in a GM-CSF ELISA.

The following protocol was used: An ELISA plate was coated with 100 μL/well 2.0 μg/mL coating antibody (anti-GM-CSF 9.1 Sanquin) in PBS and incubated 0/N at room temperature (RT). Plates were then washed 3 times with PBS supplemented with 0.05% Tween (PBST) using an Elisa-washer. Samples were diluted in PBST/0.2% BSA and standard curve samples were prepared (Standard curve: first point 1000 μg/mL, two-fold dilution curve, 10 steps and 2 blanks (Standard GM-CSF=rec GM-CSF Sandoz). 100 μL/well of samples were added to the plate and 10 μL/well of monoclonal biotinylated anti-GM-CSF (monoclonal anti-GM-CSF 16.3 Sanquin) (1 μg/mL) diluted in PBST/0.2% BSA and incubated for 2 h at RT on a shaker. After washing 3 times with PBS-T 100 μL/well Strep-poly-HRP diluted in PBST/0.2% BSA (0.1 μg/mL) was added and incubated for 20 minutes at room temperature on a shaker. For detection 1 tablet of ABTS substrate was dissolved in 50 ml ABTS-buffer (Roche) and 100 μL/well of the ABTS solution was added to well and incubated for 15-30 minutes at RT in the dark. The reaction was stopped with 100 μL/well 2% oxalic acid and incubated for 10 min in the dark. Absorbance was read at 405 nm using an EL808-Elisa-reader.

Figure 23:
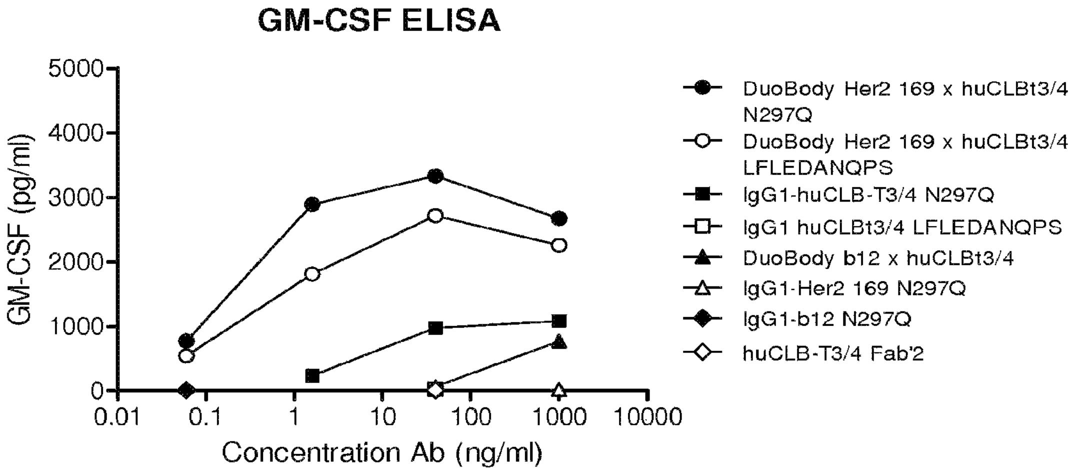
FIG. 23: GM-CSF production as a measure for T cell activation by bispecific HER2×CD3 antibodies and the contribution of non-specific Fc mediated activation.

DuoBody HER2 169×huCLB-T3/4 (both Fc variants, N297Q and LFLEDANQPS) induced a dose-dependent activation of T cells as shown by GM-CSF production (FIG. 23). The monospecific control antibody IgG1-HER2-169-N297Q and the irrelevant antibody IgG1-b12 N297Q did not induce T cell activation as expected. As observed in the TH1/TH2 cytokine profile assay monospecific IgG1-huCLB-T3/4 N297Q and DuoBody huCLB-T3/4×b12 N297Q did induce activation of T cells. The $(Fab')_2$ control and the inactive Fc mutant LFLEDANQPS of IgG1-CLB-T3/4 did not induce T cell activation suggesting that Fc mediated activation of T cells by N297Q mutants is occurring.

TABLE 14

Cytokine profile measured at day 3 of in vitro cytotoxicity assay with A. T-cells or B. PBMCs (incubated with 1000 ng/mL antibody).

A

| | Cytokines T-cells (conc. pg/mL) | | | | | |
|---|---|---|---|---|---|---|
| | INFγ | TNFα | IL2 | IL6 | IL4 | IL10 |
| DuoBody huCLB-T3/4-Q × HER2-169-Q | 4268.0 | 1005.1 | 2371.3 | 45.3 | 32.6 | 2010.1 |
| DuoBody huCLB-T3/4-Q × B12-Q | 0.5 | 0.3 | 9.3 | 0.1 | 0.1 | 1.7 |
| IgG1-hCLB-T3/4-Q | 1.6 | 1.7 | 20.5 | 0.2 | 0.3 | 2.6 |
| IgG1-HER2-169-Q | 4.8 | 0.7 | 5.1 | 0.3 | 0.2 | 0.5 |
| T-cells only | 0.1 | 0.4 | 0.2 | 0.1 | 0.0 | 0.3 |
| T-cell medium | 3.8 | 1.0 | 7.9 | 0.2 | 0.1 | 0.3 |

B

| | Cytokines PBMCs (conc. pg/mL) | | | | | |
|---|---|---|---|---|---|---|
| | INFγ | TNFα | IL2 | IL6 | IL4 | IL10 |
| DuoBody huCLB-T3/4-Q × HER2-169-Q * | 4082.6 | 1073.3 | 585.6 | 4191.9 | 13.2 | 2018.2 |
| DuoBody huCLB-T3/4-Q × B12-Q * | 1760.2 | 115.0 | 10.1 | 569.4 | 1.4 | 592.4 |
| IgG1-hCLB-T3/4-Q | 1474.2 | 92.7 | 345.2 | 116.5 | 1.7 | 1295.4 |
| IgG1-HER2-169-Q | 1.3 | 1.0 | 15.5 | 2.2 | 0.2 | 2.8 |
| T-cells only | 0.4 | 0.7 | 0.3 | 0.2 | 0.4 | 0.4 |
| T-cell medium | 1.5 | 1.0 | 8.8 | 0.2 | 0.3 | 2.2 |

* Concentration antibody = 1000 ng/mL

Example 31

In Vivo Proof of Concept

The in vivo anti-tumor efficacy of bispecific HER2×CD3 antibody was evaluated, in a subcutaneous NCI-N87 xenograft model, in which human T cells are co-inoculated in the form of unstimulated PBMCs with the tumor cells, analogous to the model described by Brischwein et al., (Mol. Immunol. 43 (2006), 1129-1143). Six to eleven weeks old female NOD-SCID (NOD.CB17-Prkdcscid/NcrCrl) mice were used. PBMC from healthy donors were isolated from a buffy coat as described in Example 21. At day 0, a mixture containing $5\times10^6$ cells of both PBMCs (and NCI-N87 cells were inoculated subcutaneously in 200 μL in the right flank of each mouse (PBMCs from two donors were used in parallel to rule out donor specific artefacts. Within one hour of injection, the mice were sorted into five groups (n=7) and each group was injected intraperitoneally (i.p.) with a single dose of (bispecific) antibody. Treatment groups are shown in Table 15. All antibody samples were supplemented with irrelevant mAb IgG1-b12 to obtain a total antibody concentration of 4 mg/kg per sample.

Figure 24A:
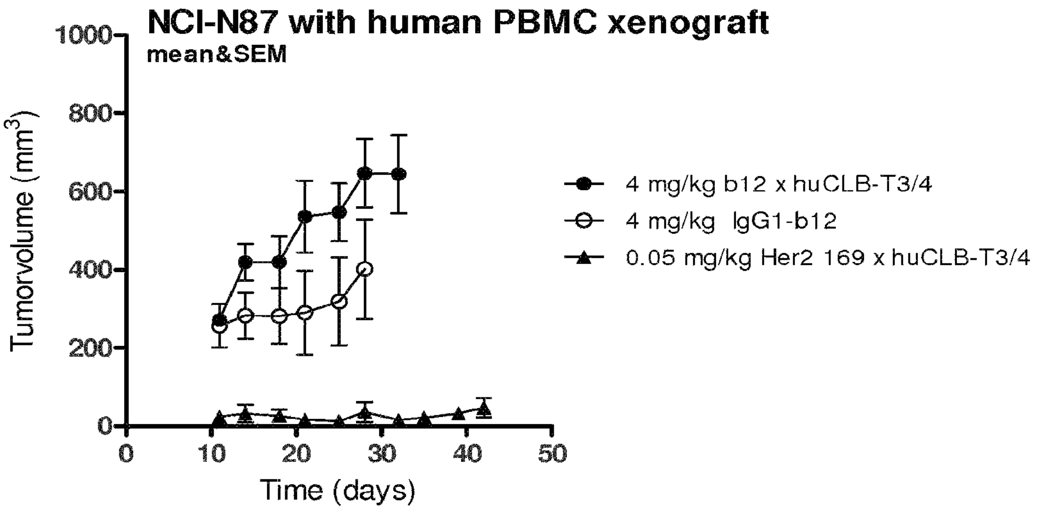
FIGS. 24A and 24B: Evaluation of the in vivo efficacy of HER2×CD3 bispecific mAb in a subcutaneous xenograft model with HER2 expressing tumor cell line and human PBMCs. In (FIG. 24A), tumor development (mean & SEM) in mice with NCI-N87 S.C. xenografts and S.C. human PBMCs treated with bispecific HER2×CD3 antibodies is shown. Three dosing schedules were being compared, and the lowest dose appeared to be most effective. In (FIG. 24B) the percentage surviving mice (with tumor sizes smaller then 500 $mm^3$) is shown in a Kaplan-Meier plot.

Tumors were measured twice per week using caliper (PLEXX) until an endpoint tumor volume of 1500 $mm^3$, tumors showed ulcerations or until the end of the study (day 50). FIG. 24A shows that on day 42 tumor outgrowth is inhibited most optimal by bispecific HER2×CD3 antibody effectively at a dose of 0.05 mg/kg.

Figure 24B:
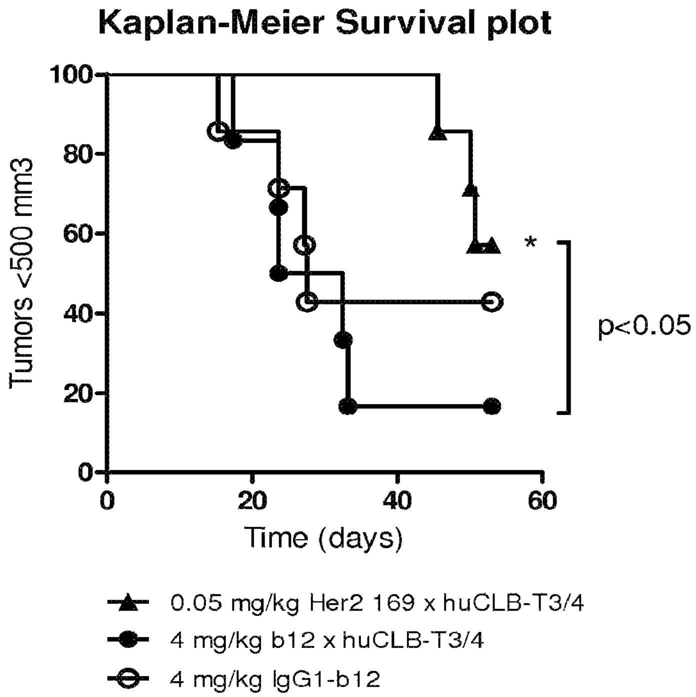

In FIG. 24B, the percentage survival (with tumor sizes smaller then 500 mm3) is shown in a Kaplan-Meier plot. Tumor formation is significantly delayed ($p<0.05$, Log Rank (Mantel-Cox)) in mice treated with HER2×CD3 antibodies (0.05 mg/kg) compared to control group treated with b12×CD3 control antibody.

TABLE 15

Treatment groups and dosing.

| Group | Antibody | Dose |
|---|---|---|
| 1 | DuoBody HER2 169 × CLB-T3/4-N297Q | 1 μg (= 0.05 mg/kg) |

TABLE 15-continued

| Treatment groups and dosing. | | |
|---|---|---|
| Group | Antibody | Dose |
| 2 | DuoBody b12 × CLB-T3/4-N297Q | 80 μg (= 4 mg/kg) |
| 3 | Neg control mAb IgG1-b12 | 80 μg (= 4 mg/kg) |

Example 32

Unraveling the Requirement of the T350I, K370T and F4051 Substitutions for Fab-Arm Exchange Engagement of Human IgG1

To further identify the determinants in the IgG1 CH3 domain that are required for IgG1 to be engaged in Fab-arm exchange, IgG1 containing the triple mutation T350I-K370T-F405L (ITL) was compared to the double mutants T350I-K370T (IT), T350I-F405L (IL) and K370T-F405L (TL) were studied using antibodies 2F8 and 7D8, respectively described in WO 02/100348 and WO 04/035607. Also the single mutant F405L (L) was tested. 2-MEA was used as a reductant to induce in vitro Fab-arm exchange (50 μg of each antibody in 100 μL PBS/25 mM 2-MEA for 90 min at 37° C.). For the single mutant F405L antibody, unpurified antibody from supernatant of a transient transfection was used after buffer-exchange to PBS using Amicon Ultra centrifugal devices (30k, Millipore, cat. no. UFC803096). To stop the reduction reaction, the reducing agent 2-MEA was removed by desalting the samples using spin columns. The generation of bispecific antibodies was determined by bispecific binding measured in an ELISA.

Figure 25A:
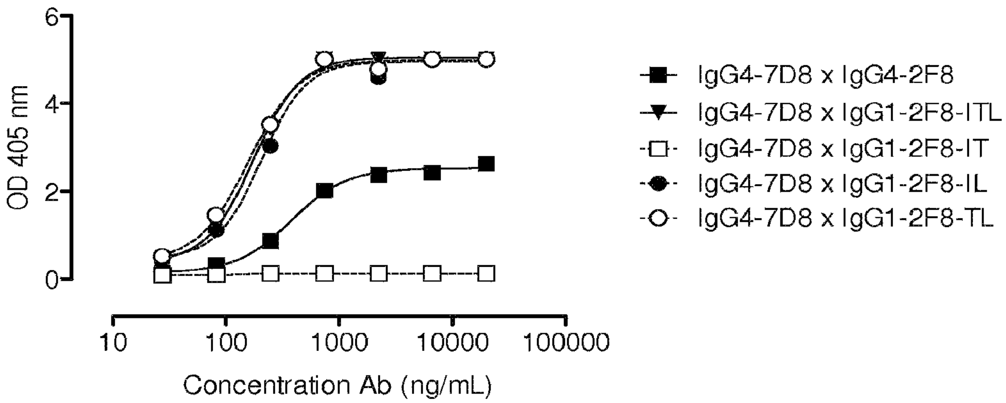
FIGS. 25A-25C: Comparison between triple mutant (ITL), double mutants (IT, IL, TL) and single mutant (L) human IgG1-2F8 in the generation of bispecific antibodies by Fab-arm exchange with human IgG4-7D8. The generation of bispecific antibodies after 2-MEA-induced in vitro Fab-arm exchange between the human IgG1-2F8 triple and double mutants and wild type IgG4-7D8 with a CPSC hinge (FIG. 25A) or mutant IgG4-7D8-CPPC with a stabilized hinge (FIG. 25B), or the single mutant IgG1-2F8-F405L and IgG4-7D8 with a wild type CPSC or stabilized CPPC hinge (FIG. 25C), was determined by an ELISA. A concentration series (total antibody) of 0-20 μg/mL or 0-10 μg/mL was analyzed in the ELISA for the experiments including the double and single mutants, respectively. Combinations with the double mutants IgG1-2F8-IL and -TL result in bispecific EGFR/CD20 binding similar as the triple mutant IgG1-ITL. Combinations with the IgG1-2F8-IT do not result in a bispecific product. Combinations with the single mutant IgG1-2F8-F405L result in bispecific EGFR/CD20 binding.
Figure 25B:
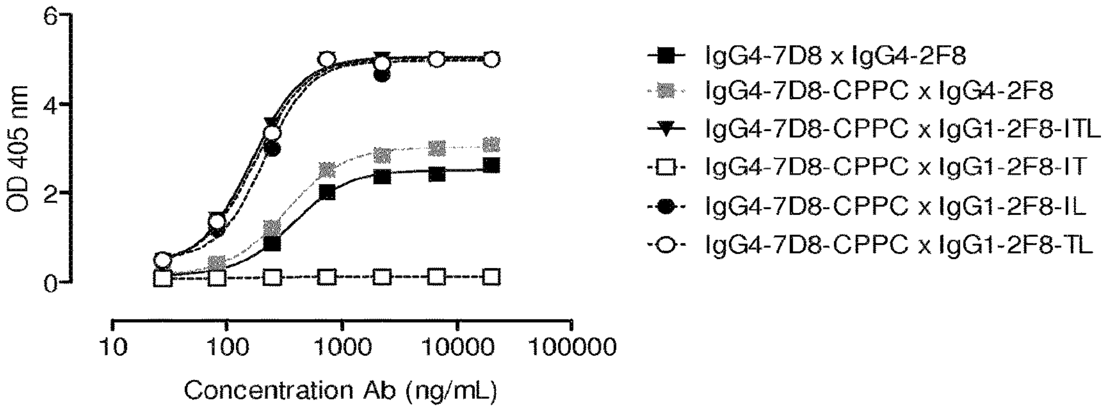
Figure 25C:
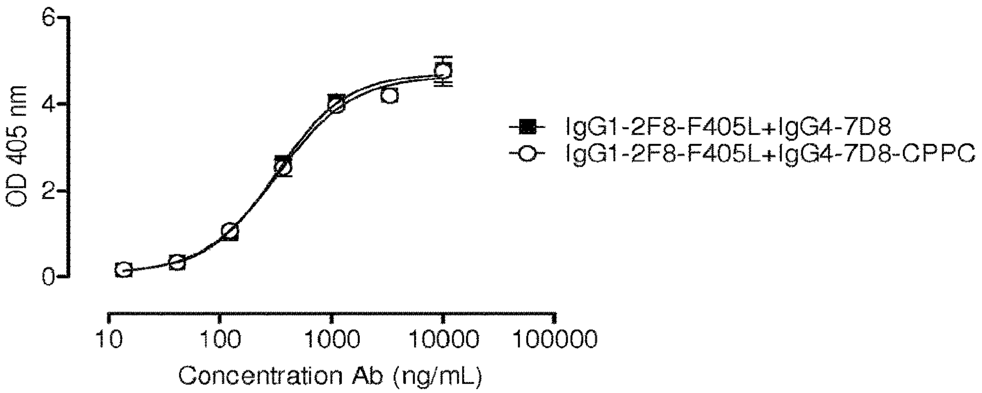

The triple (ITL), double mutations (IT, IL and TL) and single mutation (L) were introduced in IgG1-2F8. These mutants were combined with IgG4-7D8, containing a CPSC hinge (wild type) or a stabilized hinge (IgG4-7D8-CPPC), for Fab-arm exchange using 25 mM 2-MEA for 90 min at 37° C. FIGS. 25A-B show that the IgG1-2F8-IL and -TL mutants showed Fab-arm exchange to the same level as the triple mutant ITL, irrespective of the combined IgG4-7D8 (CPSC or CPPC hinge). In contrast, no bispecific binding was found for the combination with the IgG1-2F8-IT mutant. FIG. 25C shows that also the IgG1-2F8-F405L mutant showed Fab-arm exchange, irrespective of the combined IgG4-7D8 (CPSC or CPPC hinge). These data indicate that the F405L mutation is sufficient to engage human IgG1 for Fab-arm exchange under the conditions mentioned above.

Example 33

Determinants at the IgG1 409 Position for Engagement in 2-MEA-Induced Fab-Arm Exchange in Combination with IgG1-ITL 2-MEA can induce Fab-arm exchange between human IgG1-ITL and IgG4-CPPC. The CH3 interface residues of human IgG1 and IgG4 differ at position 409 only: lysine (K) in IgG1 and arginine (R) in IgG4. Therefore, it was tested whether substitution of lysine at position 409 by arginine or any other amino acid (K409X) could enable IgG1 to engage in 2-MEA-induced Fab-arm exchange with IgG1-ITL. Combinations of 10 μg human IgG1-2F8-ITL and 10 μg IgG1-7D8-K409X in 20 μl PBS/25 mM 2-MEA (final concentration of 0.5 mg/mL for each antibody) were incubated for 90 min at 37° C. Unpurified antibodies from supernatants of transient transfections were used after buffer-exchange to PBS using Amicon Ultra centrifugal devices (30k, Millipore, cat. no. UFC803096). After the Fab-arm exchange reaction, 20 μL PBS was added to each sample and the reducing agent was removed by desalting the samples using spin desalting plate. Dilution series of the antibody samples (total antibody concentration 0-20 μg/mL in 3-fold dilutions) were used in an ELISA to measure bispecific binding.

Figure 26A:
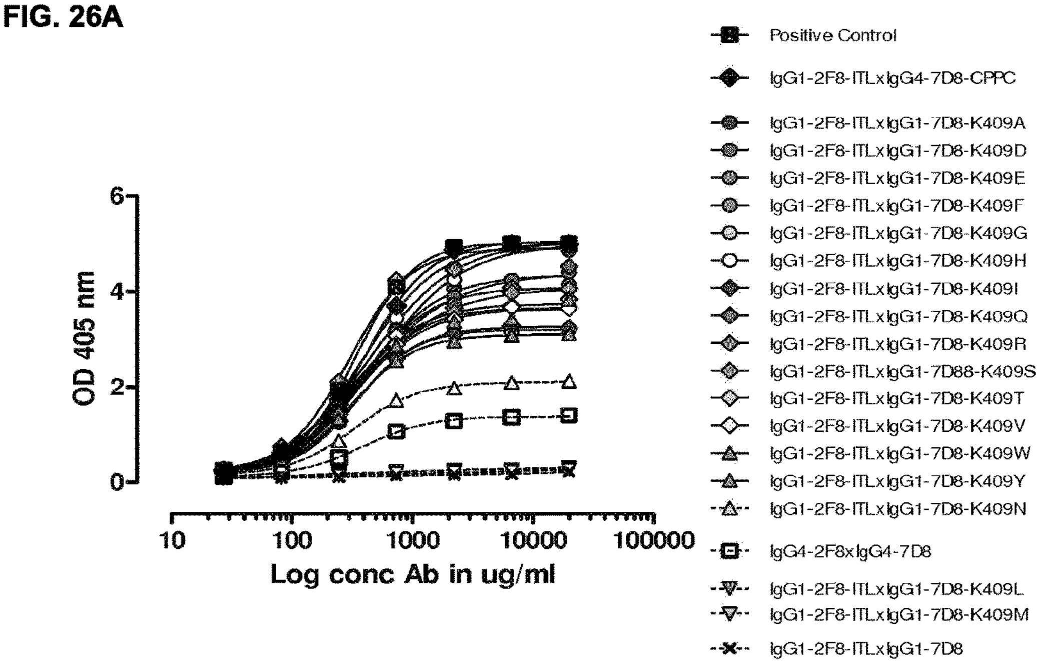
FIGS. 26A and 26B: 2-MEA-induced Fab-arm exchange between IgG1-2F8-ITL and IgG1-7D8-K409X mutants. The generation of bispecific antibodies after 2-MEA-induced in vitro Fab-arm exchange between IgG1-2F8-ITL and the indicated IgG1-7D8-K409X mutants was determined by an ELISA.
Figure 26B:
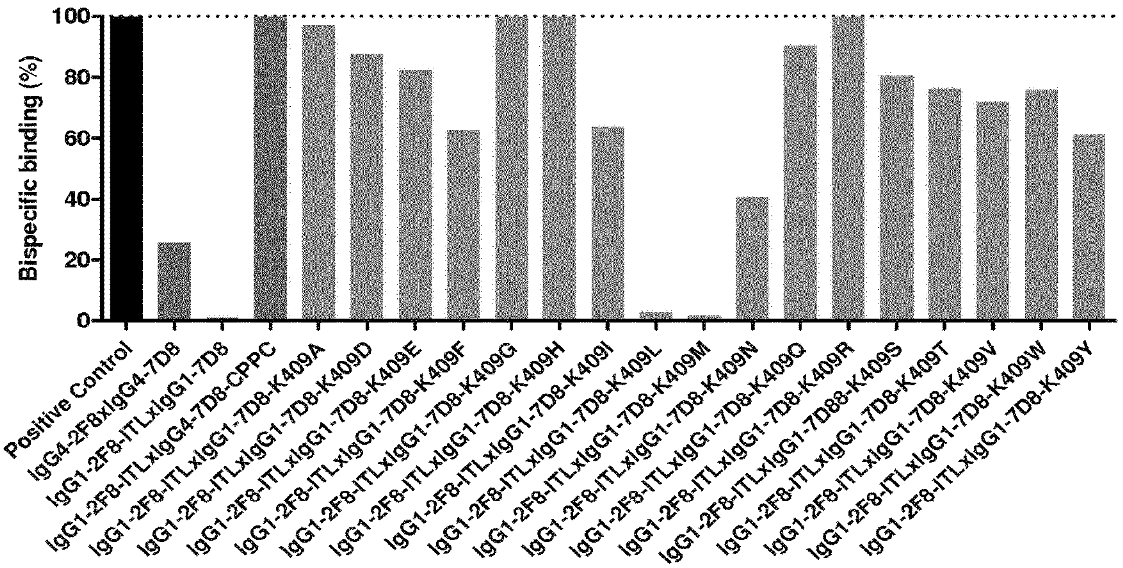

FIG. 26A shows the results of bispecific binding upon 2-MEA induced Fab-arm exchange between IgG1-2F8-ITL×IgG1-7D8-K409X. In FIG. 26B, the exchange is presented as bispecific binding relative to a purified batch of bispecific antibody derived from a 2-MEA-induced Fab-arm-exchange between IgG1-2F8-ITL and IgG4-7D8-CPPC, which was set to 100%. These data were also scored as (−) no Fab-arm exchange, (+/−) low, (+) intermediate or (++) high Fab-arm exchange, as presented in Table 1. No Fab-arm exchange (−) was found when the 409 position in IgG1-7D8 was K (=wild type IgG1), L or M. Fab-arm exchange was found to be intermediate (+) when the 409 position in IgG1-7D8 was F, I, N or Y and high (++) when the 409 position in IgG1-7D8 was A, D, E, G, H, Q, R, S, T, V or W.

TABLE 16

2-MEA-induced Fab-arm exchange between IgG1-2F8-ITL and IgG1-7D8-K409X mutants. The generation of bispecific antibodies after 2-MEA-induced in vitro Fab-arm exchange between IgG1-2F8-ITL and IgG1-7D8-K409X mutants was determined by a sandwich ELISA.

| IgG1-7D8-K409X | Fab-arm exchange × IgG1-2F8-ITL |
|---|---|
| A | ++ |
| D | ++ |
| E | ++ |
| F | + |
| G | ++ |
| H | ++ |
| I | + |
| K | − |
| L | − |
| M | − |
| N | + |
| Q | ++ |
| R | ++ |
| S | ++ |
| T | ++ |
| V | ++ |
| W | ++ |
| Y | + |

(−) no, (+/−) low, (+) intermediate, (++) high Fab-arm exchange.

Example 34

Determinants at the IgG1 405 Position for Engagement in 2-MEA-Induced Fab-Arm-Exchange in Combination with IgG1-K409R In Example 32 it is described that the F405L mutation is sufficient to enable human IgG1 to engage in Fab-arm-exchange when combined with IgG4-7D8. To further test the determinants at the IgG1 405 position for engagement in 2-MEA-induced Fab-arm-exchange in combination with human IgG1-K409R, all possible IgG1-2F8-F405X mutants (with the exception of C and P) were combined with IgG1-7D8-K409R. The procedure was performed with purified antibodies as described in Example 32.

Figure 27A:
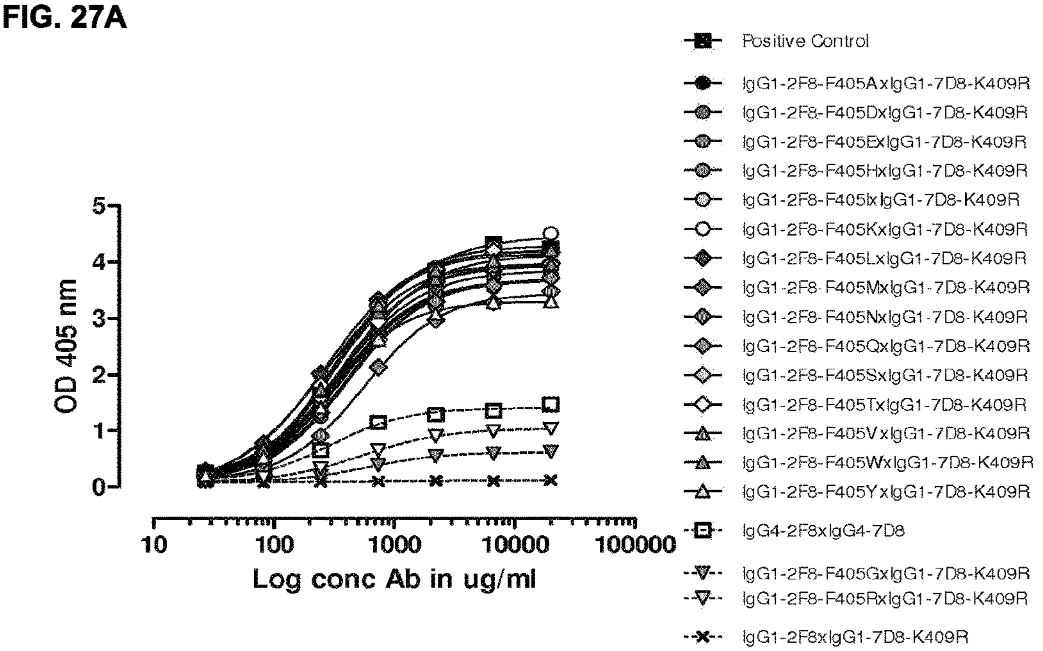
FIGS. 27A and 27B: 2-MEA-induced Fab-arm-exchange between IgG1-2F8-F405X mutants and IgG1-7D8-K409R. The generation of bispecific antibodies after 2-MEA-induced in vitro Fab-arm-exchange between the indicated IgG1-2F8-F405X mutants and IgG1-7D8-K409R was determined by an ELISA.
Figure 27B:
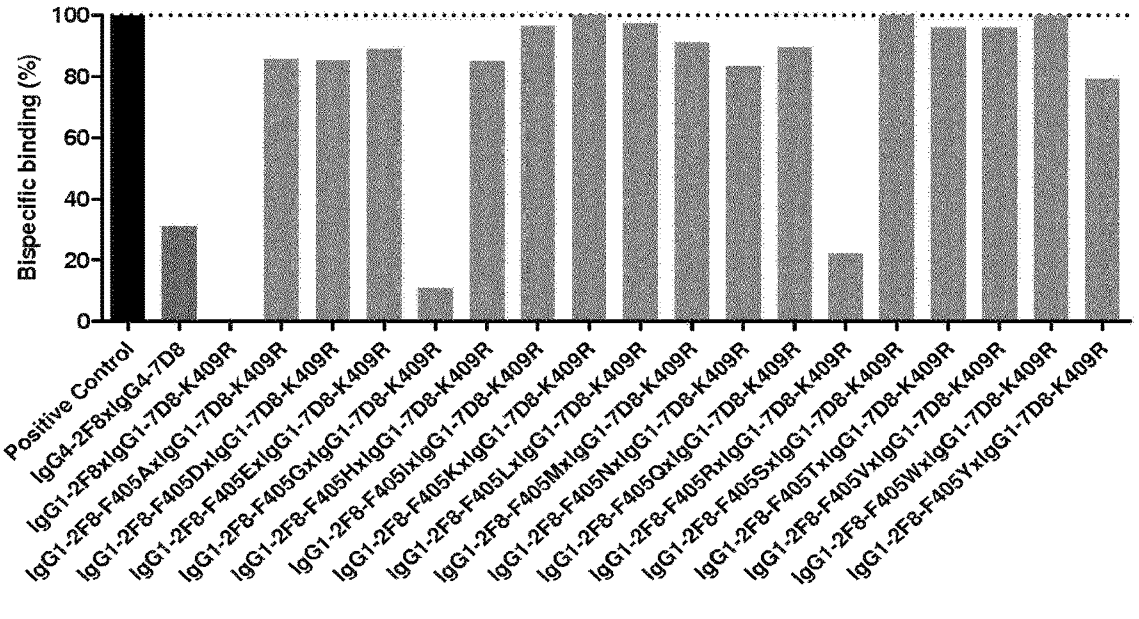

FIG. 27 shows the results of bispecific binding upon 2-MEA-induced Fab-arm-exchange between IgG1-2F8-

F405X×IgG1-7D8-K409R. These data were also scored as (−) no Fab-arm exchange, (+/−) low, (+) intermediate or (++) high Fab-arm exchange, as presented in Table 18. No Fab-arm exchange (−) was found when the 405 position in IgG1-2F8 was F (=wild type IgG1). Fab-arm exchange was found to be low (+/−) when the 405 position in IgG1-2F8 was G or R. Fab-arm exchange was found to be high (++) when the 405 position in IgG1-2F8 was A, D, E, H, I, K, L, M, N, Q, S, T, V, W or Y. These data indicate that particular mutations at the IgG1 405 position allow IgG1 to engage in 2-MEA-induced Fab-arm-exchange when combined with IgG1-K409R.

TABLE 17

2-MEA-induced Fab-arm-exchange between IgG1-2F8-F405X mutants and IgG1-7D8-K409R. The generation of bispecific antibodies after 2-MEA-induced in vitro Fab-arm-exchange between IgG1-2F8-F405X mutants and IgG1-7D8-K409R was determined by a sandwich ELISA.

| IgG1-2F8-F405X | Fab-arm-exchange × IgG1-7D8-K409R |
|---|---|
| A | ++ |
| D | ++ |
| E | ++ |
| F | − |
| G | +/− |
| H | ++ |
| I | ++ |
| K | ++ |
| L | ++ |
| M | ++ |
| N | ++ |
| Q | ++ |
| R | +/− |
| S | ++ |
| T | ++ |
| V | ++ |
| W | ++ |
| Y | ++ |

(−) no, (+/−) low, (+) intermediate, (++) high Fab-arm-exchange.

Example 35

Determinants at the IgG1 407 Position for Engagement in 2-MEA-Induced Fab-Arm-Exchange in Combination with IgG1-K409R In the previous Example, it is described that certain single mutations at position F405 are sufficient to enable human IgG1 to engage in Fab-arm-exchange when combined with IgG1-K409R. To test whether other determinants implicated in the Fc:Fc interface positions in the CH3 domain could also mediate the Fab-arm-exchange mechanism, mutagenesis of the IgG1 407 position was performed and the mutants were tested for engagement in 2-MEA-induced Fab-arm-exchange in combination with human IgG1-K409R. All possible IgG1-2F8-Y407X mutants (with the exception of C and P) were combined with IgG1-7D8-K409R. The procedure was performed with purified antibodies.

Figure 28A:
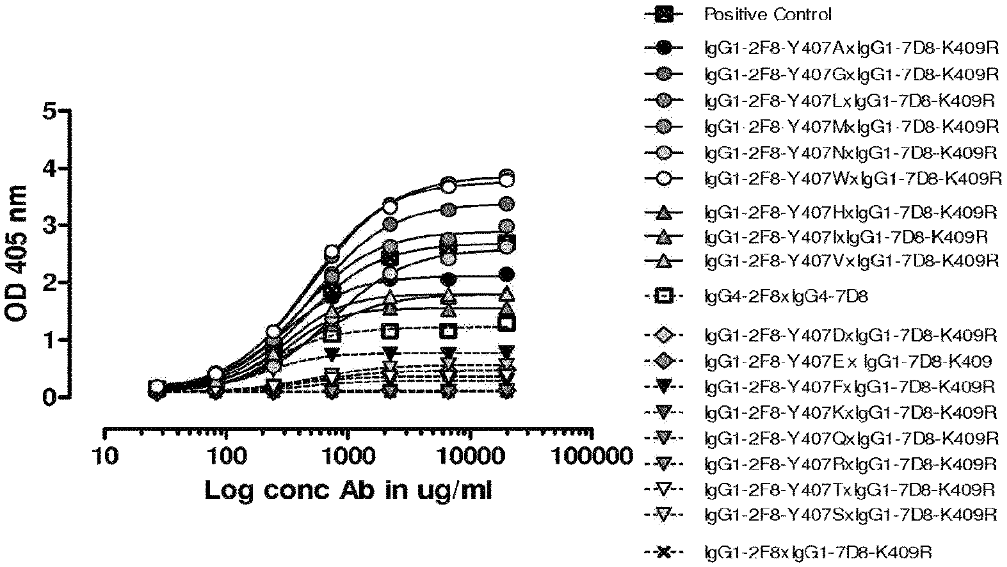
FIGS. 28A and 28B: 2-MEA-induced Fab-arm-exchange between IgG1-2F8-Y407X mutants and IgG1-7D8-K409R. The generation of bispecific antibodies after 2-MEA-induced in vitro Fab-arm-exchange between the indicated IgG1-2F8-Y407X mutants and IgG1-7D8-K409R was determined by an ELISA.
Figure 28B:
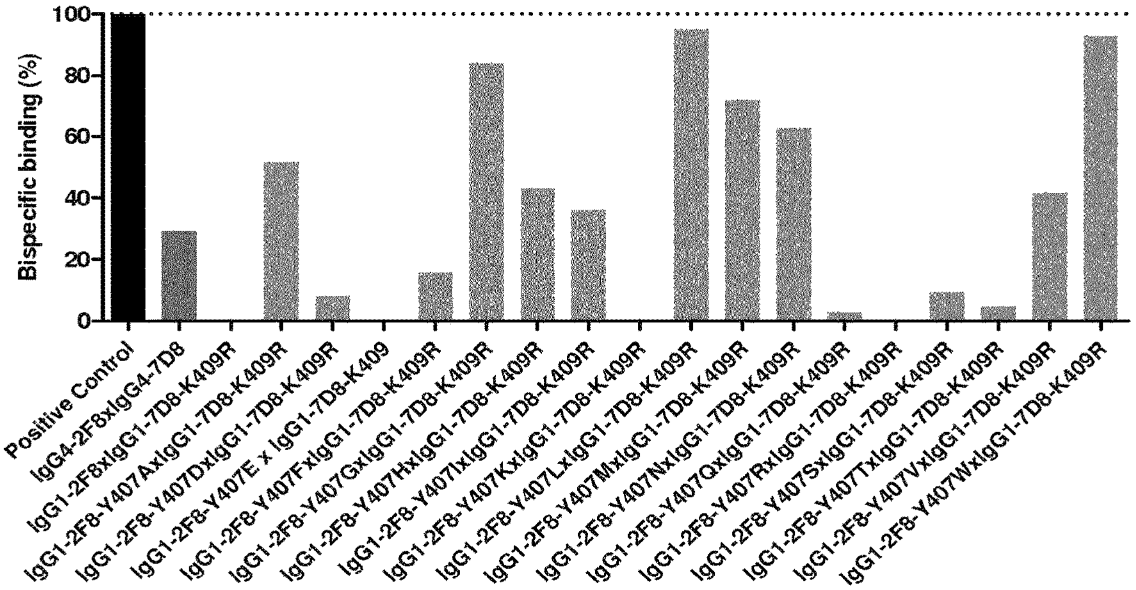

FIG. 28 shows the results of bispecific binding upon 2-MEA-induced Fab-arm-exchange between IgG1-2F8-Y407X×IgG1-7D8-K409R. These data were also scored as (−) no Fab-arm exchange, (+/−) low, (+) intermediate or (++) high Fab-arm exchange, as presented in Table 19. No Fab-arm exchange (−) was found when the 407 position in IgG1-2F8 was Y (=wild type IgG1), E, K, Q, or R. Fab-arm exchange was found to be low (+/−) when the 407 position in IgG1-2F8 was D, F, I, S or T and intermediate (+) when the 407 position in IgG1-2F8 was A, H, N or V, and high (++) when the 407 position in IgG1-2F8 was G, L, M or W.

These data indicate that particular single mutations at the IgG1 407 position allow IgG1 to engage in 2-MEA-induced Fab-arm-exchange when combined with IgG1-K409R.

TABLE 18

2-MEA-induced Fab-arm-exchange between IgG1-2F8-Y407X mutants and IgG1-7D8-K409R. The generation of bispecific antibodies after 2-MEA-induced in vitro Fab-arm exchange between IgG1-2F8-Y407X mutants and IgG1-7D8-K409R was determined by a sandwich ELISA.

| IgG1-2F8-Y407X | Fab-arm-exchange × IgG1-7D8-K409R |
|---|---|
| A | + |
| D | +/− |
| E | − |
| F | +/− |
| G | ++ |
| H | + |
| I | +/− |
| K | − |
| L | ++ |
| M | ++ |
| N | + |
| Q | − |
| R | − |
| S | +/− |
| T | +/− |
| V | + |
| W | ++ |
| Y | − |

(−) no, (+/−) low, (+) intermediate, (++) high Fab-arm-exchange.

Example 36

Determinants at the IgG1 368 Position for Engagement in 2-MEA-Induced Fab-Arm Exchange in Combination with IgG1-K409R Examples 34 and 35 show that certain single mutations at position F405 and Y407 are sufficient to enable human IgG1 to engage in Fab-arm exchange when combined with IgG1-K409R. As illustrated in this example further determinants implicated in the Fc:Fc interface positions in the CH3 domain may also mediate the Fab-arm exchange mechanism. To this effect mutagenesis of the IgG1 368 position was performed and the mutants were tested for engagement in 2-MEA-induced Fab-arm-exchange in combination with human IgG1-K409R. All possible IgG1-2F8-L368X mutants (with the exception of C and P) were combined with IgG1-7D8-K409R. The procedure was performed with purified antibodies.

Figure 29A:
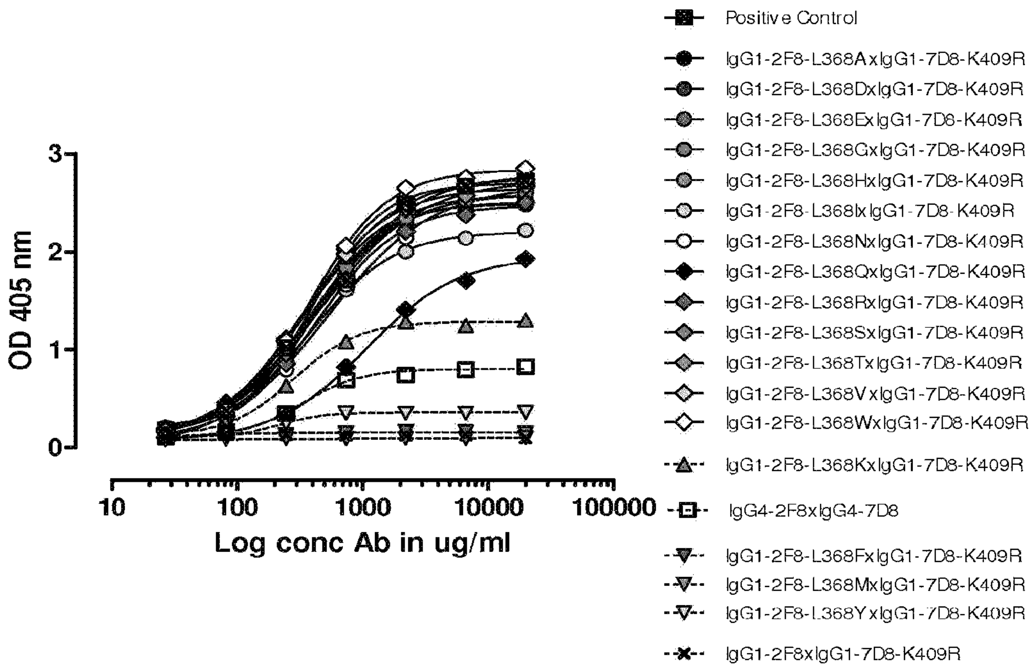
FIGS. 29A and 29B: Generation of bispecific antibodies after 2-MEA-induced in vitro Fab-arm exchange between the indicated IgG1-2F8-L368X mutants and IgG1-7D8-K409R was determined by an ELISA using a concentration series (total antibody) of 0-20 μg/mL (FIG. 29A). The positive control is a purified batch of bispecific antibody, derived from IgG1-2F8-F405L×IgG1-7D8-K409R.
Figure 29B:
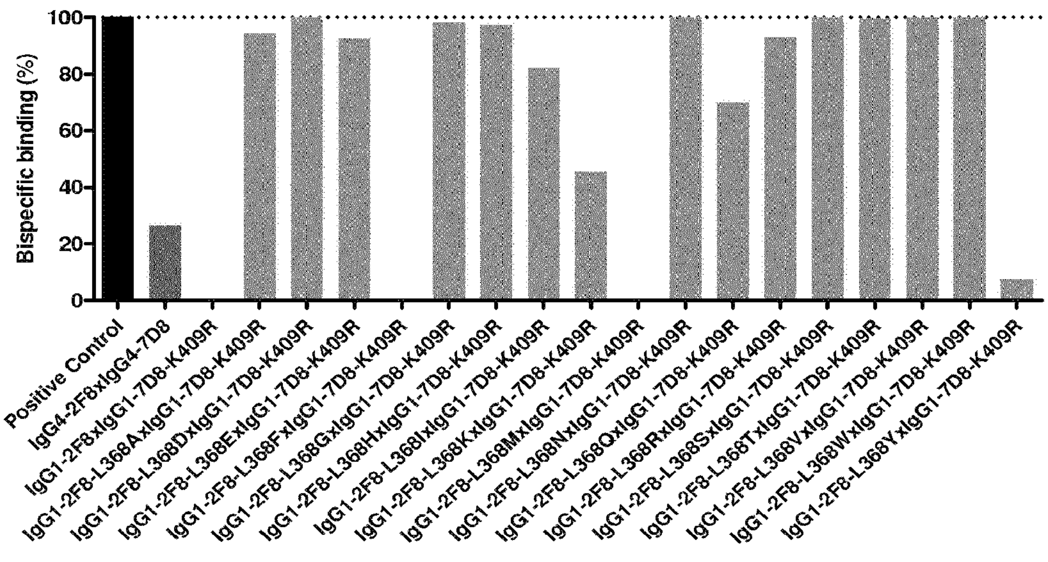

FIG. 29 shows the results of bispecific binding upon 2-MEA-induced Fab-arm exchange between IgG1-2F8-L368X×IgG1-7D8-K409R. These data were also scored as (−) no Fab-arm exchange, (+/−) low, (+) intermediate or (++) high Fab-arm exchange, as presented in Table 20. No Fab-arm exchange (−) was found when the 368 position in IgG1-2F8 was L (=wild type IgG1), F or M. Fab-arm exchange was found to be low (+/−) when the 368 position in IgG1-2F8 was Y. Fab-arm exchange was found to be intermediate (+) when the 368 position in IgG1-2F8 was K and high (++) when the 368 position in IgG1-2F8 was A, D, E, G, H, I, N, Q, R, S, T, V, or W. These data indicate that particular mutations at the IgG1 368 position allow IgG1 to engage in 2-MEA-induced Fab-arm exchange when combined with IgG1-K409R.

TABLE 19

2-MEA-induced Fab-arm exchange between IgG1-2F8-L368X mutants and IgG1-7D8-K409R. The generation of bispecific antibodies after 2-MEA-induced in vitro Fab-arm exchange between IgG1-2F8-L368X mutants and IgG1-7D8-K409R was determined by a sandwich ELISA.

| IgG1-2F8-L368X | Fab-arm exchange Fab-arm exchange × IgG1-7D8-K409R |
|---|---|
| A | ++ |
| D | ++ |
| E | ++ |
| F | – |
| G | ++ |
| H | ++ |
| I | ++ |
| K | + |
| L | – |
| M | – |
| N | ++ |
| Q | ++ |
| R | ++ |
| S | ++ |
| T | ++ |
| V | ++ |
| W | ++ |

(–) no, (+/–) low, (+) intermediate or (++) high Fab-arm exchange.

Example 37

Determinants at the IgG1 370 Position for Engagement in 2-MEA-Induced Fab-Arm Exchange in Combination with IgG1-K409R The previous Examples show that certain single mutations at positions F405, Y407 or L368 are sufficient to enable human IgG1 to engage in Fab-arm exchange when combined with IgG1-K409R. As illustrated in this example further determinants implicated in the Fc:Fc interface positions in the CH3 domain may also mediate the Fab-arm exchange mechanism. To this effect mutagenesis of the IgG1 370 position was performed and the mutants were tested for engagement in 2-MEA-induced Fab-arm-exchange in combination with human IgG1-K409R. All possible IgG1-2F8-K370X mutants (with the exception of C and P) were combined with IgG1-7D8-K409R. The procedure was performed with purified antibodies.

Figure 30A:
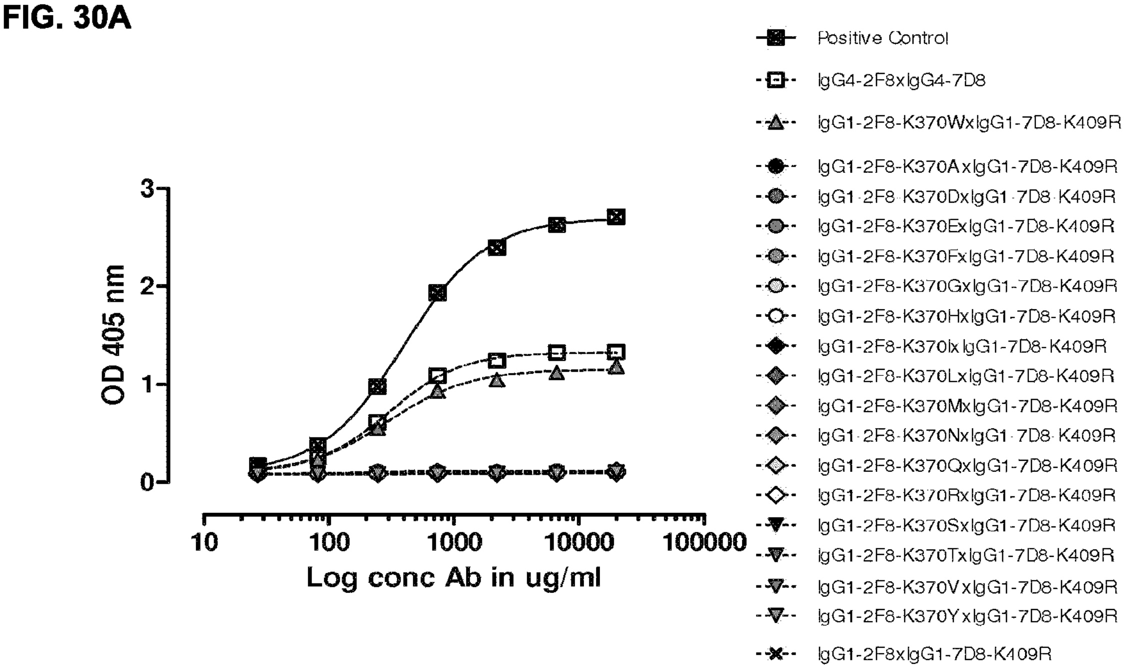
FIGS. 30A and 30B: Generation of bispecific antibodies after 2-MEA-induced in vitro Fab-arm exchange between the indicated IgG1-2F8-K370X mutants and IgG1-7D8-K409R was determined by an ELISA using a concentration series (total antibody) of 0-20 μg/mL (FIG. 30A). The positive control is a purified batch of bispecific antibody, derived from IgG1-2F8-F405L×IgG1-7D8-K409R.
Figure 30B:
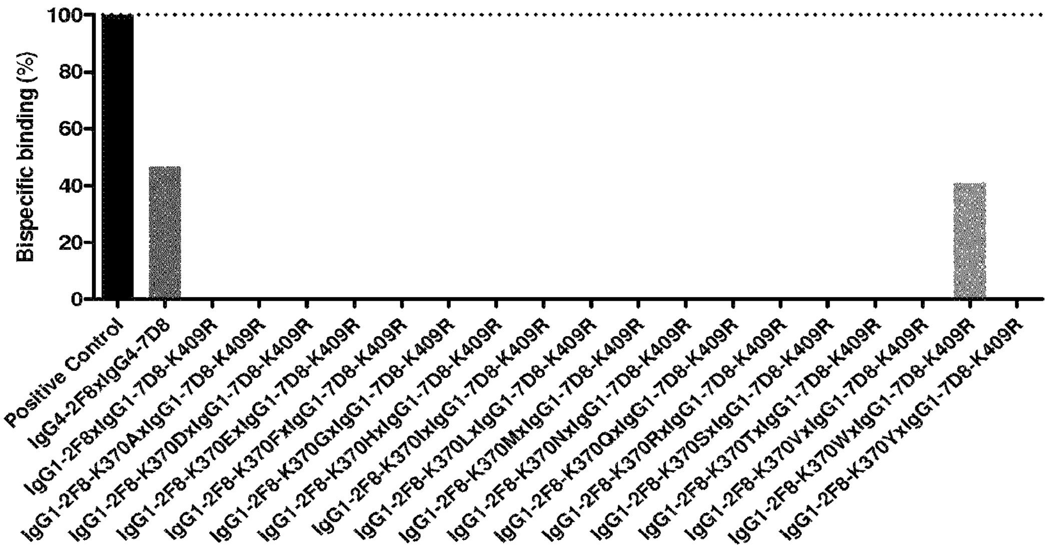

FIG. 30 shows the results of bispecific binding upon 2-MEA-induced Fab-arm exchange between IgG1-2F8-K370X×IgG1-7D8-K409R. These data were also scored as (–) no Fab-arm exchange, (+/–) low, (+) intermediate or (++) high Fab-arm exchange, as presented in Table 21. No Fab-arm exchange (–) was found when the 370 position in IgG1-2F8 was K (=wild type IgG1), A, D, E, F, G, H, I, L, M, N, Q, R, S, T, V or Y. Only substitution of K370 with W resulted in intermediate Fab-arm exchange (+). These data indicate that only one mutation at the IgG1 370 position (K370W) allows IgG1 to engage in 2-MEA-induced Fab-arm exchange when combined with IgG1-K409R.

TABLE 20

2-MEA-induced Fab-arm exchange between IgG1-2F8-K370X mutants and IgG1-7D8-K409R. The generation of bispecific antibodies after 2-MEA-induced in vitro Fab-arm exchange between IgG1-2F8-K370X mutants and IgG1-7D8-K409R was determined by a sandwich ELISA.

| IgG1-2F8-K370X | Fab-arm exchange × IgG1-7D8-K409R |
|---|---|
| A | – |
| D | – |
| E | – |
| F | – |
| G | – |
| H | – |
| I | – |
| K | – |
| L | – |
| M | – |
| N | – |
| Q | – |
| R | – |
| S | – |
| T | – |
| V | – |
| W | + |
| Y | – |

(–) no, (+/–) low, (+) intermediate or (++) high Fab-arm exchange.

Example 38

Determinants at the IgG1 399 Position for Engagement in 2-MEA-Induced Fab-Arm Exchange in Combination with IgG1-K409R The preceding Examples show that certain single mutations at positions F405, Y407, L368 or K370 are sufficient to enable human IgG1 to engage in Fab-arm exchange when combined with IgG1-K409R. As illustrated in this example further determinants implicated in the Fc:Fc interface positions in the CH3 domain may also mediate the Fab-arm exchange mechanism. To this effect mutagenesis of the IgG1 399 position was performed and the mutants were tested for engagement in 2-MEA-induced Fab-arm-exchange in combination with human IgG1-K409R. All possible IgG1-2F8-D399X mutants (with the exception of C and P) were combined with IgG1-7D8-K409R. The procedure was performed with purified antibodies as described in Example 33.

Figure 31A:
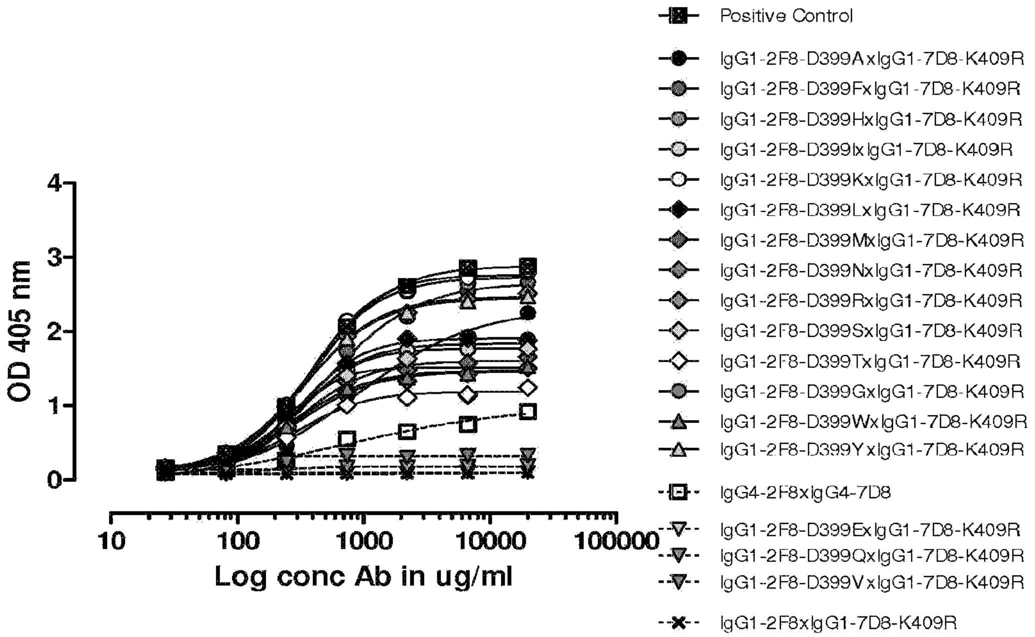
FIGS. 31A and 31B: Generation of bispecific antibodies after 2-MEA-induced in vitro Fab-arm exchange between the indicated IgG1-2F8-D399X mutants and IgG1-7D8-K409R was determined by an ELISA using a concentration series (total antibody) of 0-20 μg/mL (FIG. 31A).
Figure 31B:
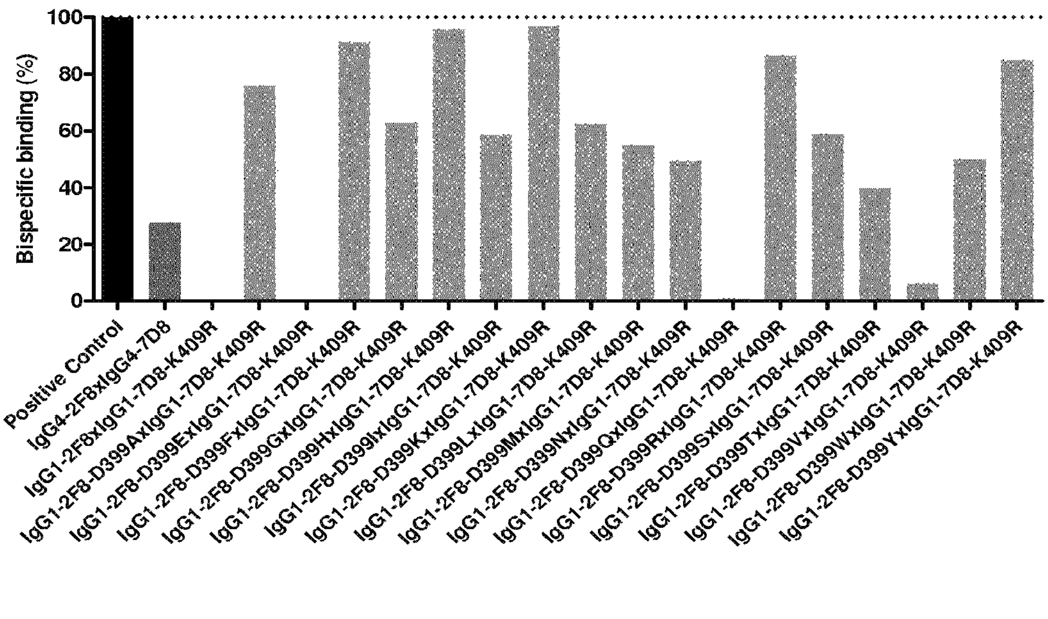

FIG. 31 shows the results of bispecific binding upon 2-MEA-induced Fab-arm exchange between IgG1-2F8-D399X×IgG1-7D8-K409R. These data were also scored as (–) no, (+/–) low, (+) intermediate or (++) high Fab-arm exchange, as presented in Table 10. No Fab-arm exchange (–) was found when the 399 position in IgG1-2F8 was D (=wild type IgG1), E and Q. Fab-arm exchange was found to be low (+/–) when the 399 position in IgG1-2F8 was V, intermediate (+) when the 399 position in IgG1-2F8 was G, I, L, M, N, S, T or W. Fab-arm exchange was found to be high (++) when the 399 position in IgG1-2F8 was A, F, H, K, R or Y. These data indicate that particular mutations at the IgG1 399 position allow IgG1 to engage in 2-MEA-induced Fab-arm exchange when combined with IgG1-K409R.

TABLE 21

2-MEA-induced Fab-arm exchange between IgG1-2F8-D399X mutants and IgG1-7D8-K409R. The generation of bispecific antibodies after 2-MEA-induced in vitro Fab-arm exchange between IgG1-2F8-D399X mutants and IgG1-7D8-K409R was determined by a sandwich ELISA.

| IgG1-2F8-D399X | Fab-arm exchange × IgG1-7D8-K409R |
|---|---|
| A | ++ |
| D | – |

TABLE 21-continued

2-MEA-induced Fab-arm exchange between IgG1-2F8-D399X mutants and IgG1-7D8-K409R. The generation of bispecific antibodies after 2-MEA-induced in vitro Fab-arm exchange between IgG1-2F8-D399X mutants and IgG1-7D8-K409R was determined by a sandwich ELISA.

| IgG1-2F8-D399X | Fab-arm exchange × IgG1-7D8-K409R |
|---|---|
| E | − |
| F | ++ |
| G | + |
| H | ++ |
| I | + |
| K | ++ |
| L | + |
| M | + |
| N | + |
| Q | − |
| R | ++ |
| S | + |
| T | + |
| V | +/− |
| W | + |
| Y | ++ |

(−) no, (+/−) low, (+) intermediate or (++) high Fab-arm exchange.

Example 39

Determinants at the IgG1 366 Position for Engagement in 2-MEA-Induced Fab-Arm Exchange in Combination with IgG1-K409R Examples 32 to 38 show that certain single mutations at positions F405, Y407, L368, K370 or D399 are sufficient to enable human IgG1 to engage in Fab-arm exchange when combined with IgG1-K409R. As illustrated in this example further determinants implicated in the Fc:Fc interface positions in the CH3 domain may also mediate the Fab-arm exchange mechanism. To this effect mutagenesis of the IgG1 366 position was performed and the mutants were tested for engagement in 2-MEA-induced Fab-arm-exchange in combination with human IgG1-K409R. All possible IgG1-2F8-T366X mutants (with the exception of C and P) were combined with IgG1-7D8-K409R. The procedure was performed with purified antibodies as described in Example 33.

Figure 32A:
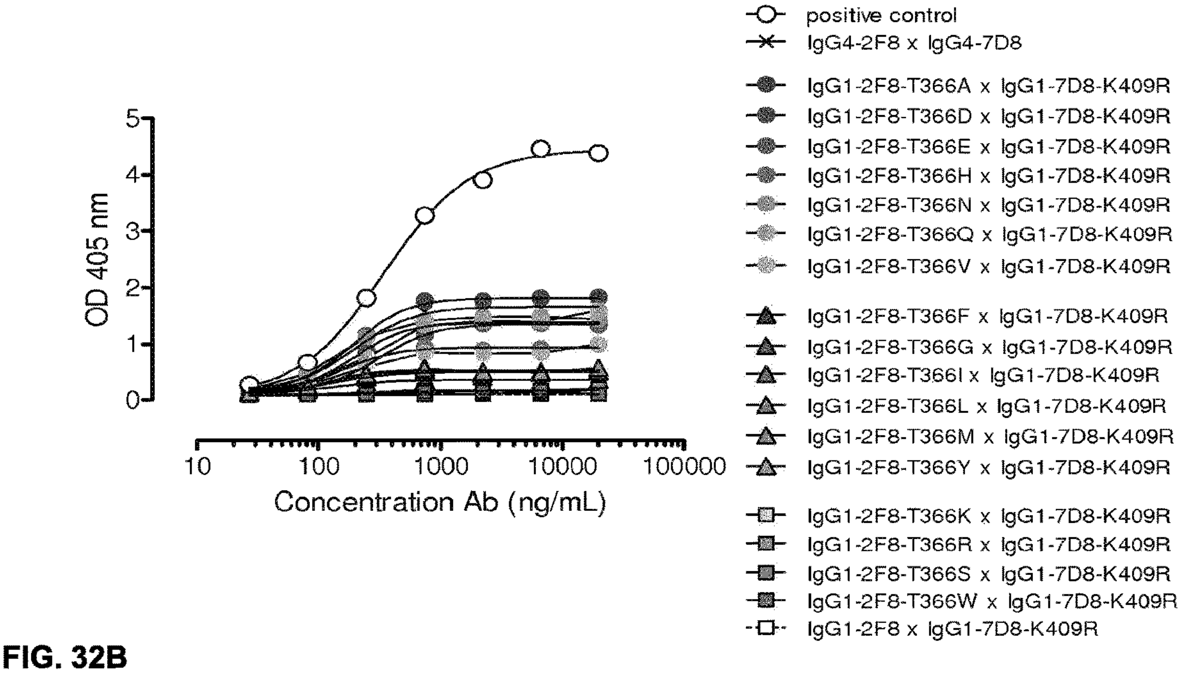
FIGS. 32A and 32B: Generation of bispecific antibodies after 2-MEA-induced in vitro Fab-arm exchange between the indicated IgG1-2F8-T366X mutants and IgG1-7D8-K409R was determined by an ELISA using a concentration series (total antibody) of 0-20 μg/mL (FIG. 32A).
Figure 32B:
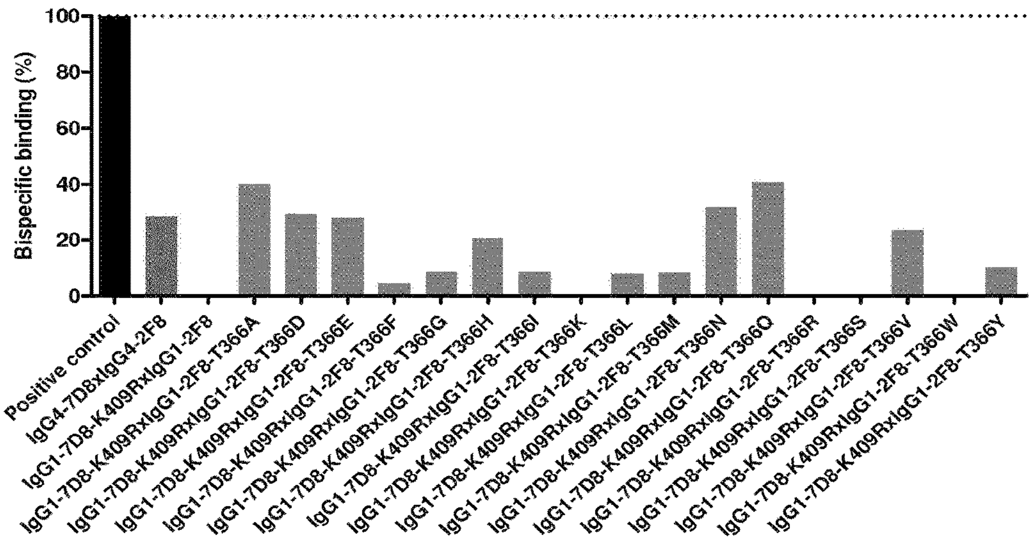

FIG. 32 shows the results of bispecific binding upon 2-MEA-induced Fab-arm exchange between IgG1-2F8-T366X×IgG1-7D8-K409R. These data were also scored as (−) no, (+/−) low, (+) intermediate or (++) high Fab-arm exchange, as presented in Table X. No Fab-arm exchange (−) was found when the 366 position in IgG1-2F8 was T (=wild type IgG1), K, R, S or W. Fab-arm exchange was found to be low (+/−) when the 366 position in IgG1-2F8 was F, G, I, L, M or Y, intermediate (+) when the 366 position in IgG1-2F8 was A, D, E, H, N, V or Q. These data indicate that particular mutations at the IgG1 366 position allow IgG1 to engage in 2-MEA-induced Fab-arm exchange when combined with IgG1-K409R.

TABLE 22

2-MEA-induced Fab-arm exchange between IgG1-2F8-T366X mutants and IgG1-7D8-K409R
The generation of bispecific antibodies after 2-MEA-induced in vitro Fab-arm exchange between IgG1-2F8-T366X mutants and IgG1-7D8-K409R was determined by a sandwich ELISA.

| IgG1-2F8-T366X | Fab-arm exchange × IgG1-7D8-K409R |
|---|---|
| A | + |
| D | + |
| E | + |
| F | +/− |
| G | +/− |
| H | + |
| I | +/− |
| K | − |
| L | +/− |
| M | +/− |
| N | + |
| Q | + |
| R | − |
| S | − |
| T | − |
| V | + |
| W | − |
| Y | +/− |

(−) no, (+/−) low, (+) intermediate or (++) high Fab-arm exchange.

Example 40

In Vivo Proof of Concept: Dose Titration

To further test the growth inhibitory effect of the bispecific HER2×CD3 antibody, different antibody doses were tested using the subcutaneous NCI-N87 xenograft model in NOD-SCID mice with subcutaneous (s.c.) co-injection of unstimulated human PBMCs (7 mice per group) as described in Example 31. This time, a single dose of antibody was administered intravenously (i.v.) 1 hour after tumor inoculation. Treatment groups are shown in Table 23.

Control groups showed a donor-specific tumor growth inhibition (alloreaction) in the absence of therapeutic antibody with PBMCs from one of the two donors (data not shown). Therefore, data received with PBMCs from that particular donor were excluded from analysis.

TABLE 23

Treatment groups and dosing

| Group | Antibody | Dose |
|---|---|---|
| 1 | DuoBody HER2 169 × CLB-T3/4-N297Q | 0.01 µg (= 0.0005 mg/kg) |
| 2 | DuoBody HER2 169 × CLB-T3/4-N297Q | 0.1 µg (= 0.005 mg/kg) |
| 3 | DuoBody HER2 169 × CLB-T3/4-N297Q | 1 µg (= 0.05 mg/kg) |
| 4 | DuoBody HER2 169 × CLB-T3/4-N297Q | 10 µg (= 0.5 mg/kg) |
| 5 | DuoBody b12 × CLB-T3/4-N297Q | 10 µg (= 0.5 mg/kg) |
| 6 | PBS | |

Figure 33A:
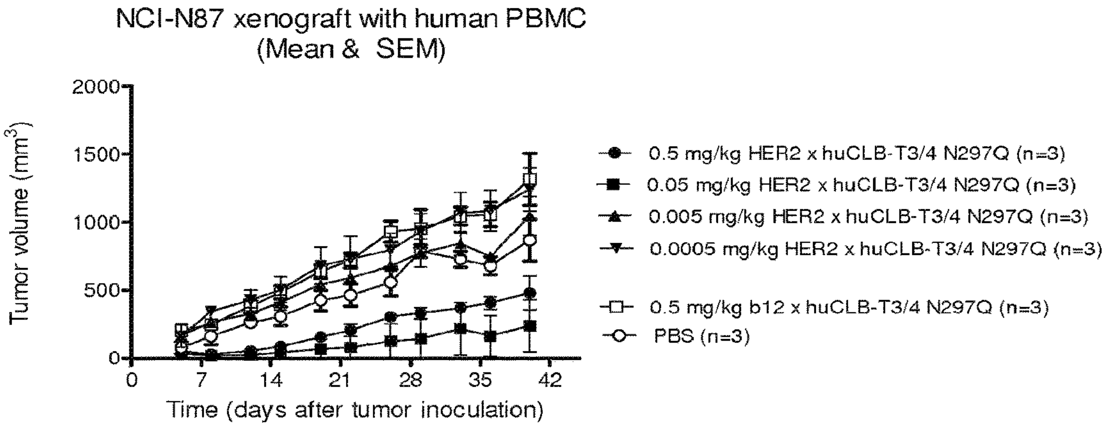
FIGS. 33A and 33B: Evaluation of the in vivo efficacy of HER2×CD3 bispecific mAb in a subcutaneous xenograft model with an HER2 expressing tumor cell line and human PBMCs. In (FIG. 33A), tumor development (mean & SEM) in mice with NCI-N87 s.c. xenografts and s.c. human PBMCs treated with bispecific HER2×CD3 antibodies is shown. Different dosing schedules were being compared, and 0.05 mg/kg and 0.5 mg/kg appeared to be effective. In (FIG. 33B), the percentage mice with tumor sizes smaller then 500 $mm^3$ is shown in a Kaplan-Meier plot.

FIG. 33A shows that tumor growth was inhibited by 0.05 mg/kg and 0.5 mg/kg HER2×CD3 N297Q.

Figure 33B:
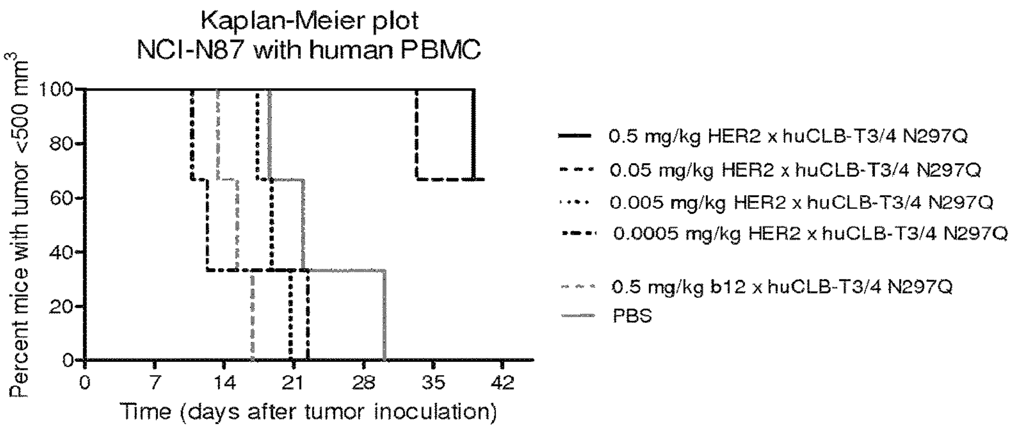

FIG. 33B shows a Kaplan-Meier plot displaying the percentage of mice with tumors <500 $mm^3$. Tumor formation is delayed in mice treated with 0.05 mg/kg and 0.5 mg/kg HER2×CD3-N297Q bispecific antibody compared to control mice treated with PBS or b12×CD3 control antibody.

The invention claimed is:

1. A bispecific antibody comprising a first antigen-binding region, a second antigen-binding region, and a first Fc region and a second Fc region, wherein the second antigen-binding region binds an epitope on human CD3 and the first antigen-binding region binds to human epidermal growth factor receptor 2 (HER2), and wherein the first antigen-binding region comprises a heavy chain variable (VH) region and a light chain variable (VL) region selected from the group consisting of:

(a) a VH region comprising the CDR1, CDR2 and CDR3 sequences set forth in SEQ ID NOs: 166, 167 and 168, respectively; and a VL region comprising the CDR1, CDR2 and CDR3 sequences set forth in SEQ ID NO: 170, GAS and SEQ ID NO: 171, respectively;

(b) a VH region comprising the CDR1, CDR2 and CDR3 sequences set forth in SEQ ID NOs: 173, 174 and 175, respectively; and a VL region comprising the CDR1, CDR2 and CDR3 sequences set forth in SEQ ID NO: 177, DAS, and SEQ ID NO: 178, respectively;

(c) a VH region comprising the CDR1, CDR2 and CDR3 sequences set forth in SEQ ID NOs: 180, 181 and 182, respectively; and a VL region comprising the CDR1, CDR2 and CDR3 sequences set forth in SEQ ID NO: 184, GAS, and SEQ ID NO: 185, respectively;

(d) a VH region comprising the CDR1, CDR2 and CDR3 sequences set forth in SEQ ID NOs: 187, 188 and 189, respectively; and a VL region comprising the CDR1, CDR2 and CDR3 sequences set forth in SEQ ID NO: 191, GAS, and SEQ ID NO: 192, respectively;

(e) a VH region comprising the CDR1, CDR2 and CDR3 sequences set forth in SEQ ID NOs: 194, 195 and 196, respectively; and a VL region comprising the CDR1, CDR2 and CDR3 sequences set forth in SEQ ID NO: 198, GAS, and SEQ ID NO: 199, respectively; and (f) a VH region comprising the CDR1, CDR2 and CDR3 sequences set forth in SEQ ID NOs: 201, 202 and 203, respectively; and a VL region comprising the CDR1, CDR2 and CDR3 sequences set forth in SEQ ID NO: 205, GAS, and SEQ ID NO: 206, respectively, and wherein the first and second Fc regions comprise a sequence independently selected from the group consisting of SEQ ID NOs: 251,254, and 255.

2. The bispecific antibody of claim 1, wherein the first antigen-binding region comprises VH and VL regions comprising amino acid sequences selected from the group consisting of:

(a) SEQ ID NOs: 165 and 169, respectively;

(b) SEQ ID NOs: 172 and 176, respectively;

(c) SEQ ID NOs: 179 and 183, respectively;

(d) SEQ ID NOs: 186 and 190, respectively;

(e) SEQ ID NOs: 193 and 197, respectively; and (f) SEQ ID NOs: 200 and 204, respectively.

3. The bispecific antibody of claim 1, wherein the second antigen-binding region comprises VH and VL regions comprising amino acid sequences selected from the group consisting of:

(a) SEQ ID NOs: 240 and 241, respectively;

(b) SEQ ID NOs: 234 and 235, respectively;

(c) SEQ ID NOs: 238 and 239, respectively; and (d) SEQ ID NOs: 236 and 237, respectively.

4. The bispecific antibody of claim 1, which is effector-function deficient.

5. The bispecific antibody of claim 1, wherein the first Fc region has an amino acid substitution at a position selected from the group consisting of 409, 366, 368, 370, 399, 405 and 407, and said second Fc region has an amino acid substitution at a position selected from the group consisting of 405, 366, 368, 370, 399, 407, and 409, wherein said first Fc region and said second Fc region are not substituted in the same positions, and wherein the numbering of amino acid positions is according to the EU Index.

6. The bispecific antibody of claim 5, wherein said first and second Fc regions, except for the specified mutations, comprise the sequence of SEQ ID NO:247 (IgG1m(a)).

7. The bispecific antibody of claim 1, wherein neither said first nor said second Fc region comprises a Cys-Pro-Ser-Cys sequence in the hinge region.

8. The bispecific antibody of claim 1, wherein both said first and second Fc regions comprise a Cys-Pro-Pro-Cys sequence in the hinge region.

9. The bispecific antibody of claim 1, wherein the first and/or the second Fc-region comprises a mutation removing the acceptor site for Asn-linked glycosylation.

10. A conjugated bispecific antibody of claim 1, wherein the antibody is conjugated to a drug, radioisotope, cytokine, or cytotoxic moiety.

11. A pharmaceutical composition comprising the bispecific antibody of claim 1 and a pharmaceutically acceptable carrier.

* * * * *

SEQUENCE LISTING

<160> NUMBER OF SEQ ID NOS: 257

<210> SEQ ID NO 1
<211> LENGTH: 121
<212> TYPE: PRT
<213> ORGANISM: homo sapiens

<400> SEQUENCE: 1

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Leu Ser Ala Tyr Ser Gly Asn Thr Ile Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Ile Val Val Arg Pro Asp Tyr Phe Asp Tyr Trp Gly
            100                 105                 110

Gln Gly Thr Leu Val Thr Val Ser Ser
        115                 120
```

<210> SEQ ID NO 2
<211> LENGTH: 8
<212> TYPE: PRT
<213> ORGANISM: homo sapiens

<400> SEQUENCE: 2

```
Gly Tyr Thr Phe Thr Asn Tyr Gly
1               5
```

<210> SEQ ID NO 3
<211> LENGTH: 8
<212> TYPE: PRT
<213> ORGANISM: homo sapiens

<400> SEQUENCE: 3

```
Leu Ser Ala Tyr Ser Gly Asn Thr
1               5
```

<210> SEQ ID NO 4
<211> LENGTH: 14
<212> TYPE: PRT
<213> ORGANISM: homo sapiens

<400> SEQUENCE: 4

```
Ala Arg Asp Arg Ile Val Val Arg Pro Asp Tyr Phe Asp Tyr
1               5                   10
```

<210> SEQ ID NO 5
<211> LENGTH: 107
<212> TYPE: PRT
<213> ORGANISM: homo sapiens

<400> SEQUENCE: 5

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105


<210> SEQ ID NO 6
<211> LENGTH: 6
<212> TYPE: PRT
<213> ORGANISM: homo sapiens

<400> SEQUENCE: 6

Gln Ser Val Ser Ser Tyr
1               5


<210> SEQ ID NO 7
<211> LENGTH: 9
<212> TYPE: PRT
<213> ORGANISM: homo sapiens

<400> SEQUENCE: 7

Gln Gln Arg Ser Asn Trp Pro Arg Thr
1               5


<210> SEQ ID NO 8
<211> LENGTH: 119
<212> TYPE: PRT
<213> ORGANISM: homo sapiens

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Arg Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Lys Ala Arg Ala Asn Trp Asp Tyr Phe Asp Tyr Trp Gly Gln Gly
            100                 105                 110

Thr Leu Val Thr Val Ser Ser
        115


<210> SEQ ID NO 9
<211> LENGTH: 8
<212> TYPE: PRT
<213> ORGANISM: homo sapiens

<400> SEQUENCE: 9
```

```
Gly Phe Thr Phe Ser Ser Tyr Ala
1               5


<210> SEQ ID NO 10
<211> LENGTH: 8
<212> TYPE: PRT
<213> ORGANISM: homo sapiens

<400> SEQUENCE: 10

Ile Ser Gly Arg Gly Gly Thr Thr
1               5


<210> SEQ ID NO 11
<211> LENGTH: 12
<212> TYPE: PRT
<213> ORGANISM: homo sapiens

<400> SEQUENCE: 11

Ala Lys Ala Arg Ala Asn Trp Asp Tyr Phe Asp Tyr
1               5                   10


<210> SEQ ID NO 12
<211> LENGTH: 107
<212> TYPE: PRT
<213> ORGANISM: homo sapiens

<400> SEQUENCE: 12

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105


<210> SEQ ID NO 13
<211> LENGTH: 6
<212> TYPE: PRT
<213> ORGANISM: homo sapiens

<400> SEQUENCE: 13

Gln Gly Ile Ser Ser Trp
1               5


<210> SEQ ID NO 14
<211> LENGTH: 9
<212> TYPE: PRT
<213> ORGANISM: homo sapiens

<400> SEQUENCE: 14

Gln Gln Ala Asn Ser Phe Pro Ile Thr
1               5


<210> SEQ ID NO 15
<211> LENGTH: 121
```

<212> TYPE: PRT
<213> ORGANISM: homo sapiens

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Thr Tyr
            20                  25                  30

Ala Ile Asn Trp Val Arg Gln Ala Pro Gly Gln Gly Leu Glu Trp Met
        35                  40                  45

Gly Arg Ile Asn Thr Val Leu Gly Ile Val Asn His Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Asn Ser Leu Arg Ser Glu Asp Thr Ala Val Tyr Tyr Cys
                85                  90                  95

Ala Arg Glu Lys Gly Val Asp Tyr Tyr Tyr Gly Ile Glu Val Trp Gly
            100                 105                 110

Gln Gly Thr Thr Val Thr Val Ser Ser
        115                 120

<210> SEQ ID NO 16
<211> LENGTH: 8
<212> TYPE: PRT
<213> ORGANISM: homo sapiens

<400> SEQUENCE: 16

Gly Gly Thr Phe Arg Thr Tyr Ala
1               5

<210> SEQ ID NO 17
<211> LENGTH: 8
<212> TYPE: PRT
<213> ORGANISM: homo sapiens

<400> SEQUENCE: 17

Ile Asn Thr Val Leu Gly Ile Val
1               5

<210> SEQ ID NO 18
<211> LENGTH: 14
<212> TYPE: PRT
<213> ORGANISM: homo sapiens

<400> SEQUENCE: 18

Ala Arg Glu Lys Gly Val Asp Tyr Tyr Tyr Gly Ile Glu Val
1               5                   10

<210> SEQ ID NO 19
<211> LENGTH: 107
<212> TYPE: PRT
<213> ORGANISM: homo sapiens

<400> SEQUENCE: 19

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

-continued

```
Tyr Val Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105


<210> SEQ ID NO 20
<211> LENGTH: 6
<212> TYPE: PRT
<213> ORGANISM: homo sapiens

<400> SEQUENCE: 20

Gln Gly Ile Ser Ser Trp
1               5


<210> SEQ ID NO 21
<211> LENGTH: 9
<212> TYPE: PRT
<213> ORGANISM: homo sapiens

<400> SEQUENCE: 21

Gln Gln Ala Asn Ser Phe Pro Leu Thr
1               5


<210> SEQ ID NO 22
<211> LENGTH: 120
<212> TYPE: PRT
<213> ORGANISM: homo sapiens

<400> SEQUENCE: 22

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile His His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Asp Ser Gly Val Tyr Tyr Phe Asp Tyr Trp Ala Gln
            100                 105                 110

Gly Thr Leu Val Thr Val Ser Ser
        115                 120


<210> SEQ ID NO 23
<211> LENGTH: 8
<212> TYPE: PRT
<213> ORGANISM: homo sapiens

<400> SEQUENCE: 23

Gly Gly Ser Phe Ser Asp Tyr Tyr
1               5


<210> SEQ ID NO 24
```

<211> LENGTH: 7
<212> TYPE: PRT
<213> ORGANISM: homo sapiens

<400> SEQUENCE: 24

Ile His His Ser Gly Ser Thr
1               5

<210> SEQ ID NO 25
<211> LENGTH: 14
<212> TYPE: PRT
<213> ORGANISM: homo sapiens

<400> SEQUENCE: 25

Ala Arg Gly Tyr Tyr Asp Ser Gly Val Tyr Tyr Phe Asp Tyr
1               5                   10

<210> SEQ ID NO 26
<211> LENGTH: 107
<212> TYPE: PRT
<213> ORGANISM: homo sapiens

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 27
<211> LENGTH: 6
<212> TYPE: PRT
<213> ORGANISM: homo sapiens

<400> SEQUENCE: 27

Gln Gly Ile Ser Arg Trp
1               5

<210> SEQ ID NO 28
<211> LENGTH: 9
<212> TYPE: PRT
<213> ORGANISM: homo sapiens

<400> SEQUENCE: 28

Gln Gln Tyr Asn Ser Tyr Pro Ile Thr
1               5

<210> SEQ ID NO 29
<211> LENGTH: 120
<212> TYPE: PRT
<213> ORGANISM: homo sapiens

<400> SEQUENCE: 29

```
Gln Val Gln Leu Gln Gln Trp Gly Ala Gly Leu Leu Lys Pro Ser Glu
1               5                   10                  15

Thr Leu Ser Leu Thr Cys Ala Val Ser Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Glu Ile Tyr His Ser Gly Asp Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Tyr Ser Val Thr Ala Ala Asp Thr Ala Val Tyr Tyr Cys Ala
                85                  90                  95

Arg Leu Tyr Phe Gly Ser Gly Ile Tyr Tyr Leu Asp Tyr Trp Gly Gln
            100                 105                 110

Gly Thr Leu Val Thr Val Ser Ser
        115                 120


<210> SEQ ID NO 30
<211> LENGTH: 8
<212> TYPE: PRT
<213> ORGANISM: homo sapiens

<400> SEQUENCE: 30

Gly Gly Ser Phe Ser Gly Tyr Tyr
1               5


<210> SEQ ID NO 31
<211> LENGTH: 14
<212> TYPE: PRT
<213> ORGANISM: homo sapiens

<400> SEQUENCE: 31

Ala Arg Leu Tyr Phe Gly Ser Gly Ile Tyr Tyr Leu Asp Tyr
1               5                   10


<210> SEQ ID NO 32
<211> LENGTH: 107
<212> TYPE: PRT
<213> ORGANISM: homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Val Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gln Gly Thr Lys Val Glu Ile Lys
            100                 105


<210> SEQ ID NO 33
<211> LENGTH: 6
<212> TYPE: PRT
```

<213> ORGANISM: homo sapiens

<400> SEQUENCE: 33

Gln Gly Ile Ser Ser Trp
1 5

<210> SEQ ID NO 34
<211> LENGTH: 9
<212> TYPE: PRT
<213> ORGANISM: homo sapiens

<400> SEQUENCE: 34

Gln Gln Tyr Asn Ser Phe Pro Pro Thr
1 5

<210> SEQ ID NO 35
<211> LENGTH: 119
<212> TYPE: PRT
<213> ORGANISM: homo sapiens

<400> SEQUENCE: 35

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Thr Phe
20 25 30

Ala Ile His Trp Val Arg Gln Ala Pro Gly Lys Gly Leu Glu Trp Val
35 40 45

Ala Val Ile Ser Tyr Asp Gly Gly His Lys Phe Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Met Tyr Tyr Cys
85 90 95

Ala Arg Gly Leu Gly Val Trp Gly Ala Phe Asp Tyr Trp Gly Gln Gly
100 105 110

Thr Leu Val Thr Val Ser Ser
115

<210> SEQ ID NO 36
<211> LENGTH: 8
<212> TYPE: PRT
<213> ORGANISM: homo sapiens

<400> SEQUENCE: 36

Gly Phe Thr Phe Ser Thr Phe Ala
1 5

<210> SEQ ID NO 37
<211> LENGTH: 8
<212> TYPE: PRT
<213> ORGANISM: homo sapiens

<400> SEQUENCE: 37

Ile Ser Tyr Asp Gly Gly His Lys
1 5

<210> SEQ ID NO 38
<211> LENGTH: 12
<212> TYPE: PRT
<213> ORGANISM: homo sapiens

<400> SEQUENCE: 38

```
Ala Arg Gly Leu Gly Val Trp Gly Ala Phe Asp Tyr
1               5                   10


<210> SEQ ID NO 39
<211> LENGTH: 106
<212> TYPE: PRT
<213> ORGANISM: homo sapiens

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Trp Thr
                85                  90                  95

Phe Gly Gln Gly Thr Lys Val Glu Ile Lys
            100                 105


<210> SEQ ID NO 40
<211> LENGTH: 6
<212> TYPE: PRT
<213> ORGANISM: homo sapiens

<400> SEQUENCE: 40

Gln Ser Val Ser Ser Tyr
1               5


<210> SEQ ID NO 41
<211> LENGTH: 8
<212> TYPE: PRT
<213> ORGANISM: homo sapiens

<400> SEQUENCE: 41

Gln Gln Arg Ser Asn Trp Trp Thr
1               5


<210> SEQ ID NO 42
<211> LENGTH: 123
<212> TYPE: PRT
<213> ORGANISM: homo sapiens

<400> SEQUENCE: 42

Glu Val Gln Leu Val Gln Ser Gly Ala Glu Val Lys Lys Pro Gly Glu
1               5                   10                  15

Ser Leu Thr Ile Ser Cys Lys Gly Ser Gly Tyr Ser Phe Ser Ile Tyr
            20                  25                  30

Trp Ile Gly Trp Val Arg Gln Met Pro Gly Lys Gly Leu Glu Trp Met
        35                  40                  45

Gly Ile Ile Phe Pro Gly Asp Ser Asp Ile Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
```

-continued

```
                85                  90                  95

Ala Arg Gln Pro Gly Asp Trp Ser Pro Arg His Trp Tyr Phe Asp Leu
            100                 105                 110

Trp Gly Arg Gly Thr Leu Val Thr Val Ser Ser
        115                 120


<210> SEQ ID NO 43
<211> LENGTH: 8
<212> TYPE: PRT
<213> ORGANISM: homo sapiens

<400> SEQUENCE: 43

Gly Tyr Ser Phe Ser Ile Tyr Trp
1               5


<210> SEQ ID NO 44
<211> LENGTH: 8
<212> TYPE: PRT
<213> ORGANISM: homo sapiens

<400> SEQUENCE: 44

Ile Phe Pro Gly Asp Ser Asp Ile
1               5


<210> SEQ ID NO 45
<211> LENGTH: 16
<212> TYPE: PRT
<213> ORGANISM: homo sapiens

<400> SEQUENCE: 45

Ala Arg Gln Pro Gly Asp Trp Ser Pro Arg His Trp Tyr Phe Asp Leu
1               5                   10                  15


<210> SEQ ID NO 46
<211> LENGTH: 107
<212> TYPE: PRT
<213> ORGANISM: homo sapiens

<400> SEQUENCE: 46

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Tyr Leu Gln Ser
65                  70                  75                  80

Glu Asp Phe Ala Thr Tyr Tyr Cys Gln Gln Tyr Tyr Ser Phe Pro Leu
                85                  90                  95

Thr Phe Gly Gly Gly Thr Lys Val Glu Ile Lys
            100                 105


<210> SEQ ID NO 47
<211> LENGTH: 6
<212> TYPE: PRT
<213> ORGANISM: homo sapiens

<400> SEQUENCE: 47

Gln Gly Ile Ser Ser Tyr
```

-continued

```
1               5


<210> SEQ ID NO 48
<211> LENGTH: 9
<212> TYPE: PRT
<213> ORGANISM: homo sapiens

<400> SEQUENCE: 48

Gln Gln Tyr Tyr Ser Phe Pro Leu Thr
1               5


<210> SEQ ID NO 49
<211> LENGTH: 126
<212> TYPE: PRT
<213> ORGANISM: homo sapiens

<400> SEQUENCE: 49

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Thr Tyr Tyr Asp Ile Leu Thr Gly Tyr Phe Asn Trp
            100                 105                 110

Phe Asp Pro Trp Gly Gln Gly Thr Leu Val Thr Val Ser Ser
        115                 120                 125


<210> SEQ ID NO 50
<211> LENGTH: 8
<212> TYPE: PRT
<213> ORGANISM: homo sapiens

<400> SEQUENCE: 50

Gly Tyr Asn Phe Thr Ser Tyr Trp
1               5


<210> SEQ ID NO 51
<211> LENGTH: 8
<212> TYPE: PRT
<213> ORGANISM: homo sapiens

<400> SEQUENCE: 51

Ile Tyr Pro Gly Asp Ser Asp Thr
1               5


<210> SEQ ID NO 52
<211> LENGTH: 15
<212> TYPE: PRT
<213> ORGANISM: homo sapiens

<400> SEQUENCE: 52

Ala Arg Trp Gly Thr Tyr Tyr Asp Ile Leu Thr Gly Tyr Phe Asn
1               5                   10                  15
```

<210> SEQ ID NO 53
<211> LENGTH: 107
<212> TYPE: PRT
<213> ORGANISM: homo sapiens

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Trp
                85                  90                  95

Thr Phe Gly Gln Gly Thr Lys Val Glu Ile Lys
            100                 105

<210> SEQ ID NO 54
<211> LENGTH: 6
<212> TYPE: PRT
<213> ORGANISM: homo sapiens

<400> SEQUENCE: 54

Gln Gly Ile Ser Ser Trp
1               5

<210> SEQ ID NO 55
<211> LENGTH: 9
<212> TYPE: PRT
<213> ORGANISM: homo sapiens

<400> SEQUENCE: 55

Gln Gln Tyr Tyr Ile Tyr Pro Trp Thr
1               5

<210> SEQ ID NO 56
<211> LENGTH: 124
<212> TYPE: PRT
<213> ORGANISM: homo sapiens

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Ala Ile Ser Gly Ser Ala Tyr Ser Thr Tyr Tyr Ala Asp Ser Val
    50                  55                  60

Lys Gly Arg Phe Thr Ile Ser Arg Asp Asn Ser Lys Asn Thr Leu Trp
65                  70                  75                  80

Leu Gln Met Asn Ser Leu Arg Ala Glu Asp Thr Ala Val Tyr Tyr Cys
                85                  90                  95

Ala Lys Ala His Tyr His Gly Ser Gly Ser Tyr Tyr Thr Leu Phe Asp
            100                 105                 110

```
Tyr Trp Gly Gln Gly Thr Leu Val Thr Val Ser Ser
        115                 120


<210> SEQ ID NO 57
<211> LENGTH: 8
<212> TYPE: PRT
<213> ORGANISM: homo sapiens

<400> SEQUENCE: 57

Gly Phe Thr Phe Ser Asn Tyr Gly
1               5


<210> SEQ ID NO 58
<211> LENGTH: 8
<212> TYPE: PRT
<213> ORGANISM: homo sapiens

<400> SEQUENCE: 58

Ile Ser Gly Ser Ala Tyr Ser Thr
1               5


<210> SEQ ID NO 59
<211> LENGTH: 17
<212> TYPE: PRT
<213> ORGANISM: homo sapiens

<400> SEQUENCE: 59

Ala Lys Ala His Tyr His Gly Ser Gly Ser Tyr Tyr Thr Leu Phe Asp
1               5                   10                  15

Tyr


<210> SEQ ID NO 60
<211> LENGTH: 107
<212> TYPE: PRT
<213> ORGANISM: homo sapiens

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105


<210> SEQ ID NO 61
<211> LENGTH: 6
<212> TYPE: PRT
<213> ORGANISM: homo sapiens

<400> SEQUENCE: 61

Gln Gly Ile Ser Ser Trp
1               5
```

<210> SEQ ID NO 62
<211> LENGTH: 9
<212> TYPE: PRT
<213> ORGANISM: homo sapiens

<400> SEQUENCE: 62

```
Gln Gln Tyr Asn Ser Tyr Pro Tyr Thr
1               5
```

<210> SEQ ID NO 63
<211> LENGTH: 121
<212> TYPE: PRT
<213> ORGANISM: homo sapiens

<400> SEQUENCE: 63

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Val Ile His Trp Val Arg Gln Ala Pro Gly Lys Gly Leu Glu Trp Val
        35                  40                  45

Thr Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Met Tyr Tyr Cys
                85                  90                  95

Ala Arg Gly Gly Ile Thr Gly Thr Thr Gly Val Phe Asp Tyr Trp Gly
            100                 105                 110

Gln Gly Thr Leu Val Thr Val Ser Ser
        115                 120
```

<210> SEQ ID NO 64
<211> LENGTH: 8
<212> TYPE: PRT
<213> ORGANISM: homo sapiens

<400> SEQUENCE: 64

```
Gly Phe Thr Phe Ser Asp Tyr Val
1               5
```

<210> SEQ ID NO 65
<211> LENGTH: 8
<212> TYPE: PRT
<213> ORGANISM: homo sapiens

<400> SEQUENCE: 65

```
Ile Ser Tyr Asp Gly Ser Asn Lys
1               5
```

<210> SEQ ID NO 66
<211> LENGTH: 14
<212> TYPE: PRT
<213> ORGANISM: homo sapiens

<400> SEQUENCE: 66

```
Ala Arg Gly Gly Ile Thr Gly Thr Thr Gly Val Phe Asp Tyr
1               5                   10
```

<210> SEQ ID NO 67
<211> LENGTH: 107
<212> TYPE: PRT

<213> ORGANISM: homo sapiens

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Asp Ala Ser Ser Leu Gln Ser Gly Val Pro Ser Arg Phe Ser Gly
    50                  55                  60

Ser Gly Tyr Gly Thr Asp Phe Ser Leu Thr Ile Ser Ser Leu Gln Pro
65                  70                  75                  80

Glu Asp Phe Ala Ile Tyr Tyr Cys Gln Gln Tyr Lys Ser Tyr Pro Ile
                85                  90                  95

Thr Phe Gly Gln Gly Thr Arg Leu Glu Ile Lys
            100                 105
```

<210> SEQ ID NO 68
<211> LENGTH: 6
<212> TYPE: PRT
<213> ORGANISM: homo sapiens

<400> SEQUENCE: 68

```
Gln Gly Ile Ser Ser Trp
1               5
```

<210> SEQ ID NO 69
<211> LENGTH: 9
<212> TYPE: PRT
<213> ORGANISM: homo sapiens

<400> SEQUENCE: 69

```
Gln Gln Tyr Lys Ser Tyr Pro Ile Thr
1               5
```

<210> SEQ ID NO 70
<211> LENGTH: 125
<212> TYPE: PRT
<213> ORGANISM: homo sapiens

<400> SEQUENCE: 70

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Ser Asn Tyr Val Gln Lys Phe
    50                  55                  60

Gln Gly Arg Val Thr Met Thr Thr Asp Thr Thr Thr Ser Thr Ala Tyr
65                  70                  75                  80

Met Glu Leu Arg Ser Leu Thr Ser Asp Asp Thr Ala Val Tyr Tyr Cys
                85                  90                  95

Ala Arg Glu Tyr Ser Tyr Asp Ser Gly Thr Tyr Phe Tyr Tyr Gly Met
            100                 105                 110

Asp Val Trp Gly Gln Gly Thr Thr Val Thr Val Ser Ser
        115                 120                 125
```

<210> SEQ ID NO 71
<211> LENGTH: 8
<212> TYPE: PRT
<213> ORGANISM: homo sapiens

<400> SEQUENCE: 71

Gly Tyr Thr Phe Thr Ser Tyr Gly
1               5

<210> SEQ ID NO 72
<211> LENGTH: 8
<212> TYPE: PRT
<213> ORGANISM: homo sapiens

<400> SEQUENCE: 72

Ile Ser Ala Tyr Asn Gly Asn Ser
1               5

<210> SEQ ID NO 73
<211> LENGTH: 18
<212> TYPE: PRT
<213> ORGANISM: homo sapiens

<400> SEQUENCE: 73

Ala Arg Glu Tyr Ser Tyr Asp Ser Gly Thr Tyr Phe Tyr Tyr Gly Met
1               5                   10                  15

Asp Val

<210> SEQ ID NO 74
<211> LENGTH: 108
<212> TYPE: PRT
<213> ORGANISM: homo sapiens

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Met
                85                  90                  95

Tyr Thr Phe Gly Gln Gly Thr Lys Leu Glu Ile Lys
            100                 105

<210> SEQ ID NO 75
<211> LENGTH: 6
<212> TYPE: PRT
<213> ORGANISM: homo sapiens

<400> SEQUENCE: 75

Gln Ser Val Ser Ser Tyr
1               5

<210> SEQ ID NO 76
<211> LENGTH: 10
<212> TYPE: PRT

<213> ORGANISM: homo sapiens

<400> SEQUENCE: 76

```
Gln Gln Arg Ser Asn Trp Pro Met Tyr Thr
1               5                   10
```

<210> SEQ ID NO 77
<211> LENGTH: 119
<212> TYPE: PRT
<213> ORGANISM: homo sapiens

<400> SEQUENCE: 77

```
Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Gly Thr Thr Tyr Tyr Ala Asp Ser Val
    50                  55                  60

Lys Gly Arg Phe Thr Ile Ser Arg Asp Asn Ser Lys Ser Thr Leu Cys
65                  70                  75                  80

Leu Gln Met Asn Ser Leu Arg Ala Glu Asp Thr Ala Val Tyr Tyr Cys
                85                  90                  95

Ala Lys Ala Arg Ala Asn Trp Asp Tyr Phe Asp Tyr Trp Gly Gln Gly
            100                 105                 110

Thr Leu Val Thr Val Ser Ser
        115
```

<210> SEQ ID NO 78
<211> LENGTH: 107
<212> TYPE: PRT
<213> ORGANISM: homo sapiens

<400> SEQUENCE: 78

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Arg Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105
```

<210> SEQ ID NO 79
<211> LENGTH: 119
<212> TYPE: PRT
<213> ORGANISM: homo sapiens

<400> SEQUENCE: 79

```
Glu Val Gln Leu Leu Glu Ser Gly Gly Asp Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Gly Thr Thr Tyr Tyr Ala Asp Ser Val
    50                  55                  60

Lys Gly Arg Phe Thr Ile Ser Arg Asp Asn Ser Lys Ser Thr Leu Cys
65                  70                  75                  80

Leu Gln Met Asn Ser Leu Arg Ala Glu Asp Thr Ala Val Tyr Tyr Cys
                85                  90                  95

Ala Lys Ala Arg Ala Asn Trp Asp Tyr Phe Asp Tyr Trp Gly Gln Gly
            100                 105                 110

Thr Leu Val Thr Val Ser Ser
        115


<210> SEQ ID NO 80
<211> LENGTH: 107
<212> TYPE: PRT
<213> ORGANISM: homo sapiens

<400> SEQUENCE: 80

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Arg Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105


<210> SEQ ID NO 81
<211> LENGTH: 119
<212> TYPE: PRT
<213> ORGANISM: homo sapiens

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Arg Gly Gly Thr Thr Tyr Tyr Ala Asp Ser Val
    50                  55                  60

Lys Gly Arg Phe Thr Ile Ser Arg Asp Asn Ser Lys Ser Thr Leu Cys
65                  70                  75                  80

Leu Gln Met Asn Ser Leu Arg Ala Glu Asp Thr Ala Val Tyr Tyr Cys
                85                  90                  95

Ala Lys Ala Arg Ala Asn Trp Asp Tyr Phe Asp Tyr Trp Gly Gln Gly
            100                 105                 110
```

```
Thr Leu Val Thr Val Ser Ser
        115


<210> SEQ ID NO 82
<211> LENGTH: 107
<212> TYPE: PRT
<213> ORGANISM: homo sapiens

<400> SEQUENCE: 82

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Arg Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105


<210> SEQ ID NO 83
<211> LENGTH: 121
<212> TYPE: PRT
<213> ORGANISM: homo sapiens

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ala Gly Tyr Thr Phe Thr Asn Tyr
            20                  25                  30

Gly Ile Ser Trp Val Arg Gln Ala Pro Gly Gln Ala Leu Glu Trp Met
        35                  40                  45

Gly Trp Ile Thr Thr Tyr Ser Ser Asn Thr Ile Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Val Val Val Arg Pro Asp Tyr Phe Asp Tyr Trp Gly
            100                 105                 110

Gln Gly Thr Leu Val Thr Val Ser Ser
        115                 120


<210> SEQ ID NO 84
<211> LENGTH: 107
<212> TYPE: PRT
<213> ORGANISM: homo sapiens

<400> SEQUENCE: 84

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
```

```
        35                  40                  45

Tyr Asp Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser His Trp Pro Arg
                85                  90                  95

Thr Phe Gly Gln Gly Thr Lys Val Glu Ile Lys
            100                 105


<210> SEQ ID NO 85
<211> LENGTH: 121
<212> TYPE: PRT
<213> ORGANISM: homo sapiens

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Leu Ser Ala Tyr Ser Gly Asn Thr Ile Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Ile Val Val Arg Pro Asp Tyr Phe Asp Tyr Trp Gly
            100                 105                 110

Gln Gly Thr Leu Val Thr Val Ser Ser
        115                 120


<210> SEQ ID NO 86
<211> LENGTH: 107
<212> TYPE: PRT
<213> ORGANISM: homo sapiens

<400> SEQUENCE: 86

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105


<210> SEQ ID NO 87
<211> LENGTH: 121
<212> TYPE: PRT
```

<213> ORGANISM: homo sapiens

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ala Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ile Thr Tyr Asn Gly Asn Thr Ile Tyr Ala Gln Arg Phe
    50                  55                  60

Gln Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Ile Ile Val Arg Pro Asp Tyr Phe Asp Tyr Trp Gly
            100                 105                 110

Gln Gly Thr Leu Val Thr Val Ser Ser
        115                 120

<210> SEQ ID NO 88
<211> LENGTH: 107
<212> TYPE: PRT
<213> ORGANISM: homo sapiens

<400> SEQUENCE: 88

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 89
<211> LENGTH: 120
<212> TYPE: PRT
<213> ORGANISM: homo sapiens

<400> SEQUENCE: 89

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

```
Lys Leu Ser Ser Val Thr Ala Ala Asp Thr Ala Val Tyr Tyr Cys Ala
                85                  90                  95

Arg Gly Asn Tyr Gly Ser Gly Tyr Tyr Tyr Phe Asp Leu Trp Gly Arg
            100                 105                 110

Gly Thr Gln Val Thr Val Ser Ser
        115                 120


<210> SEQ ID NO 90
<211> LENGTH: 107
<212> TYPE: PRT
<213> ORGANISM: homo sapiens

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Ser Phe Pro Ile
                85                  90                  95

Thr Phe Gly Gln Gly Thr Arg Leu Glu Ile Lys
            100                 105


<210> SEQ ID NO 91
<211> LENGTH: 120
<212> TYPE: PRT
<213> ORGANISM: homo sapiens

<400> SEQUENCE: 91

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile His His Ser Gly Ser Ala Asn Tyr Asn Pro Ser Leu Met
    50                  55                  60

Ser Arg Val Thr Ile Ser Val Asp Thr Ser Lys Asn Gln Phe Ser Leu
65                  70                  75                  80

Gln Leu Ser Ser Val Thr Ala Ala Asp Thr Ala Val Tyr Tyr Cys Ala
                85                  90                  95

Arg Gly Tyr Tyr Gly Ser Gly Tyr Tyr Tyr Phe Asp Tyr Trp Gly Gln
            100                 105                 110

Gly Thr Leu Val Thr Val Ser Ser
        115                 120


<210> SEQ ID NO 92
<211> LENGTH: 107
<212> TYPE: PRT
<213> ORGANISM: homo sapiens

<400> SEQUENCE: 92
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105


<210> SEQ ID NO 93
<211> LENGTH: 120
<212> TYPE: PRT
<213> ORGANISM: homo sapiens

<400> SEQUENCE: 93

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile His His Val Gly Ser Thr Asn Tyr Asn Pro Ser Leu Lys
    50                  55                  60

Ser Arg Val Thr Ile Ser Val Asp Thr Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Asp Ser Gly Val Tyr Tyr Phe Asp Tyr Trp Ala Gln
            100                 105                 110

Gly Thr Leu Val Thr Val Ser Ser
        115                 120


<210> SEQ ID NO 94
<211> LENGTH: 107
<212> TYPE: PRT
<213> ORGANISM: homo sapiens

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95
```

```
Thr Phe Gly Gln Gly Thr Arg Leu Glu Ile Lys
            100                 105


<210> SEQ ID NO 95
<211> LENGTH: 120
<212> TYPE: PRT
<213> ORGANISM: homo sapiens

<400> SEQUENCE: 95

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile His His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Ala Ser Gly Val Tyr Tyr Phe Asp Tyr Trp Gly Gln
            100                 105                 110

Gly Thr Leu Val Thr Val Ser Ser
        115                 120


<210> SEQ ID NO 96
<211> LENGTH: 107
<212> TYPE: PRT
<213> ORGANISM: homo sapiens

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105


<210> SEQ ID NO 97
<211> LENGTH: 120
<212> TYPE: PRT
<213> ORGANISM: homo sapiens

<400> SEQUENCE: 97

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Phe Trp Asn Trp Ile Arg Gln Pro Pro Gly Lys Gly Leu Glu Trp Ile
```

```
        35                  40                  45

Gly Glu Ile His His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Asn Leu Ser Ser Val Thr Ala Ala Asp Thr Ala Val Tyr Tyr Cys Ala
                85                  90                  95

Arg Gly Leu Ile Gly Ser Gly Tyr Tyr Tyr Phe Asp Tyr Trp Asp Gln
            100                 105                 110

Gly Thr Leu Val Thr Val Ser Ser
        115                 120


<210> SEQ ID NO 98
<211> LENGTH: 107
<212> TYPE: PRT
<213> ORGANISM: homo sapiens

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105


<210> SEQ ID NO 99
<211> LENGTH: 120
<212> TYPE: PRT
<213> ORGANISM: homo sapiens

<400> SEQUENCE: 99

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asp Thr Asn Tyr Asn Pro Ser Leu Thr
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Phe Tyr Gly Ser Gly Ile Tyr Tyr Phe Asp Tyr Trp Gly Gln
            100                 105                 110

Gly Thr Leu Val Thr Val Ser Ser
        115                 120
```

<210> SEQ ID NO 100
<211> LENGTH: 107
<212> TYPE: PRT
<213> ORGANISM: homo sapiens

<400> SEQUENCE: 100

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Thr Phe Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gln Gly Thr Lys Val Glu Ile Lys
            100                 105
```

<210> SEQ ID NO 101
<211> LENGTH: 120
<212> TYPE: PRT
<213> ORGANISM: homo sapiens

<400> SEQUENCE: 101

```
Gln Val Gln Leu Gln Gln Trp Gly Ala Gly Leu Leu Lys Pro Ser Glu
1               5                   10                  15

Thr Leu Ser Leu Thr Cys Ala Ile Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asp Thr Asn Tyr Asn Pro Ser Leu Thr
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Phe Tyr Gly Ser Gly Ile Tyr Tyr Phe Asp Tyr Trp Gly Gln
            100                 105                 110

Gly Thr Leu Val Thr Val Ser Ser
        115                 120
```

<210> SEQ ID NO 102
<211> LENGTH: 107
<212> TYPE: PRT
<213> ORGANISM: homo sapiens

<400> SEQUENCE: 102

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Thr Phe Arg Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gln Gly Thr Lys Val Glu Ile Lys
            100                 105


<210> SEQ ID NO 103
<211> LENGTH: 120
<212> TYPE: PRT
<213> ORGANISM: homo sapiens

<400> SEQUENCE: 103

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Tyr Tyr Gly Ser Gly Thr Tyr Tyr Phe Asp Tyr Trp Gly Gln
            100                 105                 110

Gly Thr Leu Val Thr Val Ser Ser
        115                 120


<210> SEQ ID NO 104
<211> LENGTH: 107
<212> TYPE: PRT
<213> ORGANISM: homo sapiens

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Thr Trp Tyr Gln Gln Lys Pro Glu Lys Ala Pro Lys Ser Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gln Gly Thr Lys Val Glu Ile Lys
            100                 105


<210> SEQ ID NO 105
<211> LENGTH: 120
<212> TYPE: PRT
<213> ORGANISM: homo sapiens

<400> SEQUENCE: 105
```

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile His His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Trp Tyr Gly Ser Gly Ser Tyr Tyr Phe Asp Tyr Trp Gly Gln
            100                 105                 110

Gly Thr Leu Val Thr Val Ser Ser
        115                 120


<210> SEQ ID NO 106
<211> LENGTH: 107
<212> TYPE: PRT
<213> ORGANISM: homo sapiens

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105


<210> SEQ ID NO 107
<211> LENGTH: 120
<212> TYPE: PRT
<213> ORGANISM: homo sapiens

<400> SEQUENCE: 107

Gln Val Gln Leu Gln Gln Trp Gly Ala Gly Leu Leu Lys Pro Ser Glu
1               5                   10                  15

Thr Leu Ser Leu Thr Cys Ala Val Ser Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Glu Ile Tyr His Ser Gly Asp Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Tyr Ser Val Thr Ala Ala Asp Thr Ala Val Tyr Tyr Cys Ala
                85                  90                  95
```

```
Arg Leu Tyr Phe Gly Ser Gly Ile Tyr Tyr Leu Asp Tyr Trp Gly Gln
            100                 105                 110

Gly Thr Leu Val Thr Val Ser Ser
        115                 120


<210> SEQ ID NO 108
<211> LENGTH: 107
<212> TYPE: PRT
<213> ORGANISM: homo sapiens

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Val Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gln Gly Thr Lys Val Glu Ile Lys
            100                 105


<210> SEQ ID NO 109
<211> LENGTH: 124
<212> TYPE: PRT
<213> ORGANISM: homo sapiens

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Ala Ile Ser Gly Ser Ala Tyr Ser Thr Tyr Tyr Ala Asp Ser Val
    50                  55                  60

Lys Gly Arg Phe Thr Ile Ser Arg Asp Asn Ser Lys Asn Thr Leu Trp
65                  70                  75                  80

Leu Gln Met Asn Ser Leu Arg Ala Glu Asp Thr Ala Val Tyr Tyr Cys
                85                  90                  95

Ala Lys Ala His Tyr His Gly Ser Gly Ser Tyr Tyr Thr Leu Phe Asp
            100                 105                 110

Tyr Trp Gly Gln Gly Thr Leu Val Thr Val Ser Ser
        115                 120


<210> SEQ ID NO 110
<211> LENGTH: 107
<212> TYPE: PRT
<213> ORGANISM: homo sapiens

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
```

```
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105


<210> SEQ ID NO 111
<211> LENGTH: 124
<212> TYPE: PRT
<213> ORGANISM: homo sapiens

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Gly Met Asn Trp Val Arg Gln Ala Pro Gly Lys Gly Leu Glu Trp Val
        35                  40                  45

Ser Ala Ile Ser Gly Thr Gly Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Tyr Phe Gly Ser Gly Ser Tyr Tyr Thr Leu Phe Asp
            100                 105                 110

Tyr Trp Gly Gln Gly Thr Leu Val Thr Val Ser Ser
        115                 120


<210> SEQ ID NO 112
<211> LENGTH: 107
<212> TYPE: PRT
<213> ORGANISM: homo sapiens

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105
```

<210> SEQ ID NO 113
<211> LENGTH: 124
<212> TYPE: PRT
<213> ORGANISM: homo sapiens

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Tyr Ala Thr Tyr Tyr Ala Asp Ser Val
    50                  55                  60

Lys Gly Arg Phe Thr Ile Ser Arg Asp Asn Ser Lys Thr Thr Leu Tyr
65                  70                  75                  80

Leu Gln Met Asn Ser Leu Arg Ala Glu Asp Thr Ala Val Tyr Tyr Cys
                85                  90                  95

Ala Lys Gly His Thr Leu Gly Ser Gly Ser Tyr Tyr Thr Leu Phe Asp
            100                 105                 110

Tyr Trp Gly Gln Gly Thr Leu Val Thr Val Ser Ser
        115                 120

<210> SEQ ID NO 114
<211> LENGTH: 107
<212> TYPE: PRT
<213> ORGANISM: homo sapiens

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 115
<211> LENGTH: 124
<212> TYPE: PRT
<213> ORGANISM: homo sapiens

<400> SEQUENCE: 115

Glu Val Gln Leu Trp Glu Ser Gly Gly Gly Ser Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Gly Ile Ser Gly Ser Gly Tyr Ser Thr Tyr Tyr Ala Asp Ser Val
    50                  55                  60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Tyr His Gly Ser Gly Ser Tyr Tyr Thr Ser Phe Asp
            100                 105                 110

Tyr Trp Gly Gln Gly Thr Leu Val Thr Val Ser Ser
        115                 120


<210> SEQ ID NO 116
<211> LENGTH: 107
<212> TYPE: PRT
<213> ORGANISM: homo sapiens

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105


<210> SEQ ID NO 117
<211> LENGTH: 121
<212> TYPE: PRT
<213> ORGANISM: homo sapiens

<400> SEQUENCE: 117

Gln Val Gln Leu Val Glu Ser Gly Gly Gly Val Val Gln Thr Gly Arg
1               5                   10                  15

Ser Leu Arg Leu Ser Cys Ala Ala Ser Gly Phe Thr Phe Ser Ser His
            20                  25                  30

Ala Met His Trp Val Arg Gln Ala Pro Gly Lys Gly Leu Glu Trp Val
        35                  40                  45

Ala Ala Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Ile Ser Ser Ser Gly Val Phe Asp Tyr Trp Gly
            100                 105                 110

Gln Gly Thr Leu Val Thr Val Ser Ser
        115                 120


<210> SEQ ID NO 118
<211> LENGTH: 107
<212> TYPE: PRT
<213> ORGANISM: homo sapiens
```

<400> SEQUENCE: 118

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Ile
85 90 95

Thr Phe Gly Gln Gly Thr Arg Leu Glu Ile Lys
100 105

<210> SEQ ID NO 119
<211> LENGTH: 121
<212> TYPE: PRT
<213> ORGANISM: homo sapiens

<400> SEQUENCE: 119

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser His
20 25 30

Ala Met His Trp Val Arg Gln Ala Pro Gly Lys Gly Leu Glu Trp Val
35 40 45

Ala Ala Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Met Tyr
65 70 75 80

Leu Gln Met Asn Ser Leu Arg Ala Glu Asp Thr Ala Met Cys Tyr Cys
85 90 95

Ala Arg Gly Ser Ile Thr Gly Ser Thr Gly Val Phe Asp Tyr Trp Gly
100 105 110

Gln Gly Thr Leu Val Thr Val Ser Ser
115 120

<210> SEQ ID NO 120
<211> LENGTH: 107
<212> TYPE: PRT
<213> ORGANISM: homo sapiens

<400> SEQUENCE: 120

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

```
Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105


<210> SEQ ID NO 121
<211> LENGTH: 121
<212> TYPE: PRT
<213> ORGANISM: homo sapiens

<400> SEQUENCE: 121

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ile Ile Gly Ser Thr Gly Val Phe Asp Tyr Trp Gly
            100                 105                 110

Gln Gly Thr Leu Val Thr Val Ser Ser
        115                 120


<210> SEQ ID NO 122
<211> LENGTH: 107
<212> TYPE: PRT
<213> ORGANISM: homo sapiens

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105


<210> SEQ ID NO 123
<211> LENGTH: 121
<212> TYPE: PRT
<213> ORGANISM: homo sapiens

<400> SEQUENCE: 123

Gln Val Gln Val Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

```
            20                  25                  30

Ala Met His Trp Val Arg Gln Ala Pro Gly Lys Gly Leu Glu Trp Val
        35                  40                  45

Ala Val Ile Ser Tyr Asp Gly Ser Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ile Thr Gly Ser Thr Gly Val Phe Asp Tyr Trp Gly
            100                 105                 110

Gln Gly Thr Leu Val Thr Val Ser Ser
        115                 120


<210> SEQ ID NO 124
<211> LENGTH: 107
<212> TYPE: PRT
<213> ORGANISM: homo sapiens

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Trp
            20                  25                  30

Leu Ala Trp Tyr Gln Gln Lys Pro Glu Lys Ala Pro Lys Ser Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asn Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105


<210> SEQ ID NO 125
<211> LENGTH: 121
<212> TYPE: PRT
<213> ORGANISM: homo sapiens

<400> SEQUENCE: 125

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Ile His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ile Thr Gly Ser Thr Gly Val Phe Asp Tyr Trp Gly
            100                 105                 110

Gln Gly Thr Leu Val Thr Val Ser Ser
```

```
        115                 120


<210> SEQ ID NO 126
<211> LENGTH: 107
<212> TYPE: PRT
<213> ORGANISM: homo sapiens

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105


<210> SEQ ID NO 127
<211> LENGTH: 8
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: wherein Xaa=Arg or Ser, preferably Arg
<220> FEATURE:
<221> NAME/KEY: MISC_FEATURE
<222> LOCATION: (7)..(7)
<223> OTHER INFORMATION: wherein Xaa=Thr or Ser, preferably Thr

<400> SEQUENCE: 127

Ile Ser Gly Xaa Gly Gly Xaa Thr
1               5


<210> SEQ ID NO 128
<211> LENGTH: 8
<212> TYPE: PRT
<213> ORGANISM: homo sapiens
<220> FEATURE:
<221> NAME/KEY: MISC_FEATURE
<222> LOCATION: (5)..(5)
<223> OTHER INFORMATION: wherein Xaa=Arg or Ser, preferably Arg
<220> FEATURE:
<221> NAME/KEY: MISC_FEATURE
<222> LOCATION: (6)..(6)
<223> OTHER INFORMATION: wherein Xaa=Thr or Ser, preferably Thr

<400> SEQUENCE: 128

Gly Gly Thr Phe Xaa Xaa Tyr Ala
1               5


<210> SEQ ID NO 129
<211> LENGTH: 8
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: wherein Xaa=Asn or Ile, preferably Asn
<220> FEATURE:
```

<221> NAME/KEY: MISC_FEATURE
<222> LOCATION: (3)..(3)
<223> OTHER INFORMATION: wherein Xaa=Thr or Pro, preferably Thr
<220> FEATURE:
<221> NAME/KEY: MISC_FEATURE
<222> LOCATION: (4)..(4)
<223> OTHER INFORMATION: wherein Xaa=Val or Ile, preferably Val
<220> FEATURE:
<221> NAME/KEY: MISC_FEATURE
<222> LOCATION: (8)..(8)
<223> OTHER INFORMATION: wherein Xaa=Val or Ala, preferably Val

<400> SEQUENCE: 129

Ile Xaa Xaa Xaa Leu Gly Ile Xaa
1               5

<210> SEQ ID NO 130
<211> LENGTH: 13
<212> TYPE: PRT
<213> ORGANISM: homo sapiens
<220> FEATURE:
<221> NAME/KEY: MISC_FEATURE
<222> LOCATION: (12)..(12)
<223> OTHER INFORMATION: wherein Xaa=Ile or Met, preferably Ile
<220> FEATURE:
<221> NAME/KEY: MISC_FEATURE
<222> LOCATION: (13)..(13)
<223> OTHER INFORMATION: wherein Xaa=Glu or Asp, preferably Glu

<400> SEQUENCE: 130

Ala Arg Glu Lys Gly Val Asp Tyr Tyr Tyr Gly Xaa Xaa
1               5                   10

<210> SEQ ID NO 131
<211> LENGTH: 8
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: wherein Xaa=Asn or Ser, preferably Ser

<400> SEQUENCE: 131

Gly Tyr Thr Phe Thr Xaa Tyr Gly
1               5

<210> SEQ ID NO 132
<211> LENGTH: 8
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: wherein Xaa=Ser, Thr, or Ile, preferably Ser
<220> FEATURE:
<221> NAME/KEY: MISC_FEATURE
<222> LOCATION: (3)..(3)
<223> OTHER INFORMATION: wherein Xaa=Ala or Thr, preferably Ala
<220> FEATURE:
<221> NAME/KEY: MISC_FEATURE
<222> LOCATION: (5)..(5)
<223> OTHER INFORMATION: wherein Xaa=Ser or Asn, preferably Ser

<400> SEQUENCE: 132

Ile Xaa Xaa Tyr Xaa Gly Asn Thr
1               5

<210> SEQ ID NO 133
<211> LENGTH: 14
<212> TYPE: PRT
<213> ORGANISM: homo sapiens
<220> FEATURE:
<221> NAME/KEY: MISC_FEATURE
<222> LOCATION: (5)..(5)
<223> OTHER INFORMATION: wherein Xaa=Ile or Val, preferably Ile
<220> FEATURE:
<221> NAME/KEY: MISC_FEATURE
<222> LOCATION: (6)..(6)
<223> OTHER INFORMATION: wherein Xaa=Val or Ile, preferably Val

<400> SEQUENCE: 133

Ala Arg Asp Arg Xaa Xaa Val Arg Pro Asp Tyr Phe Asp Tyr
1 5 10

<210> SEQ ID NO 134
<211> LENGTH: 8
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: wherein Xaa=Asp or Gly, preferably Asp
<220> FEATURE:
<221> NAME/KEY: MISC_FEATURE
<222> LOCATION: (8)..(8)
<223> OTHER INFORMATION: wherein Xaa=Tyr or Phe, preferably Tyr

<400> SEQUENCE: 134

Gly Gly Ser Phe Ser Xaa Tyr Xaa
1 5

<210> SEQ ID NO 135
<211> LENGTH: 7
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: wherein Xaa=His or Asn, preferably His
<220> FEATURE:
<221> NAME/KEY: MISC_FEATURE
<222> LOCATION: (4)..(4)
<223> OTHER INFORMATION: wherein Xaa=Ser or Val, preferably Ser
<220> FEATURE:
<221> NAME/KEY: MISC_FEATURE
<222> LOCATION: (7)..(7)
<223> OTHER INFORMATION: wherein Xaa=Thr or Ala, preferably Thr

<400> SEQUENCE: 135

Ile Xaa His Xaa Gly Ser Xaa
1 5

<210> SEQ ID NO 136
<211> LENGTH: 14
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: wherein Xaa=Tyr, Asn or Leu, preferably Tyr
<220> FEATURE:
<221> NAME/KEY: MISC_FEATURE
<222> LOCATION: (5)..(5)
<223> OTHER INFORMATION: wherein Xaa=Tyr or Ile, preferably Tyr
<220> FEATURE:
<221> NAME/KEY: MISC_FEATURE
<222> LOCATION: (6)..(6)
<223> OTHER INFORMATION: wherein Xaa=Asp, Gly, or Ala, preferably Asp
<220> FEATURE:
<221> NAME/KEY: MISC_FEATURE
<222> LOCATION: (9)..(9)
<223> OTHER INFORMATION: wherein Xaa=Val or Tyr, preferably Val
<220> FEATURE:
<221> NAME/KEY: MISC_FEATURE
<222> LOCATION: (14)..(14)
<223> OTHER INFORMATION: wherein Xaa=Tyr or Leu, preferably Tyr

<400> SEQUENCE: 136

Ala Arg Gly Xaa Xaa Xaa Ser Gly Xaa Tyr Tyr Phe Asp Xaa
1 5 10

<210> SEQ ID NO 137
<211> LENGTH: 8
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: wherein Xaa=Gly or Asp, preferably Gly

<400> SEQUENCE: 137

Gly Gly Ser Phe Ser Xaa Tyr Tyr
1 5

<210> SEQ ID NO 138
<211> LENGTH: 7
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: wherein Xaa=Tyr, Asn or His, preferably Tyr
<220> FEATURE:
<221> NAME/KEY: MISC_FEATURE
<222> LOCATION: (6)..(6)
<223> OTHER INFORMATION: wherein Xaa=Asp or Ser, preferably Asp

<400> SEQUENCE: 138

Ile Xaa His Ser Gly Xaa Thr
1 5

<210> SEQ ID NO 139
<211> LENGTH: 14
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: wherein Xaa=Tyr, Phe or Trp, preferably Tyr
<220> FEATURE:
<221> NAME/KEY: MISC_FEATURE
<222> LOCATION: (5)..(5)
<223> OTHER INFORMATION: wherein Xaa=Phe or Tyr, preferably Phe
<220> FEATURE:
<221> NAME/KEY: MISC_FEATURE
<222> LOCATION: (9)..(9)
<223> OTHER INFORMATION: wherein Xaa=Ile, Thr or Ser, preferably Ile
<220> FEATURE:
<221> NAME/KEY: MISC_FEATURE
<222> LOCATION: (12)..(12)
<223> OTHER INFORMATION: wherein Xaa=Leu or Phe, preferably Leu

<400> SEQUENCE: 139

Ala Arg Leu Xaa Xaa Gly Ser Gly Xaa Tyr Tyr Xaa Asp Tyr
1 5 10

<210> SEQ ID NO 140
<211> LENGTH: 8
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: wherein Xaa=Thr or Phe, preferably Thr
<220> FEATURE:

<221> NAME/KEY: MISC_FEATURE
<222> LOCATION: (7)..(7)
<223> OTHER INFORMATION: wherein Xaa=Phe or Tyr, preferably Phe

<400> SEQUENCE: 140

Gly Phe Thr Phe Ser Xaa Xaa Ala
1 5

<210> SEQ ID NO 141
<211> LENGTH: 8
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: wherein Xaa=Gly or Ser, preferably Gly
<220> FEATURE:
<221> NAME/KEY: MISC_FEATURE
<222> LOCATION: (7)..(7)
<223> OTHER INFORMATION: wherein Xaa=His or Asn, preferably His

<400> SEQUENCE: 141

Ile Ser Tyr Asp Gly Xaa Xaa Lys
1 5

<210> SEQ ID NO 142
<211> LENGTH: 12
<212> TYPE: PRT
<213> ORGANISM: homo sapiens
<220> FEATURE:
<221> NAME/KEY: MISC_FEATURE
<222> LOCATION: (9)..(9)
<223> OTHER INFORMATION: wherein Xaa=Ala or Tyr, preferably Ala

<400> SEQUENCE: 142

Ala Arg Gly Leu Gly Val Trp Gly Xaa Phe Asp Tyr
1 5 10

<210> SEQ ID NO 143
<211> LENGTH: 8
<212> TYPE: PRT
<213> ORGANISM: homo sapiens
<220> FEATURE:
<221> NAME/KEY: MISC_FEATURE
<222> LOCATION: (5)..(5)
<223> OTHER INFORMATION: wherein Xaa=Ser, Asn or Thr, preferably Ser
<220> FEATURE:
<221> NAME/KEY: MISC_FEATURE
<222> LOCATION: (6)..(6)
<223> OTHER INFORMATION: wherein Xaa=Asn, Asp or Ser, preferably Asn
<220> FEATURE:
<221> NAME/KEY: MISC_FEATURE
<222> LOCATION: (8)..(8)
<223> OTHER INFORMATION: wherein Xaa=Gly or Ala, preferably Gly

<400> SEQUENCE: 143

Gly Phe Thr Phe Xaa Xaa Tyr Xaa
1 5

<210> SEQ ID NO 144
<211> LENGTH: 8
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: wherein Xaa=Ser or Thr, preferably Ser
<220> FEATURE:
<221> NAME/KEY: MISC_FEATURE
<222> LOCATION: (5)..(5)
<223> OTHER INFORMATION: wherein Xaa=Ala or Gly, preferably Ala

```
<220> FEATURE:
<221> NAME/KEY: MISC_FEATURE
<222> LOCATION: (6)..(6)
<223> OTHER INFORMATION: wherein Xaa=Tyr or Gly, preferably Tyr
<220> FEATURE:
<221> NAME/KEY: MISC_FEATURE
<222> LOCATION: (7)..(7)
<223> OTHER INFORMATION: wherein Xaa=Ser or Ala, preferably Ser

<400> SEQUENCE: 144

Ile Ser Gly Xaa Xaa Xaa Xaa Thr
1               5


<210> SEQ ID NO 145
<211> LENGTH: 17
<212> TYPE: PRT
<213> ORGANISM: homo sapiens
<220> FEATURE:
<221> NAME/KEY: MISC_FEATURE
<222> LOCATION: (3)..(3)
<223> OTHER INFORMATION: wherein Xaa=Ala or Gly, preferably Ala
<220> FEATURE:
<221> NAME/KEY: MISC_FEATURE
<222> LOCATION: (4)..(4)
<223> OTHER INFORMATION: wherein Xaa=His or Tyr, preferably His
<220> FEATURE:
<221> NAME/KEY: MISC_FEATURE
<222> LOCATION: (5)..(5)
<223> OTHER INFORMATION: wherein Xaa=Tyr or Thr, preferably Tyr
<220> FEATURE:
<221> NAME/KEY: MISC_FEATURE
<222> LOCATION: (6)..(6)
<223> OTHER INFORMATION: wherein Xaa=His, Phe or Leu, preferably His
<220> FEATURE:
<221> NAME/KEY: MISC_FEATURE
<222> LOCATION: (14)..(14)
<223> OTHER INFORMATION: wherein Xaa=Leu or Ser, preferably Leu

<400> SEQUENCE: 145

Ala Lys Xaa Xaa Xaa Xaa Gly Ser Gly Ser Tyr Tyr Thr Xaa Phe Asp
1               5                   10                  15

Tyr


<210> SEQ ID NO 146
<211> LENGTH: 8
<212> TYPE: PRT
<213> ORGANISM: homo sapiens
<220> FEATURE:
<221> NAME/KEY: MISC_FEATURE
<222> LOCATION: (5)..(5)
<223> OTHER INFORMATION: wherein Xaa=Ser or Thr, preferably Ser
<220> FEATURE:
<221> NAME/KEY: MISC_FEATURE
<222> LOCATION: (6)..(6)
<223> OTHER INFORMATION: wherein Xaa=Ile or Ser, preferably Ile

<400> SEQUENCE: 146

Gly Tyr Ser Phe Xaa Xaa Tyr Trp
1               5


<210> SEQ ID NO 147
<211> LENGTH: 8
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: wherein Xaa=Phe or Tyr, preferably Phe
<220> FEATURE:
<221> NAME/KEY: MISC_FEATURE
<222> LOCATION: (8)..(8)
<223> OTHER INFORMATION: wherein Xaa=Ile or Thr, preferably Ile
```

<400> SEQUENCE: 147

Ile Xaa Pro Gly Asp Ser Asp Xaa
1 5

<210> SEQ ID NO 148
<211> LENGTH: 16
<212> TYPE: PRT
<213> ORGANISM: homo sapiens

<400> SEQUENCE: 148

Ala Arg Gln Pro Gly Asp Trp Ser Pro Arg His Trp Tyr Phe Asp Leu
1 5 10 15

<210> SEQ ID NO 149
<211> LENGTH: 8
<212> TYPE: PRT
<213> ORGANISM: homo sapiens
<220> FEATURE:
<221> NAME/KEY: MISC_FEATURE
<222> LOCATION: (3)..(3)
<223> OTHER INFORMATION: wherein Xaa=Asn or Ser, preferably Asn

<400> SEQUENCE: 149

Gly Tyr Xaa Phe Thr Ser Tyr Trp
1 5

<210> SEQ ID NO 150
<211> LENGTH: 8
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: wherein Xaa=Ser or Thr, preferably Ser

<400> SEQUENCE: 150

Ile Ser Ala Tyr Asn Gly Asn Xaa
1 5

<210> SEQ ID NO 151
<211> LENGTH: 18
<212> TYPE: PRT
<213> ORGANISM: homo sapiens

<400> SEQUENCE: 151

Ala Arg Glu Tyr Ser Tyr Asp Ser Gly Thr Tyr Phe Tyr Tyr Gly Met
1 5 10 15

Asp Val

<210> SEQ ID NO 152
<211> LENGTH: 8
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: wherein Xaa=Asp or Ser, preferably Asp
<220> FEATURE:
<221> NAME/KEY: MISC_FEATURE
<222> LOCATION: (7)..(7)
<223> OTHER INFORMATION: wherein Xaa=Tyr or His, preferably Tyr
<220> FEATURE:
<221> NAME/KEY: MISC_FEATURE
<222> LOCATION: (8)..(8)
<223> OTHER INFORMATION: wherein Xaa=Val or Ala, preferably Val

<400> SEQUENCE: 152

Gly Phe Thr Phe Ser Xaa Xaa Xaa
1 5

<210> SEQ ID NO 153
<211> LENGTH: 8
<212> TYPE: PRT
<213> ORGANISM: homo sapiens
<220> FEATURE:
<221> NAME/KEY: MISC_FEATURE
<222> LOCATION: (7)..(7)
<223> OTHER INFORMATION: wherein Xaa=Asn or Tyr, preferably Asn
<220> FEATURE:
<221> NAME/KEY: MISC_FEATURE
<222> LOCATION: (8)..(8)
<223> OTHER INFORMATION: wherein Xaa=Lys or Glu, preferably Lys

<400> SEQUENCE: 153

Ile Ser Tyr Asp Gly Ser Xaa Xaa
1 5

<210> SEQ ID NO 154
<211> LENGTH: 14
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: wherein Xaa=Gly, Asp or Ser, preferably Gly
<220> FEATURE:
<221> NAME/KEY: MISC_FEATURE
<222> LOCATION: (5)..(5)
<223> OTHER INFORMATION: wherein Xaa=Ile or Tyr, preferably Ile
<220> FEATURE:
<221> NAME/KEY: MISC_FEATURE
<222> LOCATION: (6)..(6)
<223> OTHER INFORMATION: wherein Xaa=Thr or Ile, preferably Thr
<220> FEATURE:
<221> NAME/KEY: MISC_FEATURE
<222> LOCATION: (7)..(7)
<223> OTHER INFORMATION: wherein Xaa=Gly or Ser, preferably Gly
<220> FEATURE:
<221> NAME/KEY: MISC_FEATURE
<222> LOCATION: (8)..(8)
<223> OTHER INFORMATION: wherein Xaa=Thr or Ser, preferably Thr
<220> FEATURE:
<221> NAME/KEY: MISC_FEATURE
<222> LOCATION: (9)..(9)
<223> OTHER INFORMATION: wherein Xaa=Thr or Ser, preferably Thr
<220> FEATURE:
<221> NAME/KEY: MISC_FEATURE
<222> LOCATION: (11)..(11)
<223> OTHER INFORMATION: wherein Xaa=Tyr or Val, preferably Val

<400> SEQUENCE: 154

Ala Arg Gly Xaa Xaa Xaa Xaa Xaa Xaa Gly Xaa Phe Asp Tyr
1 5 10

<210> SEQ ID NO 155
<211> LENGTH: 9
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: wherein Xaa=Ile or Leu

<400> SEQUENCE: 155

Gln Gln Ala Asn Ser Phe Pro Xaa Thr
1 5

<210> SEQ ID NO 156

<211> LENGTH: 9
<212> TYPE: PRT
<213> ORGANISM: homo sapiens
<220> FEATURE:
<221> NAME/KEY: MISC_FEATURE
<222> LOCATION: (5)..(5)
<223> OTHER INFORMATION: wherein Xaa=Asn or His, preferably Asn

<400> SEQUENCE: 156

Gln Gln Arg Ser Xaa Trp Pro Arg Thr
1 5

<210> SEQ ID NO 157
<211> LENGTH: 6
<212> TYPE: PRT
<213> ORGANISM: homo sapiens
<220> FEATURE:
<221> NAME/KEY: MISC_FEATURE
<222> LOCATION: (5)..(5)
<223> OTHER INFORMATION: wherein Xaa=Arg or Ser, preferably Arg

<400> SEQUENCE: 157

Gln Gly Ile Ser Xaa Trp
1 5

<210> SEQ ID NO 158
<211> LENGTH: 9
<212> TYPE: PRT
<213> ORGANISM: homo sapiens

<400> SEQUENCE: 158

Gln Gln Tyr Asn Ser Phe Pro Pro Thr
1 5

<210> SEQ ID NO 159
<211> LENGTH: 6
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: wherein Xaa=Ser or Asn, preferably Ser

<400> SEQUENCE: 159

Gln Gly Ile Xaa Ser Trp
1 5

<210> SEQ ID NO 160
<211> LENGTH: 9
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: wherein Xaa=Tyr or Leu, preferably Tyr

<400> SEQUENCE: 160

Gln Gln Tyr Asn Ser Tyr Pro Xaa Thr
1 5

<210> SEQ ID NO 161
<211> LENGTH: 6
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: wherein Xaa=Ser or Asn, preferably Ser
<220> FEATURE:

<221> NAME/KEY: MISC_FEATURE
<222> LOCATION: (5)..(5)
<223> OTHER INFORMATION: wherein Xaa=Ser or Asn, preferably Ser

<400> SEQUENCE: 161

Gln Gly Ile Xaa Xaa Trp
1 5

<210> SEQ ID NO 162
<211> LENGTH: 9
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: wherein Xaa=Lys or Asn, preferably Lys

<400> SEQUENCE: 162

Gln Gln Tyr Xaa Ser Tyr Pro Ile Thr
1 5

<210> SEQ ID NO 163
<211> LENGTH: 7
<212> TYPE: PRT
<213> ORGANISM: homo sapiens

<400> SEQUENCE: 163

Ile Tyr His Ser Gly Asp Thr
1 5

<210> SEQ ID NO 164
<211> LENGTH: 9
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: wherein Xaa=Tyr or Phe, preferably Tyr

<400> SEQUENCE: 164

Gln Gln Tyr Asn Ser Xaa Pro Ile Thr
1 5

<210> SEQ ID NO 165
<211> LENGTH: 122
<212> TYPE: PRT
<213> ORGANISM: homo sapiens

<400> SEQUENCE: 165

Glu Val Gln Leu Val Gln Ser Gly Ala Glu Val Lys Lys Pro Gly Glu
1 5 10 15

Ser Leu Lys Ile Ser Cys Lys Ala Ser Gly Tyr Ser Phe His Phe Tyr
20 25 30

Trp Ile Gly Trp Val Arg Gln Met Pro Gly Lys Gly Leu Glu Trp Met
35 40 45

Gly Ser Ile Tyr Pro Gly Asp Ser Asp Thr Arg Tyr Arg Pro Ser Phe
50 55 60

Gln Gly Gln Val Thr Ile Ser Ala Asp Lys Ser Ile Ser Thr Ala Tyr
65 70 75 80

Leu Gln Trp Thr Ser Leu Lys Ala Ser Asp Thr Ala Ile Tyr Tyr Cys
85 90 95

Ala Arg Gln Arg Gly Asp Tyr Tyr Tyr Phe Tyr Gly Met Asp Val Trp
100 105 110

-continued

```
Gly Gln Gly Thr Thr Val Thr Val Ser Ser
        115                 120


<210> SEQ ID NO 166
<211> LENGTH: 8
<212> TYPE: PRT
<213> ORGANISM: homo sapiens

<400> SEQUENCE: 166

Gly Tyr Ser Phe His Phe Tyr Trp
1               5


<210> SEQ ID NO 167
<211> LENGTH: 8
<212> TYPE: PRT
<213> ORGANISM: homo sapiens

<400> SEQUENCE: 167

Ile Tyr Pro Gly Asp Ser Asp Thr
1               5


<210> SEQ ID NO 168
<211> LENGTH: 15
<212> TYPE: PRT
<213> ORGANISM: homo sapiens

<400> SEQUENCE: 168

Ala Arg Gln Arg Gly Asp Tyr Tyr Tyr Phe Tyr Gly Met Asp Val
1               5                   10                  15


<210> SEQ ID NO 169
<211> LENGTH: 107
<212> TYPE: PRT
<213> ORGANISM: homo sapiens

<400> SEQUENCE: 169

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Val Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105


<210> SEQ ID NO 170
<211> LENGTH: 7
<212> TYPE: PRT
<213> ORGANISM: homo sapiens

<400> SEQUENCE: 170

Gln Ser Val Ser Ser Ser Tyr
1               5


<210> SEQ ID NO 171
<211> LENGTH: 8
```

```
<212> TYPE: PRT
<213> ORGANISM: homo sapiens

<400> SEQUENCE: 171

Gln Gln Tyr Gly Ser Ser Leu Thr
1               5


<210> SEQ ID NO 172
<211> LENGTH: 119
<212> TYPE: PRT
<213> ORGANISM: homo sapiens

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Leu Ile Trp Val Arg Gln Ala Pro Gly Lys Gly Leu Glu Trp Val
        35                  40                  45

Ser Ile Ile Arg Gly Gly Ala Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Arg Ile Trp Gly Pro Leu Phe Asp Tyr Trp Gly Gln Gly
            100                 105                 110

Thr Leu Val Thr Val Ser Ser
        115


<210> SEQ ID NO 173
<211> LENGTH: 8
<212> TYPE: PRT
<213> ORGANISM: homo sapiens

<400> SEQUENCE: 173

Gly Phe Thr Phe Ser Asn Tyr Ala
1               5


<210> SEQ ID NO 174
<211> LENGTH: 8
<212> TYPE: PRT
<213> ORGANISM: homo sapiens

<400> SEQUENCE: 174

Ile Arg Gly Gly Ala Gly Ser Thr
1               5


<210> SEQ ID NO 175
<211> LENGTH: 12
<212> TYPE: PRT
<213> ORGANISM: homo sapiens

<400> SEQUENCE: 175

Ala Lys Ala Arg Ile Trp Gly Pro Leu Phe Asp Tyr
1               5                   10


<210> SEQ ID NO 176
<211> LENGTH: 108
<212> TYPE: PRT
<213> ORGANISM: homo sapiens
```

<400> SEQUENCE: 176

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Pro
85 90 95

Leu Thr Phe Gly Gly Gly Thr Lys Val Glu Ile Lys
100 105

<210> SEQ ID NO 177
<211> LENGTH: 6
<212> TYPE: PRT
<213> ORGANISM: homo sapiens

<400> SEQUENCE: 177

Gln Ser Val Ser Ser Tyr
1 5

<210> SEQ ID NO 178
<211> LENGTH: 10
<212> TYPE: PRT
<213> ORGANISM: homo sapiens

<400> SEQUENCE: 178

Gln Gln Arg Ser Asn Trp Pro Pro Leu Thr
1 5 10

<210> SEQ ID NO 179
<211> LENGTH: 122
<212> TYPE: PRT
<213> ORGANISM: homo sapiens

<400> SEQUENCE: 179

Gln Val Gln Leu Val Gln Ser Gly Ala Glu Val Lys Lys Pro Gly Ala
1 5 10 15

Ser Val Arg Val Pro Cys Lys Ala Ser Gly Tyr Thr Phe Thr Arg Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Lys Thr Tyr Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Ser Pro Leu Leu Trp Phe Glu Glu Leu Tyr Phe Asp Tyr Trp
100 105 110

Gly Gln Gly Thr Leu Val Thr Val Ser Ser
115 120

<210> SEQ ID NO 180

<211> LENGTH: 8
<212> TYPE: PRT
<213> ORGANISM: homo sapiens

<400> SEQUENCE: 180

Gly Tyr Thr Phe Thr Arg Tyr Gly
1               5

<210> SEQ ID NO 181
<211> LENGTH: 8
<212> TYPE: PRT
<213> ORGANISM: homo sapiens

<400> SEQUENCE: 181

Ile Ser Ala Tyr Asn Gly Lys Thr
1               5

<210> SEQ ID NO 182
<211> LENGTH: 15
<212> TYPE: PRT
<213> ORGANISM: homo sapiens

<400> SEQUENCE: 182

Ala Arg Ser Pro Leu Leu Trp Phe Glu Glu Leu Tyr Phe Asp Tyr
1               5                   10                  15

<210> SEQ ID NO 183
<211> LENGTH: 108
<212> TYPE: PRT
<213> ORGANISM: homo sapiens

<400> SEQUENCE: 183

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Leu
                85                  90                  95

Phe Thr Phe Gly Pro Gly Thr Lys Val Asp Ile Lys
            100                 105

<210> SEQ ID NO 184
<211> LENGTH: 7
<212> TYPE: PRT
<213> ORGANISM: homo sapiens

<400> SEQUENCE: 184

Gln Ser Val Ser Ser Thr Tyr
1               5

<210> SEQ ID NO 185
<211> LENGTH: 9
<212> TYPE: PRT
<213> ORGANISM: homo sapiens

<400> SEQUENCE: 185

Gln Gln Tyr Gly Thr Ser Leu Phe Thr
1 5

<210> SEQ ID NO 186
<211> LENGTH: 122
<212> TYPE: PRT
<213> ORGANISM: homo sapiens

<400> SEQUENCE: 186

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Arg Phe Thr Ser Tyr
20 25 30

Trp Ile Gly Trp Val Arg Gln Met Pro Gly Lys Gly Leu Glu Trp Met
35 40 45

Gly Ser Ile Tyr Pro Gly Asp Ser Tyr Thr Arg Asn Ser Pro Ser Phe
50 55 60

Gln Gly Gln Val Thr Ile Ser Ala Asp Lys Ser Ile Ala Thr Ala Tyr
65 70 75 80

Leu Gln Trp Asn Ser Leu Lys Ala Ser Asp Thr Ala Met Tyr Tyr Cys
85 90 95

Ala Arg His Ala Gly Asp Phe Tyr Tyr Phe Asp Gly Leu Asp Val Trp
100 105 110

Gly Gln Gly Thr Thr Val Thr Val Ser Ser
115 120

<210> SEQ ID NO 187
<211> LENGTH: 9
<212> TYPE: PRT
<213> ORGANISM: homo sapiens

<400> SEQUENCE: 187

Gly Tyr Arg Phe Thr Thr Ser Tyr Trp
1 5

<210> SEQ ID NO 188
<211> LENGTH: 8
<212> TYPE: PRT
<213> ORGANISM: homo sapiens

<400> SEQUENCE: 188

Ile Tyr Pro Gly Asp Ser Tyr Thr
1 5

<210> SEQ ID NO 189
<211> LENGTH: 15
<212> TYPE: PRT
<213> ORGANISM: homo sapiens

<400> SEQUENCE: 189

Ala Arg His Ala Gly Asp Phe Tyr Tyr Phe Asp Gly Leu Asp Val
1 5 10 15

<210> SEQ ID NO 190
<211> LENGTH: 109
<212> TYPE: PRT
<213> ORGANISM: homo sapiens

<400> SEQUENCE: 190

Glu Ile Val Leu Thr Gln Ser Pro Gly Thr Leu Ser Leu Ser Pro Gly
1 5 10 15

```
Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Ile Thr Phe Gly Gln Gly Thr Arg Leu Glu Ile Lys
            100                 105


<210> SEQ ID NO 191
<211> LENGTH: 7
<212> TYPE: PRT
<213> ORGANISM: homo sapiens

<400> SEQUENCE: 191

Gln Ser Val Ser Ser Ser Tyr
1               5


<210> SEQ ID NO 192
<211> LENGTH: 10
<212> TYPE: PRT
<213> ORGANISM: homo sapiens

<400> SEQUENCE: 192

Gln Gln Tyr Gly Ser Ser Pro Pro Ile Thr
1               5                   10


<210> SEQ ID NO 193
<211> LENGTH: 124
<212> TYPE: PRT
<213> ORGANISM: homo sapiens

<400> SEQUENCE: 193

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Arg Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Thr Gly Asp Arg Gly Phe Asp Tyr Tyr Ser Gly Met Asp
            100                 105                 110

Val Trp Gly Gln Gly Thr Thr Val Thr Val Ser Ser
        115                 120


<210> SEQ ID NO 194
<211> LENGTH: 8
<212> TYPE: PRT
<213> ORGANISM: homo sapiens

<400> SEQUENCE: 194
```

Gly Tyr Ser Phe Thr Arg Tyr Trp
1 5

<210> SEQ ID NO 195
<211> LENGTH: 8
<212> TYPE: PRT
<213> ORGANISM: homo sapiens

<400> SEQUENCE: 195

Ile Tyr Pro Gly Asp Ser Asp Thr
1 5

<210> SEQ ID NO 196
<211> LENGTH: 17
<212> TYPE: PRT
<213> ORGANISM: homo sapiens

<400> SEQUENCE: 196

Ala Arg Leu Thr Gly Asp Arg Gly Phe Asp Tyr Tyr Ser Gly Met Asp
1 5 10 15

Val

<210> SEQ ID NO 197
<211> LENGTH: 107
<212> TYPE: PRT
<213> ORGANISM: homo sapiens

<400> SEQUENCE: 197

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Phe
85 90 95

Thr Phe Gly Pro Gly Thr Lys Val Asp Ile Lys
100 105

<210> SEQ ID NO 198
<211> LENGTH: 7
<212> TYPE: PRT
<213> ORGANISM: homo sapiens

<400> SEQUENCE: 198

Gln Ser Val Ser Ser Ser Tyr
1 5

<210> SEQ ID NO 199
<211> LENGTH: 8
<212> TYPE: PRT
<213> ORGANISM: homo sapiens

<400> SEQUENCE: 199

Gln Gln Tyr Gly Ser Ser Phe Thr
1 5

<210> SEQ ID NO 200
<211> LENGTH: 119
<212> TYPE: PRT
<213> ORGANISM: homo sapiens

<400> SEQUENCE: 200

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Gly Ile Ser Trp Val Arg Gln Ala Pro Gly Pro Gly Leu Glu Trp Met
35 40 45

Gly Arg Ile Ile Pro Ile Leu Gly Ile Ala Asn Tyr Ala Gln Lys Phe
50 55 60

Gln Gly Arg Val Thr Ile Thr Ala Asp Lys Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Asp Gln Glu Tyr Ser Ser Asn Trp Tyr Tyr Trp Gly Gln Gly
100 105 110

Thr Leu Val Thr Val Ser Ser
115

<210> SEQ ID NO 201
<211> LENGTH: 8
<212> TYPE: PRT
<213> ORGANISM: homo sapiens

<400> SEQUENCE: 201

Gly Gly Thr Phe Ser Ser Tyr Gly
1 5

<210> SEQ ID NO 202
<211> LENGTH: 8
<212> TYPE: PRT
<213> ORGANISM: homo sapiens

<400> SEQUENCE: 202

Ile Ile Pro Ile Leu Gly Ile Ala
1 5

<210> SEQ ID NO 203
<211> LENGTH: 12
<212> TYPE: PRT
<213> ORGANISM: homo sapiens

<400> SEQUENCE: 203

Ala Arg Asp Gln Glu Tyr Ser Ser Asn Trp Tyr Tyr
1 5 10

<210> SEQ ID NO 204
<211> LENGTH: 107
<212> TYPE: PRT
<213> ORGANISM: homo sapiens

<400> SEQUENCE: 204

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Arg Ser Ser
20 25 30

```
Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Leu Tyr Gly Ser Ser Pro
                85                  90                  95

Thr Phe Gly Pro Gly Thr Lys Val Asp Ile Lys
            100                 105


<210> SEQ ID NO 205
<211> LENGTH: 7
<212> TYPE: PRT
<213> ORGANISM: homo sapiens

<400> SEQUENCE: 205

Gln Ser Val Arg Ser Ser Tyr
1               5


<210> SEQ ID NO 206
<211> LENGTH: 8
<212> TYPE: PRT
<213> ORGANISM: homo sapiens

<400> SEQUENCE: 206

Gln Leu Tyr Gly Ser Ser Pro Thr
1               5


<210> SEQ ID NO 207
<211> LENGTH: 122
<212> TYPE: PRT
<213> ORGANISM: homo sapiens

<400> SEQUENCE: 207

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ser Ile Tyr Pro Gly Asp Ser His Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Lys Gly Asp Phe Tyr Tyr Phe Phe Gly Leu Asp Val Trp
            100                 105                 110

Gly Gln Gly Thr Ala Ile Thr Val Ser Ser
        115                 120


<210> SEQ ID NO 208
<211> LENGTH: 107
<212> TYPE: PRT
<213> ORGANISM: homo sapiens

<400> SEQUENCE: 208

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105


<210> SEQ ID NO 209
<211> LENGTH: 122
<212> TYPE: PRT
<213> ORGANISM: homo sapiens

<400> SEQUENCE: 209

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ser Ile Tyr Pro Gly Asp Ser His Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Ala Gly Asp Tyr Tyr Tyr Tyr Asn Gly Met Asp Val Trp
            100                 105                 110

Gly Gln Gly Thr Thr Val Thr Val Ser Ser
        115                 120


<210> SEQ ID NO 210
<211> LENGTH: 107
<212> TYPE: PRT
<213> ORGANISM: homo sapiens

<400> SEQUENCE: 210

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Thr Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105
```

<210> SEQ ID NO 211
<211> LENGTH: 122
<212> TYPE: PRT
<213> ORGANISM: homo sapiens

<400> SEQUENCE: 211

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Lys Gly Asp Tyr Tyr Tyr His Tyr Gly Leu Asp Val Trp
            100                 105                 110

Gly Gln Gly Thr Thr Val Thr Val Ser Ser
        115                 120
```

<210> SEQ ID NO 212
<211> LENGTH: 109
<212> TYPE: PRT
<213> ORGANISM: homo sapiens

<400> SEQUENCE: 212

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Leu Thr Phe Gly Gly Gly Thr Lys Val Glu Ile Lys
            100                 105
```

<210> SEQ ID NO 213
<211> LENGTH: 122
<212> TYPE: PRT
<213> ORGANISM: homo sapiens

<400> SEQUENCE: 213

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45
```

```
Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Lys Gly Asp Tyr Tyr Tyr Phe Asn Gly Leu Asp Val Trp
            100                 105                 110

Gly Gln Gly Thr Thr Val Thr Val Ser Ser
        115                 120


<210> SEQ ID NO 214
<211> LENGTH: 109
<212> TYPE: PRT
<213> ORGANISM: homo sapiens

<400> SEQUENCE: 214

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Leu Thr Phe Gly Gly Gly Thr Lys Val Glu Ile Lys
            100                 105


<210> SEQ ID NO 215
<211> LENGTH: 122
<212> TYPE: PRT
<213> ORGANISM: homo sapiens

<400> SEQUENCE: 215

Glu Val Gln Leu Val Gln Ser Gly Ala Glu Val Lys Lys Pro Gly Glu
1               5                   10                  15

Ser Leu Lys Ile Ser Cys Gln Gly Ser Gly Tyr Arg Phe Ile Ser Tyr
            20                  25                  30

Trp Ile Gly Trp Val Arg Gln Met Pro Gly Lys Gly Leu Glu Trp Met
        35                  40                  45

Gly Arg Ile Tyr Pro Gly Asp Ser Asp Thr Arg Tyr Ser Pro Ser Phe
    50                  55                  60

Gln Gly Gln Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Arg Gly Asp Tyr Tyr Tyr Phe Asn Gly Leu Asp Val Trp
            100                 105                 110

Gly Gln Gly Thr Thr Val Thr Val Ser Ser
        115                 120


<210> SEQ ID NO 216
<211> LENGTH: 107
```

<212> TYPE: PRT
<213> ORGANISM: homo sapiens

<400> SEQUENCE: 216

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Leu
85 90 95

Thr Phe Gly Gly Gly Thr Lys Val Glu Ile Lys
100 105

<210> SEQ ID NO 217
<211> LENGTH: 122
<212> TYPE: PRT
<213> ORGANISM: homo sapiens

<400> SEQUENCE: 217

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

Trp Ile Gly Trp Val Arg Gln Met Pro Gly Lys Gly Leu Glu Trp Met
35 40 45

Gly Arg Ile Tyr Pro Gly Asp Ser Asp Thr Arg Tyr Ser Pro Ser Phe
50 55 60

Gln Gly Gln Val Thr Ile Ser Ala Asp Lys Ser Ile Thr Thr Ala Tyr
65 70 75 80

Leu Gln Trp Ser Ser Leu Arg Ala Ser Asp Thr Ala Met Tyr Tyr Cys
85 90 95

Ala Arg Gln Arg Gly Asp Tyr Tyr Tyr Phe Phe Gly Leu Asp Ile Trp
100 105 110

Gly Gln Gly Thr Thr Val Thr Val Ser Leu
115 120

<210> SEQ ID NO 218
<211> LENGTH: 107
<212> TYPE: PRT
<213> ORGANISM: homo sapiens

<400> SEQUENCE: 218

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu

```
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105


<210> SEQ ID NO 219
<211> LENGTH: 122
<212> TYPE: PRT
<213> ORGANISM: homo sapiens

<400> SEQUENCE: 219

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Ser Ser Tyr
            20                  25                  30

Trp Ile Gly Trp Val Arg Gln Met Pro Gly Lys Gly Leu Glu Trp Met
        35                  40                  45

Gly Ser Ile Phe Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Ala Gly Asp Tyr Tyr Tyr Tyr Asn Gly Met Asp Val Trp
            100                 105                 110

Gly Gln Gly Thr Thr Val Thr Val Ser Ser
        115                 120


<210> SEQ ID NO 220
<211> LENGTH: 107
<212> TYPE: PRT
<213> ORGANISM: homo sapiens

<400> SEQUENCE: 220

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105


<210> SEQ ID NO 221
<211> LENGTH: 8
<212> TYPE: PRT
<213> ORGANISM: homo sapiens
<220> FEATURE:
<221> NAME/KEY: MISC_FEATURE
<222> LOCATION: (3)..(3)
<223> OTHER INFORMATION: wherein Xaa=Ser or Arg
<220> FEATURE:
```

```
<221> NAME/KEY: MISC_FEATURE
<222> LOCATION: (5)..(5)
<223> OTHER INFORMATION: wherein Xaa=Ser, Thr, His or Ile, preferably
      His or Thr
<220> FEATURE:
<221> NAME/KEY: MISC_FEATURE
<222> LOCATION: (6)..(6)
<223> OTHER INFORMATION: wherein Xaa=Ser, Arg or Phe

<400> SEQUENCE: 221

Gly Tyr Xaa Phe Xaa Xaa Tyr Trp
1               5


<210> SEQ ID NO 222
<211> LENGTH: 8
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: wherein Xaa=Tyr or Phe
<220> FEATURE:
<221> NAME/KEY: MISC_FEATURE
<222> LOCATION: (7)..(7)
<223> OTHER INFORMATION: wherein Xaa=Asp, Tyr or His, preferably Asp or
      Tyr

<400> SEQUENCE: 222

Ile Xaa Pro Gly Asp Ser Xaa Thr
1               5


<210> SEQ ID NO 223
<211> LENGTH: 17
<212> TYPE: PRT
<213> ORGANISM: homo sapiens
<220> FEATURE:
<221> NAME/KEY: MISC_FEATURE
<222> LOCATION: (3)..(3)
<223> OTHER INFORMATION: wherein Xaa=Gln, His or leu, preferably Gln
<220> FEATURE:
<221> NAME/KEY: MISC_FEATURE
<222> LOCATION: (4)..(4)
<223> OTHER INFORMATION: wherein Xaa=Arg, Ala, Thr or Lys, preferably
      Arg or Ala
<220> FEATURE:
<221> NAME/KEY: MISC_FEATURE
<222> LOCATION: (5)..(5)
<223> OTHER INFORMATION: wherein Xaa=Gly
<220> FEATURE:
<221> NAME/KEY: MISC_FEATURE
<222> LOCATION: (6)..(6)
<223> OTHER INFORMATION: wherein Xaa=Asp
<220> FEATURE:
<221> NAME/KEY: MISC_FEATURE
<222> LOCATION: (7)..(7)
<223> OTHER INFORMATION: wherein Xaa=Arg or none, preferably none
<220> FEATURE:
<221> NAME/KEY: MISC_FEATURE
<222> LOCATION: (8)..(8)
<223> OTHER INFORMATION: wherein Xaa=Gly or none, preferably none
<220> FEATURE:
<221> NAME/KEY: MISC_FEATURE
<222> LOCATION: (9)..(9)
<223> OTHER INFORMATION: wherein Xaa=Tyr or Phe
<220> FEATURE:
<221> NAME/KEY: MISC_FEATURE
<222> LOCATION: (10)..(10)
<223> OTHER INFORMATION: wherein Xaa=Tyr or Asp, preferably Tyr
<220> FEATURE:
<221> NAME/KEY: MISC_FEATURE
<222> LOCATION: (12)..(12)
<223> OTHER INFORMATION: wherein Xaa=Tyr, Phe or His, preferably Phe
<220> FEATURE:
<221> NAME/KEY: MISC_FEATURE
<222> LOCATION: (13)..(13)
```

<223> OTHER INFORMATION: wherein Xaa=Tyr, Asp, Ser, Phe or Asn,
      preferably Tyr
<220> FEATURE:
<221> NAME/KEY: MISC_FEATURE
<222> LOCATION: (15)..(15)
<223> OTHER INFORMATION: wherein Xaa=Met or Leu
<220> FEATURE:
<221> NAME/KEY: MISC_FEATURE
<222> LOCATION: (17)..(17)
<223> OTHER INFORMATION: wherein Xaa=Val or Ile, preferably Val

<400> SEQUENCE: 223

```
Ala Arg Xaa Xaa Xaa Xaa Xaa Xaa Xaa Xaa Tyr Xaa Xaa Gly Xaa Asp
1               5                   10                  15

Xaa
```

<210> SEQ ID NO 224
<211> LENGTH: 8
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: wherein Xaa=Asn or Ser, preferably Asn

<400> SEQUENCE: 224

```
Gly Phe Thr Phe Ser Xaa Tyr Ala
1               5
```

<210> SEQ ID NO 225
<211> LENGTH: 8
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: wherein Xaa=Arg or Ser, preferably Arg
<220> FEATURE:
<221> NAME/KEY: MISC_FEATURE
<222> LOCATION: (4)..(4)
<223> OTHER INFORMATION: wherein Xaa=Gly or Ser, preferably Gly
<220> FEATURE:
<221> NAME/KEY: MISC_FEATURE
<222> LOCATION: (5)..(5)
<223> OTHER INFORMATION: wherein Xaa=Ala or Gly, preferably Ala

<400> SEQUENCE: 225

```
Ile Xaa Gly Xaa Xaa Gly Ser Thr
1               5
```

<210> SEQ ID NO 226
<211> LENGTH: 11
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: wherein Xaa=Leu or Tyr, preferably Leu

<400> SEQUENCE: 226

```
Ala Lys Arg Ile Trp Gly Pro Xaa Phe Asp Tyr
1               5                   10
```

<210> SEQ ID NO 227
<211> LENGTH: 8
<212> TYPE: PRT
<213> ORGANISM: homo sapiens
<220> FEATURE:
<221> NAME/KEY: MISC_FEATURE
<222> LOCATION: (6)..(6)

<223> OTHER INFORMATION: wherein Xaa=Arg or Ser, preferably Arg

<400> SEQUENCE: 227

Gly Tyr Thr Phe Thr Xaa Tyr Gly
1 5

<210> SEQ ID NO 228
<211> LENGTH: 8
<212> TYPE: PRT
<213> ORGANISM: homo sapiens
<220> FEATURE:
<221> NAME/KEY: MISC_FEATURE
<222> LOCATION: (7)..(7)
<223> OTHER INFORMATION: wherein Xaa=Lys or Asn, preferably Lys

<400> SEQUENCE: 228

Ile Ser Ala Tyr Asn Gly Xaa Thr
1 5

<210> SEQ ID NO 229
<211> LENGTH: 15
<212> TYPE: PRT
<213> ORGANISM: homo sapiens

<400> SEQUENCE: 229

Ala Arg Ser Pro Leu Leu Trp Phe Glu Glu Leu Tyr Phe Asp Tyr
1 5 10 15

<210> SEQ ID NO 230
<211> LENGTH: 8
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: wherein Xaa=Gly or Ala, preferably Gly

<400> SEQUENCE: 230

Gly Gly Thr Phe Ser Ser Tyr Xaa
1 5

<210> SEQ ID NO 231
<211> LENGTH: 11
<212> TYPE: PRT
<213> ORGANISM: homo sapiens
<220> FEATURE:
<221> NAME/KEY: MISC_FEATURE
<222> LOCATION: (9)..(9)
<223> OTHER INFORMATION: wherein Xaa=Asn or Tyr, preferably Asn
<220> FEATURE:
<221> NAME/KEY: MISC_FEATURE
<222> LOCATION: (10)..(10)
<223> OTHER INFORMATION: wherein Xaa=Trp or Phe, preferably Trp
<220> FEATURE:
<221> NAME/KEY: MISC_FEATURE
<222> LOCATION: (11)..(11)
<223> OTHER INFORMATION: wherein Xaa=Tyr or Asp, preferably Tyr

<400> SEQUENCE: 231

Ala Arg Asp Gln Glu Tyr Ser Ser Xaa Xaa Xaa
1 5 10

<210> SEQ ID NO 232
<211> LENGTH: 7
<212> TYPE: PRT
<213> ORGANISM: homo sapiens
<220> FEATURE:
<221> NAME/KEY: MISC_FEATURE
<222> LOCATION: (4)..(4)

```
<223> OTHER INFORMATION: wherein Xaa=Ser or Arg
<220> FEATURE:
<221> NAME/KEY: MISC_FEATURE
<222> LOCATION: (6)..(6)
<223> OTHER INFORMATION: wherein Xaa=Ser or Thr

<400> SEQUENCE: 232

Gln Ser Val Xaa Ser Xaa Tyr
1               5


<210> SEQ ID NO 233
<211> LENGTH: 10
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: wherein Xaa=Gln or Leu
<220> FEATURE:
<221> NAME/KEY: MISC_FEATURE
<222> LOCATION: (5)..(5)
<223> OTHER INFORMATION: wherein Xaa=Ser or Thr
<220> FEATURE:
<221> NAME/KEY: MISC_FEATURE
<222> LOCATION: (7)..(7)
<223> OTHER INFORMATION: wherein Xaa=Pro or none
<220> FEATURE:
<221> NAME/KEY: MISC_FEATURE
<222> LOCATION: (8)..(8)
<223> OTHER INFORMATION: wherein Xaa=Pro, Leu, Arg or none, preferably
      Pro, Leu or none
<220> FEATURE:
<221> NAME/KEY: MISC_FEATURE
<222> LOCATION: (9)..(9)
<223> OTHER INFORMATION: wherein Xaa=Leu, Phe, Ile or none

<400> SEQUENCE: 233

Gln Xaa Tyr Gly Xaa Ser Xaa Xaa Xaa Thr
1               5                   10


<210> SEQ ID NO 234
<211> LENGTH: 119
<212> TYPE: PRT
<213> ORGANISM: homo sapiens

<400> SEQUENCE: 234

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Pro Met Ala Trp Val Arg Gln Ala Pro Gly Lys Gly Leu Glu Trp Val
        35                  40                  45

Ser Thr Ile Ser Thr Ser Gly Gly Arg Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Gln Tyr Ser Gly Gly Phe Asp Tyr Trp Gly Gln Gly
            100                 105                 110

Thr Leu Val Thr Val Ser Ser
        115


<210> SEQ ID NO 235
<211> LENGTH: 110
<212> TYPE: PRT
```

<213> ORGANISM: homo sapiens

<400> SEQUENCE: 235

Asp Ile Gln Leu Thr Gln Pro Asn Ser Val Ser Thr Ser Leu Gly Ser
1 5 10 15

Thr Val Lys Leu Ser Cys Thr Leu Ser Ser Gly Asn Ile Glu Asn Asn
20 25 30

Tyr Val His Trp Tyr Gln Leu Tyr Glu Gly Arg Ser Pro Thr Thr Met
35 40 45

Ile Tyr Asp Asp Asp Lys Arg Pro Asp Gly Val Pro Asp Arg Phe Ser
50 55 60

Gly Ser Ile Asp Arg Ser Ser Asn Ser Ala Phe Leu Thr Ile His Asn
65 70 75 80

Val Ala Ile Glu Asp Glu Ala Ile Tyr Phe Cys His Ser Tyr Val Ser
85 90 95

Ser Phe Asn Val Phe Gly Gly Gly Thr Lys Leu Thr Val Leu
100 105 110

<210> SEQ ID NO 236
<211> LENGTH: 120
<212> TYPE: PRT
<213> ORGANISM: homo sapiens

<400> SEQUENCE: 236

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ile Ser Tyr
20 25 30

Thr Met His Trp Val Arg Gln Ala Pro Gly Gln Gly Leu Glu Trp Met
35 40 45

Gly Tyr Ile Asn Pro Arg Ser Gly Tyr Thr His Tyr Asn Gln Lys Leu
50 55 60

Lys Asp Lys Ala Thr Leu Thr Ala Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Ala Tyr Tyr Asp Tyr Asp Gly Phe Ala Tyr Trp Gly Gln
100 105 110

Gly Thr Leu Val Thr Val Ser Ser
115 120

<210> SEQ ID NO 237
<211> LENGTH: 106
<212> TYPE: PRT
<213> ORGANISM: homo sapiens

<400> SEQUENCE: 237

Asp Ile Gln Met Thr Gln Ser Pro Ser Ser Leu Ser Ala Ser Val Gly
1 5 10 15

Asp Arg Val Thr Ile Thr Cys Ser Ala Ser Ser Ser Val Ser Tyr Met
20 25 30

Asn Trp Tyr Gln Gln Lys Pro Gly Lys Ala Pro Lys Arg Leu Ile Tyr
35 40 45

Asp Thr Ser Lys Leu Ala Ser Gly Val Pro Ser Arg Phe Ser Gly Ser
50 55 60

Gly Ser Gly Thr Asp Phe Thr Leu Thr Ile Ser Ser Leu Gln Pro Glu
65 70 75 80

```
Asp Phe Ala Thr Tyr Tyr Cys Gln Gln Trp Ser Ser Asn Pro Pro Thr
                85                  90                  95

Phe Gly Gly Gly Thr Lys Val Glu Ile Lys
            100                 105


<210> SEQ ID NO 238
<211> LENGTH: 119
<212> TYPE: PRT
<213> ORGANISM: homo sapiens

<400> SEQUENCE: 238

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser
        115


<210> SEQ ID NO 239
<211> LENGTH: 106
<212> TYPE: PRT
<213> ORGANISM: homo sapiens

<400> SEQUENCE: 239

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr
            100                 105


<210> SEQ ID NO 240
<211> LENGTH: 119
<212> TYPE: PRT
<213> ORGANISM: homo sapiens

<400> SEQUENCE: 240

Glu Val Gln Leu Val Glu Ser Gly Gly Gly Leu Val Lys Pro Gly Gly
1               5                   10                  15
```

-continued

```
Ser Leu Arg Leu Ser Cys Ala Ala Ser Gly Phe Thr Phe Ser Ser Tyr
            20                  25                  30

Gly Met Phe Trp Val Arg Gln Ala Pro Gly Lys Gly Leu Glu Trp Val
        35                  40                  45

Ala Thr Ile Ser Arg Tyr Ser Arg Tyr Ile Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Leu Tyr Gly Ser Ser Pro Asp Tyr Trp Gly Gln Gly
            100                 105                 110

Thr Leu Val Thr Val Ser Ser
        115


<210> SEQ ID NO 241
<211> LENGTH: 106
<212> TYPE: PRT
<213> ORGANISM: homo sapiens

<400> SEQUENCE: 241

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Thr Tyr Val
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Gly Tyr Pro Leu Thr
                85                  90                  95

Phe Gly Ser Gly Thr Lys Leu Glu Met Arg
            100                 105


<210> SEQ ID NO 242
<211> LENGTH: 8
<212> TYPE: PRT
<213> ORGANISM: homo sapiens

<400> SEQUENCE: 242

Gly Phe Thr Phe Ser Ser Tyr Gly
1               5


<210> SEQ ID NO 243
<211> LENGTH: 8
<212> TYPE: PRT
<213> ORGANISM: homo sapiens

<400> SEQUENCE: 243

Ile Ser Arg Tyr Ser Arg Tyr Ile
1               5


<210> SEQ ID NO 244
<211> LENGTH: 12
<212> TYPE: PRT
<213> ORGANISM: homo sapiens

<400> SEQUENCE: 244
```

```
Ala Arg Arg Pro Leu Tyr Gly Ser Ser Pro Asp Tyr
1               5                   10


<210> SEQ ID NO 245
<211> LENGTH: 5
<212> TYPE: PRT
<213> ORGANISM: homo sapiens

<400> SEQUENCE: 245

Ser Ser Val Thr Tyr
1               5


<210> SEQ ID NO 246
<211> LENGTH: 9
<212> TYPE: PRT
<213> ORGANISM: homo sapiens

<400> SEQUENCE: 246

Phe Gln Gly Ser Gly Tyr Pro Leu Thr
1               5


<210> SEQ ID NO 247
<211> LENGTH: 330
<212> TYPE: PRT
<213> ORGANISM: homo sapiens

<400> SEQUENCE: 247

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

-continued

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 248
<211> LENGTH: 330
<212> TYPE: PRT
<213> ORGANISM: homo sapiens

<400> SEQUENCE: 248

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285
```

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 249
<211> LENGTH: 330
<212> TYPE: PRT
<213> ORGANISM: homo sapiens

<400> SEQUENCE: 249

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Arg Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys 325 330

<210> SEQ ID NO 250
<211> LENGTH: 330
<212> TYPE: PRT
<213> ORGANISM: homo sapiens

<400> SEQUENCE: 250

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Gln Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 251
<211> LENGTH: 330
<212> TYPE: PRT
<213> ORGANISM: homo sapiens

<400> SEQUENCE: 251

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 252
<211> LENGTH: 330
<212> TYPE: PRT
<213> ORGANISM: homo sapiens

<400> SEQUENCE: 252

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 253
<211> LENGTH: 330
<212> TYPE: PRT
<213> ORGANISM: homo sapiens

<400> SEQUENCE: 253

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 254
<211> LENGTH: 330
<212> TYPE: PRT
<213> ORGANISM: homo sapiens

<400> SEQUENCE: 254

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
```

```
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 255
<211> LENGTH: 330
<212> TYPE: PRT
<213> ORGANISM: homo sapiens

<400> SEQUENCE: 255

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160
```

-continued

```
Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 256
<211> LENGTH: 127
<212> TYPE: PRT
<213> ORGANISM: homo sapiens

<400> SEQUENCE: 256

```
Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met
        35                  40                  45

Gly Trp Ile Asn Pro Tyr Asn Gly Asn Lys Glu Phe Ser Ala Lys Phe
    50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
            100                 105                 110

Tyr Met Asp Val Trp Gly Lys Gly Thr Thr Val Ile Val Ser Ser
        115                 120                 125
```

<210> SEQ ID NO 257
<211> LENGTH: 108
<212> TYPE: PRT
<213> ORGANISM: homo sapiens

<400> SEQUENCE: 257

```
Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
            20                  25                  30
```

-continued

```
Arg Val Ala Trp Tyr Gln His Lys Pro Gly Gln Ala Pro Arg Leu Val
        35                  40                  45

Ile His Gly Val Ser Asn Arg Ala Ser Gly Ile Ser Asp Arg Phe Ser
    50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys
            100                 105
```